US010494409B2

(12) United States Patent
Baum et al.

(10) Patent No.: US 10,494,409 B2
(45) Date of Patent: Dec. 3, 2019

(54) CHIMERIC INSECTICIDAL PROTEINS TOXIC OR INHIBITORY TO LEPIDOPTERAN PESTS

(71) Applicant: Monsanto Technology LLC, St. Louis, MO (US)

(72) Inventors: James A. Baum, Webster Groves, MO (US); Thomas A. Cerruti, Newton, MA (US); Crystal L. Dart, Norton, MA (US); Leigh H. English, Chesterfield, MO (US); Stanislaw Flasinski, Chesterfield, MO (US); Xiaoran Fu, Belmont, MA (US); Victor M. Guzov, Cambridge, MA (US); Arlene R. Howe, Chesterfield, MO (US); Jay P. Morgenstern, Boston, MA (US); James K. Roberts, Chesterfield, MO (US); Sara A. Salvador, Wildwood, MO (US); Jinling Wang, Belmont, MA (US)

(73) Assignee: Monsanto Technology LLC, St. Louis, MO (US)

(*) Notice: Subject to any disclaimer, the term of this patent is extended or adjusted under 35 U.S.C. 154(b) by 70 days.

(21) Appl. No.: 15/848,852

(22) Filed: Dec. 20, 2017

(65) Prior Publication Data

US 2018/0127773 A1 May 10, 2018

Related U.S. Application Data

(63) Continuation of application No. 14/884,469, filed on Oct. 15, 2015, now Pat. No. 10,233,217.

(60) Provisional application No. 62/064,989, filed on Oct. 16, 2014.

(51) Int. Cl.

| | |
|---|---|
| ***C07K 14/325*** | (2006.01) |
| ***C12N 15/82*** | (2006.01) |
| ***A01N 63/02*** | (2006.01) |
| *C12N 15/62* | (2006.01) |

(52) U.S. Cl.

CPC ............ *C07K 14/325* (2013.01); *A01N 63/02* (2013.01); *C12N 15/8286* (2013.01); *C07K 2319/00* (2013.01); *C12N 15/62* (2013.01); *Y02A 40/162* (2018.01)

(58) Field of Classification Search

None

See application file for complete search history.

(56) References Cited

U.S. PATENT DOCUMENTS

| | | | | |
|---|---|---|---|---|
| 5,188,642 | A | 2/1993 | Shah et al. | |
| 5,312,910 | A | 5/1994 | Kishore et al. | |
| 5,500,365 | A | 3/1996 | Fischhoff et al. | |
| 5,510,471 | A | 4/1996 | Lebrun et al. | |
| 5,627,061 | A | 5/1997 | Barry et al. | |
| 5,633,435 | A | 5/1997 | Barry et al. | |
| 5,633,448 | A | 5/1997 | Lebrun et al. | |
| 5,728,925 | A | 3/1998 | Herrera-Estrella et al. | |
| 5,880,275 | A | 3/1999 | Fischhoff et al. | |
| 6,017,534 | A | 1/2000 | Marlvar et al. | |
| 6,033,874 | A | 3/2000 | Baum et al. | |
| 6,204,246 | B1 | 3/2001 | Bosch et al. | |
| 6,218,188 | B1 * | 4/2001 | Cardineau | C07K 14/325 435/468 |
| 6,501,009 | B1 | 12/2002 | Romano | |
| 6,713,063 | B1 | 3/2004 | Malvar et al. | |
| 6,962,705 | B2 | 11/2005 | Malvar et al. | |
| 7,064,249 | B2 | 6/2006 | Corbin et al. | |
| 7,070,982 | B2 | 7/2006 | Malvar et al. | |
| 7,193,133 | B2 | 3/2007 | Lassner et al. | |
| 7,510,878 | B2 | 3/2009 | Abad et al. | |
| 7,772,465 | B2 | 8/2010 | Abad et al. | |
| 7,812,129 | B1 | 10/2010 | Abad et al. | |
| 8,344,207 | B2 | 1/2013 | Bogdanova et al. | |
| 8,609,936 | B2 | 12/2013 | Baum et al. | |
| 2003/0119158 | A1 * | 6/2003 | Malvar | C07K 14/325 435/184 |
| 2006/0021087 | A1 | 1/2006 | Baum et al. | |
| 2006/0112447 | A1 | 5/2006 | Bogdanova et al. | |
| 2008/0172762 | A1 | 7/2008 | Cerf et al. | |
| 2008/0256667 | A1 | 10/2008 | Dersch et al. | |
| 2008/0280361 | A1 | 11/2008 | Calabotta et al. | |
| 2008/0282432 | A1 | 11/2008 | Duncan et al. | |
| 2009/0138985 | A1 | 5/2009 | Martinell et al. | |
| 2009/0142837 | A1 | 6/2009 | Adams, Jr. et al. | |
| 2009/0313721 | A1 | 12/2009 | Abad et al. | |

(Continued)

FOREIGN PATENT DOCUMENTS

| | | | |
|---|---|---|---|
| EP | 0189707 | A2 | 8/1986 |
| EP | 0508909 | A1 | 10/1992 |

(Continued)

OTHER PUBLICATIONS

Fourgoux-Nicol et al Plant Mol. Biol. (1999) 40: 857-872.*
Pardo Lopez et al, Peptides (2009) 30:589-595.*
Aronson et al, FEMS Microbiol. Lett. (2001) 195:1-8.*
Herrero et al., Biochem. J. (2004) 384, 507-513.*
Abdul-Rauf et al, Curr. Microbiol. (1999) 39, 94-98.*
UniProt Accession No. Q45739, Integrated into UniProt on May 30, 2000; initial submission on Nov. 1, 1996.*
Abdul-Rauf et al., "Mutations of Loop 2 and Loop 3 Residues in Domain II of *Bacillus thuringiensis* Cry1C δ-Endotoxin Affect Insecticidal Specificity and Initial Binding to *Spodoptera littoralis* and *Aedes aegypti* Midgut Membranes," *Current Microbiology*, 39:94-98 (1999).

(Continued)

*Primary Examiner* — Mykola V. Kovalenko
(74) *Attorney, Agent, or Firm* — Timothy K. Ball; Carine M. Doyle; Arnold & Porter Kaye Scholer LLP

(57) ABSTRACT

Nucleotide sequences are disclosed that encode novel chimeric insecticidal proteins exhibiting Lepidopteran inhibitory activity. Particular embodiments provide compositions and transformed plants, plant parts, and seeds containing the recombinant nucleic acid molecules encoding one or more of the chimeric insecticidal proteins.

19 Claims, No Drawings

Specification includes a Sequence Listing.

(56) References Cited

U.S. PATENT DOCUMENTS

| | | | | |
|---|---|---|---|---|
| 2009/0313722 | A1* | 12/2009 | Abad | C07K 14/32 800/279 |
| 2010/0004176 | A1 | 1/2010 | Sampson et al. | |
| 2010/0017914 | A1 | 1/2010 | Hart et al. | |
| 2010/0077507 | A1 | 3/2010 | Abad et al. | |
| 2010/0077508 | A1 | 3/2010 | Abad et al. | |
| 2010/0137216 | A1 | 6/2010 | Carozzi et al. | |
| 2010/0160231 | A1 | 6/2010 | Sampson et al. | |
| 2010/0192256 | A1 | 6/2010 | Abad et al. | |
| 2010/0197592 | A1 | 8/2010 | Heinrichs | |
| 2010/0269221 | A1 | 10/2010 | Abad et al. | |
| 2010/0317569 | A1 | 12/2010 | Lira et al. | |
| 2010/0319092 | A1 | 12/2010 | Lira et al. | |
| 2010/0319093 | A1 | 12/2010 | Lira et al. | |
| 2011/0030096 | A1 | 2/2011 | Lira et al. | |
| 2011/0055968 | A1 | 3/2011 | Cerf et al. | |
| 2011/0112013 | A1 | 5/2011 | Abad et al. | |
| 2011/0154536 | A1 | 6/2011 | Abad et al. | |
| 2012/0047606 | A1 | 2/2012 | Abad et al. | |
| 2012/0117690 | A1 | 5/2012 | Cerf et al. | |
| 2012/0167259 | A1 | 6/2012 | Liu et al. | |
| 2012/0192310 | A1 | 7/2012 | Abad et al. | |
| 2012/0210462 | A1 | 8/2012 | Bermudez et al. | |
| 2012/0233726 | A1 | 9/2012 | Abad et al. | |
| 2012/0317681 | A1 | 12/2012 | Meade et al. | |
| 2013/0055469 | A1 | 2/2013 | Sampson et al. | |
| 2013/0097735 | A1 | 4/2013 | Bowen et al. | |
| 2013/0104259 | A1 | 4/2013 | Sampson et al. | |
| 2013/0117884 | A1 | 5/2013 | Hargiss et al. | |
| 2013/0167264 | A1 | 6/2013 | Sampson et al. | |
| 2013/0219570 | A1 | 8/2013 | Lira et al. | |
| 2013/0269060 | A1 | 10/2013 | Baum et al. | |
| 2013/0303440 | A1 | 11/2013 | Sampson et al. | |
| 2013/0310543 | A1 | 11/2013 | Sampson et al. | |
| 2014/0007292 | A1 | 1/2014 | Cerf et al. | |
| 2014/0033361 | A1 | 1/2014 | Altier et al. | |
| 2014/0033363 | A1 | 1/2014 | Sampson | |
| 2014/0196175 | A1 | 7/2014 | Sampson et al. | |
| 2014/0223599 | A1 | 8/2014 | Sampson et al. | |
| 2014/0245491 | A1 | 8/2014 | Sampson et al. | |
| 2014/0298538 | A1 | 10/2014 | Heinrichs et al. | |
| 2014/0366227 | A1 | 12/2014 | Gatehouse et al. | |
| 2014/0373195 | A1 | 12/2014 | Sampson et al. | |

FOREIGN PATENT DOCUMENTS

| | | | |
|---|---|---|---|
| EP | 0218571 | B1 | 2/1993 |
| EP | 0924299 | A1 | 6/1999 |
| JP | 2009-505679 | A | 2/2009 |
| JP | 2013-514769 | A | 5/2013 |
| WO | WO 90/10076 | | 9/1990 |
| WO | WO 99/24581 | A2 | 5/1999 |
| WO | WO 01/14562 | A1 | 3/2001 |
| WO | WO 01/19859 | A2 | 3/2001 |
| WO | WO 02/14517 | A1 | 2/2002 |
| WO | WO 2004/020636 | A1 | 3/2004 |
| WO | WO2007027777 | A1 | 3/2007 |
| WO | WO 2011/075588 | A1 | 6/2011 |
| WO | WO2011075588 | A1 | 6/2011 |
| WO | WO 2014/008054 | A2 | 1/2014 |
| WO | WO 2014/055881 | A1 | 4/2014 |

OTHER PUBLICATIONS

Aronson et al., "Why *Bacillus thuringiensis* insecticidal toxins are so effective: unique features of their mode of action," *FEMS Microbiology Letters*, 195:1-8 (2001).

Baig et al., "cry Genes profiling and the toxicity of isolates of *Bacillus thuringiensis* from soil samples against American bollworm, *Helicoverpa armigera," Journal of Applied Microbiology*, 109:1967-1978 (2010).

Bravo et al., "Mode of action of *Bacillus thuringiensis* Cry and Cyt toxins and their potential for insect control," *Toxins*, 49:423-435 (2007).

Database UniProt, Database accession No. D9U3MO (2010).

De Maagd et al., "*Bacillus thuringiensis* delta-endotoxin Cry1C domain III Can Function as a Specificity Determinant for *Spodoptera exigua* in Different, but Not All, Cry1-Cry1C Hybrids," *Applied and Environmental Microbiology*, 66(4):1559-1563 (2000).

Della-Cioppa et al., "Translocation of the precursor of 5-enolpyruvylshikimate-3-phosphate synthase into chloroplasts of higher plants in vitro," *Proc. Natl. Acad. Sci. USA*, 83:6873-6877, (1986).

Forgoux-Nicol et al., "Isolation of repeseed genes expressed early and specifically during development of the male gametophyte," *Plant Molecular Biology*, 40:857-872 (1999).

Herrero et al., "Mutations in the *Bacillus thuringiensis* Cry1Ca toxin demonstrate the role of domains II and III in specificity towards *Spodoptera exigua* larvae," *Biochem J.*, 384:507-513 (2004).

International Search Report dated Jun. 6, 2016, in International Patent Application No. PCT US2015/055800.

IUPAC-IUB Joint Commission on Biochemical Nomenclature, "Nomenclature and Symbolism for Amino Acids and Peptides," *Eur. J. Biochem*. 138:9-37(1984) .

Klee et al., "Cloning of an *Arabidopsis thaliana* gene encoding 5-enolpyruvylshikimate-3-phosphate synthase: sequence analysis and manipulation to obtain glyphosate-tolerant plants," *Mol Gen Genet*, 210:437-442 (1987).

Knight et al., "A Strategy for Shuffling Numerous *Bacillus thuringiensis* Crystal Protein Domains," *Journal of Economic Entomology*, 97:1805-1813 (2004).

James, "Global Status of Commercialized Biotech/GM Crops: 2012," *ISAAA*, Brief No. 44 (2012).

Lucena et al., "Molecular Approaches to Improve the Insecticidal Activity of Bacillus thuringiensis Cry toxins," *Toxins*, 6(8):2393-2423 (2014).

Pardo-Lopez et al., "Strategies to improve the insecticidal activity of Cry toxins from *Bacillus thuringiensis," Peptides*, 30:589-595 (2009).

Pardo-Lopez et al., "*Bacillus thuringiensis* insecticidal three-domain Cry toxins: mode of action, insect resistance and consequences for crop protection," *FEMS Microbiology Reviews*, 37:3-22 (2013).

Thompson et al., "CLUSTAL W: improving the sensitivity of progressive multiple sequence alignment through sequence weighting, position-specific gap penalties and weight matrix choice," *Nucleic Acids Research*, 22:4673-4680 (1994).

Bravo et al., "Evolution of *Bacillus thuringiencis* Cry toxins insecticidal activity," *Microbial Biotechnology*,6:17-26 (2012).

Gen Bank Database, Apr. 25, 1994, Accession No. AAA 22344.1.

GenBank Database, Aug. 24, 1998, Accession No. AAC 32850.1.

GenBank Database, Apr. 18, 2005, Accession No. CAA 31951.1.

GenBank Database, Dec. 31, 2013, Accession No. AEH 31431.1.

GenBank Database, Apr. 26, 1993, Accession No. AAA 22561.1.

Gen Bank Database, Apr. 26, 1993, Accession No. AAA 22331.1.

GenBank Database, Nov. 18, 2005, Accession No. ABB 766664.1.

Maagd R. A. et al., "*Bacillus thuringiencis* Delta-Endotoxin Cry1C Domain III Can Function as a Specificity Determinant for *Spodoptera exigua* in Different, but Not All, Cry1-Cry1C Hybrids," *Applied and Environmental Microbiology*, 66(4):1559-1563 (2000).

Office Action in corresponding Application No. JP 2017-0520352, dated Feb. 5, 2019.

Periak et al., Insect Resistant Cotton Plants, *FEMS Microbiology Reviews*, 37:3-22 (2013).

* cited by examiner

SEQUENCE LISTING

```
<160> NUMBER OF SEQ ID NOS: 53

<210> SEQ ID NO 1
<211> LENGTH: 3570
<212> TYPE: DNA
<213> ORGANISM: Artificial
<220> FEATURE:
<223> OTHER INFORMATION: Recombinant nucleotide sequence used for
      expression in a bacterial cell encoding TIC1100.
```

<400> SEQUENCE: 1

```
atggagatag tgaataatca gaatcaatgc gtgccttata attgtttgaa taatcccgaa      60
atcgaaatat tagaaggcgg aagaatatca gttggtaata ccccaattga tatttctctt     120
tcgcttactc agtttctttt gagtgaattt gtcccaggtg cggggtttgt attaggatta     180
attgatttaa tatggggatt tgtaggtcct tcccaatggg acgcatttct tgctcaagtg     240
gaacagttaa ttaaccaaag aatagcagaa gctgtaagaa atacagcaat tcaggaatta     300
gagggaatgg cacgggttta tagaacctat gctactgctt ttgctgagtg ggaaaaagct     360
cctgatgacc cagagctaag agaagcacta cgtacacaat ttacagcaac tgagacttat     420
ataagtggaa gaatatccgt tttaaaaatt caaacttttg aagtacagct gttatcagtg     480
tttgcccaag ctgcaaattt acatttatct ttattaagag acgttgtgtt ttttgggcaa     540
agatggggtt tttcaacgac aaccgtaaat aattactaca atgatttaac agaagggatt     600
agtacctata cagattatgc tgtacgctgg tacaatacgg gattagaacg tgtatgggga     660
ccggattcta gagattgggt aaggtataat caatttagaa gagaattaac actaactgta     720
ttagatatcg ttgctctgtt cccgaattat gatagtagaa gatatccaat tcgaacagtt     780
tcccaattaa caagagaaat ttatacaaac ccagtattag aaaattttga tggtagtttt     840
cgaggctcgg ctcagggcat agaaagaagt attaggagtc cacatttgat ggatatactt     900
aacagtataa ccatctatac ggatgctcat aggggttatt attattggtc agggcatcaa     960
ataatggctt ctcctgtcgg tttttcgggg ccagaattca cgtttccgct atatggaacc    1020
atgggaaatg cagctccaca acaacgtatt gttgctcaac taggtcaggg cgtgtataga    1080
acattatcgt ccactttata tagaagacct tttaatatag ggataaataa tcaacaacta    1140
tctgttcttg acgggacaga atttgcttat ggaacctcct caaatttgcc atccgctgta    1200
tacagaaaaa gcggaacggt agattcgctg gatgaaatac cgccacagaa taacaacgtg    1260
ccacctaggc aaggatttag tcatcgatta agccatgttt caatgtttcg ttcaggcttt    1320
agtaatagta gtgtaagtat aataagagct cctatgttct cttggataca tcgtagtgct    1380
gaatttaata atataattgc atcggatagt attaatcaaa tacctttagt gaaaggattt    1440
agagtttggg ggggcacctc tgtcattaca ggaccaggat ttacaggagg ggatatcctt    1500
cgaagaaata cctttggtga ttttgtatct ctacaagtca atattaattc accaattacc    1560
caaagatacc gtttaagatt tcgttacgct tccagtaggg atgcacgagt tatagtatta    1620
acaggagcgg catccacagg agtgggaggc caagttagtg taaatatgcc tcttcagaaa    1680
actatggaaa taggggagaa cttaacatct agaacattta gatataccga ttttagtaat    1740
ccttttttcat ttagagctaa tccagatata attgggataa gtgaacaacc tctatttggt    1800
gcaggttcta ttagtagcgg tgaactttat atagataaaa ttgaaattat tctagcagat    1860
gcaacatttg aagcagaatc tgatttagaa agagcgcaga aggcggtgaa tgcgctgttt    1920
acgtctacaa accaactagg gctaaaaaca aatgtaacgg attatcatat tgatcaagtg    1980
tccaatttag ttacgtattt atcggatgaa ttttgtctgg atgaaaagcg agaattgtcc    2040
gagaaagtca aacatgcgaa gcgactcagt gatgaacgca atttactcca agattcaaat    2100
ttcaaagaca ttaataggca accagaacgt gggtggggcg gaagtacagg gattaccatc    2160
caaggagggg atgacgtatt taaagaaaat tacgtcacac tatcaggtac ctttgatgag    2220
tgctatccaa catatttgta tcaaaaaatc gatgaatcaa aattaaaagc ctttacccgt    2280
tatcaattaa gagggtatat cgaagatagt caagacttag aaatctattt aattcgctac    2340
```

```
aatgcaaaac atgaaacagt aaatgtgcca ggtacgggtt ccttatggcc gctttcagcc   2400

caaagtccaa tcggaaagtg tggagagccg aatcgatgcg cgccacacct tgaatggaat   2460

cctgacttag attgttcgtg tagggatgga gaaaagtgtg cccatcattc gcatcatttc   2520

tccttagaca ttgatgtagg atgtacagac ttaaatgagg acctaggtgt atgggtgatc   2580

tttaagatta agacgcaaga tgggcacgca agactaggga atctagagtt tctcgaagag   2640

aaaccattag taggagaagc gctagctcgt gtgaaaagag cggagaaaaa atggagagac   2700

aaacgtgaaa aattggaatg ggaaacaaat atcgtttata aagaggcaaa agaatctgta   2760

gatgctttat ttgtaaactc tcaatatgat caattacaag cggatacgaa tattgccatg   2820

attcatgcgg cagataaacg tgttcatagc attcgagaag cttatctgcc tgagctgtct   2880

gtgattccgg gtgtcaatgc ggctattttt gaagaattag aagggcgtat tttcactgca   2940

ttctccctat atgatgcgag aaatgtcatt aaaaatggtg attttaataa tggcttatcc   3000

tgctggaacg tgaaagggca tgtagatgta gaagaacaaa acaaccaacg ttcggtcctt   3060

gttgttccgg aatgggaagc agaagtgtca caagaagttc gtgtctgtcc gggtcgtggc   3120

tatatccttc gtgtcacagc gtacaaggag ggatatggag aaggttgcgt aaccattcat   3180

gagatcgaga acaatacaga cgaactgaag tttagcaact gcgtagaaga ggaaatctat   3240

ccaaataaca cggtaacgtg taatgattat actgtaaatc aagaagaata cggaggtgcg   3300

tacacttctc gtaatcgagg atataacgaa gctccttccg taccagctga ttatgcgtca   3360

gtctatgaag aaaaatcgta tacagatgga cgaagagaga atccttgtga atttaacaga   3420

gggtataggg attacacgcc actaccagtt ggttatgtga caaaagaatt agaatacttc   3480

ccagaaaccg ataaggtatg gattgagatt ggagaaacgg aaggaacatt tatcgtggac   3540

agcgtggaat tactccttat ggaggaatga                                    3570
```

```
<210> SEQ ID NO 2
<211> LENGTH: 3570
<212> TYPE: DNA
<213> ORGANISM: Artificial
<220> FEATURE:
<223> OTHER INFORMATION: Synthetic nucleotide sequence designed for
      expression in a plant cell encoding TIC1100.

<400> SEQUENCE: 2
```

```
atggagattg tgaacaacca gaaccagtgc gttccttaca actgcttgaa caaccctgag     60

attgagattc ttgagggtgg tagaatttct gttggcaaca ctcctattga catctctttg    120

agtttgactc aattcttgtt gagtgagttc gttcctggtg ctggtttcgt cttgggtttg    180

attgatttga tttggggttt cgttggtcct agtcaatggg atgctttctt ggctcaagtt    240

gagcaattga ttaaccagag gatcgctgag gctgtgagga acactgctat tcaagagttg    300

gagggtatgg ctagagttta cagaacttac gctactgctt tcgctgagtg ggagaaggct    360

cctgatgacc ctgagttgag ggaggctttg agaactcaat tcactgctac tgagacttac    420

atcagtggta gaatcagtgt cttgaagatt caaactttcg aggttcaatt gctttctgtg    480

ttcgctcaag ctgcaaactt gcacttgtct ttgcttagag atgttgtgtt ctttggtcaa    540

agatggggtt tctccactac taccgtgaac aattactaca acgatttgac tgagggtatt    600

tctacttaca ctgattacgc tgttagatgg tacaacactg gtttggagag agtttggggt    660

ccagattcca gagattgggt cagatacaac cagttcagaa gggagttgac tttgactgtc    720

ttggacattg ttgctctctt ccctaactac gatagtcgtc gttaccctat tagaactgtt    780
```

-continued

```
tctcaactta ctagggaaat ctacactaac cctgttcttg agaacttcga tggtagtttc    840
cgtggtagtg ctcaagggat tgagcgttct attcgttctc ctcatcttat ggacattctt    900
aactctatta ctatctacac tgatgctcat cgtggttact attactggtc tggtcatcaa    960
attatggcta gtcctgttgg tttcagtggt cctgagttca ctttccctct ttacggtact   1020
atgggcaacg ctgcacctca acagaggatc gttgctcaac ttggtcaagg tgtttacagg   1080
actctttctt caacccttta caggcgtcct ttcaacattg ggatcaacaa ccagcagctt   1140
tctgttcttg atggaaccga gttcgcttac ggaacctctt caaaccttcc tagtgctgtt   1200
tacaggaagt ctggaaccgt tgacagtctt gatgagattc caccgcagaa caataacgtt   1260
ccacccaggc aaggcttcag tcataggctt tctcatgttt ctatgttccg ctctggattc   1320
agcaactctt cagtttctat tatcagggct ccaatgttct cgtggattca taggtctgcc   1380
gagttcaaca acattatcgc ttccgatagc attaaccaga ttccacttgt taagggattc   1440
cgtgtttggg gaggcacctc tgttattacc ggaccaggct tcaccggagg cgacattctt   1500
cgtcgtaaca ccttcggaga tttcgtttca cttcaagtga acattaactc accaatcacc   1560
cagcgctaca ggcttcgctt ccgctacgca tcatccaggg atgcaagggt gatcgtgctt   1620
accggagcag cctcaaccgg agtgggaggc caagtgagcg tgaacatgcc acttcagaag   1680
acgatggaga tcggcgagaa ccttacctca agaacctttc gttacaccga tttcagcaac   1740
ccattcagct ttcgtgcaaa cccagacatc atagggatct cagagcagcc actgtttgga   1800
gctggatcaa tctcatccgg agagctttac atcgacaaga tcgagatcat actcgcagat   1860
gcaaccttcg aggctgagag cgatctggag cgtgcacaga aggcagtgaa cgcactcttt   1920
acctctacca accagctcgg actcaagacc aacgtgaccg attaccacat cgaccaagtg   1980
agcaacctcg tgacctacct ctcagatgag ttctgcttgg atgagaaacg cgaactcagc   2040
gagaaggtga agcacgcaaa gcgtctctca gatgagcgta acctcctcca ggatagcaat   2100
ttcaaggaca tcaatcgtca gccagagcgt ggatggggag gctcaaccgg aatcaccatc   2160
cagggaggcg atgatgtgtt taaggagaat tacgtgacac tctccggaac attcgatgag   2220
tgctacccaa catacctcta tcagaagatc gacgagtcca agctcaaggc gttcacccgt   2280
tatcagctcc gtggctacat cgaggatagt caagacctgg aaatctacct catccgctac   2340
aatgcaaagc acgagacagt gaatgtgcca ggaacaggct ccctctggcc actctccgca   2400
cagtctccaa tcggcaagtg cggcgagcca aatcgctgcg cgccacacct ggagtggaat   2460
cccgacctgg actgctcctg ccgcgacggc gagaagtgcg cccaccactc ccaccacttt   2520
agcctggaca tcgacgtggg ctgtacagac ctgaatgagg atctgggcgt gtgggtgatc   2580
tttaagatca agacacagga cggccacgcc cgcctgggca atctggagtt tctggaggag   2640
aagcctctgg tgggcgaagc cctggcccgc gtgaagcgcg ccgagaagaa atggcgcgac   2700
aaacgcgaga aactggaatg ggaaacaaac atcgtgtaca aagaagccaa agaatccgtg   2760
gacgccctat ttgtgaactc ccagtatgac cagctacagg ccgacacaaa catcgcgatg   2820
atccacgctg cggacaagcg cgtgcactcc atacgcgaag cctatctacc cgaactatcc   2880
gtgatacccg gcgtcaatgc cgcgatcttt gaagaattgg aaggccgcat cttcacagcc   2940
tttagcctct atgacgcccg aaatgtcatc aagaatggcg actttaacaa tgggctatcc   3000
tgttggaatg tcaaagggca cgtggacgtc gaagagcaga acaatcagcg atccgtctta   3060
gtcgtacccg aatgggaagc cgaagtctcc caggaagtcc gagtctgtcc tggtagaggt   3120
```

```
tacatcttga gagtgactgc ttacaaggag ggttacggtg agggatgcgt gactattcac   3180

gagattgaga acaacactga tgagttgaag ttcagtaact gcgtggagga ggaaatctac   3240

cccaacaaca ctgtgacttg taacgattac accgtgaacc aggaggaata cggaggcgct   3300

tacacctcca gaaaccgtgg atacaatgag gctccctcgg tccccgctga ttatgcctcc   3360

gtctatgagg agaagtccta caccgatgga aggcgcgaga atccctgcga gttcaatcgc   3420

ggctatcgag actacactcc gctacccgtt ggctatgtca caaaggaact ggaatacttc   3480

ccggaaacag acaaagtctg gatcgaaatc ggcgaaacag aagggacgtt catagtcgat   3540

agcgtagaac ttctccttat ggaagaatga                                    3570
```

```
<210> SEQ ID NO 3
<211> LENGTH: 3570
<212> TYPE: DNA
<213> ORGANISM: Artificial
<220> FEATURE:
<223> OTHER INFORMATION: Synthetic nucleotide sequence designed for
      expression in a plant cell encoding TIC1100.

<400> SEQUENCE: 3

atggagattg tgaacaacca gaaccagtgc gttccttaca actgcttgaa caaccctgag     60

attgagattc ttgagggtgg tagaatttct gttggcaaca ctcctattga catctctttg    120

agtttgactc aattcttgtt gagtgagttc gttcctggtg ctggtttcgt cttgggtttg    180

attgatttga tttggggttt cgttggtcct agtcaatggg atgctttctt ggctcaagtt    240

gagcaattga ttaaccagag gatcgctgag gctgtgagga acactgctat tcaagagttg    300

gagggtatgg ctagagttta cagaacttac gctactgctt tcgctgagtg ggagaaggct    360

cctgatgacc ctgagttgag ggaggctttg agaactcaat tcactgctac tgagacttac    420

atcagtggta gaatcagtgt cttgaagatt caaactttcg aggttcaatt gctttctgtg    480

ttcgctcaag ctgcaaactt gcacttgtct ttgcttagag atgttgtgtt ctttggtcaa    540

agatggggtt tctccactac taccgtgaac aattactaca acgatttgac tgagggtatt    600

tctacttaca ctgattacgc tgttagatgg tacaacactg gtttggagag agtttggggt    660

ccagattcca gagattgggt cagatacaac cagttcagaa gggagttgac tttgactgtc    720

ttggacattg ttgctctctt ccctaactac gatagtcgtc gttaccctat tagaactgtt    780

tctcaactta ctagggaaat ctacactaac cctgttcttg agaacttcga tggtagtttc    840

cgtggtagtg ctcaagggat tgagcgttct attcgttctc ctcatcttat ggacattctt    900

aactctatta ctatctacac tgatgctcat cgtggttact attactggtc tggtcatcaa    960

attatggcta gtcctgttgg tttcagtggt cctgagttca ctttccctct ttacggtact   1020

atgggcaacg ctgcacctca acagaggatc gttgctcaac ttggtcaagg tgtttacagg   1080

actctttctt caaccctta caggcgtcct ttcaacattg ggatcaacaa ccagcagctt   1140

tctgttcttg atggaaccga gttcgcttac ggaacctctt caaaccttcc tagtgctgtt   1200

tacaggaagt ctggaaccgt tgacagtctt gatgagattc caccgcagaa caataacgtt   1260

ccacccaggc aaggcttcag tcataggctt tctcatgttt ctatgttccg ctctggattc   1320

agcaactctt cagtttctat tatcagggct ccaatgttct cgtggattca taggtctgcc   1380

gagttcaaca acattatcgc ttccgatagc attaaccaga ttccacttgt taagggattc   1440

cgtgtttggg gaggcacctc tgttattacc ggaccaggct tcaccggagg cgacattctt   1500

cgtcgtaaca ccttcggaga tttcgtttca cttcaagtga acattaactc accaatcacc   1560
```

-continued cagcgctaca ggcttcgctt ccgctacgca tcatccaggg atgcaagggt gatcgtgctt 1620
accggagcag cctcaaccgg agtgggaggc caagtgagcg tgaacatgcc acttcagaag 1680
acgatggaga tcggcgagaa ccttacctca agaacctttc gttacaccga tttcagcaac 1740
ccattcagct ttcgtgcaaa cccagacatc atagggatct cagagcagcc actgtttgga 1800
gctggatcaa tctcatccgg agagctttac atcgacaaga tcgagatcat actcgcagat 1860
gcaaccttcg aggctgagag cgatctggag cgtgcacaga aggcagtgaa cgcactcttt 1920
acctctacca accagctcgg actcaagacc aacgtgaccg attaccacat cgaccaagtg 1980
agcaacctcg tgacctacct ctcagatgag ttctgcttgg atgagaaacg cgaactcagc 2040
gagaaggtga agcacgcaaa gcgtctctca gatgagcgta acctcctcca ggatagcaat 2100
ttcaaggaca tcaatcgtca gccagagcgt ggatggggag gctcaaccgg aatcaccatc 2160
cagggaggcg atgatgtgtt taaggagaat tacgtgacac tctccggaac attcgatgag 2220
tgctacccaa catacctcta tcagaagatc gacgagtcca agctcaaggc gttcacccgt 2280
tatcagctcc gtggctacat cgaggatagt caagacctgg aaatctacct catccgctac 2340
aatgcaaagc acgagacagt gaatgtacca ggaacaggct ccctctggcc actctccgca 2400
cagtctccaa tcggcaagtg cggcgagcca aatcgctgcg cgccacacct ggagtggaat 2460
cccgacctgg actgctcctg ccgcgacggc gagaagtgcg cccaccactc ccaccacttt 2520
agcctggaca tcgacgtggg ctgtacagac ctgaatgagg atctgggcgt gtgggtgatc 2580
tttaagatca agacacagga cggccacgcc cgcctgggca atctggagtt tctggaggag 2640
aagcctctgg tgggcgaagc cctggcccgc gtgaagcgcg ccgagaagaa atggcgcgac 2700
aaacgcgaga aactggaatg ggaaacaaac atcgtgtaca aagaagccaa agaatccgtg 2760
gacgccctat ttgtgaactc ccagtatgac cagctacagg ccgacacaaa catcgcgatg 2820
atccacgctg cggacaagcg cgtgcactcc atacgcgaag cctatctacc cgaactatcc 2880
gtgatacccg gcgtcaatgc cgcgatcttt gaagaattgg aaggccgcat cttcacagcc 2940
tttagcctct atgacgcccg aaatgtcatc aagaatggcg actttaacaa tgggctatcc 3000
tgttggaatg tcaaagggca cgtggacgtc gaagagcaga acaatcagcg atccgtctta 3060
gtcgtacccg aatgggaagc cgaagtctcc caggaagtcc gagtctgtcc tggtagaggt 3120
tacatcttga gagtgactgc ttacaaggag ggttacggtg agggatgcgt gactattcac 3180
gagattgaga acaacactga tgagttgaag ttcagtaact gcgtggagga ggaaatctac 3240
cccaacaaca ctgtgacttg taacgattac accgtgaacc aggaggaata cggaggcgct 3300
tacacctcca gaaaccgtgg atacaatgag gctccctcgg tccccgctga ttatgcctcc 3360
gtctatgagg agaagtccta caccgatgga aggcgcgaga atccctgcga gttcaatcgc 3420
ggctatcgag actacactcc gctacccgtt ggctatgtca caaaggaact ggaatacttc 3480
ccggaaacag acaaagtctg gatcgaaatc ggcgaaacag aagggacgtt catagtcgat 3540
agcgtagaac ttctccttat ggaagaatga 3570

<210> SEQ ID NO 4
<211> LENGTH: 1189
<212> TYPE: PRT
<213> ORGANISM: Artificial
<220> FEATURE:
<223> OTHER INFORMATION: Amino acid sequence of the chimeric protein TIC1100.

<400> SEQUENCE: 4

-continued

```
Met Glu Ile Val Asn Asn Gln Asn Gln Cys Val Pro Tyr Asn Cys Leu
1               5                   10                  15

Asn Asn Pro Glu Ile Glu Ile Leu Glu Gly Gly Arg Ile Ser Val Gly
            20                  25                  30

Asn Thr Pro Ile Asp Ile Ser Leu Ser Leu Thr Gln Phe Leu Leu Ser
        35                  40                  45

Glu Phe Val Pro Gly Ala Gly Phe Val Leu Gly Leu Ile Asp Leu Ile
    50                  55                  60

Trp Gly Phe Val Gly Pro Ser Gln Trp Asp Ala Phe Leu Ala Gln Val
65                  70                  75                  80

Glu Gln Leu Ile Asn Gln Arg Ile Ala Glu Ala Val Arg Asn Thr Ala
                85                  90                  95

Ile Gln Glu Leu Glu Gly Met Ala Arg Val Tyr Arg Thr Tyr Ala Thr
            100                 105                 110

Ala Phe Ala Glu Trp Glu Lys Ala Pro Asp Asp Pro Glu Leu Arg Glu
        115                 120                 125

Ala Leu Arg Thr Gln Phe Thr Ala Thr Glu Thr Tyr Ile Ser Gly Arg
    130                 135                 140

Ile Ser Val Leu Lys Ile Gln Thr Phe Glu Val Gln Leu Leu Ser Val
145                 150                 155                 160

Phe Ala Gln Ala Ala Asn Leu His Leu Ser Leu Leu Arg Asp Val Val
                165                 170                 175

Phe Phe Gly Gln Arg Trp Gly Phe Ser Thr Thr Thr Val Asn Asn Tyr
            180                 185                 190

Tyr Asn Asp Leu Thr Glu Gly Ile Ser Thr Tyr Thr Asp Tyr Ala Val
        195                 200                 205

Arg Trp Tyr Asn Thr Gly Leu Glu Arg Val Trp Gly Pro Asp Ser Arg
    210                 215                 220

Asp Trp Val Arg Tyr Asn Gln Phe Arg Arg Glu Leu Thr Leu Thr Val
225                 230                 235                 240

Leu Asp Ile Val Ala Leu Phe Pro Asn Tyr Asp Ser Arg Arg Tyr Pro
                245                 250                 255

Ile Arg Thr Val Ser Gln Leu Thr Arg Glu Ile Tyr Thr Asn Pro Val
            260                 265                 270

Leu Glu Asn Phe Asp Gly Ser Phe Arg Gly Ser Ala Gln Gly Ile Glu
        275                 280                 285

Arg Ser Ile Arg Ser Pro His Leu Met Asp Ile Leu Asn Ser Ile Thr
    290                 295                 300

Ile Tyr Thr Asp Ala His Arg Gly Tyr Tyr Tyr Trp Ser Gly His Gln
305                 310                 315                 320

Ile Met Ala Ser Pro Val Gly Phe Ser Gly Pro Glu Phe Thr Phe Pro
                325                 330                 335

Leu Tyr Gly Thr Met Gly Asn Ala Ala Pro Gln Gln Arg Ile Val Ala
            340                 345                 350

Gln Leu Gly Gln Gly Val Tyr Arg Thr Leu Ser Ser Thr Leu Tyr Arg
        355                 360                 365

Arg Pro Phe Asn Ile Gly Ile Asn Asn Gln Gln Leu Ser Val Leu Asp
    370                 375                 380

Gly Thr Glu Phe Ala Tyr Gly Thr Ser Ser Asn Leu Pro Ser Ala Val
385                 390                 395                 400

Tyr Arg Lys Ser Gly Thr Val Asp Ser Leu Asp Glu Ile Pro Pro Gln
                405                 410                 415

Asn Asn Asn Val Pro Pro Arg Gln Gly Phe Ser His Arg Leu Ser His
```

-continued

```
            420                 425                 430

Val Ser Met Phe Arg Ser Gly Phe Ser Asn Ser Ser Val Ser Ile Ile
        435                 440                 445

Arg Ala Pro Met Phe Ser Trp Ile His Arg Ser Ala Glu Phe Asn Asn
    450                 455                 460

Ile Ile Ala Ser Asp Ser Ile Asn Gln Ile Pro Leu Val Lys Gly Phe
465                 470                 475                 480

Arg Val Trp Gly Gly Thr Ser Val Ile Thr Gly Pro Gly Phe Thr Gly
                485                 490                 495

Gly Asp Ile Leu Arg Arg Asn Thr Phe Gly Asp Phe Val Ser Leu Gln
            500                 505                 510

Val Asn Ile Asn Ser Pro Ile Thr Gln Arg Tyr Arg Leu Arg Phe Arg
        515                 520                 525

Tyr Ala Ser Ser Arg Asp Ala Arg Val Ile Val Leu Thr Gly Ala Ala
    530                 535                 540

Ser Thr Gly Val Gly Gly Gln Val Ser Val Asn Met Pro Leu Gln Lys
545                 550                 555                 560

Thr Met Glu Ile Gly Glu Asn Leu Thr Ser Arg Thr Phe Arg Tyr Thr
                565                 570                 575

Asp Phe Ser Asn Pro Phe Ser Phe Arg Ala Asn Pro Asp Ile Ile Gly
            580                 585                 590

Ile Ser Glu Gln Pro Leu Phe Gly Ala Gly Ser Ile Ser Ser Gly Glu
        595                 600                 605

Leu Tyr Ile Asp Lys Ile Glu Ile Ile Leu Ala Asp Ala Thr Phe Glu
    610                 615                 620

Ala Glu Ser Asp Leu Glu Arg Ala Gln Lys Ala Val Asn Ala Leu Phe
625                 630                 635                 640

Thr Ser Thr Asn Gln Leu Gly Leu Lys Thr Asn Val Thr Asp Tyr His
                645                 650                 655

Ile Asp Gln Val Ser Asn Leu Val Thr Tyr Leu Ser Asp Glu Phe Cys
            660                 665                 670

Leu Asp Glu Lys Arg Glu Leu Ser Glu Lys Val Lys His Ala Lys Arg
        675                 680                 685

Leu Ser Asp Glu Arg Asn Leu Leu Gln Asp Ser Asn Phe Lys Asp Ile
    690                 695                 700

Asn Arg Gln Pro Glu Arg Gly Trp Gly Gly Ser Thr Gly Ile Thr Ile
705                 710                 715                 720

Gln Gly Gly Asp Asp Val Phe Lys Glu Asn Tyr Val Thr Leu Ser Gly
                725                 730                 735

Thr Phe Asp Glu Cys Tyr Pro Thr Tyr Leu Tyr Gln Lys Ile Asp Glu
            740                 745                 750

Ser Lys Leu Lys Ala Phe Thr Arg Tyr Gln Leu Arg Gly Tyr Ile Glu
        755                 760                 765

Asp Ser Gln Asp Leu Glu Ile Tyr Leu Ile Arg Tyr Asn Ala Lys His
    770                 775                 780

Glu Thr Val Asn Val Pro Gly Thr Gly Ser Leu Trp Pro Leu Ser Ala
785                 790                 795                 800

Gln Ser Pro Ile Gly Lys Cys Gly Glu Pro Asn Arg Cys Ala Pro His
                805                 810                 815

Leu Glu Trp Asn Pro Asp Leu Asp Cys Ser Cys Arg Asp Gly Glu Lys
            820                 825                 830

Cys Ala His His Ser His His Phe Ser Leu Asp Ile Asp Val Gly Cys
        835                 840                 845
```

```
Thr Asp Leu Asn Glu Asp Leu Gly Val Trp Val Ile Phe Lys Ile Lys
    850                 855                 860

Thr Gln Asp Gly His Ala Arg Leu Gly Asn Leu Glu Phe Leu Glu Glu
865                 870                 875                 880

Lys Pro Leu Val Gly Glu Ala Leu Ala Arg Val Lys Arg Ala Glu Lys
                885                 890                 895

Lys Trp Arg Asp Lys Arg Glu Lys Leu Glu Trp Glu Thr Asn Ile Val
            900                 905                 910

Tyr Lys Glu Ala Lys Glu Ser Val Asp Ala Leu Phe Val Asn Ser Gln
        915                 920                 925

Tyr Asp Gln Leu Gln Ala Asp Thr Asn Ile Ala Met Ile His Ala Ala
    930                 935                 940

Asp Lys Arg Val His Ser Ile Arg Glu Ala Tyr Leu Pro Glu Leu Ser
945                 950                 955                 960

Val Ile Pro Gly Val Asn Ala Ala Ile Phe Glu Glu Leu Glu Gly Arg
                965                 970                 975

Ile Phe Thr Ala Phe Ser Leu Tyr Asp Ala Arg Asn Val Ile Lys Asn
            980                 985                 990

Gly Asp Phe Asn Asn Gly Leu Ser  Cys Trp Asn Val Lys  Gly His Val
        995                 1000                1005

Asp Val  Glu Glu Gln Asn Asn  Gln Arg Ser Val Leu  Val Val Pro
    1010                1015                1020

Glu Trp  Glu Ala Glu Val Ser  Gln Glu Val Arg Val  Cys Pro Gly
    1025                1030                1035

Arg Gly  Tyr Ile Leu Arg Val  Thr Ala Tyr Lys Glu  Gly Tyr Gly
    1040                1045                1050

Glu Gly  Cys Val Thr Ile His  Glu Ile Glu Asn Asn  Thr Asp Glu
    1055                1060                1065

Leu Lys  Phe Ser Asn Cys Val  Glu Glu Glu Ile Tyr  Pro Asn Asn
    1070                1075                1080

Thr Val  Thr Cys Asn Asp Tyr  Thr Val Asn Gln Glu  Glu Tyr Gly
    1085                1090                1095

Gly Ala  Tyr Thr Ser Arg Asn  Arg Gly Tyr Asn Glu  Ala Pro Ser
    1100                1105                1110

Val Pro  Ala Asp Tyr Ala Ser  Val Tyr Glu Glu Lys  Ser Tyr Thr
    1115                1120                1125

Asp Gly  Arg Arg Glu Asn Pro  Cys Glu Phe Asn Arg  Gly Tyr Arg
    1130                1135                1140

Asp Tyr  Thr Pro Leu Pro Val  Gly Tyr Val Thr Lys  Glu Leu Glu
    1145                1150                1155

Tyr Phe  Pro Glu Thr Asp Lys  Val Trp Ile Glu Ile  Gly Glu Thr
    1160                1165                1170

Glu Gly  Thr Phe Ile Val Asp  Ser Val Glu Leu Leu  Leu Met Glu
    1175                1180                1185

Glu
```

<210> SEQ ID NO 5
<211> LENGTH: 3672
<212> TYPE: DNA
<213> ORGANISM: Artificial
<220> FEATURE:
<223> OTHER INFORMATION: Recombinant nucleotide sequence used for expression in a bacterial cell encoding TIC860.

<400> SEQUENCE: 5

-continued

```
atgacttcaa ataggaaaaa tgagaatgaa attataaatg ctttatcgat tccaacggta     60
tcgaatcctt ccacgcaaat gaatctatca ccagatgctc gtattgaaga tagcttgtgt    120
gtagccgagg tgaacaatat tgatccattt gttagcgcat caacagtcca aacgggtata    180
aacatagctg gtagaatatt gggcgtatta ggtgtgccgt ttgctggaca actagctagt    240
ttttatagtt ttcttgttgg ggaattatgg cctagtggca gagatccatg ggaaattttc    300
ctggaacatg tagaacaact tataagacaa caagtaacag aaaatactag gaatacggct    360
attgctcgat tagaaggtct aggaagaggc tatagatctt accagcaggc tcttgaaact    420
tggttagata accgaaatga tgcaagatca agaagcatta ttcttgagcg ctatgttgct    480
ttagaacttg acattactac tgctataccg cttttcagaa tacgaaatga agaagttcca    540
ttattaatgg tatatgctca agctgcaaat ttacacctat tattattgag agacgcatcc    600
ctttttggta gtgaatgggg gatggcatct tccgatgtta accaatatta ccaagaacaa    660
atcagatata cagaggaata ttctaaccat tgcgtacaat ggtataatac agggctaaat    720
aacttaagag ggacaaatgc tgaaagttgg ttgcggtata atcaattccg tagagaccta    780
acgttagggg tattagattt agtagcccta ttcccaagct atgatactcg cacttatcca    840
atcaatacga gtgctcagtt aacaagagaa atttatacag atccaattgg gagaacaaat    900
gcaccttcag gatttgcaag tacgaattgg tttaataata atgcaccatc gttttctgcc    960
atagaggctg ccattttcag gcctccgcat ctacttgatt ttccagaaca acttacaatt   1020
tacagtgcat caagccgttg gagtagcact caacatatga attattgggt gggacatagg   1080
cttaacttcc gcccaatagg agggacatta aatacctcaa cacaaggact tactaataat   1140
acttcaatta atcctgtaac attacagttt acgtctcgag acgtttatag aacagaatca   1200
aatgcaggga caaatatact atttactact cctgtgaatg gagtaccttg ggctagattt   1260
aattttataa accctcagaa tatttatgaa agaggcgcca ctacctacag tcaaccgtat   1320
cagggagttg ggattcaatt atttgattca gaaactgaat taccaccaga aacaacagaa   1380
cgaccaaatt atgaatcata tagtcataga ttatctcata taggactaat cataggaaac   1440
actttgagag caccagtcta ttcttggacg catcgtagtg cagatcgtac gaatacgatt   1500
ggaccaaata gaattaatca aatacccttta gtgaaaggat ttagagtttg ggggggcacc   1560
tctgtcatta caggaccagg atttacagga ggggatatcc ttcgaagaaa tacctttggt   1620
gattttgtat ctctacaagt caatattaat tcaccaatta cccaaagata ccgtttaaga   1680
tttcgttacg cttccagtag ggatgcacga gttatagtat taacaggagc ggcatccaca   1740
ggagtgggag gccaagttag tgtaaatatg cctcttcaga aaactatgga aataggggag   1800
aacttaacat ctagaacatt tagatatacc gattttagta atcctttttc atttagagct   1860
aatccagata taattgggat aagtgaacaa cctctatttg gtgcaggttc tattagtagc   1920
ggtgaacttt atatagataa aattgaaatt attctagcag atgcaacatt tgaagcagaa   1980
tctgatttag aaagagcgca gaaggcggtg aatgcgctgt ttacgtctac aaaccaacta   2040
gggctaaaaa caaatgtaac ggattatcat attgatcaag tgtccaattt agttacgtat   2100
ttatcggatg aattttgtct ggatgaaaag cgagaattgt ccgagaaagt caaacatgcg   2160
aagcgactca gtgatgaacg caatttactc caagattcaa atttcaaaga cattaatagg   2220
caaccagaac gtgggtgggg cggaagtaca gggattacca tccaaggagg ggatgacgta   2280
tttaaagaaa attacgtcac actatcaggt acctttgatg agtgctatcc aacatatttg   2340
```

```
tatcaaaaaa tcgatgaatc aaaattaaaa gcctttaccc gttatcaatt aagagggtat   2400

atcgaagata gtcaagactt agaaatctat ttaattcgct acaatgcaaa acatgaaaca   2460

gtaaatgtgc caggtacggg ttccttatgg ccgctttcag cccaaagtcc aatcggaaag   2520

tgtggagagc cgaatcgatg cgcgccacac cttgaatgga atcctgactt agattgttcg   2580

tgtagggatg gagaaaagtg tgcccatcat tcgcatcatt tctccttaga cattgatgta   2640

ggatgtacag acttaaatga ggacctaggt gtatgggtga tctttaagat taagacgcaa   2700

gatgggcacg caagactagg gaatctagag tttctcgaag agaaaccatt agtaggagaa   2760

gcgctagctc gtgtgaaaag agcggagaaa aaatggagag acaaacgtga aaaattggaa   2820

tgggaaacaa atatcgttta taaagaggca aaagaatctg tagatgcttt atttgtaaac   2880

tctcaatatg atcaattaca agcggatacg aatattgcca tgattcatgc ggcagataaa   2940

cgtgttcata gcattcgaga agcttatctg cctgagctgt ctgtgattcc gggtgtcaat   3000

gcggctattt ttgaagaatt agaagggcgt attttcactg cattctccct atatgatgcg   3060

agaaatgtca ttaaaaatgg tgattttaat aatggcttat cctgctggaa cgtgaaaggg   3120

catgtagatg tagaagaaca aaacaaccaa cgttcggtcc ttgttgttcc ggaatgggaa   3180

gcagaagtgt cacaagaagt tcgtgtctgt ccgggtcgtg gctatatcct tcgtgtcaca   3240

gcgtacaagg agggatatgg agaaggttgc gtaaccattc atgagatcga gaacaataca   3300

gacgaactga agtttagcaa ctgcgtagaa gaggaaatct atccaaataa cacggtaacg   3360

tgtaatgatt atactgtaaa tcaagaagaa tacggaggtg cgtacacttc tcgtaatcga   3420

ggatataacg aagctccttc cgtaccagct gattatgcgt cagtctatga agaaaaatcg   3480

tatacagatg gacgaagaga gaatccttgt gaatttaaca gagggtatag ggattacacg   3540

ccactaccag ttggttatgt gacaaaagaa ttagaatact tcccagaaac cgataaggta   3600

tggattgaga ttggagaaac ggaaggaaca tttatcgtgg acagcgtgga attactcctt   3660

atggaggaat ag                                                       3672
```

```
<210> SEQ ID NO 6
<211> LENGTH: 3672
<212> TYPE: DNA
<213> ORGANISM: Artificial
<220> FEATURE:
<223> OTHER INFORMATION: Synthetic nucleotide sequence designed for
      expression in a plant cell encoding TIC860.

<400> SEQUENCE: 6

atgaccagca accggaagaa cgagaacgag atcatcaacg ccctgagcat cccgaccgtg     60

agcaacccta gcacccagat gaacctgagc cctgacgctc gcatcgagga ctccctctgc    120

gtggctgagg tgaacaacat cgacccgttc gtgtccgcct ccaccgtgca gaccggcatc    180

aacatcgcgg gccgcatcct cggcgtgctc ggcgtgccct ttgcgggcca gctcgcctcc    240

ttctactcct tcctcgtggg agagctgtgg ccctccggcc gcgacccgtg ggagatcttc    300

ctggagcacg tggagcagct catccgccag caagtcaccg agaacacccg caacaccgcc    360

atcgcccgcc tggagggcct gggccgtggc taccgctcct accagcaagc cctggagacc    420

tggctcgaca accgcaacga cgcccgctcc cgctccatca tcctggagcg ctacgtcgcc    480

ctggaactgg acatcaccac tgccatccca ctcttccgca tcaggaacga ggaggtgcct    540

ctgctgatgg tgtacgccca ggctgcgaac ctgcacctgc tgctgctgcg cgacgcaagc    600

ctgtttggct ccgagtgggg tatggcaagc tccgacgtca accagtacta ccaggagcag    660
```

-continued

```
atccgctaca ccgaggagta cagcaaccac tgcgtccagt ggtacaacac cggtctgaac    720
aatctcagag ggaccaacgc tgagagctgg ctgcgctaca accagttccg gcgggatctg    780
accctaggtg tcctggatct ggtcgctctg ttcccgagct acgataccag gacgtaccct    840
atcaacacct ctgctcagct taccagggag atctacactg atcctatcgg taggactaac    900
gctcctagtg gtttcgccag cactaactgg ttcaacaaca acgcgcctag tttctctgcc    960
atcgaggcgg cgatcttccg gcctcctcac ctcctcgact tcccggagca gcttactatc   1020
tactctgcgt cttcgcggtg gtcttcgact cagcacatga actactgggt tggtcaccgg   1080
cttaacttcc gcccgattgg aggaactctt aacaccagta cgcaaggtct tacgaacaac   1140
acttccatca acccggttac gttgcagttc acgtctcggg acgtttaccg gacggagtcg   1200
aatgctggga cgaacatcct gttcacgaca ccggtgaatg gtgttccgtg ggcacgtttc   1260
aacttcatca acccgcagaa catctacgag cgtggagcaa cgacatactc gcaaccatac   1320
caaggcgttg gcatccaact gtttgactcg gagacggaac tgccaccaga gacgacagaa   1380
cgtccgaatt acgagtcata ctcacacaga ctatcacaca ttggactcat tatcggaaac   1440
acactgagag caccagtgta ctcatggaca catcggtcag cagatcgtac gaacaccatc   1500
ggacccaatc ggatcaacca gatcccgctc gtgaagggct tccgcgtgtg gggcggcacc   1560
tccgtcatca ccggtccggg cttcaccggc ggcgacatcc tccgccgcaa caccttcggc   1620
gacttcgtgt cactccaagt gaacatcaac agcccgatca cccagcgcta tcgcctccgc   1680
ttccgctacg cctcctcccg cgacgctaga gtgatcgtgc tcaccggagc ggcgtccaca   1740
ggcgtaggcg gccaagtgtc tgtgaacatg ccgctccaga agactatgga gattggtgag   1800
aacctcacct ctcgcacctt ccgctacacc gacttctcca atccgttctc cttcagagcc   1860
aacccagaca tcatcggcat ctccgagcag cctctctttg gcgctggctc catctcctcc   1920
ggcgagctgt acatcgacaa gattgagatc atccttgccg acgccacctt cgaagctgag   1980
tccgatctcg agcgcgccca gaaggccgtg aacgccctct tcactagcac taaccagctc   2040
ggcctcaaga ctaacgtgac cgactaccac attgaccaag tgagcaacct agtgacctac   2100
cttagcgacg agttctgcct tgacgagaag cgtgagctga gcgagaaggt gaagcacgcc   2160
aagcgcctct ccgacgagcg caacctcctc caggactcca acttcaagga catcaaccgc   2220
cagcccgagc gcggctgggg cggtagcacc ggcatcacca tccagggcgg tgacgatgtg   2280
ttcaaggaga actacgtgac cctctccggc accttcgacg agtgctaccc gacctacctc   2340
taccagaaga tcgacgagtc caagctcaag gcgttcaccc gctaccagct tcgcggctac   2400
atcgaggact cccaggatct ggagatctac ctcatccgct acaacgccaa gcacgagacc   2460
gtgaacgtgc ccggcaccgg ctccctctgg ccgctctccg cccagagccc tatcggcaag   2520
tgcggcgagc ccaaccgctg cgcgcctcac ctggagtgga accctgacct cgactgctcc   2580
tgccgcgacg gcgagaagtg cgcccaccat agccaccact tctctctcga catcgacgtg   2640
ggctgcaccg acctcaacga ggatctgggc gtgtgggtga tcttcaagat caagacccag   2700
gacggccacg ccaggctggg caacctggag ttcctggagg agaagcctct ggtgggtgag   2760
gccctggcca gggtcaagag ggctgagaag aaatggaggg acaagaggga gaagctggag   2820
tgggagacca acatcgtgta caaggaggct aaggagtccg tggacgctct gttcgtcaac   2880
tctcagtacg atcagctcca ggctgacacc aacatcgcta tgatccacgc tgcggataag   2940
agggtccact ctatcaggga ggcttacctg cctgagcttt ctgtcatccc tggtgtcaac   3000
gcggcaatct tcgaggaact tgagggccgc atcttcactg cgttctcgct ttacgatgcg   3060
```

```
cggaacgtca ttaagaacgg tgacttcaac aatggtcttt cgtgctggaa cgtcaagggt   3120

catgtcgatg tcgaggaaca gaacaaccag cggtcggtcc ttgtcgttcc cgagtgggag   3180

gccgaggtct cgcaagaggt ccgggtctgc cctgggcgcg ggtacattct tcgtgtcact   3240

gcgtacaagg agggctacgg cgagggctgc gttactattc atgagattga gaacaatacg   3300

gatgagctta agtttagtaa ctgtgttgag gaggagatct acccgaacaa tacggttacg   3360

tgcaatgatt acacggtgaa ccaggaggaa tacggcggag catacacctc acgtaataga   3420

gggtacaatg aggcaccgtc agttccggca gattatgcct cagtttatga ggagaagtcc   3480

tacacggatg gaagacgcga gaatccatgt gagtttaata gaggataccg agactacaca   3540

ccactcccag ttggatacgt tacaaaggag ttggaatact tcccagaaac agataaagtt   3600

tggatagaga tcggagaaac agaaggaacc ttcatcgtgg acagtgtaga actgctgctg   3660

atggaagaat ga                                                         3672
```

<210> SEQ ID NO 7
<211> LENGTH: 1223
<212> TYPE: PRT
<213> ORGANISM: Artificial
<220> FEATURE:
<223> OTHER INFORMATION: Amino acid sequence of the chimeric protein TIC860.

<400> SEQUENCE: 7

```
Met Thr Ser Asn Arg Lys Asn Glu Asn Glu Ile Ile Asn Ala Leu Ser
1               5                   10                  15

Ile Pro Thr Val Ser Asn Pro Ser Thr Gln Met Asn Leu Ser Pro Asp
            20                  25                  30

Ala Arg Ile Glu Asp Ser Leu Cys Val Ala Glu Val Asn Asn Ile Asp
        35                  40                  45

Pro Phe Val Ser Ala Ser Thr Val Gln Thr Gly Ile Asn Ile Ala Gly
    50                  55                  60

Arg Ile Leu Gly Val Leu Gly Val Pro Phe Ala Gly Gln Leu Ala Ser
65                  70                  75                  80

Phe Tyr Ser Phe Leu Val Gly Glu Leu Trp Pro Ser Gly Arg Asp Pro
                85                  90                  95

Trp Glu Ile Phe Leu Glu His Val Glu Gln Leu Ile Arg Gln Gln Val
            100                 105                 110

Thr Glu Asn Thr Arg Asn Thr Ala Ile Ala Arg Leu Glu Gly Leu Gly
        115                 120                 125

Arg Gly Tyr Arg Ser Tyr Gln Gln Ala Leu Glu Thr Trp Leu Asp Asn
    130                 135                 140

Arg Asn Asp Ala Arg Ser Arg Ser Ile Ile Leu Glu Arg Tyr Val Ala
145                 150                 155                 160

Leu Glu Leu Asp Ile Thr Thr Ala Ile Pro Leu Phe Arg Ile Arg Asn
                165                 170                 175

Glu Glu Val Pro Leu Leu Met Val Tyr Ala Gln Ala Ala Asn Leu His
            180                 185                 190

Leu Leu Leu Leu Arg Asp Ala Ser Leu Phe Gly Ser Glu Trp Gly Met
        195                 200                 205

Ala Ser Ser Asp Val Asn Gln Tyr Tyr Gln Glu Gln Ile Arg Tyr Thr
    210                 215                 220

Glu Glu Tyr Ser Asn His Cys Val Gln Trp Tyr Asn Thr Gly Leu Asn
225                 230                 235                 240
```

-continued

```
Asn Leu Arg Gly Thr Asn Ala Glu Ser Trp Leu Arg Tyr Asn Gln Phe
                245                 250                 255

Arg Arg Asp Leu Thr Leu Gly Val Leu Asp Leu Val Ala Leu Phe Pro
            260                 265                 270

Ser Tyr Asp Thr Arg Thr Tyr Pro Ile Asn Thr Ser Ala Gln Leu Thr
        275                 280                 285

Arg Glu Ile Tyr Thr Asp Pro Ile Gly Arg Thr Asn Ala Pro Ser Gly
    290                 295                 300

Phe Ala Ser Thr Asn Trp Phe Asn Asn Asn Ala Pro Ser Phe Ser Ala
305                 310                 315                 320

Ile Glu Ala Ala Ile Phe Arg Pro Pro His Leu Leu Asp Phe Pro Glu
                325                 330                 335

Gln Leu Thr Ile Tyr Ser Ala Ser Ser Arg Trp Ser Ser Thr Gln His
            340                 345                 350

Met Asn Tyr Trp Val Gly His Arg Leu Asn Phe Arg Pro Ile Gly Gly
        355                 360                 365

Thr Leu Asn Thr Ser Thr Gln Gly Leu Thr Asn Asn Thr Ser Ile Asn
    370                 375                 380

Pro Val Thr Leu Gln Phe Thr Ser Arg Asp Val Tyr Arg Thr Glu Ser
385                 390                 395                 400

Asn Ala Gly Thr Asn Ile Leu Phe Thr Thr Pro Val Asn Gly Val Pro
                405                 410                 415

Trp Ala Arg Phe Asn Phe Ile Asn Pro Gln Asn Ile Tyr Glu Arg Gly
            420                 425                 430

Ala Thr Thr Tyr Ser Gln Pro Tyr Gln Gly Val Gly Ile Gln Leu Phe
        435                 440                 445

Asp Ser Glu Thr Glu Leu Pro Pro Glu Thr Thr Glu Arg Pro Asn Tyr
    450                 455                 460

Glu Ser Tyr Ser His Arg Leu Ser His Ile Gly Leu Ile Ile Gly Asn
465                 470                 475                 480

Thr Leu Arg Ala Pro Val Tyr Ser Trp Thr His Arg Ser Ala Asp Arg
                485                 490                 495

Thr Asn Thr Ile Gly Pro Asn Arg Ile Asn Gln Ile Pro Leu Val Lys
            500                 505                 510

Gly Phe Arg Val Trp Gly Gly Thr Ser Val Ile Thr Gly Pro Gly Phe
        515                 520                 525

Thr Gly Gly Asp Ile Leu Arg Arg Asn Thr Phe Gly Asp Phe Val Ser
    530                 535                 540

Leu Gln Val Asn Ile Asn Ser Pro Ile Thr Gln Arg Tyr Arg Leu Arg
545                 550                 555                 560

Phe Arg Tyr Ala Ser Ser Arg Asp Ala Arg Val Ile Val Leu Thr Gly
                565                 570                 575

Ala Ala Ser Thr Gly Val Gly Gly Gln Val Ser Val Asn Met Pro Leu
            580                 585                 590

Gln Lys Thr Met Glu Ile Gly Glu Asn Leu Thr Ser Arg Thr Phe Arg
        595                 600                 605

Tyr Thr Asp Phe Ser Asn Pro Phe Ser Phe Arg Ala Asn Pro Asp Ile
    610                 615                 620

Ile Gly Ile Ser Glu Gln Pro Leu Phe Gly Ala Gly Ser Ile Ser Ser
625                 630                 635                 640

Gly Glu Leu Tyr Ile Asp Lys Ile Glu Ile Ile Leu Ala Asp Ala Thr
                645                 650                 655

Phe Glu Ala Glu Ser Asp Leu Glu Arg Ala Gln Lys Ala Val Asn Ala
```

```
            660                 665                 670

Leu Phe Thr Ser Thr Asn Gln Leu Gly Leu Lys Thr Asn Val Thr Asp
        675                 680                 685

Tyr His Ile Asp Gln Val Ser Asn Leu Val Thr Tyr Leu Ser Asp Glu
    690                 695                 700

Phe Cys Leu Asp Glu Lys Arg Glu Leu Ser Glu Lys Val Lys His Ala
705                 710                 715                 720

Lys Arg Leu Ser Asp Glu Arg Asn Leu Leu Gln Asp Ser Asn Phe Lys
                725                 730                 735

Asp Ile Asn Arg Gln Pro Glu Arg Gly Trp Gly Gly Ser Thr Gly Ile
            740                 745                 750

Thr Ile Gln Gly Gly Asp Asp Val Phe Lys Glu Asn Tyr Val Thr Leu
        755                 760                 765

Ser Gly Thr Phe Asp Glu Cys Tyr Pro Thr Tyr Leu Tyr Gln Lys Ile
    770                 775                 780

Asp Glu Ser Lys Leu Lys Ala Phe Thr Arg Tyr Gln Leu Arg Gly Tyr
785                 790                 795                 800

Ile Glu Asp Ser Gln Asp Leu Glu Ile Tyr Leu Ile Arg Tyr Asn Ala
                805                 810                 815

Lys His Glu Thr Val Asn Val Pro Gly Thr Gly Ser Leu Trp Pro Leu
            820                 825                 830

Ser Ala Gln Ser Pro Ile Gly Lys Cys Gly Glu Pro Asn Arg Cys Ala
        835                 840                 845

Pro His Leu Glu Trp Asn Pro Asp Leu Asp Cys Ser Cys Arg Asp Gly
    850                 855                 860

Glu Lys Cys Ala His His Ser His His Phe Ser Leu Asp Ile Asp Val
865                 870                 875                 880

Gly Cys Thr Asp Leu Asn Glu Asp Leu Gly Val Trp Val Ile Phe Lys
                885                 890                 895

Ile Lys Thr Gln Asp Gly His Ala Arg Leu Gly Asn Leu Glu Phe Leu
            900                 905                 910

Glu Glu Lys Pro Leu Val Gly Glu Ala Leu Ala Arg Val Lys Arg Ala
        915                 920                 925

Glu Lys Lys Trp Arg Asp Lys Arg Glu Lys Leu Glu Trp Glu Thr Asn
    930                 935                 940

Ile Val Tyr Lys Glu Ala Lys Glu Ser Val Asp Ala Leu Phe Val Asn
945                 950                 955                 960

Ser Gln Tyr Asp Gln Leu Gln Ala Asp Thr Asn Ile Ala Met Ile His
                965                 970                 975

Ala Ala Asp Lys Arg Val His Ser Ile Arg Glu Ala Tyr Leu Pro Glu
            980                 985                 990

Leu Ser Val Ile Pro Gly Val Asn  Ala Ala Ile Phe Glu  Glu Leu Glu
        995                 1000                1005

Gly Arg  Ile Phe Thr Ala Phe  Ser Leu Tyr Asp Ala  Arg Asn Val
    1010                1015                1020

Ile Lys  Asn Gly Asp Phe Asn  Asn Gly Leu Ser Cys  Trp Asn Val
    1025                1030                1035

Lys Gly  His Val Asp Val Glu  Glu Gln Asn Asn Gln  Arg Ser Val
    1040                1045                1050

Leu Val  Val Pro Glu Trp Glu  Ala Glu Val Ser Gln  Glu Val Arg
    1055                1060                1065

Val Cys  Pro Gly Arg Gly Tyr  Ile Leu Arg Val Thr  Ala Tyr Lys
    1070                1075                1080
```

```
Glu Gly  Tyr Gly Glu Gly Cys  Val Thr Ile His Glu  Ile Glu Asn
    1085                 1090                 1095

Asn Thr  Asp Glu Leu Lys Phe  Ser Asn Cys Val Glu  Glu Glu Ile
    1100                 1105                 1110

Tyr Pro  Asn Asn Thr Val Thr  Cys Asn Asp Tyr Thr  Val Asn Gln
    1115                 1120                 1125

Glu Glu  Tyr Gly Gly Ala Tyr  Thr Ser Arg Asn Arg  Gly Tyr Asn
    1130                 1135                 1140

Glu Ala  Pro Ser Val Pro Ala  Asp Tyr Ala Ser Val  Tyr Glu Glu
    1145                 1150                 1155

Lys Ser  Tyr Thr Asp Gly Arg  Arg Glu Asn Pro Cys  Glu Phe Asn
    1160                 1165                 1170

Arg Gly  Tyr Arg Asp Tyr Thr  Pro Leu Pro Val Gly  Tyr Val Thr
    1175                 1180                 1185

Lys Glu  Leu Glu Tyr Phe Pro  Glu Thr Asp Lys Val  Trp Ile Glu
    1190                 1195                 1200

Ile Gly  Glu Thr Glu Gly Thr  Phe Ile Val Asp Ser  Val Glu Leu
    1205                 1210                 1215

Leu Leu  Met Glu Glu
    1220
```

```
<210> SEQ ID NO 8
<211> LENGTH: 3564
<212> TYPE: DNA
<213> ORGANISM: Artificial
<220> FEATURE:
<223> OTHER INFORMATION: Recombinant nucleotide sequence used for
      expression in a bacterial cell encoding TIC867.

<400> SEQUENCE: 8

atgacttcaa ataggaaaaa tgagaatgaa attataaatg ctttatcgat tccagctgta     60

tcgaatcatt ccgcacaaat gaatctatca accgatgctc gtattgagga tagcttgtgt    120

atagccgagg ggaacaatat cgatccattt gttagcgcat caacagtcca aacgggtatt    180

aacatagctg gtagaatact aggtgtatta ggcgtaccgt ttgctggaca aatagctagt    240

ttttatagtt ttcttgttgg tgaattatgg ccccgcggca gagatccttg ggaaattttc    300

ctagaacatg tcgaacaact tataagacaa caagtaacag aaaatactag ggatacggct    360

cttgctcgat tacaaggttt aggaaattcc tttagagcct atcaacagtc acttgaagat    420

tggctagaaa accgtgatga tgcaagaacg agaagtgttc tttataccca atatatagcc    480

ttagaacttg attttcttaa tgcgatgccg cttttcgcaa ttagaaacca agaagttcca    540

ttattaatgg tatatgctca agctgcaaat ttacacctat tattattgag agatgcctct    600

ctttttggta gtgaatttgg gcttacatcc caagaaattc aacgttatta tgagcgccaa    660

gtggaaaaaa cgagagaata ttctgattat tgcgcaagat ggtataatac gggtttaaat    720

aatttgagag ggacaaatgc tgaaagttgg ttgcgatata atcaattccg tagagactta    780

acgctaggag tattagatct agtggcacta ttcccaagct atgacacgcg tgtttatcca    840

atgaatacca gtgctcaatt aacaagagaa atttatacag atccaattgg gagaacaaat    900

gcaccttcag gatttgcaag tacgaattgg tttaataata atgcaccatc gttttctgcc    960

atagaggctg ccgttattag gcctccgcat ctacttgatt ttccagaaca gcttacaatt   1020

ttcagcgtat taagtcgatg gagtaatact caatatatga attactgggt gggacataga   1080

cttgaatcgc gaacaataag gggtcatta agtacctcga cacacggaaa taccaatact    1140
```

```
tctattaatc ctgtaacatt acagttcaca tctcgagacg tttatagaac agaatcattt   1200
gcagggataa atatacttct aactactcct gtgaatggag taccttgggc tagatttaat   1260
tggagaaatc ccctgaattc tcttagaggt agccttctct atactatagg gtatactgga   1320
gtggggacac aactatttga ttcagaaact gaattaccac cagaaacaac agaacgacca   1380
aattatgaat cttacagtca tagattatct aatataagac taatatcagg aaacactttg   1440
agagcaccag tatattcttg gacgcaccgt agtgcagatc gtacaaatac cattagttca   1500
gatagcatta cacaaatacc attggtaaag gcgcataccc tccaatcggg taccactgta   1560
gtaaaagggc cagggtttac aggaggggat atcctccgtc gaacaagtgg aggaccattt   1620
gcttttagta atgttaatct agattttaac ttgtcacaaa ggtatcgtgc tagaattcgt   1680
tatgcctcta ctactaacct aagaatttac gtaacggttg caggtgaacg aatttttgct   1740
ggtcaatttg acaaaactat ggatgctggt gccccattaa cattccaatc ttttagttac   1800
gcaactatta atacagcttt tacattccca gaaagatcga gcagcttgac tgtaggtgcc   1860
gatacgttta gttcaggtaa tgaagtttat gtagatagat ttgaattaat cccagttact   1920
gcaaccttcg aggcagaatc tgatttagaa agagcacaaa aggcggtgaa tgagctgttt   1980
acttcttcca atcaaatcgg gttaaaaaca gatgtgacgg attatcatat tgatcaagta   2040
tccaatttag ttgagtgttt atctgatgaa ttttgtctgg atgaaaaaaa agaattgtcc   2100
gagaaagtca aacatgcgaa gcgacttagt gatgagcgga atttacttca agatccaaac   2160
tttagaggga tcaatagaca actagaccgt ggctggagag gaagtacgga tattaccatc   2220
caaggaggcg atgacgtatt caaagagaat tacgttacgc tattgggtac ctttgatgag   2280
tgctatccaa cgtatttata tcaaaaaata gatgagtcga aattaaaagc ctatacccgt   2340
taccaattaa gagggtatat cgaagatagt caagacttag aaatctattt aattcgctac   2400
aatgccaaac acgaaacagt aaatgtgcca ggtacgggtt ccttatggcc gctttcagcc   2460
ccaagtccaa tcggaaaatg tgcccatcat tcccatcatt tctccttgga cattgatgtt   2520
ggatgtacag acttaaatga ggacttaggt gtatgggtga tattcaagat taagacgcaa   2580
gatggccatg caagactagg aaatctagaa tttctcgaag agaaaccatt agtaggagaa   2640
gcactagctc gtgtgaaaag agcggagaaa aaatggagag acaaacgtga aaaattggaa   2700
tgggaaacaa atattgttta taaagaggca aaagaatctg tagatgcttt atttgtaaac   2760
tctcaatatg atagattaca agcggatacc aacatcgcga tgattcatgc ggcagataaa   2820
cgcgttcata gcattcgaga agcttatctg cctgagctgt ctgtgattcc gggtgtcaat   2880
gcggctattt ttgaagaatt agaagggcgt attttcactg cattctccct atatgatgcg   2940
agaaatgtca ttaaaaatgg tgattttaat aatggcttat cctgctggaa cgtgaaaggg   3000
catgtagatg tagaagaaca aaacaaccac cgttcggtcc ttgttgttcc ggaatgggaa   3060
gcagaagtgt cacaagaagt tcgtgtctgt ccgggtcgtg gctatatcct tcgtgtcaca   3120
gcgtacaagg agggatatgg agaaggttgc gtaaccattc atgagatcga gaacaataca   3180
gacgaactga agtttagcaa ctgtgtagaa gaggaagtat atccaaacaa cacggtaacg   3240
tgtaatgatt atactgcgac tcaagaagaa tatgagggta cgtacacttc tcgtaatcga   3300
ggatatgacg gagcctatga aagcaattct tctgtaccag ctgattatgc atcagcctat   3360
gaagaaaaag catatacaga tggacgaaga gacaatcctt gtgaatctaa cagaggatat   3420
ggggattaca caccactacc agctggctat gtgacaaaag aattagagta cttcccagaa   3480
```

accgataagg tatggattga gatcggagaa acggaaggaa cattcatcgt ggacagcgtg 3540
gaattacttc ttatggagga atag 3564

<210> SEQ ID NO 9
<211> LENGTH: 3564
<212> TYPE: DNA
<213> ORGANISM: Artificial
<220> FEATURE:
<223> OTHER INFORMATION: Synthetic nucleotide sequence designed for expression in a plant cell encoding TIC867.

<400> SEQUENCE: 9
atgaccagca accgaaagaa cgagaacgag atcatcaacg ccctgtccat accggccgtg 60
tcaaaccact ccgcccagat gaacctctcc accgacgcga ggatcgagga ctccctctgc 120
atcgccgagg gcaacaacat cgacccgttc gtgtctgcaa gcacggtcca gaccggcatc 180
aacatcgcgg gccgcatcct gggcgtgctc ggcgtgccct tcgcgggtca aatcgcctct 240
ttctactcat tcctcgtggg cgagctgtgg ccgcgcggac gtgacccgtg ggaaatcttc 300
ctggagcacg ttgagcagct catccggcag caagtgaccg agaacaccag ggacaccgca 360
ctggcacggc tccagggcct tggcaacagc ttccgcgcct accagcagtc gctggaggac 420
tggctggaga accgagacga cgccagaacc cgctcagttc tgtacacaca gtacatcgcc 480
ctagagctgg acttcctcaa cgctatgccg ctcttcgcca tccgtaacca ggaagtaccg 540
cttctgatgg tgtacgcaca agcagcgaac ctccatctgc tcctgctgcg agacgcatct 600
ctgttcggca gtgagttcgg gctgacgagc caggagatcc agcgctacta cgagcgccaa 660
gtggagaaga ctcgtgagta cagcgactac tgcgcgcgct ggtacaacac gggcttgaac 720
aaccttcgcg ggacaaacgc cgaatcctgg cttcgctaca accagttccg ccgcgacctc 780
acgctgggtg tgctggacct ggtcgcgctc ttcccgtcct acgacacacg ggtgtaccca 840
atgaacacga gcgcacagct cacccgtgag atctacacag atcccatcgg ccgcaccaac 900
gctcccagtg gcttcgcaag cacgaattgg ttcaacaata acgctccttc tttctctgcc 960
atcgaggccg ctgtcatcag accgccgcac ttactcgatt tcccggagca gctcactatc 1020
ttctctgtgt tgtcccggtg gtcgaacacg cagtacatga actactgggt gggccacagg 1080
ctagagagcc ggaccatccg tggcagtctc tcaacctcga cccacggcaa cacgaacacg 1140
agcatcaacc ctgtcactct ccagtttaca tctagggacg tttacaggac agagtcgttc 1200
gctggcatta acattctgtt gaccactccg gtgaacggcg tcccttgggc ccgcttcaac 1260
tggaggaatc ctctgaactc actgcgcggc agccttctct acactatcgg ctacaccggc 1320
gttgggacgc aactcttcga ctcggagacc gagctgccgc ccgagaccac cgagcggcct 1380
aactacgaga gttattcaca caggctctcc aacatccgct tgatttctgg gaacaccttg 1440
cgggctccgg tgtactcctg gacgcaccgc agcgccgaca gaactaatac catcagctcc 1500
gactcgatca cccagatccc gctggtgaag gctcacacgc ttcagtcggg caccacagtc 1560
gtcaagggcc ctggcttcac cggcggcgac atcctgcgtc gcacatctgg cggacccttc 1620
gccttcagca acgtgaactt ggacttcaat ttgtcacagc ggtatcgtgc cagaatccgg 1680
tacgccagca ctacgaacct gcgaatctat gttactgtgg cgggcgagcg gatcttcgcc 1740
gggcaattcg acaagacgat ggacgcggga gcacctctga cattccagtc attctcttac 1800
gccacgatca acacggcatt cacgtttccg gagcgttcca gtagcctgac cgtgggcgct 1860
gataccttca gtagcgggaa cgaggtgtac gttgaccgtt tcgagctgat cccggtcacc 1920

```
gccaccttcg aagctgagtc ggacctggag cgtgcacaga aggcagtcaa cgagctgttc   1980
acctctagca accagatcgg cctcaagacc gacgtcacag actaccacat cgaccaagtg   2040
tccaacctgg tcgagtgcct tagcgacgag ttctgcctag acgagaagaa ggagctgtcg   2100
gagaaggtca aacacgccaa gcgtctgagc gatgagcgca acctgctcca agaccctaac   2160
ttccgtggca tcaacaggca gcttgaccgt ggctggcgcg gctcgacgga catcacgatc   2220
cagggtggcg acgacgtatt caaggagaat tacgtgacct tgcttgggac gtttgacgag   2280
tgctatccca cctacctcta ccagaagatt gatgaatcga aattgaaggc gtacacgaga   2340
taccagctcc gtggctacat cgaggacagc caggacttgg agatctacct catacgctac   2400
aacgctaaac atgagaccgt gaacgtccct gggacgggca gtctgtggcc actctctgct   2460
cctagcccta tcggcaagtg cgctcaccac tcgcaccact tcagccttga catcgacgtg   2520
ggatgtactg acctcaacga agacctgggc gtctgggtta tcttcaagat caagacccag   2580
gacggccacg cccgactcgg caacctggag ttcctggagg agaaaccact ggtgggcgag   2640
gcgctcgccc gcgtgaagcg tgccgagaag aagtggcggg acaagaggga gaagctagaa   2700
tgggagacga acatcgtgta caaggaggcc aaggaaagcg tcgatgccct gttcgtgaac   2760
tcacagtacg accgtctcca ggcggacacg aacatcgcca tgatccacgc ggctgacaag   2820
cgcgtccact ccatccgcga ggcgtactta ccggagctgt cggtgatccc aggcgtaaac   2880
gcggcgatct tcgaggagct agagggacgc atcttcacag cgttcagcct gtacgacgca   2940
cgcaacgtca tcaagaacgg cgatttcaac aacggactgt cctgctggaa cgtgaagggc   3000
cacgtcgatg tcgaggaaca gaacaaccac cgctctgtcc tggtggtccc agagtgggag   3060
gccgaggtct cccaggaggt ccgcgtgtgc cctgggcgtg gctacatcct ccgtgtgaca   3120
gcctacaagg agggctacgg tgagggctgc gtcaccattc acgagatcga gaacaacact   3180
gacgaactca agttctcgaa ttgcgtggag gaggaggtgt acccgaacaa tacggtgacg   3240
tgcaacgact acacggcaac ccaagaggag tacgagggca cctacaccag taggaaccgt   3300
ggctacgacg gtgcctacga gtcgaactcc agcgtccctg cggactacgc cagcgcgtac   3360
gaggagaagg cttacaccga cggacgccgg gacaacccat gcgagagcaa ccgtggctac   3420
ggcgactaca ctcctctccc ggccggatac gtcacaaagg agctggagta tttcccagag   3480
acggacaagg tgtggatcga aatcggagag acagagggaa ccttcatcgt ggacagcgtg   3540
gagctgctcc tcatggagga gtga                                          3564
```

<210> SEQ ID NO 10
<211> LENGTH: 1187
<212> TYPE: PRT
<213> ORGANISM: Artificial
<220> FEATURE:
<223> OTHER INFORMATION: Amino acid sequence of the chimeric protein TIC867.

<400> SEQUENCE: 10

```
Met Thr Ser Asn Arg Lys Asn Glu Asn Glu Ile Ile Asn Ala Leu Ser
1               5                   10                  15

Ile Pro Ala Val Ser Asn His Ser Ala Gln Met Asn Leu Ser Thr Asp
            20                  25                  30

Ala Arg Ile Glu Asp Ser Leu Cys Ile Ala Glu Gly Asn Asn Ile Asp
        35                  40                  45

Pro Phe Val Ser Ala Ser Thr Val Gln Thr Gly Ile Asn Ile Ala Gly
    50                  55                  60
```

-continued

```
Arg Ile Leu Gly Val Leu Gly Val Pro Phe Ala Gly Gln Ile Ala Ser
65                  70                  75                  80

Phe Tyr Ser Phe Leu Val Gly Glu Leu Trp Pro Arg Gly Arg Asp Pro
                85                  90                  95

Trp Glu Ile Phe Leu Glu His Val Glu Gln Leu Ile Arg Gln Gln Val
            100                 105                 110

Thr Glu Asn Thr Arg Asp Thr Ala Leu Ala Arg Leu Gln Gly Leu Gly
        115                 120                 125

Asn Ser Phe Arg Ala Tyr Gln Gln Ser Leu Glu Asp Trp Leu Glu Asn
    130                 135                 140

Arg Asp Asp Ala Arg Thr Arg Ser Val Leu Tyr Thr Gln Tyr Ile Ala
145                 150                 155                 160

Leu Glu Leu Asp Phe Leu Asn Ala Met Pro Leu Phe Ala Ile Arg Asn
                165                 170                 175

Gln Glu Val Pro Leu Leu Met Val Tyr Ala Gln Ala Ala Asn Leu His
            180                 185                 190

Leu Leu Leu Leu Arg Asp Ala Ser Leu Phe Gly Ser Glu Phe Gly Leu
        195                 200                 205

Thr Ser Gln Glu Ile Gln Arg Tyr Tyr Glu Arg Gln Val Glu Lys Thr
    210                 215                 220

Arg Glu Tyr Ser Asp Tyr Cys Ala Arg Trp Tyr Asn Thr Gly Leu Asn
225                 230                 235                 240

Asn Leu Arg Gly Thr Asn Ala Glu Ser Trp Leu Arg Tyr Asn Gln Phe
                245                 250                 255

Arg Arg Asp Leu Thr Leu Gly Val Leu Asp Leu Val Ala Leu Phe Pro
            260                 265                 270

Ser Tyr Asp Thr Arg Val Tyr Pro Met Asn Thr Ser Ala Gln Leu Thr
        275                 280                 285

Arg Glu Ile Tyr Thr Asp Pro Ile Gly Arg Thr Asn Ala Pro Ser Gly
    290                 295                 300

Phe Ala Ser Thr Asn Trp Phe Asn Asn Asn Ala Pro Ser Phe Ser Ala
305                 310                 315                 320

Ile Glu Ala Ala Val Ile Arg Pro Pro His Leu Leu Asp Phe Pro Glu
                325                 330                 335

Gln Leu Thr Ile Phe Ser Val Leu Ser Arg Trp Ser Asn Thr Gln Tyr
            340                 345                 350

Met Asn Tyr Trp Val Gly His Arg Leu Glu Ser Arg Thr Ile Arg Gly
        355                 360                 365

Ser Leu Ser Thr Ser Thr His Gly Asn Thr Asn Thr Ser Ile Asn Pro
    370                 375                 380

Val Thr Leu Gln Phe Thr Ser Arg Asp Val Tyr Arg Thr Glu Ser Phe
385                 390                 395                 400

Ala Gly Ile Asn Ile Leu Leu Thr Thr Pro Val Asn Gly Val Pro Trp
                405                 410                 415

Ala Arg Phe Asn Trp Arg Asn Pro Leu Asn Ser Leu Arg Gly Ser Leu
            420                 425                 430

Leu Tyr Thr Ile Gly Tyr Thr Gly Val Gly Thr Gln Leu Phe Asp Ser
        435                 440                 445

Glu Thr Glu Leu Pro Pro Glu Thr Thr Glu Arg Pro Asn Tyr Glu Ser
    450                 455                 460

Tyr Ser His Arg Leu Ser Asn Ile Arg Leu Ile Ser Gly Asn Thr Leu
465                 470                 475                 480

Arg Ala Pro Val Tyr Ser Trp Thr His Arg Ser Ala Asp Arg Thr Asn
```

-continued

```
                485                 490                 495

Thr Ile Ser Ser Asp Ser Ile Thr Gln Ile Pro Leu Val Lys Ala His
            500                 505                 510

Thr Leu Gln Ser Gly Thr Thr Val Val Lys Gly Pro Gly Phe Thr Gly
        515                 520                 525

Gly Asp Ile Leu Arg Arg Thr Ser Gly Gly Pro Phe Ala Phe Ser Asn
    530                 535                 540

Val Asn Leu Asp Phe Asn Leu Ser Gln Arg Tyr Arg Ala Arg Ile Arg
545                 550                 555                 560

Tyr Ala Ser Thr Thr Asn Leu Arg Ile Tyr Val Thr Val Ala Gly Glu
                565                 570                 575

Arg Ile Phe Ala Gly Gln Phe Asp Lys Thr Met Asp Ala Gly Ala Pro
            580                 585                 590

Leu Thr Phe Gln Ser Phe Ser Tyr Ala Thr Ile Asn Thr Ala Phe Thr
        595                 600                 605

Phe Pro Glu Arg Ser Ser Ser Leu Thr Val Gly Ala Asp Thr Phe Ser
    610                 615                 620

Ser Gly Asn Glu Val Tyr Val Asp Arg Phe Glu Leu Ile Pro Val Thr
625                 630                 635                 640

Ala Thr Phe Glu Ala Glu Ser Asp Leu Glu Arg Ala Gln Lys Ala Val
                645                 650                 655

Asn Glu Leu Phe Thr Ser Ser Asn Gln Ile Gly Leu Lys Thr Asp Val
            660                 665                 670

Thr Asp Tyr His Ile Asp Gln Val Ser Asn Leu Val Glu Cys Leu Ser
        675                 680                 685

Asp Glu Phe Cys Leu Asp Glu Lys Lys Glu Leu Ser Glu Lys Val Lys
    690                 695                 700

His Ala Lys Arg Leu Ser Asp Glu Arg Asn Leu Leu Gln Asp Pro Asn
705                 710                 715                 720

Phe Arg Gly Ile Asn Arg Gln Leu Asp Arg Gly Trp Arg Gly Ser Thr
                725                 730                 735

Asp Ile Thr Ile Gln Gly Gly Asp Asp Val Phe Lys Glu Asn Tyr Val
            740                 745                 750

Thr Leu Leu Gly Thr Phe Asp Glu Cys Tyr Pro Thr Tyr Leu Tyr Gln
        755                 760                 765

Lys Ile Asp Glu Ser Lys Leu Lys Ala Tyr Thr Arg Tyr Gln Leu Arg
    770                 775                 780

Gly Tyr Ile Glu Asp Ser Gln Asp Leu Glu Ile Tyr Leu Ile Arg Tyr
785                 790                 795                 800

Asn Ala Lys His Glu Thr Val Asn Val Pro Gly Thr Gly Ser Leu Trp
                805                 810                 815

Pro Leu Ser Ala Pro Ser Pro Ile Gly Lys Cys Ala His His Ser His
            820                 825                 830

His Phe Ser Leu Asp Ile Asp Val Gly Cys Thr Asp Leu Asn Glu Asp
        835                 840                 845

Leu Gly Val Trp Val Ile Phe Lys Ile Lys Thr Gln Asp Gly His Ala
    850                 855                 860

Arg Leu Gly Asn Leu Glu Phe Leu Glu Glu Lys Pro Leu Val Gly Glu
865                 870                 875                 880

Ala Leu Ala Arg Val Lys Arg Ala Glu Lys Lys Trp Arg Asp Lys Arg
                885                 890                 895

Glu Lys Leu Glu Trp Glu Thr Asn Ile Val Tyr Lys Glu Ala Lys Glu
            900                 905                 910
```

```
Ser Val Asp Ala Leu Phe Val Asn Ser Gln Tyr Asp Arg Leu Gln Ala
        915                 920                 925

Asp Thr Asn Ile Ala Met Ile His Ala Ala Asp Lys Arg Val His Ser
    930                 935                 940

Ile Arg Glu Ala Tyr Leu Pro Glu Leu Ser Val Ile Pro Gly Val Asn
945                 950                 955                 960

Ala Ala Ile Phe Glu Glu Leu Glu Gly Arg Ile Phe Thr Ala Phe Ser
                965                 970                 975

Leu Tyr Asp Ala Arg Asn Val Ile Lys Asn Gly Asp Phe Asn Asn Gly
            980                 985                 990

Leu Ser Cys Trp Asn Val Lys Gly  His Val Asp Val Glu  Glu Gln Asn
        995                 1000                1005

Asn His  Arg Ser Val Leu Val  Val Pro Glu Trp Glu  Ala Glu Val
    1010                1015                1020

Ser Gln  Glu Val Arg Val Cys  Pro Gly Arg Gly Tyr  Ile Leu Arg
    1025                1030                1035

Val Thr  Ala Tyr Lys Glu Gly  Tyr Gly Glu Gly Cys  Val Thr Ile
    1040                1045                1050

His Glu  Ile Glu Asn Asn Thr  Asp Glu Leu Lys Phe  Ser Asn Cys
    1055                1060                1065

Val Glu  Glu Glu Val Tyr Pro  Asn Asn Thr Val Thr  Cys Asn Asp
    1070                1075                1080

Tyr Thr  Ala Thr Gln Glu Glu  Tyr Glu Gly Thr Tyr  Thr Ser Arg
    1085                1090                1095

Asn Arg  Gly Tyr Asp Gly Ala  Tyr Glu Ser Asn Ser  Ser Val Pro
    1100                1105                1110

Ala Asp  Tyr Ala Ser Ala Tyr  Glu Glu Lys Ala Tyr  Thr Asp Gly
    1115                1120                1125

Arg Arg  Asp Asn Pro Cys Glu  Ser Asn Arg Gly Tyr  Gly Asp Tyr
    1130                1135                1140

Thr Pro  Leu Pro Ala Gly Tyr  Val Thr Lys Glu Leu  Glu Tyr Phe
    1145                1150                1155

Pro Glu  Thr Asp Lys Val Trp  Ile Glu Ile Gly Glu  Thr Glu Gly
    1160                1165                1170

Thr Phe  Ile Val Asp Ser Val  Glu Leu Leu Leu Met  Glu Glu
    1175                1180                1185


<210> SEQ ID NO 11
<211> LENGTH: 3642
<212> TYPE: DNA
<213> ORGANISM: Artificial
<220> FEATURE:
<223> OTHER INFORMATION: Recombinant nucleotide sequence used for
      expression in a bacterial cell encoding TIC867_20.

<400> SEQUENCE: 11

atgacttcaa ataggaaaaa tgagaatgaa attataaatg ctttatcgat tccagctgta      60

tcgaatcatt ccgcacaaat gaatctatca accgatgctc gtattgagga tagcttgtgt     120

atagccgagg ggaacaatat cgatccattt gttagcgcat caacagtcca aacgggtatt     180

aacatagctg gtagaatact aggtgtatta ggcgtaccgt ttgctggaca aatagctagt     240

ttttatagtt ttcttgttgg tgaattatgg ccccgcggca gagatccttg ggaaattttc     300

ctagaacatg tcgaacaact tataagacaa caagtaacag aaaatactag ggatacggct     360

cttgctcgat tacaaggttt aggaaattcc tttagagcct atcaacagtc acttgaagat     420
```

-continued

```
tggctagaaa accgtgatga tgcaagaacg agaagtgttc tttataccca atatatagcc    480
ttagaacttg attttcttaa tgcgatgccg cttttcgcaa ttagaaacca agaagttcca    540
ttattaatgg tatatgctca agctgcaaat ttacacctat tattattgag agatgcctct    600
ctttttggta gtgaatttgg gcttacatcc caagaaattc aacgttatta tgagcgccaa    660
gtggaaaaaa cgagagaata ttctgattat tgcgcaagat ggtataatac gggtttaaat    720
aatttgagag ggacaaatgc tgaaagttgg ttgcgatata atcaattccg tagagactta    780
acgctaggag tattagatct agtggcacta ttcccaagct atgacacgcg tgtttatcca    840
atgaatacca gtgctcaatt aacaagagaa atttatacag atccaattgg gagaacaaat    900
gcaccttcag gatttgcaag tacgaattgg tttaataata atgcaccatc gttttctgcc    960
atagaggctg ccgttattag gcctccgcat ctacttgatt ttccagaaca gcttacaatt   1020
ttcagcgtat taagtcgatg gagtaatact caatatatga attactgggt gggacataga   1080
cttgaatcgc gaacaataag gggtcatta agtacctcga cacacggaaa taccaatact   1140
tctattaatc ctgtaacatt acagttcaca tctcgagacg tttatagaac agaatcattt   1200
gcagggataa atatacttct aactactcct gtgaatggag taccttgggc tagatttaat   1260
tggagaaatc ccctgaattc tcttagaggt agccttctct atactatagg gtatactgga   1320
gtggggacac aactatttga ttcagaaact gaattaccac cagaaacaac agaacgacca   1380
aattatgaat cttacagtca tagattatct aatataagac taatatcagg aaacactttg   1440
agagcaccag tatattcttg gacgcaccgt agtgcagatc gtacaaatac cattagttca   1500
gatagcatta cacaaatacc attggtaaag gcgcataccc tccaatcggg taccactgta   1560
gtaaaagggc cagggtttac aggaggggat atcctccgtc gaacaagtgg aggaccattt   1620
gcttttagta atgttaatct agattttaac ttgtcacaaa ggtatcgtgc tagaattcgt   1680
tatgcctcta ctactaacct aagaatttac gtaacggttg caggtgaacg aatttttgct   1740
ggtcaatttg acaaaactat ggatgctggt gccccattaa cattccaatc ttttagttac   1800
gcaactatta atacagcttt tacattccca gaaagatcga gcagcttgac tgtaggtgcc   1860
gatacgttta gttcaggtaa tgaagtttat gtagatagat ttgaattaat cccagttact   1920
gcaacctttg aggcagaata tgatttagaa agagcgcaaa aggtggtgaa tgccctgttt   1980
acgtctacaa accaactagg gctaaaaaca gatgtgacgg attatcatat tgatcaggta   2040
tccaatctag ttgcgtgttt atcggatgaa ttttgtctgg atgaaaagag agaattgtcc   2100
gagaaagtta aacatgcaaa gcgactcagt gatgagcgga atttacttca agatccaaac   2160
ttcagaggga tcaataggca accagaccgt ggctggagag gaagtacgga tattactatc   2220
caaggaggag atgacgtatt caaagagaat tacgttacgc taccgggtac ctttgatgag   2280
tgctatccaa cgtatttata tcaaaaaata gatgagtcga aattaaaagc ctatacccgt   2340
tatcaattaa gagggtatat cgaagatagt caagacttag aaatctattt aattcgttac   2400
aatgcaaaac acgaaatagt aaatgtacca ggtacaggaa gtttatggcc tctttctgta   2460
gaaaatcaaa ttggaccttg tggagaaccg aatcgatgcg cgccacacct tgaatggaat   2520
cctgatttac actgttcctg cagagacggg gaaaaatgtg cacatcattc tcatcatttc   2580
tctttggaca ttgatgttgg atgtacagac ttaaatgagg acttaggtgt atgggtgata   2640
ttcaagatta agacgcaaga tggccacgca cgactaggga atctagagtt tctcgaagag   2700
aaaccattat taggagaagc actagctcgt gtgaaaagag cggagaaaaa atggagagac   2760
```

```
aaacgcgaaa cattacaatt ggaaacaact atcgtttata aagaggcaaa agaatctgta   2820

gatgctttat ttgtaaactc tcaatatgat agattacaag cggatacgaa catcgcgatg   2880

attcatgcgg cagataaacg cgttcataga attcgagaag cgtatctgcc ggagctgtct   2940

gtgattccgg gtgtcaatgc ggctattttt gaagaattag aagagcgtat tttcactgca   3000

ttttccctat atgatgcgag aaatattatt aaaaatggcg atttcaataa tggcttatta   3060

tgctggaacg tgaaagggca tgtagaggta gaagaacaaa acaatcaccg ttcagtcctg   3120

gttatcccag aatgggaggc agaagtgtca caagaggttc gtgtctgtcc aggtcgtggc   3180

tatatccttc gtgttacagc gtacaaagag ggatatggag aaggttgcgt aacgatccat   3240

gagatcgaga acaatacaga cgaactgaaa ttcaacaact gtgtagaaga ggaagtatat   3300

ccaaacaaca cggtaacgtg tattaattat actgcgactc aagaagaata tgagggtacg   3360

tacacttctc gtaatcgagg atatgacgaa gcctatggta ataacccttc cgtaccagct   3420

gattatgcgt cagtctatga agaaaaatcg tatacagata gacgaagaga gaatccttgt   3480

gaatctaaca gaggatatgg agattacaca ccactaccag ctggttatgt aacaaaggaa   3540

ttagagtact tcccagagac cgataaggta tggattgaga ttggagaaac agaaggaaca   3600

ttcatcgtgg acagcgtgga attactcctt atggaggaat ag                      3642
```

<210> SEQ ID NO 12
<211> LENGTH: 3642
<212> TYPE: DNA
<213> ORGANISM: Artificial
<220> FEATURE:
<223> OTHER INFORMATION: Synthetic nucleotide sequence designed for expression in a plant cell encoding TIC867_20.

<400> SEQUENCE: 12

```
atgaccagca accgaaagaa cgagaacgag atcatcaacg ccctgtccat accggccgtg     60

tcaaaccact ccgcccagat gaacctctcc accgacgcga ggatcgagga ctccctctgc    120

atcgccgagg gcaacaacat cgacccgttc gtgtctgcaa gcacggtcca gaccggcatc    180

aacatcgcgg gccgcatcct gggcgtgctc ggcgtgccct tcgcgggtca aatcgcctct    240

ttctactcat tcctcgtggg cgagctgtgg ccgcgcggac gtgacccgtg ggaaatcttc    300

ctggagcacg ttgagcagct catccggcag caagtgaccg agaacaccag ggacaccgca    360

ctggcacggc tccagggcct tggcaacagc ttccgcgcct accagcagtc gctggaggac    420

tggctggaga accgagacga cgccagaacc cgctcagttc tgtacacaca gtacatcgcc    480

ctagagctgg acttcctcaa cgctatgccg ctcttcgcca tccgtaacca ggaagtaccg    540

cttctgatgg tgtacgcaca agcagcgaac ctccatctgc tcctgctgcg agacgcatct    600

ctgttcggca gtgagttcgg gctgacgagc caggagatcc agcgctacta cgagcgccaa    660

gtggagaaga ctcgtgagta cagcgactac tgcgcgcgct ggtacaacac gggcttgaac    720

aaccttcgcg ggacaaacgc cgaatcctgg cttcgctaca accagttccg ccgcgacctc    780

acgctgggtg tgctggacct ggtcgcgctc ttcccgtcct acgacacacg ggtgtaccca    840

atgaacacga gcgcacagct cacccgtgag atctacacag atcccatcgg ccgcaccaac    900

gctcccagtg gcttcgcaag cacgaattgg ttcaacaata acgctccttc tttctctgcc    960

atcgaggccg ctgtcatcag accgccgcac ttactcgatt tcccggagca gctcactatc   1020

ttctctgtgt tgtcccggtg gtcgaacacg cagtacatga actactgggt gggccacagg   1080

ctagagagcc ggaccatccg tggcagtctc tcaacctcga cccacggcaa cacgaacacg   1140
```

-continued

```
agcatcaacc ctgtcactct ccagtttaca tctagggacg tttacaggac agagtcgttc   1200
gctggcatta acattctgtt gaccactccg gtgaacggcg tcccttgggc ccgcttcaac   1260
tggaggaatc ctctgaactc actgcgcggc agccttctct acactatcgg ctacaccggc   1320
gttgggacgc aactcttcga ctcggagacc gagctgccgc ccgagaccac cgagcggcct   1380
aactacgaga gttattcaca caggctctcc aacatccgct tgatttctgg gaacaccttg   1440
cgggctccgg tgtactcctg gacgcaccgc agcgccgaca gaactaatac catcagctcc   1500
gactcgatca cccagatccc gctggtgaag gctcacacgc ttcagtcggg caccacagtc   1560
gtcaagggcc ctggcttcac cggcggcgac atcctgcgtc gcacatctgg cggacccttc   1620
gccttcagca acgtgaactt ggacttcaat ttgtcacagc ggtatcgtgc cagaatccgg   1680
tacgccagca ctacgaacct gcgaatctat gttactgtgg cgggcgagcg gatcttcgcc   1740
gggcaattcg acaagacgat ggacgcggga gcacctctga cattccagtc attctcttac   1800
gccacgatca acacggcatt cacgtttccg gagcgttcca gtagcctgac cgtgggcgct   1860
gataccttca gtagcgggaa cgaggtgtac gttgaccgtt tcgagctgat cccggtcacc   1920
gccaccttcg aggccgagta cgaccttgag cgcgcccaga aggtggtgaa cgccctcttc   1980
actagcacta accagctagg cctgaagact gacgtgaccg actaccacat cgaccaagtg   2040
agcaacctag tggcctgcct ctccgacgag ttctgcctcg acgagaagcg cgagctgtcc   2100
gagaaggtga agcacgccaa gcgcctctcc gacgagcgca acctgctcca ggaccccaac   2160
ttcaggggca tcaacaggca gcccgaccgc ggctggcgcg gctccaccga catcaccatc   2220
cagggcggtg acgacgtatt caaggagaac tacgttaccc tccccggcac cttcgacgag   2280
tgttacccca cctacctcta ccagaagatc gacgagtcca agctgaaggc ctacacccgc   2340
taccagctcc gcggctacat cgaggactcc caggacctgg aaatctacct catccgctac   2400
aacgccaagc acgagatcgt gaacgtgcct ggcaccggca gcctctggcc tctcagcgtg   2460
gagaaccaga tcggcccttg cggcgagcct aaccgctgcg cccctcacct cgagtggaac   2520
cctgacctcc actgctcgtg cagggacggc gagaagtgcg cccaccatag ccaccacttc   2580
tctctggaca tcgacgtggg ctgcaccgac ctgaacgagg acctgggcgt gtgggttatc   2640
ttcaagatca agacccagga cggtcacgcc aggctgggta acctggagtt ccttgaggaa   2700
aagcctctgc tgggtgaggc cctggccagg gtcaagaggg ctgagaagaa atggagggat   2760
aagagggaga ccctgcagct ggagaccact atcgtctaca aggaggctaa ggagtctgtc   2820
gatgctctgt tcgtcaactc tcagtacgat agactgcaag ctgataccaa catcgctatg   2880
atccacgctg cggataagcg ggtccaccgg atccgggagg cttaccttcc ggagctttct   2940
gtcatcccgg gtgtcaacgc tgcgatcttc gaggaacttg aggaacggat cttcactgcg   3000
tttagtcttt acgatgcgcg gaacatcatc aagaacgggg acttcaacaa tggtctgctg   3060
tgctggaacg tcaagggtca tgtcgaggtc gaggaacaaa acaatcatcg tagtgtcctt   3120
gtcattcctg agtgggaggc ggaggtctct caagaggtcc gtgtttgccc ggggcgtggg   3180
tacattcttc gtgttactgc gtacaaggag gggtacgggg aggggtgcgt tactattcat   3240
gagattgaga acaatactga tgagcttaag ttcaacaatt gtgttgagga ggaggtttac   3300
ccgaacaata ctgttacgtg catcaactac acggcaacgc aagaggaata cgaggggacg   3360
tacacctcgc gtaatagagg gtatgatgag gcgtacggaa acaacccgtc ggttccagca   3420
gattatgcct cggtttatga ggagaagtcg tacacggata gacgacgcga gaatccatgt   3480
gagtcaaatc gaggatacgg agattacaca ccattaccag caggatacgt tacaaaggag   3540
```

ttggaatact tcccggaaac agataaagtt tggattgaaa tcggagaaac agaaggaaca 3600
ttcatcgtcg actcagtaga attgttgttg atggaagaat ga 3642

<210> SEQ ID NO 13
<211> LENGTH: 1213
<212> TYPE: PRT
<213> ORGANISM: Artificial
<220> FEATURE:
<223> OTHER INFORMATION: Amino acid sequence of the chimeric protein variant TIC867_20.

<400> SEQUENCE: 13

Met Thr Ser Asn Arg Lys Asn Glu Asn Glu Ile Ile Asn Ala Leu Ser
1 5 10 15

Ile Pro Ala Val Ser Asn His Ser Ala Gln Met Asn Leu Ser Thr Asp
20 25 30

Ala Arg Ile Glu Asp Ser Leu Cys Ile Ala Glu Gly Asn Asn Ile Asp
35 40 45

Pro Phe Val Ser Ala Ser Thr Val Gln Thr Gly Ile Asn Ile Ala Gly
50 55 60

Arg Ile Leu Gly Val Leu Gly Val Pro Phe Ala Gly Gln Ile Ala Ser
65 70 75 80

Phe Tyr Ser Phe Leu Val Gly Glu Leu Trp Pro Arg Gly Arg Asp Pro
85 90 95

Trp Glu Ile Phe Leu Glu His Val Glu Gln Leu Ile Arg Gln Gln Val
100 105 110

Thr Glu Asn Thr Arg Asp Thr Ala Leu Ala Arg Leu Gln Gly Leu Gly
115 120 125

Asn Ser Phe Arg Ala Tyr Gln Gln Ser Leu Glu Asp Trp Leu Glu Asn
130 135 140

Arg Asp Asp Ala Arg Thr Arg Ser Val Leu Tyr Thr Gln Tyr Ile Ala
145 150 155 160

Leu Glu Leu Asp Phe Leu Asn Ala Met Pro Leu Phe Ala Ile Arg Asn
165 170 175

Gln Glu Val Pro Leu Leu Met Val Tyr Ala Gln Ala Ala Asn Leu His
180 185 190

Leu Leu Leu Leu Arg Asp Ala Ser Leu Phe Gly Ser Glu Phe Gly Leu
195 200 205

Thr Ser Gln Glu Ile Gln Arg Tyr Tyr Glu Arg Gln Val Glu Lys Thr
210 215 220

Arg Glu Tyr Ser Asp Tyr Cys Ala Arg Trp Tyr Asn Thr Gly Leu Asn
225 230 235 240

Asn Leu Arg Gly Thr Asn Ala Glu Ser Trp Leu Arg Tyr Asn Gln Phe
245 250 255

Arg Arg Asp Leu Thr Leu Gly Val Leu Asp Leu Val Ala Leu Phe Pro
260 265 270

Ser Tyr Asp Thr Arg Val Tyr Pro Met Asn Thr Ser Ala Gln Leu Thr
275 280 285

Arg Glu Ile Tyr Thr Asp Pro Ile Gly Arg Thr Asn Ala Pro Ser Gly
290 295 300

Phe Ala Ser Thr Asn Trp Phe Asn Asn Asn Ala Pro Ser Phe Ser Ala
305 310 315 320

Ile Glu Ala Ala Val Ile Arg Pro Pro His Leu Leu Asp Phe Pro Glu
325 330 335

-continued

```
Gln Leu Thr Ile Phe Ser Val Leu Ser Arg Trp Ser Asn Thr Gln Tyr
            340                 345                 350

Met Asn Tyr Trp Val Gly His Arg Leu Glu Ser Arg Thr Ile Arg Gly
        355                 360                 365

Ser Leu Ser Thr Ser Thr His Gly Asn Thr Asn Thr Ser Ile Asn Pro
    370                 375                 380

Val Thr Leu Gln Phe Thr Ser Arg Asp Val Tyr Arg Thr Glu Ser Phe
385                 390                 395                 400

Ala Gly Ile Asn Ile Leu Leu Thr Thr Pro Val Asn Gly Val Pro Trp
                405                 410                 415

Ala Arg Phe Asn Trp Arg Asn Pro Leu Asn Ser Leu Arg Gly Ser Leu
            420                 425                 430

Leu Tyr Thr Ile Gly Tyr Thr Gly Val Gly Thr Gln Leu Phe Asp Ser
        435                 440                 445

Glu Thr Glu Leu Pro Pro Glu Thr Thr Glu Arg Pro Asn Tyr Glu Ser
    450                 455                 460

Tyr Ser His Arg Leu Ser Asn Ile Arg Leu Ile Ser Gly Asn Thr Leu
465                 470                 475                 480

Arg Ala Pro Val Tyr Ser Trp Thr His Arg Ser Ala Asp Arg Thr Asn
                485                 490                 495

Thr Ile Ser Ser Asp Ser Ile Thr Gln Ile Pro Leu Val Lys Ala His
            500                 505                 510

Thr Leu Gln Ser Gly Thr Thr Val Val Lys Gly Pro Gly Phe Thr Gly
        515                 520                 525

Gly Asp Ile Leu Arg Arg Thr Ser Gly Gly Pro Phe Ala Phe Ser Asn
    530                 535                 540

Val Asn Leu Asp Phe Asn Leu Ser Gln Arg Tyr Arg Ala Arg Ile Arg
545                 550                 555                 560

Tyr Ala Ser Thr Thr Asn Leu Arg Ile Tyr Val Thr Val Ala Gly Glu
                565                 570                 575

Arg Ile Phe Ala Gly Gln Phe Asp Lys Thr Met Asp Ala Gly Ala Pro
            580                 585                 590

Leu Thr Phe Gln Ser Phe Ser Tyr Ala Thr Ile Asn Thr Ala Phe Thr
        595                 600                 605

Phe Pro Glu Arg Ser Ser Ser Leu Thr Val Gly Ala Asp Thr Phe Ser
    610                 615                 620

Ser Gly Asn Glu Val Tyr Val Asp Arg Phe Glu Leu Ile Pro Val Thr
625                 630                 635                 640

Ala Thr Phe Glu Ala Glu Tyr Asp Leu Glu Arg Ala Gln Lys Val Val
                645                 650                 655

Asn Ala Leu Phe Thr Ser Thr Asn Gln Leu Gly Leu Lys Thr Asp Val
            660                 665                 670

Thr Asp Tyr His Ile Asp Gln Val Ser Asn Leu Val Ala Cys Leu Ser
        675                 680                 685

Asp Glu Phe Cys Leu Asp Glu Lys Arg Glu Leu Ser Glu Lys Val Lys
    690                 695                 700

His Ala Lys Arg Leu Ser Asp Glu Arg Asn Leu Leu Gln Asp Pro Asn
705                 710                 715                 720

Phe Arg Gly Ile Asn Arg Gln Pro Asp Arg Gly Trp Arg Gly Ser Thr
                725                 730                 735

Asp Ile Thr Ile Gln Gly Gly Asp Asp Val Phe Lys Glu Asn Tyr Val
            740                 745                 750

Thr Leu Pro Gly Thr Phe Asp Glu Cys Tyr Pro Thr Tyr Leu Tyr Gln
```

-continued

```
        755                 760                 765

Lys Ile Asp Glu Ser Lys Leu Lys Ala Tyr Thr Arg Tyr Gln Leu Arg
    770                 775                 780

Gly Tyr Ile Glu Asp Ser Gln Asp Leu Glu Ile Tyr Leu Ile Arg Tyr
785                 790                 795                 800

Asn Ala Lys His Glu Ile Val Asn Val Pro Gly Thr Gly Ser Leu Trp
                805                 810                 815

Pro Leu Ser Val Glu Asn Gln Ile Gly Pro Cys Gly Glu Pro Asn Arg
            820                 825                 830

Cys Ala Pro His Leu Glu Trp Asn Pro Asp Leu His Cys Ser Cys Arg
        835                 840                 845

Asp Gly Glu Lys Cys Ala His His Ser His His Phe Ser Leu Asp Ile
    850                 855                 860

Asp Val Gly Cys Thr Asp Leu Asn Glu Asp Leu Gly Val Trp Val Ile
865                 870                 875                 880

Phe Lys Ile Lys Thr Gln Asp Gly His Ala Arg Leu Gly Asn Leu Glu
                885                 890                 895

Phe Leu Glu Glu Lys Pro Leu Leu Gly Glu Ala Leu Ala Arg Val Lys
            900                 905                 910

Arg Ala Glu Lys Lys Trp Arg Asp Lys Arg Glu Thr Leu Gln Leu Glu
        915                 920                 925

Thr Thr Ile Val Tyr Lys Glu Ala Lys Glu Ser Val Asp Ala Leu Phe
    930                 935                 940

Val Asn Ser Gln Tyr Asp Arg Leu Gln Ala Asp Thr Asn Ile Ala Met
945                 950                 955                 960

Ile His Ala Ala Asp Lys Arg Val His Arg Ile Arg Glu Ala Tyr Leu
                965                 970                 975

Pro Glu Leu Ser Val Ile Pro Gly Val Asn Ala Ala Ile Phe Glu Glu
            980                 985                 990

Leu Glu Glu Arg Ile Phe Thr Ala  Phe Ser Leu Tyr Asp  Ala Arg Asn
        995                 1000                1005

Ile Ile  Lys Asn Gly Asp Phe  Asn Asn Gly Leu Leu  Cys Trp Asn
    1010                1015                1020

Val Lys  Gly His Val Glu Val  Glu Glu Gln Asn Asn  His Arg Ser
    1025                1030                1035

Val Leu  Val Ile Pro Glu Trp  Glu Ala Glu Val Ser  Gln Glu Val
    1040                1045                1050

Arg Val  Cys Pro Gly Arg Gly  Tyr Ile Leu Arg Val  Thr Ala Tyr
    1055                1060                1065

Lys Glu  Gly Tyr Gly Glu Gly  Cys Val Thr Ile His  Glu Ile Glu
    1070                1075                1080

Asn Asn  Thr Asp Glu Leu Lys  Phe Asn Asn Cys Val  Glu Glu Glu
    1085                1090                1095

Val Tyr  Pro Asn Asn Thr Val  Thr Cys Ile Asn Tyr  Thr Ala Thr
    1100                1105                1110

Gln Glu  Glu Tyr Glu Gly Thr  Tyr Thr Ser Arg Asn  Arg Gly Tyr
    1115                1120                1125

Asp Glu  Ala Tyr Gly Asn Asn  Pro Ser Val Pro Ala  Asp Tyr Ala
    1130                1135                1140

Ser Val  Tyr Glu Glu Lys Ser  Tyr Thr Asp Arg Arg  Arg Glu Asn
    1145                1150                1155

Pro Cys  Glu Ser Asn Arg Gly  Tyr Gly Asp Tyr Thr  Pro Leu Pro
    1160                1165                1170
```

```
Ala Gly Tyr Val Thr Lys Glu Leu Glu Tyr Phe Pro Glu Thr Asp
    1175                1180                1185

Lys Val Trp Ile Glu Ile Gly Glu Thr Glu Gly Thr Phe Ile Val
    1190                1195                1200

Asp Ser Val Glu Leu Leu Leu Met Glu Glu
    1205                1210


<210> SEQ ID NO 14
<211> LENGTH: 3690
<212> TYPE: DNA
<213> ORGANISM: Artificial
<220> FEATURE:
<223> OTHER INFORMATION: Recombinant nucleotide sequence used for
      expression in a bacterial cell encoding TIC867_21.

<400> SEQUENCE: 14

atgacttcaa ataggaaaaa tgagaatgaa attataaatg ctttatcgat tccagctgta     60

tcgaatcatt ccgcacaaat gaatctatca accgatgctc gtattgagga tagcttgtgt    120

atagccgagg ggaacaatat cgatccattt gttagcgcat caacagtcca aacgggtatt    180

aacatagctg gtagaatact aggtgtatta ggcgtaccgt ttgctggaca aatagctagt    240

ttttatagtt ttcttgttgg tgaattatgg ccccgcggca gagatccttg ggaaattttc    300

ctagaacatg tcgaacaact tataagacaa caagtaacag aaaatactag ggatacggct    360

cttgctcgat tacaaggttt aggaaattcc tttagagcct atcaacagtc acttgaagat    420

tggctagaaa accgtgatga tgcaagaacg agaagtgttc tttataccca atatatagcc    480

ttagaacttg attttcttaa tgcgatgccg cttttcgcaa ttagaaacca agaagttcca    540

ttattaatgg tatatgctca agctgcaaat ttacacctat tattattgag agatgcctct    600

ctttttggta gtgaatttgg gcttacatcc caagaaattc aacgttatta tgagcgccaa    660

gtggaaaaaa cgagagaata ttctgattat tgcgcaagat ggtataatac gggtttaaat    720

aatttgagag ggacaaatgc tgaaagttgg ttgcgatata atcaattccg tagagactta    780

acgctaggag tattagatct agtggcacta ttcccaagct atgacacgcg tgtttatcca    840

atgaatacca gtgctcaatt aacaagagaa atttatacag atccaattgg gagaacaaat    900

gcaccttcag gatttgcaag tacgaattgg tttaataata atgcaccatc gttttctgcc    960

atagaggctg ccgttattag gcctccgcat ctacttgatt ttccagaaca gcttacaatt   1020

ttcagcgtat taagtcgatg gagtaatact caatatatga attactgggt gggacataga   1080

cttgaatcgc gaacaataag gggtcatta agtacctcga cacacggaaa taccaatact   1140

tctattaatc ctgtaacatt acagttcaca tctcgagacg tttatagaac agaatcattt   1200

gcagggataa atatacttct aactactcct gtgaatggag taccttgggc tagatttaat   1260

tggagaaatc ccctgaattc tcttagaggt agccttctct atactatagg gtatactgga   1320

gtggggacac aactatttga ttcagaaact gaattaccac cagaaacaac agaacgacca   1380

aattatgaat cttacagtca tagattatct aatataagac taatatcagg aaacactttg   1440

agagcaccag tatattcttg gacgcaccgt agtgcagatc gtacaaatac cattagttca   1500

gatagcatta cacaaatacc attggtaaag gcgcataccc tccaatcggg taccactgta   1560

gtaaaagggc cagggtttac aggaggggat atcctccgtc gaacaagtgg aggaccattt   1620

gcttttagta atgttaatct agattttaac ttgtcacaaa ggtatcgtgc tagaattcgt   1680

tatgcctcta ctactaacct aagaatttac gtaacggttg caggtgaacg aatttttgct   1740
```

-continued

```
ggtcaatttg acaaaactat ggatgctggt gccccattaa cattccaatc ttttagttac   1800
gcaactatta atacagcttt tacattccca gaaagatcga gcagcttgac tgtaggtgcc   1860
gatacgttta gttcaggtaa tgaagtttat gtagatagat ttgaattaat cccagttact   1920
gcaaccggaa cgacaaccta tgagtatgaa gagaagcaga atctagaaaa agcgcagaaa   1980
gcgttgaacg ctttgtttac ggatggcacg aatggctatc tacaaatgga tgccactgat   2040
tatgatatca atcaaactgc aaacttaata gaatgtgtat cagatgaatt gtatgcaaaa   2100
gaaaagatag ttttattaga tgaagtcaaa tatgcgaagc ggcttagcat atcacgtaac   2160
ctacttttga acgatgattt agaattttca gatggatttg gagaaaacgg atggacgaca   2220
agtgataata tttcaatcca ggcggataat ccccttttta aggggaatta tttaaaaatg   2280
tttggggcaa gagatattga tggaacccta tttccaactt atctctatca aaaaatagat   2340
gagtccaggt taaaaccata tacacgttat cgagtaagag ggtttgtggg aagtagtaaa   2400
aatctaaaat tagtggtaac acgctatgag aaagaaattg atgccattat gaatgttcca   2460
aatgatttgg cacatatgca gcttaaccct tcatgtggag attatcgctg tgaatcatcg   2520
tcccagtttt tggtgaacca agtgcatcct acaccaacag ctggatatgc tcttgatatg   2580
tatgcatgcc cgtcaagttc agataaaaaa catattatgt gtcacgatcg tcatccattt   2640
gattttcata ttgacaccgg agaattaaat ccaaacacaa acctgggtat tgatgtcttg   2700
tttaaaattt ctaatccaaa tggatacgct acattaggga atctagaagt cattgaagaa   2760
ggaccactaa cagatgaagc attggtacat gtaaaacaaa aggaaaagaa atggcgtcag   2820
cacatggaga aaaaacgaat ggaaacacaa caagcctatg atccagcaaa acaagctgta   2880
gatgcattat ttacaaatga acaagagtta gactatcata ctactttaga tcatattcag   2940
aacgccgatc agctggtaca ggcgattccc tatgtacacc atgcttggtt accggatgct   3000
ccaggtatga actatgatgt atatcaaggg ttaaacgcac gtatcatgca ggcgtacaat   3060
ttatatgatg cacgaaatgt cataataaat ggtgacttta cacaaggact acaaggatgg   3120
cacgcaacag gaaaagcagc ggtacaacaa atagatggag cttcagtatt agttctatca   3180
aactggagtg ccgaggtatc tcagaatctg catgcccaag atcatcatgg atatatgtta   3240
cgtgtgattg ccaaaaaaga aggtcctgga aaagggtatg taatgatgat ggattttaat   3300
ggaaagcagg aaacacttac gttcacttct tgtgaagaag gatatataac aaaaacaata   3360
gaggtattcc cggaaagtga tcgaatacga attgaaatgg gagaaacaga gggtacgttt   3420
tatgtagata gcatcgagtt gctttgtatg caaggatatg ctagcgataa taacccgcac   3480
acgggtaata tgtatgagca aagttataat ggaaattata atcaaaatac tagcgatgtg   3540
tatcaccaag gatatataaa caactataac caaaattcta gtagtatgta taatcaaaat   3600
tatattaaca atgatgacct gcattccggt tgcacatgta accaagggca taactctggc   3660
tgtacatgta atcaaggata taaccgttag                                    3690
```

<210> SEQ ID NO 15
<211> LENGTH: 3690
<212> TYPE: DNA
<213> ORGANISM: Artificial
<220> FEATURE:
<223> OTHER INFORMATION: Synthetic nucleotide sequence designed for expression in a plant cell encoding TIC867_21.

<400> SEQUENCE: 15

```
atgaccagca accgaaagaa cgagaacgag atcatcaacg ccctgtccat accggccgtg     60
```

-continued

```
tcaaaccact ccgcccagat gaacctctcc accgacgcga ggatcgagga ctccctctgc    120
atcgccgagg gcaacaacat cgacccgttc gtgtctgcaa gcacggtcca gaccggcatc    180
aacatcgcgg gccgcatcct gggcgtgctc ggcgtgccct tcgcgggtca aatcgcctct    240
ttctactcat tcctcgtggg cgagctgtgg ccgcgcggac gtgacccgtg ggaaatcttc    300
ctggagcacg ttgagcagct catccggcag caagtgaccg agaacaccag ggacaccgca    360
ctggcacggc tccagggcct tggcaacagc ttccgcgcct accagcagtc gctggaggac    420
tggctggaga accgagacga cgccagaacc cgctcagttc tgtacacaca gtacatcgcc    480
ctagagctgg acttcctcaa cgctatgccg ctcttcgcca tccgtaacca ggaagtaccg    540
cttctgatgg tgtacgcaca agcagcgaac ctccatctgc tcctgctgcg agacgcatct    600
ctgttcggca gtgagttcgg gctgacgagc caggagatcc agcgctacta cgagcgccaa    660
gtggagaaga ctcgtgagta cagcgactac tgcgcgcgct ggtacaacac gggcttgaac    720
aaccttcgcg ggacaaacgc cgaatcctgg cttcgctaca accagttccg ccgcgacctc    780
acgctgggtg tgctggacct ggtcgcgctc ttcccgtcct acgacacacg ggtgtaccca    840
atgaacacga gcgcacagct cacccgtgag atctacacag atcccatcgg ccgcaccaac    900
gctcccagtg gcttcgcaag cacgaattgg ttcaacaata acgctccttc tttctctgcc    960
atcgaggccg ctgtcatcag accgccgcac ttactcgatt tcccggagca gctcactatc   1020
ttctctgtgt tgtcccggtg gtcgaacacg cagtacatga actactgggt gggccacagg   1080
ctagagagcc ggaccatccg tggcagtctc tcaacctcga cccacggcaa cacgaacacg   1140
agcatcaacc ctgtcactct ccagtttaca tctagggacg tttacaggac agagtcgttc   1200
gctggcatta acattctgtt gaccactccg gtgaacggcg tcccttgggc ccgcttcaac   1260
tggaggaatc ctctgaactc actgcgcggc agccttctct acactatcgg ctacaccggc   1320
gttgggacgc aactcttcga ctcggagacc gagctgccgc ccgagaccac cgagcggcct   1380
aactacgaga gttattcaca caggctctcc aacatccgct tgatttctgg gaacaccttg   1440
cgggctccgg tgtactcctg gacgcaccgc agcgccgaca gaactaatac catcagctcc   1500
gactcgatca cccagatccc gctggtgaag gctcacacgc ttcagtcggg caccacagtc   1560
gtcaagggcc ctggcttcac cggcggcgac atcctgcgtc gcacatctgg cggaccettc   1620
gccttcagca acgtgaactt ggacttcaat ttgtcacagc ggtatcgtgc cagaatccgg   1680
tacgccagca ctacgaacct gcgaatctat gttactgtgg cgggcgagcg gatcttcgcc   1740
gggcaattcg acaagacgat ggacgcggga gcacctctga cattccagtc attctcttac   1800
gccacgatca acacggcatt cacgtttccg gagcgttcca gtagcctgac cgtgggcgct   1860
gataccttca gtagcgggaa cgaggtgtac gttgaccgtt tcgagctgat cccggtcacc   1920
gccaccggga ctaccaccta cgagtacgag gagaagcaga atctcgagaa ggctcagaag   1980
gctctgaacg ctctgttcac tgacgggacc aacggctacc tccagatgga cgccactgac   2040
tacgacatca accagacagc taacctgatt gagtgtgtga gtgacgaact gtacgctaag   2100
gagaagatcg tactcctgga cgaggtgaag tacgctaagc gcctgagcat tagccgtaac   2160
ctgctgctga acgacgatct ggagttcagc gacggctttg gcgagaacgg ctggaccacc   2220
agcgacaaca tctccatcca ggccgacaat ccactcttca aaggcaacta cctcaagatg   2280
ttcggagcca gggacatcga cggcaccctc tttccgacct acctctacca gaagatcgac   2340
gagtcccgcc tcaaacccta cacccgctac agggtgcgcg gcttcgtggg cagcagcaag   2400
aacctcaagc tcgtggtcac acggtatgag aaggagatcg acgccatcat gaacgtgccc   2460
```

```
aacgatctcg cccacatgca gctcaatcca tcctgcggcg actaccggtg cgagtccagc   2520

tcccagttcc tcgtgaacca ggtgcaccct actccgaccg ctggctatgc cctggacatg   2580

tacgcctgcc ctagttcctc cgacaagaag cacatcatgt gccacgaccg tcatccgttc   2640

gacttccaca tcgacaccgg cgaactgaac ccgaacacca acctgggcat cgacgtactg   2700

ttcaagattt ccaacccgaa cggtacgcc  accttgggca acctggaggt catcgaagaa   2760

ggcccgctga ccgacgaggc cctggtccac gtcaaacaga aggagaagaa gtggcggcag   2820

cacatggaga agaagcggat ggagactcaa caagcctacg acccggccaa gcaagctgtg   2880

gacgctctgt tcaccaacga gcaagagctt gactaccaca ctactcttga ccacatccag   2940

aatgctgacc agcttgtcca ggctattccg tacgtccacc acgcttggct accggacgct   3000

ccagggatga actacgatgt gtaccagggt ctgaacgcgc ggatcatgca agcgtacaac   3060

ctgtacgacg cgcgtaacgt catcatcaac ggtgacttca ctcagggtct tcaaggttgg   3120

cacgcgactg gcaaagcggc agtccagcag attgatggtg cgtctgttct tgtgttgagc   3180

aactggtctg cggaggtttc tcagaacctg cacgcacagg atcaccacgg ctacatgctg   3240

agggtgattg ctaagaagga gggccctggc aaaggctacg tcatgatgat ggacttcaac   3300

ggaaagcaag aaaccctgac cttcactagc tgtgaggagg gctacatcac taagaccatt   3360

gaggtctttc cggagtctga ccgcatccgg atcgagatgg gcgagaccga aggcacgttc   3420

tacgtggact ccatcgaact cctctgcatg caaggctacg cctccgacaa caacccacac   3480

acgggcaaca tgtacgagca gtcctacaac gggaactaca accagaacac ctccgatgtg   3540

taccatcagg gctacatcaa caactacaac cagaacagca gcagcatgta caaccagaac   3600

tacatcaaca acgatgactt gcactcgggt tgcacctgca accagggtca caacagtggg   3660

tgcacgtgca accagggata caaccgttga                                    3690
```

<210> SEQ ID NO 16
<211> LENGTH: 1229
<212> TYPE: PRT
<213> ORGANISM: Artificial
<220> FEATURE:
<223> OTHER INFORMATION: Amino acid sequence of the chimeric protein variant TIC867_21.

<400> SEQUENCE: 16

```
Met Thr Ser Asn Arg Lys Asn Glu Asn Glu Ile Ile Asn Ala Leu Ser
1               5                   10                  15

Ile Pro Ala Val Ser Asn His Ser Ala Gln Met Asn Leu Ser Thr Asp
            20                  25                  30

Ala Arg Ile Glu Asp Ser Leu Cys Ile Ala Glu Gly Asn Asn Ile Asp
        35                  40                  45

Pro Phe Val Ser Ala Ser Thr Val Gln Thr Gly Ile Asn Ile Ala Gly
    50                  55                  60

Arg Ile Leu Gly Val Leu Gly Val Pro Phe Ala Gly Gln Ile Ala Ser
65                  70                  75                  80

Phe Tyr Ser Phe Leu Val Gly Glu Leu Trp Pro Arg Gly Arg Asp Pro
                85                  90                  95

Trp Glu Ile Phe Leu Glu His Val Glu Gln Leu Ile Arg Gln Gln Val
            100                 105                 110

Thr Glu Asn Thr Arg Asp Thr Ala Leu Ala Arg Leu Gln Gly Leu Gly
        115                 120                 125

Asn Ser Phe Arg Ala Tyr Gln Gln Ser Leu Glu Asp Trp Leu Glu Asn
```

-continued

```
    130                 135                 140

Arg Asp Asp Ala Arg Thr Arg Ser Val Leu Tyr Thr Gln Tyr Ile Ala
145                 150                 155                 160

Leu Glu Leu Asp Phe Leu Asn Ala Met Pro Leu Phe Ala Ile Arg Asn
                165                 170                 175

Gln Glu Val Pro Leu Leu Met Val Tyr Ala Gln Ala Ala Asn Leu His
            180                 185                 190

Leu Leu Leu Leu Arg Asp Ala Ser Leu Phe Gly Ser Glu Phe Gly Leu
        195                 200                 205

Thr Ser Gln Glu Ile Gln Arg Tyr Tyr Glu Arg Gln Val Glu Lys Thr
    210                 215                 220

Arg Glu Tyr Ser Asp Tyr Cys Ala Arg Trp Tyr Asn Thr Gly Leu Asn
225                 230                 235                 240

Asn Leu Arg Gly Thr Asn Ala Glu Ser Trp Leu Arg Tyr Asn Gln Phe
                245                 250                 255

Arg Arg Asp Leu Thr Leu Gly Val Leu Asp Leu Val Ala Leu Phe Pro
            260                 265                 270

Ser Tyr Asp Thr Arg Val Tyr Pro Met Asn Thr Ser Ala Gln Leu Thr
        275                 280                 285

Arg Glu Ile Tyr Thr Asp Pro Ile Gly Arg Thr Asn Ala Pro Ser Gly
    290                 295                 300

Phe Ala Ser Thr Asn Trp Phe Asn Asn Asn Ala Pro Ser Phe Ser Ala
305                 310                 315                 320

Ile Glu Ala Ala Val Ile Arg Pro Pro His Leu Leu Asp Phe Pro Glu
                325                 330                 335

Gln Leu Thr Ile Phe Ser Val Leu Ser Arg Trp Ser Asn Thr Gln Tyr
            340                 345                 350

Met Asn Tyr Trp Val Gly His Arg Leu Glu Ser Arg Thr Ile Arg Gly
        355                 360                 365

Ser Leu Ser Thr Ser Thr His Gly Asn Thr Asn Thr Ser Ile Asn Pro
    370                 375                 380

Val Thr Leu Gln Phe Thr Ser Arg Asp Val Tyr Arg Thr Glu Ser Phe
385                 390                 395                 400

Ala Gly Ile Asn Ile Leu Leu Thr Thr Pro Val Asn Gly Val Pro Trp
                405                 410                 415

Ala Arg Phe Asn Trp Arg Asn Pro Leu Asn Ser Leu Arg Gly Ser Leu
            420                 425                 430

Leu Tyr Thr Ile Gly Tyr Thr Gly Val Gly Thr Gln Leu Phe Asp Ser
        435                 440                 445

Glu Thr Glu Leu Pro Pro Glu Thr Thr Glu Arg Pro Asn Tyr Glu Ser
    450                 455                 460

Tyr Ser His Arg Leu Ser Asn Ile Arg Leu Ile Ser Gly Asn Thr Leu
465                 470                 475                 480

Arg Ala Pro Val Tyr Ser Trp Thr His Arg Ser Ala Asp Arg Thr Asn
                485                 490                 495

Thr Ile Ser Ser Asp Ser Ile Thr Gln Ile Pro Leu Val Lys Ala His
            500                 505                 510

Thr Leu Gln Ser Gly Thr Thr Val Val Lys Gly Pro Gly Phe Thr Gly
        515                 520                 525

Gly Asp Ile Leu Arg Arg Thr Ser Gly Gly Pro Phe Ala Phe Ser Asn
    530                 535                 540

Val Asn Leu Asp Phe Asn Leu Ser Gln Arg Tyr Arg Ala Arg Ile Arg
545                 550                 555                 560
```

-continued

```
Tyr Ala Ser Thr Thr Asn Leu Arg Ile Tyr Val Thr Val Ala Gly Glu
                565                 570                 575

Arg Ile Phe Ala Gly Gln Phe Asp Lys Thr Met Asp Ala Gly Ala Pro
            580                 585                 590

Leu Thr Phe Gln Ser Phe Ser Tyr Ala Thr Ile Asn Thr Ala Phe Thr
        595                 600                 605

Phe Pro Glu Arg Ser Ser Ser Leu Thr Val Gly Ala Asp Thr Phe Ser
    610                 615                 620

Ser Gly Asn Glu Val Tyr Val Asp Arg Phe Glu Leu Ile Pro Val Thr
625                 630                 635                 640

Ala Thr Gly Thr Thr Thr Tyr Glu Tyr Glu Glu Lys Gln Asn Leu Glu
                645                 650                 655

Lys Ala Gln Lys Ala Leu Asn Ala Leu Phe Thr Asp Gly Thr Asn Gly
            660                 665                 670

Tyr Leu Gln Met Asp Ala Thr Asp Tyr Asp Ile Asn Gln Thr Ala Asn
        675                 680                 685

Leu Ile Glu Cys Val Ser Asp Glu Leu Tyr Ala Lys Glu Lys Ile Val
    690                 695                 700

Leu Leu Asp Glu Val Lys Tyr Ala Lys Arg Leu Ser Ile Ser Arg Asn
705                 710                 715                 720

Leu Leu Leu Asn Asp Asp Leu Glu Phe Ser Asp Gly Phe Gly Glu Asn
                725                 730                 735

Gly Trp Thr Thr Ser Asp Asn Ile Ser Ile Gln Ala Asp Asn Pro Leu
            740                 745                 750

Phe Lys Gly Asn Tyr Leu Lys Met Phe Gly Ala Arg Asp Ile Asp Gly
        755                 760                 765

Thr Leu Phe Pro Thr Tyr Leu Tyr Gln Lys Ile Asp Glu Ser Arg Leu
    770                 775                 780

Lys Pro Tyr Thr Arg Tyr Arg Val Arg Gly Phe Val Gly Ser Ser Lys
785                 790                 795                 800

Asn Leu Lys Leu Val Val Thr Arg Tyr Glu Lys Glu Ile Asp Ala Ile
                805                 810                 815

Met Asn Val Pro Asn Asp Leu Ala His Met Gln Leu Asn Pro Ser Cys
            820                 825                 830

Gly Asp Tyr Arg Cys Glu Ser Ser Ser Gln Phe Leu Val Asn Gln Val
        835                 840                 845

His Pro Thr Pro Thr Ala Gly Tyr Ala Leu Asp Met Tyr Ala Cys Pro
    850                 855                 860

Ser Ser Ser Asp Lys Lys His Ile Met Cys His Asp Arg His Pro Phe
865                 870                 875                 880

Asp Phe His Ile Asp Thr Gly Glu Leu Asn Pro Asn Thr Asn Leu Gly
                885                 890                 895

Ile Asp Val Leu Phe Lys Ile Ser Asn Pro Asn Gly Tyr Ala Thr Leu
            900                 905                 910

Gly Asn Leu Glu Val Ile Glu Glu Gly Pro Leu Thr Asp Glu Ala Leu
        915                 920                 925

Val His Val Lys Gln Lys Glu Lys Lys Trp Arg Gln His Met Glu Lys
    930                 935                 940

Lys Arg Met Glu Thr Gln Gln Ala Tyr Asp Pro Ala Lys Gln Ala Val
945                 950                 955                 960

Asp Ala Leu Phe Thr Asn Glu Gln Glu Leu Asp Tyr His Thr Thr Leu
                965                 970                 975
```

-continued

```
Asp His Ile Gln Asn Ala Asp Gln Leu Val Gln Ala Ile Pro Tyr Val
            980                 985                 990

His His Ala Trp Leu Pro Asp Ala  Pro Gly Met Asn Tyr  Asp Val Tyr
        995                 1000                1005

Gln Gly  Leu Asn Ala Arg Ile  Met Gln Ala Tyr Asn  Leu Tyr Asp
    1010                 1015                 1020

Ala Arg  Asn Val Ile Ile Asn  Gly Asp Phe Thr Gln  Gly Leu Gln
    1025                 1030                 1035

Gly Trp  His Ala Thr Gly Lys  Ala Ala Val Gln Gln  Ile Asp Gly
    1040                 1045                 1050

Ala Ser  Val Leu Val Leu Ser  Asn Trp Ser Ala Glu  Val Ser Gln
    1055                 1060                 1065

Asn Leu  His Ala Gln Asp His  His Gly Tyr Met Leu  Arg Val Ile
    1070                 1075                 1080

Ala Lys  Lys Glu Gly Pro Gly  Lys Gly Tyr Val Met  Met Met Asp
    1085                 1090                 1095

Phe Asn  Gly Lys Gln Glu Thr  Leu Thr Phe Thr Ser  Cys Glu Glu
    1100                 1105                 1110

Gly Tyr  Ile Thr Lys Thr Ile  Glu Val Phe Pro Glu  Ser Asp Arg
    1115                 1120                 1125

Ile Arg  Ile Glu Met Gly Glu  Thr Glu Gly Thr Phe  Tyr Val Asp
    1130                 1135                 1140

Ser Ile  Glu Leu Leu Cys Met  Gln Gly Tyr Ala Ser  Asp Asn Asn
    1145                 1150                 1155

Pro His  Thr Gly Asn Met Tyr  Glu Gln Ser Tyr Asn  Gly Asn Tyr
    1160                 1165                 1170

Asn Gln  Asn Thr Ser Asp Val  Tyr His Gln Gly Tyr  Ile Asn Asn
    1175                 1180                 1185

Tyr Asn  Gln Asn Ser Ser Ser  Met Tyr Asn Gln Asn  Tyr Ile Asn
    1190                 1195                 1200

Asn Asp  Asp Leu His Ser Gly  Cys Thr Cys Asn Gln  Gly His Asn
    1205                 1210                 1215

Ser Gly  Cys Thr Cys Asn Gln  Gly Tyr Asn Arg
    1220                 1225
```

<210> SEQ ID NO 17
<211> LENGTH: 3432
<212> TYPE: DNA
<213> ORGANISM: Artificial
<220> FEATURE:
<223> OTHER INFORMATION: Recombinant nucleotide sequence used for expression in a bacterial cell encoding TIC867_22.

<400> SEQUENCE: 17

```
atgacttcaa ataggaaaaa tgagaatgaa attataaatg ctttatcgat tccagctgta      60

tcgaatcatt ccgcacaaat gaatctatca accgatgctc gtattgagga tagcttgtgt     120

atagccgagg ggaacaatat cgatccattt gttagcgcat caacagtcca aacgggtatt     180

aacatagctg gtagaatact aggtgtatta ggcgtaccgt ttgctggaca aatagctagt     240

ttttatagtt ttcttgttgg tgaattatgg ccccgcggca gagatccttg ggaaattttc     300

ctagaacatg tcgaacaact tataagacaa caagtaacag aaaatactag ggatacggct     360

cttgctcgat tacaaggttt aggaaattcc tttagagcct atcaacagtc acttgaagat     420

tggctagaaa accgtgatga tgcaagaacg agaagtgttc tttataccca atatatagcc     480

ttagaacttg atttcttaa tgcgatgccg cttttcgcaa ttagaaacca agaagttcca     540
```

-continued

```
ttattaatgg tatatgctca agctgcaaat ttacacctat tattattgag agatgcctct    600
ctttttggta gtgaatttgg gcttacatcc caagaaattc aacgttatta tgagcgccaa    660
gtggaaaaaa cgagagaata ttctgattat tgcgcaagat ggtataatac gggtttaaat    720
aatttgagag ggacaaatgc tgaaagttgg ttgcgatata atcaattccg tagagactta    780
acgctaggag tattagatct agtggcacta ttcccaagct atgacacgcg tgtttatcca    840
atgaatacca gtgctcaatt aacaagagaa atttatacag atccaattgg gagaacaaat    900
gcaccttcag gatttgcaag tacgaattgg tttaataata atgcaccatc gttttctgcc    960
atagaggctg ccgttattag gcctccgcat ctacttgatt ttccagaaca gcttacaatt   1020
ttcagcgtat taagtcgatg gagtaatact caatatatga attactgggt gggacataga   1080
cttgaatcgc gaacaataag gggtcatta agtacctcga cacacggaaa taccaatact    1140
tctattaatc ctgtaacatt acagttcaca tctcgagacg tttatagaac agaatcattt   1200
gcagggataa atatacttct aactactcct gtgaatggag taccttgggc tagatttaat   1260
tggagaaatc ccctgaattc tcttagaggt agccttctct atactatagg gtatactgga   1320
gtggggacac aactatttga ttcagaaact gaattaccac cagaaacaac agaacgacca   1380
aattatgaat cttacagtca tagattatct aatataagac taatatcagg aaacactttg   1440
agagcaccag tatattcttg gacgcaccgt agtgcagatc gtacaaatac cattagttca   1500
gatagcatta cacaaatacc attggtaaag gcgcataccc tccaatcggg taccactgta   1560
gtaaaagggc cagggtttac aggaggggat atcctccgtc gaacaagtgg aggaccattt   1620
gcttttagta atgttaatct agattttaac ttgtcacaaa ggtatcgtgc tagaattcgt   1680
tatgcctcta ctactaacct aagaatttac gtaacggttg caggtgaacg aatttttgct   1740
ggtcaatttg acaaaactat ggatgctggt gccccattaa cattccaatc ttttagttac   1800
gcaactatta atacagcttt tacattccca gaaagatcga gcagcttgac tgtaggtgcc   1860
gatacgttta gttcaggtaa tgaagtttat gtagatagat ttgaattaat cccagttact   1920
gcaaccaatc cgacgcgaga ggcggaagag gatctagaag cagcgaagaa agcggtggcg   1980
agcttgttta cacgtacaag ggacggatta caagtaaatg tgacagatta tcaagtcgat   2040
caagcggcaa atttagtgtc atgcttatca gatgaacaat atgggcatga caaaaagatg   2100
ttattggaag cggtaagagc ggcaaaacgc ctcagccgag aacgcaactt acttcaggat   2160
ccagatttta atacaatcaa tagtacagaa gaaaatggat ggaaagcaag taacggcgtt   2220
actattagcg agggcggtcc attctataaa ggccgtgcgc ttcagctagc aagcgcaaga   2280
gaaaattacc caacatacat ttatcaaaaa gtaaatgcat cagagttaaa gccgtataca   2340
cgttatagac tggatgggtt cgtgaagagt agtcaagatt tagaaattga tctcattcac   2400
catcataaag tccatctcgt gaaaaatgta ccagataatt tagtatccga tacttactcg   2460
gatggttctt gcagtggaat gaatcgatgt gaggaacaac agatggtaaa tgcgcaactg   2520
gaaacagaac atcatcatcc gatggattgc tgtgaagcgg ctcaaacaca tgagttttct   2580
tcctatatta atacaggcga tctaaattca agtgtagatc aaggcatttg ggttgtattg   2640
aaagttcgaa caaccgatgg ttatgcgacg ctaggaaatc ttgaattggt agaggtcgga   2700
ccgttatcgg gtgaatctct agaacgtgaa caaagggata atgcgaaatg gagtgcagag   2760
ctaggaagaa agcgtgcaga aacagatcgc gtgtatcaag atgccaaaca atccatcaat   2820
catttatttg tggattatca agatcaacaa ttaaatccag aaatagggat ggcagatatt   2880
```

attgacgctc aaaatcttgt cgcatcaatt tcagatgtgt atagcgatgc agtactgcaa 2940
atccctggaa ttaactatga gatttacaca gagctatcca atcgcttaca acaagcatcg 3000
tatctgtata cgtctcgaaa tgcggtgcaa aatggggact ttaacagcgg tctagatagt 3060
tggaatgcaa caggggggc tacggtacaa caggatggca atacgcattt cttagttctt 3120
tctcattggg atgcacaagt ttctcaacaa tttagagtgc agccgaattg taaatatgta 3180
ttacgtgtaa cagcagagaa agtaggcggc ggagacggat acgtgacaat ccgggatggt 3240
gctcatcata cagaaaagct tacatttaat gcatgtgatt atgatataaa tggcacgtac 3300
gtgactgata atacgtatct aacaaaagaa gtggtattct attcacatac agaacacatg 3360
tgggtagagg taagtgaaac agaaggtgca tttcatatag atagtattga attcgttgaa 3420
acagaaaagt ag 3432

<210> SEQ ID NO 18
<211> LENGTH: 3432
<212> TYPE: DNA
<213> ORGANISM: Artificial
<220> FEATURE:
<223> OTHER INFORMATION: Synthetic nucleotide sequence designed for expression in a plant cell encoding TIC867_22.

<400> SEQUENCE: 18
atgaccagca accgaaagaa cgagaacgag atcatcaacg ccctgtccat accggccgtg 60
tcaaaccact ccgcccagat gaacctctcc accgacgcga ggatcgagga ctccctctgc 120
atcgccgagg gcaacaacat cgacccgttc gtgtctgcaa gcacggtcca gaccggcatc 180
aacatcgcgg gccgcatcct gggcgtgctc ggcgtgccct tcgcgggtca aatcgcctct 240
ttctactcat tcctcgtggg cgagctgtgg ccgcgcggac gtgacccgtg ggaaatcttc 300
ctggagcacg ttgagcagct catccggcag caagtgaccg agaacaccag ggacaccgca 360
ctggcacggc tccagggcct tggcaacagc ttccgcgcct accagcagtc gctggaggac 420
tggctggaga accgagacga cgccagaacc cgctcagttc tgtacacaca gtacatcgcc 480
ctagagctgg acttcctcaa cgctatgccg ctcttcgcca tccgtaacca ggaagtaccg 540
cttctgatgg tgtacgcaca agcagcgaac ctccatctgc tcctgctgcg agacgcatct 600
ctgttcggca gtgagttcgg gctgacgagc caggagatcc agcgctacta cgagcgccaa 660
gtggagaaga ctcgtgagta cagcgactac tgcgcgcgct ggtacaacac gggcttgaac 720
aaccttcgcg ggacaaacgc cgaatcctgg cttcgctaca accagttccg ccgcgacctc 780
acgctgggtg tgctggacct ggtcgcgctc ttcccgtcct acgacacacg ggtgtaccca 840
atgaacacga gcgcacagct cacccgtgag atctacacag atcccatcgg ccgcaccaac 900
gctcccagtg gcttcgcaag cacgaattgg ttcaacaata acgctccttc tttctctgcc 960
atcgaggccg ctgtcatcag accgccgcac ttactcgatt tcccggagca gctcactatc 1020
ttctctgtgt tgtcccggtg gtcgaacacg cagtacatga actactgggt gggccacagg 1080
ctagagagcc ggaccatccg tggcagtctc tcaacctcga cccacggcaa cacgaacacg 1140
agcatcaacc ctgtcactct ccagtttaca tctagggacg tttacaggac agagtcgttc 1200
gctggcatta acattctgtt gaccactccg gtgaacggcg tcccttgggc ccgcttcaac 1260
tggaggaatc ctctgaactc actgcgcggc agccttctct acactatcgg ctacaccggc 1320
gttgggacgc aactcttcga ctcggagacc gagctgccgc ccgagaccac cgagcggcct 1380
aactacgaga gttattcaca caggctctcc aacatccgct tgatttctgg gaacaccttg 1440

-continued

```
cgggctccgg tgtactcctg gacgcaccgc agcgccgaca gaactaatac catcagctcc   1500

gactcgatca cccagatccc gctggtgaag gctcacacgc ttcagtcggg caccacagtc   1560

gtcaagggcc ctggcttcac cggcggcgac atcctgcgtc gcacatctgg cggacccttc   1620

gccttcagca acgtgaactt ggacttcaat ttgtcacagc ggtatcgtgc cagaatccgg   1680

tacgccagca ctacgaacct gcgaatctat gttactgtgg cgggcgagcg gatcttcgcc   1740

gggcaattcg acaagacgat ggacgcggga gcacctctga cattccagtc attctcttac   1800

gccacgatca acacggcatt cacgtttccg gagcgttcca gtagcctgac cgtgggcgct   1860

gataccttca gtagcgggaa cgaggtgtac gttgaccgtt tcgagctgat cccggtcacc   1920

gccaccaacc cgacgcggga agctgaggaa gacttggaag ccgccaagaa agcggtcgcc   1980

agcctgttta ctcggacgcg ggacgggctc caagtgaatg tgacggacta tcaagtggat   2040

caggccgcta acctcgtgtc atgcctgagc gacgagcagt acggtcacga caagaaaatg   2100

ctgctggagg ccgtccgggc cgccaagcgg ctgtccaggg agcgtaacct gctacaagat   2160

cccgacttta acacgatcaa cagcacagag gagaatggct ggaaggccag caacggagtt   2220

acgataagcg agggcggtcc gttctacaag ggtcgtgccc tccagctcgc ctctgcaagg   2280

gagaactatc caacctacat ctatcagaag gtgaacgcat ccgagcttaa gccctacaca   2340

cgctaccgcc tggacgggtt cgttaagtcc agtcaagacc tagagataga cctcatccac   2400

caccacaaag tgcatctggt caagaacgtt cccgataatc tcgtgagcga tacctactca   2460

gacggctcat gctctggcat gaacagatgt gaggagcaac agatggttaa tgctcaactc   2520

gaaaccgagc atcatcatcc tatggattgc tgcgaggccg cgcagaccca tgagttcagc   2580

tcttacatca acaccggaga cctcaacagt agcgtggatc agggaatttg ggtggtgctt   2640

aaagtgcgta caaccgacgg ctacgccacc ctcggcaacc ttgagcttgt cgaggtcgga   2700

ccacttagcg gcgagtccct ggaacgtgag cagcgggaca acgccaaatg gagcgcagag   2760

ctagggcgca aacgcgcgga gacggaccgg gtttatcagg acgcgaagca gtccatcaat   2820

cacctcttcg tggattatca ggaccagcag cttaatccag agatcggcat ggccgacatc   2880

atcgacgccc agaacctagt agcgtcgatt tccgatgtct attccgacgc cgtgcttcaa   2940

atacctggca tcaactacga gatctacaca gagttgtcca acaggctcca gcaagcgtca   3000

tacctctaca ccagccgcaa cgccgtccag aatggcgact tcaattccgg actagactcc   3060

tggaacgcca cgggcggagc tacggtgcaa caagacggca acacccactt cctcgtactt   3120

agccactggg acgctcaagt gagtcagcaa ttccgggttc agccgaactg caagtacgtc   3180

ctgcgcgtaa cggccgagaa ggttggaggc ggagacggct acgttaccat ccgcgacggc   3240

gctcaccaca ccgagaaact gacgttcaac gcttgtgact acgacatcaa cggcacttac   3300

gtgacggaca acacctacct gacgaaggag gtggtgttct attctcacac cgagcacatg   3360

tgggttgagg tcagcgagac cgagggagcc ttccacattg acagcatcga gttcgtggag   3420

actgagaagt ga                                                       3432
```

<210> SEQ ID NO 19
<211> LENGTH: 1143
<212> TYPE: PRT
<213> ORGANISM: Artificial
<220> FEATURE:
<223> OTHER INFORMATION: Amino acid sequence of the chimeric protein variant TIC867_22.

<400> SEQUENCE: 19

```
Met Thr Ser Asn Arg Lys Asn Glu Asn Glu Ile Ile Asn Ala Leu Ser
1               5                   10                  15

Ile Pro Ala Val Ser Asn His Ser Ala Gln Met Asn Leu Ser Thr Asp
            20                  25                  30

Ala Arg Ile Glu Asp Ser Leu Cys Ile Ala Glu Gly Asn Asn Ile Asp
        35                  40                  45

Pro Phe Val Ser Ala Ser Thr Val Gln Thr Gly Ile Asn Ile Ala Gly
    50                  55                  60

Arg Ile Leu Gly Val Leu Gly Val Pro Phe Ala Gly Gln Ile Ala Ser
65                  70                  75                  80

Phe Tyr Ser Phe Leu Val Gly Glu Leu Trp Pro Arg Gly Arg Asp Pro
                85                  90                  95

Trp Glu Ile Phe Leu Glu His Val Glu Gln Leu Ile Arg Gln Gln Val
            100                 105                 110

Thr Glu Asn Thr Arg Asp Thr Ala Leu Ala Arg Leu Gln Gly Leu Gly
        115                 120                 125

Asn Ser Phe Arg Ala Tyr Gln Gln Ser Leu Glu Asp Trp Leu Glu Asn
    130                 135                 140

Arg Asp Asp Ala Arg Thr Arg Ser Val Leu Tyr Thr Gln Tyr Ile Ala
145                 150                 155                 160

Leu Glu Leu Asp Phe Leu Asn Ala Met Pro Leu Phe Ala Ile Arg Asn
                165                 170                 175

Gln Glu Val Pro Leu Leu Met Val Tyr Ala Gln Ala Ala Asn Leu His
            180                 185                 190

Leu Leu Leu Leu Arg Asp Ala Ser Leu Phe Gly Ser Glu Phe Gly Leu
        195                 200                 205

Thr Ser Gln Glu Ile Gln Arg Tyr Tyr Glu Arg Gln Val Glu Lys Thr
    210                 215                 220

Arg Glu Tyr Ser Asp Tyr Cys Ala Arg Trp Tyr Asn Thr Gly Leu Asn
225                 230                 235                 240

Asn Leu Arg Gly Thr Asn Ala Glu Ser Trp Leu Arg Tyr Asn Gln Phe
                245                 250                 255

Arg Arg Asp Leu Thr Leu Gly Val Leu Asp Leu Val Ala Leu Phe Pro
            260                 265                 270

Ser Tyr Asp Thr Arg Val Tyr Pro Met Asn Thr Ser Ala Gln Leu Thr
        275                 280                 285

Arg Glu Ile Tyr Thr Asp Pro Ile Gly Arg Thr Asn Ala Pro Ser Gly
    290                 295                 300

Phe Ala Ser Thr Asn Trp Phe Asn Asn Asn Ala Pro Ser Phe Ser Ala
305                 310                 315                 320

Ile Glu Ala Ala Val Ile Arg Pro Pro His Leu Leu Asp Phe Pro Glu
                325                 330                 335

Gln Leu Thr Ile Phe Ser Val Leu Ser Arg Trp Ser Asn Thr Gln Tyr
            340                 345                 350

Met Asn Tyr Trp Val Gly His Arg Leu Glu Ser Arg Thr Ile Arg Gly
        355                 360                 365

Ser Leu Ser Thr Ser Thr His Gly Asn Thr Asn Thr Ser Ile Asn Pro
    370                 375                 380

Val Thr Leu Gln Phe Thr Ser Arg Asp Val Tyr Arg Thr Glu Ser Phe
385                 390                 395                 400

Ala Gly Ile Asn Ile Leu Leu Thr Thr Pro Val Asn Gly Val Pro Trp
                405                 410                 415

Ala Arg Phe Asn Trp Arg Asn Pro Leu Asn Ser Leu Arg Gly Ser Leu
```

-continued

```
        420                 425                 430

Leu Tyr Thr Ile Gly Tyr Thr Gly Val Gly Thr Gln Leu Phe Asp Ser
        435                 440                 445

Glu Thr Glu Leu Pro Pro Glu Thr Thr Glu Arg Pro Asn Tyr Glu Ser
    450                 455                 460

Tyr Ser His Arg Leu Ser Asn Ile Arg Leu Ile Ser Gly Asn Thr Leu
465                 470                 475                 480

Arg Ala Pro Val Tyr Ser Trp Thr His Arg Ser Ala Asp Arg Thr Asn
                485                 490                 495

Thr Ile Ser Ser Asp Ser Ile Thr Gln Ile Pro Leu Val Lys Ala His
            500                 505                 510

Thr Leu Gln Ser Gly Thr Thr Val Val Lys Gly Pro Gly Phe Thr Gly
        515                 520                 525

Gly Asp Ile Leu Arg Arg Thr Ser Gly Gly Pro Phe Ala Phe Ser Asn
    530                 535                 540

Val Asn Leu Asp Phe Asn Leu Ser Gln Arg Tyr Arg Ala Arg Ile Arg
545                 550                 555                 560

Tyr Ala Ser Thr Thr Asn Leu Arg Ile Tyr Val Thr Val Ala Gly Glu
                565                 570                 575

Arg Ile Phe Ala Gly Gln Phe Asp Lys Thr Met Asp Ala Gly Ala Pro
            580                 585                 590

Leu Thr Phe Gln Ser Phe Ser Tyr Ala Thr Ile Asn Thr Ala Phe Thr
        595                 600                 605

Phe Pro Glu Arg Ser Ser Ser Leu Thr Val Gly Ala Asp Thr Phe Ser
    610                 615                 620

Ser Gly Asn Glu Val Tyr Val Asp Arg Phe Glu Leu Ile Pro Val Thr
625                 630                 635                 640

Ala Thr Asn Pro Thr Arg Glu Ala Glu Glu Asp Leu Glu Ala Ala Lys
                645                 650                 655

Lys Ala Val Ala Ser Leu Phe Thr Arg Thr Arg Asp Gly Leu Gln Val
            660                 665                 670

Asn Val Thr Asp Tyr Gln Val Asp Gln Ala Ala Asn Leu Val Ser Cys
        675                 680                 685

Leu Ser Asp Glu Gln Tyr Gly His Asp Lys Lys Met Leu Leu Glu Ala
    690                 695                 700

Val Arg Ala Ala Lys Arg Leu Ser Arg Glu Arg Asn Leu Leu Gln Asp
705                 710                 715                 720

Pro Asp Phe Asn Thr Ile Asn Ser Thr Glu Glu Asn Gly Trp Lys Ala
                725                 730                 735

Ser Asn Gly Val Thr Ile Ser Glu Gly Gly Pro Phe Tyr Lys Gly Arg
            740                 745                 750

Ala Leu Gln Leu Ala Ser Ala Arg Glu Asn Tyr Pro Thr Tyr Ile Tyr
        755                 760                 765

Gln Lys Val Asn Ala Ser Glu Leu Lys Pro Tyr Thr Arg Tyr Arg Leu
    770                 775                 780

Asp Gly Phe Val Lys Ser Ser Gln Asp Leu Glu Ile Asp Leu Ile His
785                 790                 795                 800

His His Lys Val His Leu Val Lys Asn Val Pro Asp Asn Leu Val Ser
                805                 810                 815

Asp Thr Tyr Ser Asp Gly Ser Cys Ser Gly Met Asn Arg Cys Glu Glu
            820                 825                 830

Gln Gln Met Val Asn Ala Gln Leu Glu Thr Glu His His His Pro Met
        835                 840                 845
```

```
Asp Cys Cys Glu Ala Ala Gln Thr His Glu Phe Ser Ser Tyr Ile Asn
    850                 855                 860

Thr Gly Asp Leu Asn Ser Ser Val Asp Gln Gly Ile Trp Val Val Leu
865                 870                 875                 880

Lys Val Arg Thr Thr Asp Gly Tyr Ala Thr Leu Gly Asn Leu Glu Leu
                885                 890                 895

Val Glu Val Gly Pro Leu Ser Gly Glu Ser Leu Glu Arg Glu Gln Arg
            900                 905                 910

Asp Asn Ala Lys Trp Ser Ala Glu Leu Gly Arg Lys Arg Ala Glu Thr
        915                 920                 925

Asp Arg Val Tyr Gln Asp Ala Lys Gln Ser Ile Asn His Leu Phe Val
    930                 935                 940

Asp Tyr Gln Asp Gln Gln Leu Asn Pro Glu Ile Gly Met Ala Asp Ile
945                 950                 955                 960

Ile Asp Ala Gln Asn Leu Val Ala Ser Ile Ser Asp Val Tyr Ser Asp
                965                 970                 975

Ala Val Leu Gln Ile Pro Gly Ile Asn Tyr Glu Ile Tyr Thr Glu Leu
            980                 985                 990

Ser Asn Arg Leu Gln Gln Ala Ser  Tyr Leu Tyr Thr Ser  Arg Asn Ala
        995                 1000                1005

Val Gln  Asn Gly Asp Phe Asn  Ser Gly Leu Asp Ser  Trp Asn Ala
    1010                1015                1020

Thr Gly  Gly Ala Thr Val Gln  Gln Asp Gly Asn Thr  His Phe Leu
    1025                1030                1035

Val Leu  Ser His Trp Asp Ala  Gln Val Ser Gln Gln  Phe Arg Val
    1040                1045                1050

Gln Pro  Asn Cys Lys Tyr Val  Leu Arg Val Thr Ala  Glu Lys Val
    1055                1060                1065

Gly Gly  Gly Asp Gly Tyr Val  Thr Ile Arg Asp Gly  Ala His His
    1070                1075                1080

Thr Glu  Lys Leu Thr Phe Asn  Ala Cys Asp Tyr Asp  Ile Asn Gly
    1085                1090                1095

Thr Tyr  Val Thr Asp Asn Thr  Tyr Leu Thr Lys Glu  Val Val Phe
    1100                1105                1110

Tyr Ser  His Thr Glu His Met  Trp Val Glu Val Ser  Glu Thr Glu
    1115                1120                1125

Gly Ala  Phe His Ile Asp Ser  Ile Glu Phe Val Glu  Thr Glu Lys
    1130                1135                1140


<210> SEQ ID NO 20
<211> LENGTH: 3696
<212> TYPE: DNA
<213> ORGANISM: Artificial
<220> FEATURE:
<223> OTHER INFORMATION: Synthetic nucleotide sequence designed for
      expression in a plant cell encoding TIC867_23.

<400> SEQUENCE: 20

atgaccagca accgaaagaa cgagaacgag atcatcaacg ccctgtccat accggccgtg     60

tcaaaccact ccgcccagat gaacctctcc accgacgcga ggatcgagga ctccctctgc    120

atcgccgagg gcaacaacat cgacccgttc gtgtctgcaa gcacggtcca gaccggcatc    180

aacatcgcgg gccgcatcct gggcgtgctc ggcgtgccct tcgcgggtca aatcgcctct    240

ttctactcat tcctcgtggg cgagctgtgg ccgcgcggac gtgacccgtg ggaaatcttc    300
```

-continued

```
ctggagcacg ttgagcagct catccggcag caagtgaccg agaacaccag ggacaccgca    360
ctggcacggc tccagggcct tggcaacagc ttccgcgcct accagcagtc gctggaggac    420
tggctggaga accgagacga cgccagaacc cgctcagttc tgtacacaca gtacatcgcc    480
ctagagctgg acttcctcaa cgctatgccg ctcttcgcca tccgtaacca ggaagtaccg    540
cttctgatgg tgtacgcaca agcagcgaac ctccatctgc tcctgctgcg agacgcatct    600
ctgttcggca gtgagttcgg gctgacgagc caggagatcc agcgctacta cgagcgccaa    660
gtggagaaga ctcgtgagta cagcgactac tgcgcgcgct ggtacaacac gggcttgaac    720
aaccttcgcg ggacaaacgc cgaatcctgg cttcgctaca accagttccg ccgcgacctc    780
acgctgggtg tgctggacct ggtcgcgctc ttcccgtcct acgacacacg ggtgtaccca    840
atgaacacga gcgcacagct cacccgtgag atctacacag atcccatcgg ccgcaccaac    900
gctcccagtg gcttcgcaag cacgaattgg ttcaacaata acgctccttc tttctctgcc    960
atcgaggccg ctgtcatcag accgccgcac ttactcgatt tcccggagca gctcactatc   1020
ttctctgtgt tgtcccggtg gtcgaacacg cagtacatga actactgggt gggccacagg   1080
ctagagagcc ggaccatccg tggcagtctc tcaacctcga cccacggcaa cacgaacacg   1140
agcatcaacc ctgtcactct ccagtttaca tctagggacg tttacaggac agagtcgttc   1200
gctggcatta acattctgtt gaccactccg gtgaacggcg tcccttgggc ccgcttcaac   1260
tggaggaatc ctctgaactc actgcgcggc agccttctct acactatcgg ctacaccggc   1320
gttgggacgc aactcttcga ctcggagacc gagctgccgc ccgagaccac cgagcggcct   1380
aactacgaga gttattcaca caggctctcc aacatccgct tgatttctgg gaacaccttg   1440
cgggctccgg tgtactcctg gacgcaccgc agcgccgaca gaactaatac catcagctcc   1500
gactcgatca cccagatccc gctggtgaag gctcacacgc ttcagtcggg caccacagtc   1560
gtcaagggcc ctggcttcac cggcggcgac atcctgcgtc gcacatctgg cggacccttc   1620
gccttcagca acgtgaactt ggacttcaat ttgtcacagc ggtatcgtgc cagaatccgg   1680
tacgccagca ctacgaacct gcgaatctat gttactgtgg cgggcgagcg gatcttcgcc   1740
gggcaattcg acaagacgat ggacgcggga gcacctctga cattccagtc attctcttac   1800
gccacgatca acacggcatt cacgtttccg gagcgttcca gtagcctgac cgtgggcgct   1860
gataccttca gtagcgggaa cgaggtgtac gttgaccgtt tcgagctgat cccggtcacc   1920
gccaccacgg cgaccttcga ggcggagtat gacttggagc gggctcagga ggccgtcaac   1980
gcgctgttca caaacaccaa tcctcgccgc ctcaagacgg gtgtgactga ttaccacatt   2040
gacgaggtct ccaacttggt cgcgtgtctg tccgatgagt tctgcctgga cgagaagcgg   2100
gaactgctgg agaaggtcaa gtacgccaag cgcctctccg acgaaaggaa cctcctccaa   2160
gatcccaact ttacttccat taacaagcag ccggacttca tctccaccaa cgagcagtcc   2220
aacttcacct caatccacga gcagtcggag cacgggtggt ggggcagcga gaacatcacc   2280
atccaagagg gcaacgacgt cttcaaggag aactacgtga tcctgcccgg caccttcaac   2340
gagtgttacc cgacctatct ctaccagaag attggcgaag cggaactcaa ggcttacacc   2400
cgttaccaac tgagtggcta cattgaggac tcacaagacc tggaaatcta cctgatccgc   2460
tacaacgcca agcacgagac cctcgacgtg cctggcacgg agtccgtctg gcccttgagc   2520
gtggagtctc ctatcggtcg ttgcggcgag cccaatcgct gcgctccgca ctttgagtgg   2580
aatcctgatt tggattgctc ctgccgagac ggtgagaaat gcgcccacca ctcgcaccac   2640
ttcagcctag acatcgacgt gggctgcatc gacctgcacg agaacttggg cgtctgggtc   2700
```

```
gtgttcaaga tcaagacaca ggagggccat gctcggcttg ggaacctgga gttcatcgag   2760

gagaagccac tgctgggtga agccttgtca cgggtgaaac gcgccgagaa gaagtggcgg   2820

gacaaacggg agaagctcca gttggagaca aagcgtgtgt acacagaggc caaggaggcc   2880

gtggatgcct tgttcgtgga cagtcagtac gacaggctgc aagcggacac caacatcggg   2940

atgatccacg cggctgataa gcttgttcac agaatccgcg aggcgtacct gtcagagctt   3000

agcgtgatcc caggcgtcaa cgccgaaatc ttcgaggaac tggagggccg cattatcacg   3060

gcaatctcac tttatgacgc gaggaatgtg gtcaagaacg gtgacttcaa caacggcttg   3120

gcgtgttgga acgttaaagg gcacgtggat gtacaacagt cacaccacag aagtgtcttg   3180

gtcatcccgg agtgggaggc ggaagtgagc caggccgtcc gggtctgccc tgggcgcggt   3240

tacatcctcc gcgtgacagc gtacaaggag ggctacggtg agggctgcgt gacgatccac   3300

gagattgaga acaacacgga cgagcttaag ttcaagaact gcgaggagga ggaagtgtac   3360

ccgacagaca ccggcacctg caacgactac accgcccacc aagggaccgc cgcctgcaac   3420

agccgcaacg cgggctatga agatgcgtac gaggttgata ccaccgcctc agtgaactac   3480

aaaccgactt atgaggagga gacatacacg gacgtcaggc gcgacaacca ttgtgagtac   3540

gaccgtggct acgtgaacta tccgccggtg ccagcgggct acatgacgaa ggagctagaa   3600

tacttccctg agacggacaa ggtgtggatt gaaatcggcg agaccgaggg caagtttatc   3660

gtggattctg tcgagctgct gctaatggag gagtag                            3696


<210> SEQ ID NO 21
<211> LENGTH: 1231
<212> TYPE: PRT
<213> ORGANISM: Artificial
<220> FEATURE:
<223> OTHER INFORMATION: Amino acid sequence of the chimeric protein
      variant TIC867_23.

<400> SEQUENCE: 21

Met Thr Ser Asn Arg Lys Asn Glu Asn Glu Ile Ile Asn Ala Leu Ser
1               5                   10                  15

Ile Pro Ala Val Ser Asn His Ser Ala Gln Met Asn Leu Ser Thr Asp
            20                  25                  30

Ala Arg Ile Glu Asp Ser Leu Cys Ile Ala Glu Gly Asn Asn Ile Asp
        35                  40                  45

Pro Phe Val Ser Ala Ser Thr Val Gln Thr Gly Ile Asn Ile Ala Gly
    50                  55                  60

Arg Ile Leu Gly Val Leu Gly Val Pro Phe Ala Gly Gln Ile Ala Ser
65                  70                  75                  80

Phe Tyr Ser Phe Leu Val Gly Glu Leu Trp Pro Arg Gly Arg Asp Pro
                85                  90                  95

Trp Glu Ile Phe Leu Glu His Val Glu Gln Leu Ile Arg Gln Gln Val
            100                 105                 110

Thr Glu Asn Thr Arg Asp Thr Ala Leu Ala Arg Leu Gln Gly Leu Gly
        115                 120                 125

Asn Ser Phe Arg Ala Tyr Gln Gln Ser Leu Glu Asp Trp Leu Glu Asn
    130                 135                 140

Arg Asp Asp Ala Arg Thr Arg Ser Val Leu Tyr Thr Gln Tyr Ile Ala
145                 150                 155                 160

Leu Glu Leu Asp Phe Leu Asn Ala Met Pro Leu Phe Ala Ile Arg Asn
                165                 170                 175
```

-continued

```
Gln Glu Val Pro Leu Leu Met Val Tyr Ala Gln Ala Ala Asn Leu His
            180                 185                 190

Leu Leu Leu Leu Arg Asp Ala Ser Leu Phe Gly Ser Glu Phe Gly Leu
        195                 200                 205

Thr Ser Gln Glu Ile Gln Arg Tyr Tyr Glu Arg Gln Val Glu Lys Thr
    210                 215                 220

Arg Glu Tyr Ser Asp Tyr Cys Ala Arg Trp Tyr Asn Thr Gly Leu Asn
225                 230                 235                 240

Asn Leu Arg Gly Thr Asn Ala Glu Ser Trp Leu Arg Tyr Asn Gln Phe
                245                 250                 255

Arg Arg Asp Leu Thr Leu Gly Val Leu Asp Leu Val Ala Leu Phe Pro
            260                 265                 270

Ser Tyr Asp Thr Arg Val Tyr Pro Met Asn Thr Ser Ala Gln Leu Thr
        275                 280                 285

Arg Glu Ile Tyr Thr Asp Pro Ile Gly Arg Thr Asn Ala Pro Ser Gly
    290                 295                 300

Phe Ala Ser Thr Asn Trp Phe Asn Asn Asn Ala Pro Ser Phe Ser Ala
305                 310                 315                 320

Ile Glu Ala Ala Val Ile Arg Pro Pro His Leu Leu Asp Phe Pro Glu
                325                 330                 335

Gln Leu Thr Ile Phe Ser Val Leu Ser Arg Trp Ser Asn Thr Gln Tyr
            340                 345                 350

Met Asn Tyr Trp Val Gly His Arg Leu Glu Ser Arg Thr Ile Arg Gly
        355                 360                 365

Ser Leu Ser Thr Ser Thr His Gly Asn Thr Asn Thr Ser Ile Asn Pro
    370                 375                 380

Val Thr Leu Gln Phe Thr Ser Arg Asp Val Tyr Arg Thr Glu Ser Phe
385                 390                 395                 400

Ala Gly Ile Asn Ile Leu Leu Thr Thr Pro Val Asn Gly Val Pro Trp
                405                 410                 415

Ala Arg Phe Asn Trp Arg Asn Pro Leu Asn Ser Leu Arg Gly Ser Leu
            420                 425                 430

Leu Tyr Thr Ile Gly Tyr Thr Gly Val Gly Thr Gln Leu Phe Asp Ser
        435                 440                 445

Glu Thr Glu Leu Pro Pro Glu Thr Thr Glu Arg Pro Asn Tyr Glu Ser
    450                 455                 460

Tyr Ser His Arg Leu Ser Asn Ile Arg Leu Ile Ser Gly Asn Thr Leu
465                 470                 475                 480

Arg Ala Pro Val Tyr Ser Trp Thr His Arg Ser Ala Asp Arg Thr Asn
                485                 490                 495

Thr Ile Ser Ser Asp Ser Ile Thr Gln Ile Pro Leu Val Lys Ala His
            500                 505                 510

Thr Leu Gln Ser Gly Thr Thr Val Val Lys Gly Pro Gly Phe Thr Gly
        515                 520                 525

Gly Asp Ile Leu Arg Arg Thr Ser Gly Gly Pro Phe Ala Phe Ser Asn
    530                 535                 540

Val Asn Leu Asp Phe Asn Leu Ser Gln Arg Tyr Arg Ala Arg Ile Arg
545                 550                 555                 560

Tyr Ala Ser Thr Thr Asn Leu Arg Ile Tyr Val Thr Val Ala Gly Glu
                565                 570                 575

Arg Ile Phe Ala Gly Gln Phe Asp Lys Thr Met Asp Ala Gly Ala Pro
            580                 585                 590

Leu Thr Phe Gln Ser Phe Ser Tyr Ala Thr Ile Asn Thr Ala Phe Thr
```

```
        595                 600                 605

Phe Pro Glu Arg Ser Ser Ser Leu Thr Val Gly Ala Asp Thr Phe Ser
    610                 615                 620

Ser Gly Asn Glu Val Tyr Val Asp Arg Phe Glu Leu Ile Pro Val Thr
625                 630                 635                 640

Ala Thr Thr Ala Thr Phe Glu Ala Glu Tyr Asp Leu Glu Arg Ala Gln
                645                 650                 655

Glu Ala Val Asn Ala Leu Phe Thr Asn Thr Asn Pro Arg Arg Leu Lys
            660                 665                 670

Thr Gly Val Thr Asp Tyr His Ile Asp Glu Val Ser Asn Leu Val Ala
        675                 680                 685

Cys Leu Ser Asp Glu Phe Cys Leu Asp Glu Lys Arg Glu Leu Leu Glu
    690                 695                 700

Lys Val Lys Tyr Ala Lys Arg Leu Ser Asp Glu Arg Asn Leu Leu Gln
705                 710                 715                 720

Asp Pro Asn Phe Thr Ser Ile Asn Lys Gln Pro Asp Phe Ile Ser Thr
                725                 730                 735

Asn Glu Gln Ser Asn Phe Thr Ser Ile His Glu Gln Ser Glu His Gly
            740                 745                 750

Trp Trp Gly Ser Glu Asn Ile Thr Ile Gln Glu Gly Asn Asp Val Phe
        755                 760                 765

Lys Glu Asn Tyr Val Ile Leu Pro Gly Thr Phe Asn Glu Cys Tyr Pro
    770                 775                 780

Thr Tyr Leu Tyr Gln Lys Ile Gly Glu Ala Glu Leu Lys Ala Tyr Thr
785                 790                 795                 800

Arg Tyr Gln Leu Ser Gly Tyr Ile Glu Asp Ser Gln Asp Leu Glu Ile
                805                 810                 815

Tyr Leu Ile Arg Tyr Asn Ala Lys His Glu Thr Leu Asp Val Pro Gly
            820                 825                 830

Thr Glu Ser Val Trp Pro Leu Ser Val Glu Ser Pro Ile Gly Arg Cys
        835                 840                 845

Gly Glu Pro Asn Arg Cys Ala Pro His Phe Glu Trp Asn Pro Asp Leu
    850                 855                 860

Asp Cys Ser Cys Arg Asp Gly Glu Lys Cys Ala His His Ser His His
865                 870                 875                 880

Phe Ser Leu Asp Ile Asp Val Gly Cys Ile Asp Leu His Glu Asn Leu
                885                 890                 895

Gly Val Trp Val Val Phe Lys Ile Lys Thr Gln Glu Gly His Ala Arg
            900                 905                 910

Leu Gly Asn Leu Glu Phe Ile Glu Glu Lys Pro Leu Leu Gly Glu Ala
        915                 920                 925

Leu Ser Arg Val Lys Arg Ala Glu Lys Lys Trp Arg Asp Lys Arg Glu
    930                 935                 940

Lys Leu Gln Leu Glu Thr Lys Arg Val Tyr Thr Glu Ala Lys Glu Ala
945                 950                 955                 960

Val Asp Ala Leu Phe Val Asp Ser Gln Tyr Asp Arg Leu Gln Ala Asp
                965                 970                 975

Thr Asn Ile Gly Met Ile His Ala Ala Asp Lys Leu Val His Arg Ile
            980                 985                 990

Arg Glu Ala Tyr Leu Ser Glu Leu  Ser Val Ile Pro Gly  Val Asn Ala
        995                 1000                1005

Glu Ile  Phe Glu Glu Leu Glu  Gly Arg Ile Ile Thr  Ala Ile Ser
    1010                1015                1020
```

```
Leu Tyr  Asp Ala Arg Asn Val  Val Lys Asn Gly Asp  Phe Asn Asn
    1025                 1030                 1035

Gly Leu  Ala Cys Trp Asn Val  Lys Gly His Val Asp  Val Gln Gln
    1040                 1045                 1050

Ser His  His Arg Ser Val Leu  Val Ile Pro Glu Trp  Glu Ala Glu
    1055                 1060                 1065

Val Ser  Gln Ala Val Arg Val  Cys Pro Gly Arg Gly  Tyr Ile Leu
    1070                 1075                 1080

Arg Val  Thr Ala Tyr Lys Glu  Gly Tyr Gly Glu Gly  Cys Val Thr
    1085                 1090                 1095

Ile His  Glu Ile Glu Asn Asn  Thr Asp Glu Leu Lys  Phe Lys Asn
    1100                 1105                 1110

Cys Glu  Glu Glu Glu Val Tyr  Pro Thr Asp Thr Gly  Thr Cys Asn
    1115                 1120                 1125

Asp Tyr  Thr Ala His Gln Gly  Thr Ala Ala Cys Asn  Ser Arg Asn
    1130                 1135                 1140

Ala Gly  Tyr Glu Asp Ala Tyr  Glu Val Asp Thr Thr  Ala Ser Val
    1145                 1150                 1155

Asn Tyr  Lys Pro Thr Tyr Glu  Glu Glu Thr Tyr Thr  Asp Val Arg
    1160                 1165                 1170

Arg Asp  Asn His Cys Glu Tyr  Asp Arg Gly Tyr Val  Asn Tyr Pro
    1175                 1180                 1185

Pro Val  Pro Ala Gly Tyr Met  Thr Lys Glu Leu Glu  Tyr Phe Pro
    1190                 1195                 1200

Glu Thr  Asp Lys Val Trp Ile  Glu Ile Gly Glu Thr  Glu Gly Lys
    1205                 1210                 1215

Phe Ile  Val Asp Ser Val Glu  Leu Leu Leu Met Glu  Glu
    1220                 1225                 1230
```

<210> SEQ ID NO 22
<211> LENGTH: 3666
<212> TYPE: DNA
<213> ORGANISM: Artificial
<220> FEATURE:
<223> OTHER INFORMATION: Synthetic nucleotide sequence designed for expression in a plant cell encoding TIC867_24.

<400> SEQUENCE: 22

```
atgaccagca accgaaagaa cgagaacgag atcatcaacg ccctgtccat accggccgtg     60

tcaaaccact ccgcccagat gaacctctcc accgacgcga ggatcgagga ctccctctgc    120

atcgccgagg gcaacaacat cgacccgttc gtgtctgcaa gcacggtcca gaccggcatc    180

aacatcgcgg gccgcatcct gggcgtgctc ggcgtgccct tcgcgggtca aatcgcctct    240

ttctactcat tcctcgtggg cgagctgtgg ccgcgcggac gtgacccgtg ggaaatcttc    300

ctggagcacg ttgagcagct catccggcag caagtgaccg agaacaccag ggacaccgca    360

ctggcacggc tccagggcct tggcaacagc ttccgcgcct accagcagtc gctggaggac    420

tggctggaga accgagacga cgccagaacc cgctcagttc tgtacacaca gtacatcgcc    480

ctagagctgg acttcctcaa cgctatgccg ctcttcgcca tccgtaacca ggaagtaccg    540

cttctgatgg tgtacgcaca agcagcgaac ctccatctgc tcctgctgcg agacgcatct    600

ctgttcggca gtgagttcgg gctgacgagc caggagatcc agcgctacta cgagcgccaa    660

gtggagaaga ctcgtgagta cagcgactac tgcgcgcgct ggtacaacac gggcttgaac    720

aaccttcgcg ggacaaacgc cgaatcctgg cttcgctaca accagttccg ccgcgacctc    780
```

```
acgctgggtg tgctggacct ggtcgcgctc ttcccgtcct acgacacacg ggtgtaccca    840
atgaacacga gcgcacagct cacccgtgag atctacacag atcccatcgg ccgcaccaac    900
gctcccagtg gcttcgcaag cacgaattgg ttcaacaata acgctccttc tttctctgcc    960
atcgaggccg ctgtcatcag accgccgcac ttactcgatt tcccggagca gctcactatc   1020
ttctctgtgt tgtcccggtg gtcgaacacg cagtacatga actactgggt gggccacagg   1080
ctagagagcc ggaccatccg tggcagtctc tcaacctcga cccacggcaa cacgaacacg   1140
agcatcaacc ctgtcactct ccagtttaca tctagggacg tttacaggac agagtcgttc   1200
gctggcatta acattctgtt gaccactccg gtgaacggcg tcccttgggc ccgcttcaac   1260
tggaggaatc ctctgaactc actgcgcggc agccttctct acactatcgg ctacaccggc   1320
gttgggacgc aactcttcga ctcggagacc gagctgccgc ccgagaccac cgagcggcct   1380
aactacgaga gttattcaca caggctctcc aacatccgct tgatttctgg gaacaccttg   1440
cgggctccgg tgtactcctg gacgcaccgc agcgccgaca gaactaatac catcagctcc   1500
gactcgatca cccagatccc gctggtgaag gctcacacgc ttcagtcggg caccacagtc   1560
gtcaagggcc ctggcttcac cggcggcgac atcctgcgtc gcacatctgg cggacccttc   1620
gccttcagca acgtgaactt ggacttcaat ttgtcacagc ggtatcgtgc cagaatccgg   1680
tacgccagca ctacgaacct gcgaatctat gttactgtgg cgggcgagcg gatcttcgcc   1740
gggcaattcg acaagacgat ggacgcggga gcacctctga cattccagtc attctcttac   1800
gccacgatca acacggcatt cacgtttccg gagcgttcca gtagcctgac cgtgggcgct   1860
gataccttca gtagcgggaa cgaggtgtac gttgaccgtt tcgagctgat cccggtcacc   1920
gccaccaccg cgacgtttga agctgaatcc gacctcgagc gtgcgcgcaa ggcggtgaac   1980
gctctgttca cgagcaccaa ccctcgtggc ttgaagacgg atgtgacgga ctaccacatc   2040
gaccaagtct cgaacctcgt ggagtgcctg agcgacgagt tctgtcttga caagaagcgc   2100
gagctgctgg aggaggtgaa gtacgccaag cgcctctccg atgagcgcaa cctgctccaa   2160
gatcctacct tcacgtcgat ttccggccaa accgaccgtg gatggatcgg ctcgactggc   2220
atctccatcc agggcggcga cgacatcttc aaggagaact atgttcggct gccgggcacg   2280
gtggacgagt gttacccgac gtacctctac cagaagatag acgagagtca actcaagtcc   2340
tacacgcggt atcagttacg tggctacatt gaagactccc aggacttgga aatctatctc   2400
atacggtaca acgccaagca cgagacctta agcgtgccgg gaacggagtc gccctggcca   2460
agctctggcg tgtacccttc cggtaggtgc ggcgagccca accgctgtgc acctcgaatc   2520
gaatggaacc cggaccttga ctgctcttgc cggtacggcg agaagtgcgt ccatcattct   2580
caccacttca gcttggacat tgacgtcggc tgcaccgacc tcaatgaaga cctcggagtg   2640
tgggtcatct tcaagatcaa gacacaggac gggcacgcga aactaggaaa cctggagttc   2700
atcgaggaga agccactcct cggcaaggca ctttccaggg tcaagcgggc cgagaagaaa   2760
tggagggaca agtacgagaa actccagctc gaaacaaagc gggtgtacac ggaggcaaag   2820
gaatccgtgg acgccctgtt cgtggactct cagtacgaca agctccaggc gaacacaaac   2880
attggcatca tccacggtgc ggacaagcaa gtgcacagga tacgggagcc ttacctctcg   2940
gagctgccgg tgattccctc gatcaacgcg gcgatcttcg aggaactgga gggccacatc   3000
ttcaaggcgt attctctgta cgacgcgcgt aacgtcatca agaacggcga cttcaacaat   3060
gggctgtcct gctggaacgt taaaggccac gtcgatgtcc agcagaacca ccataggtca   3120
```

```
gtcctggtgc tgagcgagtg ggaggcggag gtgtcccaga aggtgcgcgt gtgcccggat   3180

cgcggctaca tcttgagggt gacagcctac aaggagggct acggcgaggg ctgtgtcacg   3240

atccatgagt tcgaggacaa cacggatgtc ctgaaattcc gtaacttcgt cgaggaggag   3300

gtctatccca acaacaccgt gacctgcaac gactacacga ccaatcagtc ggctgagggc   3360

agtaccgatg cctgcaacag ctacaaccgt ggttacgaag atggatacga gaaccgctac   3420

gagcccaatc cttcggctcc cgtgaattac actcccacgt acgaggaggg catgtacact   3480

gacactcagg gctacaacca ttgcgtcagc gaccgtggct accgcaacca cacgccgctc   3540

ccagcgggct acgtgacgct ggagctggaa tactttcccg agacagaaca agtgtggata   3600

gagatcggcg agaccgaggg cacattcatc gtgggctctg tggaattgct cctcatggag   3660

gagtaa                                                              3666
```

```
<210> SEQ ID NO 23
<211> LENGTH: 1221
<212> TYPE: PRT
<213> ORGANISM: Artificial
<220> FEATURE:
<223> OTHER INFORMATION: Amino acid sequence of the chimeric protein
      variant TIC867_24.

<400> SEQUENCE: 23

Met Thr Ser Asn Arg Lys Asn Glu Asn Glu Ile Ile Asn Ala Leu Ser
1               5                   10                  15

Ile Pro Ala Val Ser Asn His Ser Ala Gln Met Asn Leu Ser Thr Asp
            20                  25                  30

Ala Arg Ile Glu Asp Ser Leu Cys Ile Ala Glu Gly Asn Asn Ile Asp
        35                  40                  45

Pro Phe Val Ser Ala Ser Thr Val Gln Thr Gly Ile Asn Ile Ala Gly
    50                  55                  60

Arg Ile Leu Gly Val Leu Gly Val Pro Phe Ala Gly Gln Ile Ala Ser
65                  70                  75                  80

Phe Tyr Ser Phe Leu Val Gly Glu Leu Trp Pro Arg Gly Arg Asp Pro
                85                  90                  95

Trp Glu Ile Phe Leu Glu His Val Glu Gln Leu Ile Arg Gln Gln Val
            100                 105                 110

Thr Glu Asn Thr Arg Asp Thr Ala Leu Ala Arg Leu Gln Gly Leu Gly
        115                 120                 125

Asn Ser Phe Arg Ala Tyr Gln Gln Ser Leu Glu Asp Trp Leu Glu Asn
    130                 135                 140

Arg Asp Asp Ala Arg Thr Arg Ser Val Leu Tyr Thr Gln Tyr Ile Ala
145                 150                 155                 160

Leu Glu Leu Asp Phe Leu Asn Ala Met Pro Leu Phe Ala Ile Arg Asn
                165                 170                 175

Gln Glu Val Pro Leu Leu Met Val Tyr Ala Gln Ala Ala Asn Leu His
            180                 185                 190

Leu Leu Leu Leu Arg Asp Ala Ser Leu Phe Gly Ser Glu Phe Gly Leu
        195                 200                 205

Thr Ser Gln Glu Ile Gln Arg Tyr Tyr Glu Arg Gln Val Glu Lys Thr
    210                 215                 220

Arg Glu Tyr Ser Asp Tyr Cys Ala Arg Trp Tyr Asn Thr Gly Leu Asn
225                 230                 235                 240

Asn Leu Arg Gly Thr Asn Ala Glu Ser Trp Leu Arg Tyr Asn Gln Phe
                245                 250                 255
```

-continued

```
Arg Arg Asp Leu Thr Leu Gly Val Leu Asp Leu Val Ala Leu Phe Pro
            260                 265                 270

Ser Tyr Asp Thr Arg Val Tyr Pro Met Asn Thr Ser Ala Gln Leu Thr
        275                 280                 285

Arg Glu Ile Tyr Thr Asp Pro Ile Gly Arg Thr Asn Ala Pro Ser Gly
    290                 295                 300

Phe Ala Ser Thr Asn Trp Phe Asn Asn Asn Ala Pro Ser Phe Ser Ala
305                 310                 315                 320

Ile Glu Ala Ala Val Ile Arg Pro Pro His Leu Leu Asp Phe Pro Glu
                325                 330                 335

Gln Leu Thr Ile Phe Ser Val Leu Ser Arg Trp Ser Asn Thr Gln Tyr
            340                 345                 350

Met Asn Tyr Trp Val Gly His Arg Leu Glu Ser Arg Thr Ile Arg Gly
        355                 360                 365

Ser Leu Ser Thr Ser Thr His Gly Asn Thr Asn Thr Ser Ile Asn Pro
    370                 375                 380

Val Thr Leu Gln Phe Thr Ser Arg Asp Val Tyr Arg Thr Glu Ser Phe
385                 390                 395                 400

Ala Gly Ile Asn Ile Leu Leu Thr Thr Pro Val Asn Gly Val Pro Trp
                405                 410                 415

Ala Arg Phe Asn Trp Arg Asn Pro Leu Asn Ser Leu Arg Gly Ser Leu
            420                 425                 430

Leu Tyr Thr Ile Gly Tyr Thr Gly Val Gly Thr Gln Leu Phe Asp Ser
        435                 440                 445

Glu Thr Glu Leu Pro Pro Glu Thr Thr Glu Arg Pro Asn Tyr Glu Ser
    450                 455                 460

Tyr Ser His Arg Leu Ser Asn Ile Arg Leu Ile Ser Gly Asn Thr Leu
465                 470                 475                 480

Arg Ala Pro Val Tyr Ser Trp Thr His Arg Ser Ala Asp Arg Thr Asn
                485                 490                 495

Thr Ile Ser Ser Asp Ser Ile Thr Gln Ile Pro Leu Val Lys Ala His
            500                 505                 510

Thr Leu Gln Ser Gly Thr Thr Val Val Lys Gly Pro Gly Phe Thr Gly
        515                 520                 525

Gly Asp Ile Leu Arg Arg Thr Ser Gly Gly Pro Phe Ala Phe Ser Asn
    530                 535                 540

Val Asn Leu Asp Phe Asn Leu Ser Gln Arg Tyr Arg Ala Arg Ile Arg
545                 550                 555                 560

Tyr Ala Ser Thr Thr Asn Leu Arg Ile Tyr Val Thr Val Ala Gly Glu
                565                 570                 575

Arg Ile Phe Ala Gly Gln Phe Asp Lys Thr Met Asp Ala Gly Ala Pro
            580                 585                 590

Leu Thr Phe Gln Ser Phe Ser Tyr Ala Thr Ile Asn Thr Ala Phe Thr
        595                 600                 605

Phe Pro Glu Arg Ser Ser Ser Leu Thr Val Gly Ala Asp Thr Phe Ser
    610                 615                 620

Ser Gly Asn Glu Val Tyr Val Asp Arg Phe Glu Leu Ile Pro Val Thr
625                 630                 635                 640

Ala Thr Thr Ala Thr Phe Glu Ala Glu Ser Asp Leu Glu Arg Ala Arg
                645                 650                 655

Lys Ala Val Asn Ala Leu Phe Thr Ser Thr Asn Pro Arg Gly Leu Lys
            660                 665                 670

Thr Asp Val Thr Asp Tyr His Ile Asp Gln Val Ser Asn Leu Val Glu
```

-continued

```
        675                 680                 685

Cys Leu Ser Asp Glu Phe Cys Leu Asp Lys Lys Arg Glu Leu Leu Glu
    690                 695                 700

Glu Val Lys Tyr Ala Lys Arg Leu Ser Asp Glu Arg Asn Leu Leu Gln
705                 710                 715                 720

Asp Pro Thr Phe Thr Ser Ile Ser Gly Gln Thr Asp Arg Gly Trp Ile
                725                 730                 735

Gly Ser Thr Gly Ile Ser Ile Gln Gly Gly Asp Asp Ile Phe Lys Glu
            740                 745                 750

Asn Tyr Val Arg Leu Pro Gly Thr Val Asp Glu Cys Tyr Pro Thr Tyr
        755                 760                 765

Leu Tyr Gln Lys Ile Asp Glu Ser Gln Leu Lys Ser Tyr Thr Arg Tyr
    770                 775                 780

Gln Leu Arg Gly Tyr Ile Glu Asp Ser Gln Asp Leu Glu Ile Tyr Leu
785                 790                 795                 800

Ile Arg Tyr Asn Ala Lys His Glu Thr Leu Ser Val Pro Gly Thr Glu
                805                 810                 815

Ser Pro Trp Pro Ser Ser Gly Val Tyr Pro Ser Gly Arg Cys Gly Glu
            820                 825                 830

Pro Asn Arg Cys Ala Pro Arg Ile Glu Trp Asn Pro Asp Leu Asp Cys
        835                 840                 845

Ser Cys Arg Tyr Gly Glu Lys Cys Val His His Ser His His Phe Ser
    850                 855                 860

Leu Asp Ile Asp Val Gly Cys Thr Asp Leu Asn Glu Asp Leu Gly Val
865                 870                 875                 880

Trp Val Ile Phe Lys Ile Lys Thr Gln Asp Gly His Ala Lys Leu Gly
                885                 890                 895

Asn Leu Glu Phe Ile Glu Glu Lys Pro Leu Leu Gly Lys Ala Leu Ser
            900                 905                 910

Arg Val Lys Arg Ala Glu Lys Lys Trp Arg Asp Lys Tyr Glu Lys Leu
        915                 920                 925

Gln Leu Glu Thr Lys Arg Val Tyr Thr Glu Ala Lys Glu Ser Val Asp
    930                 935                 940

Ala Leu Phe Val Asp Ser Gln Tyr Asp Lys Leu Gln Ala Asn Thr Asn
945                 950                 955                 960

Ile Gly Ile Ile His Gly Ala Asp Lys Gln Val His Arg Ile Arg Glu
                965                 970                 975

Pro Tyr Leu Ser Glu Leu Pro Val Ile Pro Ser Ile Asn Ala Ala Ile
            980                 985                 990

Phe Glu Glu Leu Glu Gly His Ile  Phe Lys Ala Tyr Ser  Leu Tyr Asp
        995                 1000                1005

Ala Arg  Asn Val Ile Lys Asn  Gly Asp Phe Asn Asn  Gly Leu Ser
    1010                1015                1020

Cys Trp  Asn Val Lys Gly His  Val Asp Val Gln Gln  Asn His His
    1025                1030                1035

Arg Ser  Val Leu Val Leu Ser  Glu Trp Glu Ala Glu  Val Ser Gln
    1040                1045                1050

Lys Val  Arg Val Cys Pro Asp  Arg Gly Tyr Ile Leu  Arg Val Thr
    1055                1060                1065

Ala Tyr  Lys Glu Gly Tyr Gly  Glu Gly Cys Val Thr  Ile His Glu
    1070                1075                1080

Phe Glu  Asp Asn Thr Asp Val  Leu Lys Phe Arg Asn  Phe Val Glu
    1085                1090                1095
```

```
Glu Glu  Val Tyr Pro Asn Asn  Thr Val Thr Cys Asn  Asp Tyr Thr
    1100                 1105                 1110

Thr Asn  Gln Ser Ala Glu Gly  Ser Thr Asp Ala Cys  Asn Ser Tyr
    1115                 1120                 1125

Asn Arg  Gly Tyr Glu Asp Gly  Tyr Glu Asn Arg Tyr  Glu Pro Asn
    1130                 1135                 1140

Pro Ser  Ala Pro Val Asn Tyr  Thr Pro Thr Tyr Glu  Glu Gly Met
    1145                 1150                 1155

Tyr Thr  Asp Thr Gln Gly Tyr  Asn His Cys Val Ser  Asp Arg Gly
    1160                 1165                 1170

Tyr Arg  Asn His Thr Pro Leu  Pro Ala Gly Tyr Val  Thr Leu Glu
    1175                 1180                 1185

Leu Glu  Tyr Phe Pro Glu Thr  Glu Gln Val Trp Ile  Glu Ile Gly
    1190                 1195                 1200

Glu Thr  Glu Gly Thr Phe Ile  Val Gly Ser Val Glu  Leu Leu Leu
    1205                 1210                 1215

Met Glu  Glu
    1220


<210> SEQ ID NO 24
<211> LENGTH: 3651
<212> TYPE: DNA
<213> ORGANISM: Artificial
<220> FEATURE:
<223> OTHER INFORMATION: Synthetic nucleotide sequence designed for
      expression in a plant cell encoding TIC867_25.

<400> SEQUENCE: 24

atgaccagca accgaaagaa cgagaacgag atcatcaacg ccctgtccat accggccgtg     60

tcaaaccact ccgcccagat gaacctctcc accgacgcga ggatcgagga ctccctctgc    120

atcgccgagg gcaacaacat cgacccgttc gtgtctgcaa gcacggtcca gaccggcatc    180

aacatcgcgg gccgcatcct gggcgtgctc ggcgtgccct tcgcgggtca aatcgcctct    240

ttctactcat tcctcgtggg cgagctgtgg ccgcgcggac gtgacccgtg ggaaatcttc    300

ctggagcacg ttgagcagct catccggcag caagtgaccg agaacaccag ggacaccgca    360

ctggcacggc tccagggcct tggcaacagc ttccgcgcct accagcagtc gctggaggac    420

tggctggaga accgagacga cgccagaacc cgctcagttc tgtacacaca gtacatcgcc    480

ctagagctgg acttcctcaa cgctatgccg ctcttcgcca tccgtaacca ggaagtaccg    540

cttctgatgg tgtacgcaca agcagcgaac ctccatctgc tcctgctgcg agacgcatct    600

ctgttcggca gtgagttcgg gctgacgagc caggagatcc agcgctacta cgagcgccaa    660

gtggagaaga ctcgtgagta cagcgactac tgcgcgcgct ggtacaacac gggcttgaac    720

aaccttcgcg ggacaaacgc cgaatcctgg cttcgctaca accagttccg ccgcgacctc    780

acgctgggtg tgctggacct ggtcgcgctc ttcccgtcct acgacacacg ggtgtaccca    840

atgaacacga gcgcacagct cacccgtgag atctacacag atcccatcgg ccgcaccaac    900

gctcccagtg gcttcgcaag cacgaattgg ttcaacaata acgctccttc tttctctgcc    960

atcgaggccg ctgtcatcag accgccgcac ttactcgatt tcccggagca gctcactatc   1020

ttctctgtgt tgtcccggtg gtcgaacacg cagtacatga actactgggt gggccacagg   1080

ctagagagcc ggaccatccg tggcagtctc tcaacctcga cccacggcaa cacgaacacg   1140

agcatcaacc ctgtcactct ccagtttaca tctagggacg tttacaggac agagtcgttc   1200
```

-continued

```
gctggcatta acattctgtt gaccactccg gtgaacggcg tcccttgggc ccgcttcaac   1260
tggaggaatc ctctgaactc actgcgcggc agccttctct acactatcgg ctacaccggc   1320
gttgggacgc aactcttcga ctcggagacc gagctgccgc ccgagaccac cgagcggcct   1380
aactacgaga gttattcaca caggctctcc aacatccgct tgatttctgg gaacaccttg   1440
cgggctccgg tgtactcctg gacgcaccgc agcgccgaca gaactaatac catcagctcc   1500
gactcgatca cccagatccc gctggtgaag gctcacacgc ttcagtcggg caccacagtc   1560
gtcaagggcc ctggcttcac cggcggcgac atcctgcgtc gcacatctgg cggacccttc   1620
gccttcagca acgtgaactt ggacttcaat ttgtcacagc ggtatcgtgc cagaatccgg   1680
tacgccagca ctacgaacct gcgaatctat gttactgtgg cgggcgagcg gatcttcgcc   1740
gggcaattcg acaagacgat ggacgcggga gcacctctga cattccagtc attctcttac   1800
gccacgatca acacggcatt cacgtttccg gagcgttcca gtagcctgac cgtgggcgct   1860
gataccttca gtagcgggaa cgaggtgtac gttgaccgtt tcgagctgat cccggtcacc   1920
gccaccgatg ctacctttga agcagagtcc gacttggaac gtgcacagaa ggcagtgaac   1980
gcactcttca cctcaagcaa ccagatcgga ttgaagacag atgtgacaga ttaccacatc   2040
gaccaagtga gcaacttggt ggattgcttg tcagatgagt tctgcttgga tgagaagcgt   2100
gaactctccg agaaggtgaa gcacgcaaag cgtctctcag atgaacgtaa tctccttcaa   2160
gaccctaact ttcgtggtat caatcgtcag ccagatcgtg gatggcgtgg atcaacagac   2220
atcaccatcc agggaggcga tgatgtgttc aaggagaact acgtgaccct cccaggaacc   2280
gtggatgaat gctacccaac ctacctctac cagaagatcg acgagtcaaa gctcaaggct   2340
tacacccgtt atgaactccg tggctacatc gaagatagcc aggatctcga aatctatctc   2400
atccgttaca atgctaagca cgaaatcgtg aatgtgccag gaaccggctc actctggcca   2460
ctctcagcac agtcaccaat cggcaagtgc ggcgaaccca atcgctgcgc tcctcatctc   2520
gaatggaatc ccgatctcga ctgctcctgc cgagacggcg agaagtgtgc acatcactca   2580
caccacttca ccctcgacat cgacgtgggc tgcaccgacc tcaatgaaga cctgggcgtg   2640
tgggtgatct tcaagatcaa gacccaggac ggccacgcac gactgggcaa tctggagttt   2700
ctggaggaga agccactgct tggcgaggca ctggcacgag tgaaacgagc cgagaagaaa   2760
tggcgagaca aacgtgagaa gctgcaactg gagaccaaca tcgtgtacaa agaggccaaa   2820
gagtcagttg acgccctgtt tgtcaatagc cagtatgacc gactgcaagt tgacaccaac   2880
atcgccatga tccacgctgc ggacaagcgc gtccaccgca tccgcgaggc ttatctgccc   2940
gagctgagcg tcattcccgg cgtcaatgcc gcgatcttcg aggagttaga gggccgcatc   3000
ttcaccgcct acagcctcta tgacgcccgc aatgtcatta agaatggcga cttcaacaat   3060
ggcttactat gctggaatgt caaagggcac gttgacgtcg aggagcagaa caatcaccgc   3120
agcgtcttag tcatacccga gtgggaggcc gaagtcagcc aggaagtccg cgtctgtcca   3180
gggcgcgggt acatcctgcg ggtcaccgcc tacaaagagg gatacggcga gggttgtgtc   3240
accatacacg agatagagga caataccgac gaactcaagt tcagcaattg tgtcgaggag   3300
gaagtctatc ccaacaatac cgtaacctgc aacaactaca ccggaaccca ggaggagtat   3360
gaagggacgt acacctcgcg gaaccagggc tatgacgaag cctatgggaa caaccccgtcg   3420
gtgcctgctg actatgcgtc ggtctatgag gagaaatcgt acacggacgg gcggcgggag   3480
aatccgtgtg agtcgaatcg cgggtatggt gactacacgc cgctaccggc gggctatgta   3540
acgaaagacc tggaatactt cccggagacg gacaaagtat ggatagagat aggcgagacg   3600
```

gagggaacgt tcatcgtgga ctcggtagag ctgctgctca tggaggagtg a 3651

<210> SEQ ID NO 25
<211> LENGTH: 1216
<212> TYPE: PRT
<213> ORGANISM: Artificial
<220> FEATURE:
<223> OTHER INFORMATION: Amino acid sequence of the chimeric protein variant TIC867_25.

<400> SEQUENCE: 25

```
Met Thr Ser Asn Arg Lys Asn Glu Asn Glu Ile Ile Asn Ala Leu Ser
1               5                   10                  15

Ile Pro Ala Val Ser Asn His Ser Ala Gln Met Asn Leu Ser Thr Asp
            20                  25                  30

Ala Arg Ile Glu Asp Ser Leu Cys Ile Ala Glu Gly Asn Asn Ile Asp
        35                  40                  45

Pro Phe Val Ser Ala Ser Thr Val Gln Thr Gly Ile Asn Ile Ala Gly
    50                  55                  60

Arg Ile Leu Gly Val Leu Gly Val Pro Phe Ala Gly Gln Ile Ala Ser
65                  70                  75                  80

Phe Tyr Ser Phe Leu Val Gly Glu Leu Trp Pro Arg Gly Arg Asp Pro
                85                  90                  95

Trp Glu Ile Phe Leu Glu His Val Glu Gln Leu Ile Arg Gln Gln Val
            100                 105                 110

Thr Glu Asn Thr Arg Asp Thr Ala Leu Ala Arg Leu Gln Gly Leu Gly
        115                 120                 125

Asn Ser Phe Arg Ala Tyr Gln Gln Ser Leu Glu Asp Trp Leu Glu Asn
    130                 135                 140

Arg Asp Asp Ala Arg Thr Arg Ser Val Leu Tyr Thr Gln Tyr Ile Ala
145                 150                 155                 160

Leu Glu Leu Asp Phe Leu Asn Ala Met Pro Leu Phe Ala Ile Arg Asn
                165                 170                 175

Gln Glu Val Pro Leu Leu Met Val Tyr Ala Gln Ala Ala Asn Leu His
            180                 185                 190

Leu Leu Leu Leu Arg Asp Ala Ser Leu Phe Gly Ser Glu Phe Gly Leu
        195                 200                 205

Thr Ser Gln Glu Ile Gln Arg Tyr Tyr Glu Arg Gln Val Glu Lys Thr
    210                 215                 220

Arg Glu Tyr Ser Asp Tyr Cys Ala Arg Trp Tyr Asn Thr Gly Leu Asn
225                 230                 235                 240

Asn Leu Arg Gly Thr Asn Ala Glu Ser Trp Leu Arg Tyr Asn Gln Phe
                245                 250                 255

Arg Arg Asp Leu Thr Leu Gly Val Leu Asp Leu Val Ala Leu Phe Pro
            260                 265                 270

Ser Tyr Asp Thr Arg Val Tyr Pro Met Asn Thr Ser Ala Gln Leu Thr
        275                 280                 285

Arg Glu Ile Tyr Thr Asp Pro Ile Gly Arg Thr Asn Ala Pro Ser Gly
    290                 295                 300

Phe Ala Ser Thr Asn Trp Phe Asn Asn Asn Ala Pro Ser Phe Ser Ala
305                 310                 315                 320

Ile Glu Ala Ala Val Ile Arg Pro Pro His Leu Leu Asp Phe Pro Glu
                325                 330                 335

Gln Leu Thr Ile Phe Ser Val Leu Ser Arg Trp Ser Asn Thr Gln Tyr
            340                 345                 350
```

-continued

```
Met Asn Tyr Trp Val Gly His Arg Leu Glu Ser Arg Thr Ile Arg Gly
        355                 360                 365

Ser Leu Ser Thr Ser Thr His Gly Asn Thr Asn Thr Ser Ile Asn Pro
    370                 375                 380

Val Thr Leu Gln Phe Thr Ser Arg Asp Val Tyr Arg Thr Glu Ser Phe
385                 390                 395                 400

Ala Gly Ile Asn Ile Leu Leu Thr Thr Pro Val Asn Gly Val Pro Trp
                405                 410                 415

Ala Arg Phe Asn Trp Arg Asn Pro Leu Asn Ser Leu Arg Gly Ser Leu
            420                 425                 430

Leu Tyr Thr Ile Gly Tyr Thr Gly Val Gly Thr Gln Leu Phe Asp Ser
        435                 440                 445

Glu Thr Glu Leu Pro Pro Glu Thr Thr Glu Arg Pro Asn Tyr Glu Ser
    450                 455                 460

Tyr Ser His Arg Leu Ser Asn Ile Arg Leu Ile Ser Gly Asn Thr Leu
465                 470                 475                 480

Arg Ala Pro Val Tyr Ser Trp Thr His Arg Ser Ala Asp Arg Thr Asn
                485                 490                 495

Thr Ile Ser Ser Asp Ser Ile Thr Gln Ile Pro Leu Val Lys Ala His
            500                 505                 510

Thr Leu Gln Ser Gly Thr Thr Val Val Lys Gly Pro Gly Phe Thr Gly
        515                 520                 525

Gly Asp Ile Leu Arg Arg Thr Ser Gly Gly Pro Phe Ala Phe Ser Asn
    530                 535                 540

Val Asn Leu Asp Phe Asn Leu Ser Gln Arg Tyr Arg Ala Arg Ile Arg
545                 550                 555                 560

Tyr Ala Ser Thr Thr Asn Leu Arg Ile Tyr Val Thr Val Ala Gly Glu
                565                 570                 575

Arg Ile Phe Ala Gly Gln Phe Asp Lys Thr Met Asp Ala Gly Ala Pro
            580                 585                 590

Leu Thr Phe Gln Ser Phe Ser Tyr Ala Thr Ile Asn Thr Ala Phe Thr
        595                 600                 605

Phe Pro Glu Arg Ser Ser Ser Leu Thr Val Gly Ala Asp Thr Phe Ser
    610                 615                 620

Ser Gly Asn Glu Val Tyr Val Asp Arg Phe Glu Leu Ile Pro Val Thr
625                 630                 635                 640

Ala Thr Asp Ala Thr Phe Glu Ala Glu Ser Asp Leu Glu Arg Ala Gln
                645                 650                 655

Lys Ala Val Asn Ala Leu Phe Thr Ser Ser Asn Gln Ile Gly Leu Lys
            660                 665                 670

Thr Asp Val Thr Asp Tyr His Ile Asp Gln Val Ser Asn Leu Val Asp
        675                 680                 685

Cys Leu Ser Asp Glu Phe Cys Leu Asp Glu Lys Arg Glu Leu Ser Glu
    690                 695                 700

Lys Val Lys His Ala Lys Arg Leu Ser Asp Glu Arg Asn Leu Leu Gln
705                 710                 715                 720

Asp Pro Asn Phe Arg Gly Ile Asn Arg Gln Pro Asp Arg Gly Trp Arg
                725                 730                 735

Gly Ser Thr Asp Ile Thr Ile Gln Gly Gly Asp Asp Val Phe Lys Glu
            740                 745                 750

Asn Tyr Val Thr Leu Pro Gly Thr Val Asp Glu Cys Tyr Pro Thr Tyr
        755                 760                 765
```

```
Leu Tyr Gln Lys Ile Asp Glu Ser Lys Leu Lys Ala Tyr Thr Arg Tyr
    770                 775                 780

Glu Leu Arg Gly Tyr Ile Glu Asp Ser Gln Asp Leu Glu Ile Tyr Leu
785                 790                 795                 800

Ile Arg Tyr Asn Ala Lys His Glu Ile Val Asn Val Pro Gly Thr Gly
                805                 810                 815

Ser Leu Trp Pro Leu Ser Ala Gln Ser Pro Ile Gly Lys Cys Gly Glu
            820                 825                 830

Pro Asn Arg Cys Ala Pro His Leu Glu Trp Asn Pro Asp Leu Asp Cys
        835                 840                 845

Ser Cys Arg Asp Gly Glu Lys Cys Ala His His Ser His His Phe Thr
    850                 855                 860

Leu Asp Ile Asp Val Gly Cys Thr Asp Leu Asn Glu Asp Leu Gly Val
865                 870                 875                 880

Trp Val Ile Phe Lys Ile Lys Thr Gln Asp Gly His Ala Arg Leu Gly
                885                 890                 895

Asn Leu Glu Phe Leu Glu Glu Lys Pro Leu Leu Gly Glu Ala Leu Ala
            900                 905                 910

Arg Val Lys Arg Ala Glu Lys Lys Trp Arg Asp Lys Arg Glu Lys Leu
        915                 920                 925

Gln Leu Glu Thr Asn Ile Val Tyr Lys Glu Ala Lys Glu Ser Val Asp
    930                 935                 940

Ala Leu Phe Val Asn Ser Gln Tyr Asp Arg Leu Gln Val Asp Thr Asn
945                 950                 955                 960

Ile Ala Met Ile His Ala Ala Asp Lys Arg Val His Arg Ile Arg Glu
                965                 970                 975

Ala Tyr Leu Pro Glu Leu Ser Val Ile Pro Gly Val Asn Ala Ala Ile
            980                 985                 990

Phe Glu Glu Leu Glu Gly Arg Ile  Phe Thr Ala Tyr Ser  Leu Tyr Asp
        995                 1000                1005

Ala Arg  Asn Val Ile Lys Asn  Gly Asp Phe Asn Asn  Gly Leu Leu
    1010                1015                1020

Cys Trp  Asn Val Lys Gly His  Val Asp Val Glu Glu  Gln Asn Asn
    1025                1030                1035

His Arg  Ser Val Leu Val Ile  Pro Glu Trp Glu Ala  Glu Val Ser
    1040                1045                1050

Gln Glu  Val Arg Val Cys Pro  Gly Arg Gly Tyr Ile  Leu Arg Val
    1055                1060                1065

Thr Ala  Tyr Lys Glu Gly Tyr  Gly Glu Gly Cys Val  Thr Ile His
    1070                1075                1080

Glu Ile  Glu Asp Asn Thr Asp  Glu Leu Lys Phe Ser  Asn Cys Val
    1085                1090                1095

Glu Glu  Glu Val Tyr Pro Asn  Asn Thr Val Thr Cys  Asn Asn Tyr
    1100                1105                1110

Thr Gly  Thr Gln Glu Glu Tyr  Glu Gly Thr Tyr Thr  Ser Arg Asn
    1115                1120                1125

Gln Gly  Tyr Asp Glu Ala Tyr  Gly Asn Asn Pro Ser  Val Pro Ala
    1130                1135                1140

Asp Tyr  Ala Ser Val Tyr Glu  Glu Lys Ser Tyr Thr  Asp Gly Arg
    1145                1150                1155

Arg Glu  Asn Pro Cys Glu Ser  Asn Arg Gly Tyr Gly  Asp Tyr Thr
    1160                1165                1170

Pro Leu  Pro Ala Gly Tyr Val  Thr Lys Asp Leu Glu  Tyr Phe Pro
```

```
    1175                1180                1185

Glu Thr  Asp Lys Val Trp Ile  Glu Ile Gly Glu Thr  Glu Gly Thr
    1190                1195                1200

Phe Ile  Val Asp Ser Val Glu  Leu Leu Leu Met Glu  Glu
    1205                1210                1215


<210> SEQ ID NO 26
<211> LENGTH: 3600
<212> TYPE: DNA
<213> ORGANISM: Artificial
<220> FEATURE:
<223> OTHER INFORMATION: Recombinant nucleotide sequence used for
      expression in a bacterial cell encoding TIC868.

<400> SEQUENCE: 26

atgacttcaa ataggaaaaa tgagaatgaa attataaatg ctttatcgat tccagctgta     60

tcgaatcatt ccgcacaaat gaatctatca accgatgctc gtattgagga tagcttgtgt    120

atagccgagg ggaacaatat cgatccattt gttagcgcat caacagtcca aacgggtatt    180

aacatagctg gtagaatact aggtgtatta ggcgtaccgt ttgctggaca aatagctagt    240

ttttatagtt ttcttgttgg tgaattatgg ccccgcggca gagatccttg ggaaattttc    300

ctagaacatg tcgaacaact tataagacaa caagtaacag aaaatactag ggatacggct    360

cttgctcgat tacaaggttt aggaaattcc tttagagcct atcaacagtc acttgaagat    420

tggctagaaa accgtgatga tgcaagaacg agaagtgttc tttataccca atatatagcc    480

ttagaacttg attttcttaa tgcgatgccg cttttcgcaa ttagaaacca agaagttcca    540

ttattaatgg tatatgctca agctgcaaat ttacacctat tattattgag agatgcctct    600

ctttttggta gtgaatttgg gcttacatcc caagaaattc aacgttatta tgagcgccaa    660

gtggaaaaaa cgagagaata ttctgattat tgcgcaagat ggtataatac gggtttaaat    720

aatttgagag ggacaaatgc tgaaagttgg ttgcgatata atcaattccg tagagactta    780

acgctaggag tattagatct agtggcacta ttcccaagct atgacacgcg tgtttatcca    840

atgaatacca gtgctcaatt aacaagagaa atttatacag atccaattgg gagaacaaat    900

gcaccttcag gatttgcaag tacgaattgg tttaataata atgcaccatc gttttctgcc    960

atagaggctg ccgttattag gcctccgcat ctacttgatt ttccagaaca gcttacaatt   1020

ttcagcgtat taagtcgatg gagtaatact caatatatga attactgggt gggacataga   1080

cttgaatcgc gaacaataag gggtcatta agtacctcga cacacggaaa taccaatact   1140

tctattaatc ctgtaacatt acagttcaca tctcgagacg tttatagaac agaatcattt   1200

gcagggataa atatacttct aactactcct gtgaatggag taccttgggc tagatttaat   1260

tggagaaatc ccctgaattc tcttagaggt agccttctct atactatagg gtatactgga   1320

gtggggacac aactatttga ttcagaaact gaattaccac cagaaacaac agaacgacca   1380

aattatgaat cttacagtca tagattatct aatataagac taatatcagg aaacactttg   1440

agagcaccag tatattcttg gacgcaccgt agtgcagatc gtacaaatac cattagttca   1500

gatagcatta atcaaatacc tttagtgaaa ggatttagag tttggggggg cacctctgtc   1560

attacaggac caggatttac aggaggggat atccttcgaa gaaatacctt tggtgatttt   1620

gtatctctac aagtcaatat taattcacca attacccaaa gataccgttt aagatttcgt   1680

tacgcttcca gtagggatgc acgagttata gtattaacag gagcggcatc cacaggagtg   1740

ggaggccaag ttagtgtaaa tatgcctctt cagaaaacta tggaaatagg ggagaactta   1800
```

-continued acatctagaa catttagata taccgatttt agtaatcctt tttcatttag agctaatcca 1860
gatataattg ggataagtga acaacctcta tttggtgcag gttctattag tagcggtgaa 1920
ctttatatag ataaaattga aattattcta gcagatgcaa catttgaagc agaatctgat 1980
ttagaaagag cacaaaaggc ggtgaatgag ctgtttactt cttccaatca aatcgggtta 2040
aaaacagatg tgacggatta tcatattgat caagtatcca atttagttga gtgtttatct 2100
gatgaatttt gtctggatga aaaaaaagaa ttgtccgaga aagtcaaaca tgcgaagcga 2160
cttagtgatg agcggaattt acttcaagat ccaaacttta gagggatcaa tagacaacta 2220
gaccgtggct ggagaggaag tacggatatt accatccaag gaggcgatga cgtattcaaa 2280
gagaattacg ttacgctatt gggtaccttt gatgagtgct atccaacgta tttatatcaa 2340
aaaatagatg agtcgaaatt aaaagcctat acccgttacc aattaagagg gtatatcgaa 2400
gatagtcaag acttagaaat ctatttaatt cgctacaatg ccaaacacga aacagtaaat 2460
gtgccaggta cgggttcctt atggccgctt tcagccccaa gtccaatcgg aaaatgtgcc 2520
catcattccc atcatttctc cttggacatt gatgttggat gtacagactt aaatgaggac 2580
ttaggtgtat gggtgatatt caagattaag acgcaagatg gccatgcaag actaggaaat 2640
ctagaatttc tcgaagagaa accattagta ggagaagcac tagctcgtgt gaaaagagcg 2700
gagaaaaaat ggagagacaa acgtgaaaaa ttggaatggg aaacaaatat tgtttataaa 2760
gaggcaaaag aatctgtaga tgctttattt gtaaactctc aatatgatag attacaagcg 2820
gataccaaca tcgcgatgat tcatgcggca gataaacgcg ttcatagcat tcgagaagct 2880
tatctgcctg agctgtctgt gattccgggt gtcaatgcgg ctatttttga agaattagaa 2940
gggcgtattt tcactgcatt ctccctatat gatgcgagaa atgtcattaa aaatggtgat 3000
tttaataatg gcttatcctg ctggaacgtg aaagggcatg tagatgtaga agaacaaaac 3060
aaccaccgtt cggtccttgt tgttccggaa tgggaagcag aagtgtcaca agaagttcgt 3120
gtctgtccgg gtcgtggcta tatccttcgt gtcacagcgt acaaggaggg atatggagaa 3180
ggttgcgtaa ccattcatga gatcgagaac aatacagacg aactgaagtt tagcaactgt 3240
gtagaagagg aagtatatcc aaacaacacg gtaacgtgta atgattatac tgcgactcaa 3300
gaagaatatg agggtacgta cacttctcgt aatcgaggat atgacggagc ctatgaaagc 3360
aattcttctg taccagctga ttatgcatca gcctatgaag aaaaagcata tacagatgga 3420
cgaagagaca atccttgtga atctaacaga ggatatgggg attacacacc actaccagct 3480
ggctatgtga caaaagaatt agagtacttc ccagaaaccg ataaggtatg gattgagatc 3540
ggagaaacgg aaggaacatt catcgtggac agcgtggaat tacttcttat ggaggaatag 3600

<210> SEQ ID NO 27
<211> LENGTH: 3600
<212> TYPE: DNA
<213> ORGANISM: Artificial
<220> FEATURE:
<223> OTHER INFORMATION: Synthetic nucleotide sequence designed for expression in a plant cell encoding TIC868.

<400> SEQUENCE: 27
atgacgagca accggaagaa cgagaacgag atcatcaacg ccctctcgat ccctgctgtt 60
tcaaaccact ccgcgcagat gaacctgtcc accgacgcgc gcatcgagga ctccctctgc 120
atagccgagg gcaacaacat cgacccattc gtgtcggcca gcacggttca gaccggcatc 180
aacatcgcgg gccgtatcct cggcgtcctc ggtgtcccat tcgccggtca gatcgcgtcc 240

-continued

```
ttctactcgt tccttgtggg cgagctgtgg cctcgcggtc gtgacccgtg ggagatcttc    300
ctggagcatg tggagcagtt gatccggcag caagtcacgg agaacacccg cgatactgct    360
ctggccaggc tacagggcct gggaaactcc tttcgggcat accagcagtc actggaggac    420
tggttggaga acagggatga cgcgcgaaca cgctcggtac tctacaccca gtacatcgct    480
ctcgaactcg acttcctgaa cgctatgccg ctgttcgcca tcaggaacca ggaagttcca    540
ctccttatgg tgtacgccca ggccgccaac ttacatctgc tcctgctgcg ggacgccagc    600
ctgttcggct ccgagttcgg actcacatct caagaaatcc agcgttacta cgagcgccaa    660
gtggagaaga cccgtgagta cagtgactac tgcgctcgat ggtacaacac agggctcaac    720
aacctgcgcg gcaccaacgc tgagtcatgg ctccgttaca accagttccg ccgcgacttg    780
actttgggtg tcctagacct ggtggcgcta ttcccgtctt acgacacacg ggtgtaccca    840
atgaacacta gcgcgcaact cacgcgggag atctacacag acccaatcgg ccggacgaac    900
gcaccctccg gtttcgcatc cacgaattgg ttcaacaaca acgcaccctc cttctcggca    960
atcgaggccg ccgtcatccg ccctcctcac ctgctcgact ttcccgagca gctcacgatc   1020
ttctccgtgc tctcacgctg gtccaacaca cagtacatga actactgggt cgggcaccga   1080
ttggagagta ggacgatccg tggcagcttg agcaccagta cccacggcaa caccaacacc   1140
tccatcaacc cagttacgct acagttcacg agccgcgacg tttaccggac tgagtcgttc   1200
gcgggcatta acatccttct gacaacgccc gtcaacggcg tcccgtgggc ccggttcaac   1260
tggcgtaacc cgttgaactc cctgcgcggg tcattgctct acaccatcgg gtacacgggc   1320
gtcggcaccc agctcttcga cagtgaaact gagctgccgc ccgagaccac ggaacgcccg   1380
aactacgagt cctacagcca ccgcctgtcc aacatccggc tcatctctgg caacacgctg   1440
cgtgcgccgg tgtactcctg gacacaccgc agcgccgacc ggaccaacac gatctcttcc   1500
gactccatta accagatccc gctcgtgaag ggcttccgtg tgtggggtgg cacgagcgtc   1560
atcaccggtc cgggcttcac cggtggagac atactgcggc gcaacacttt cggcgacttc   1620
gtttcgttgc aagtgaacat caactcgccg atcacccagc gttaccgtct gaggttccgc   1680
tacgcttcaa gccgcgacgc gagggtcatt gtcctgaccg gagccgcgtc cacaggcgtg   1740
ggaggccaag tctcagtcaa catgcctctc cagaagacga tggagatagg cgagaacttg   1800
actagccgaa ccttccggta cactgatttc tcgaaccctt tctcattcag agcgaaccct   1860
gacatcattg ggatctccga gcaaccgctg ttcggtgctg gctccatcag ctctggcgaa   1920
ctgtacatcg acaagattga gatcatcctg gcggatgcga cgttcgaggc cgagtctgac   1980
ctggagcggg ctcagaaggc tgtcaacgaa ctgttcacca gcagcaacca gattgggctc   2040
aagaccgacg tcacggacta tcacattgac caagtgtcca accttgtgga gtgcctgtcc   2100
gacgagttct gcctcgacga gaagaaggag ctgtccgaga aggtcaaaca cgcgaagcgt   2160
ctgagtgacg agcggaattt gctccaggac ccgaacttcc gtggcatcaa ccgccagctc   2220
gaccgtggtt ggcgcgggag tacagacatc accatccagg gaggcgacga tgtgttcaag   2280
gagaactatg tgacgctgct cgggactttc gacgaatgct acccgacgta tctctaccag   2340
aagatagacg agagtaaatt gaaggcgtac acccgctacc agcttcgcgg gtacatcgag   2400
gatagtcagg acctggaaat ctacctgatc cgatacaacg ccaagcacga gacagtgaac   2460
gtgccaggca cgggctcact ttggccattg agcgctccct ctccaatcgg aaagtgcgct   2520
caccactcgc accacttctc tctggacatc gacgtgggct gcaccgacct caacgaggac   2580
ctgggtgtct gggttatctt caagattaag acccaggacg gacatgcccg cctcggcaac   2640
```

ctggagttcc ttgaggagaa gcctctcgtg ggcgaggccc tcgctcgtgt gaagcgcgcc 2700
gagaagaaat ggcgagacaa gcgggagaag ctggagtggg agaccaacat cgtgtacaag 2760
gaggccaagg agtcagtgga cgcactcttc gtcaacagcc agtacgaccg cctccaggct 2820
gacaccaaca tcgccatgat ccacgcggct gacaagcggg tccacagcat ccgtgaggcg 2880
tacctgcccg agctgtcagt gatccctggt gtgaacgcgg cgatcttcga ggaactggag 2940
ggccgcatct tcacagcatt cagcctgtac gatgccagga atgttattaa gaacggtgac 3000
ttcaacaacg ggctgagttg ctggaacgtc aagggccatg tggacgtcga ggagcagaac 3060
aaccaccggt ccgtgctggt cgtgccggag tgggaggcag aggtgagcca ggaggtccgc 3120
gtctgccctg gtcgcggcta catcctccgt gtgactgcgt acaaggaagg ctacggtgaa 3180
ggctgcgtga ctatccacga gatcgagaac aacaccgacg agctcaagtt ctcgaactgt 3240
gtggaggagg aggtgtaccc gaacaacacc gttacttgca acgactacac tgccacgcaa 3300
gaggagtacg agggcactta cacttcccgg aatcgcggct atgatggcgc gtacgagtcc 3360
aacagcagcg tgcctgcgga ttatgcgtcc gcttacgagg agaaggcgta caccgacgga 3420
cggagggaca acccttgcga gtccaaccgt ggctacggtg actacactcc gctgcccgcc 3480
gggtacgtca ccaaggagct ggagtacttc ccggagaccg acaaagtctg gatcgagatc 3540
ggcgagacgg agggcacttt catcgtggac tcggtcgagc tgctactgat ggaggagtga 3600

<210> SEQ ID NO 28
<211> LENGTH: 1199
<212> TYPE: PRT
<213> ORGANISM: Artificial
<220> FEATURE:
<223> OTHER INFORMATION: Amino acid sequence of the chimeric protein TIC868.

<400> SEQUENCE: 28

Met Thr Ser Asn Arg Lys Asn Glu Asn Glu Ile Ile Asn Ala Leu Ser
1 5 10 15

Ile Pro Ala Val Ser Asn His Ser Ala Gln Met Asn Leu Ser Thr Asp
20 25 30

Ala Arg Ile Glu Asp Ser Leu Cys Ile Ala Glu Gly Asn Asn Ile Asp
35 40 45

Pro Phe Val Ser Ala Ser Thr Val Gln Thr Gly Ile Asn Ile Ala Gly
50 55 60

Arg Ile Leu Gly Val Leu Gly Val Pro Phe Ala Gly Gln Ile Ala Ser
65 70 75 80

Phe Tyr Ser Phe Leu Val Gly Glu Leu Trp Pro Arg Gly Arg Asp Pro
85 90 95

Trp Glu Ile Phe Leu Glu His Val Glu Gln Leu Ile Arg Gln Gln Val
100 105 110

Thr Glu Asn Thr Arg Asp Thr Ala Leu Ala Arg Leu Gln Gly Leu Gly
115 120 125

Asn Ser Phe Arg Ala Tyr Gln Gln Ser Leu Glu Asp Trp Leu Glu Asn
130 135 140

Arg Asp Asp Ala Arg Thr Arg Ser Val Leu Tyr Thr Gln Tyr Ile Ala
145 150 155 160

Leu Glu Leu Asp Phe Leu Asn Ala Met Pro Leu Phe Ala Ile Arg Asn
165 170 175

Gln Glu Val Pro Leu Leu Met Val Tyr Ala Gln Ala Ala Asn Leu His
180 185 190

-continued

```
Leu Leu Leu Leu Arg Asp Ala Ser Leu Phe Gly Ser Glu Phe Gly Leu
        195                 200                 205

Thr Ser Gln Glu Ile Gln Arg Tyr Tyr Glu Arg Gln Val Glu Lys Thr
    210                 215                 220

Arg Glu Tyr Ser Asp Tyr Cys Ala Arg Trp Tyr Asn Thr Gly Leu Asn
225                 230                 235                 240

Asn Leu Arg Gly Thr Asn Ala Glu Ser Trp Leu Arg Tyr Asn Gln Phe
                245                 250                 255

Arg Arg Asp Leu Thr Leu Gly Val Leu Asp Leu Val Ala Leu Phe Pro
            260                 265                 270

Ser Tyr Asp Thr Arg Val Tyr Pro Met Asn Thr Ser Ala Gln Leu Thr
        275                 280                 285

Arg Glu Ile Tyr Thr Asp Pro Ile Gly Arg Thr Asn Ala Pro Ser Gly
    290                 295                 300

Phe Ala Ser Thr Asn Trp Phe Asn Asn Asn Ala Pro Ser Phe Ser Ala
305                 310                 315                 320

Ile Glu Ala Ala Val Ile Arg Pro Pro His Leu Leu Asp Phe Pro Glu
                325                 330                 335

Gln Leu Thr Ile Phe Ser Val Leu Ser Arg Trp Ser Asn Thr Gln Tyr
            340                 345                 350

Met Asn Tyr Trp Val Gly His Arg Leu Glu Ser Arg Thr Ile Arg Gly
        355                 360                 365

Ser Leu Ser Thr Ser Thr His Gly Asn Thr Asn Thr Ser Ile Asn Pro
    370                 375                 380

Val Thr Leu Gln Phe Thr Ser Arg Asp Val Tyr Arg Thr Glu Ser Phe
385                 390                 395                 400

Ala Gly Ile Asn Ile Leu Leu Thr Thr Pro Val Asn Gly Val Pro Trp
                405                 410                 415

Ala Arg Phe Asn Trp Arg Asn Pro Leu Asn Ser Leu Arg Gly Ser Leu
            420                 425                 430

Leu Tyr Thr Ile Gly Tyr Thr Gly Val Gly Thr Gln Leu Phe Asp Ser
        435                 440                 445

Glu Thr Glu Leu Pro Pro Glu Thr Thr Glu Arg Pro Asn Tyr Glu Ser
    450                 455                 460

Tyr Ser His Arg Leu Ser Asn Ile Arg Leu Ile Ser Gly Asn Thr Leu
465                 470                 475                 480

Arg Ala Pro Val Tyr Ser Trp Thr His Arg Ser Ala Asp Arg Thr Asn
                485                 490                 495

Thr Ile Ser Ser Asp Ser Ile Asn Gln Ile Pro Leu Val Lys Gly Phe
            500                 505                 510

Arg Val Trp Gly Gly Thr Ser Val Ile Thr Gly Pro Gly Phe Thr Gly
        515                 520                 525

Gly Asp Ile Leu Arg Arg Asn Thr Phe Gly Asp Phe Val Ser Leu Gln
    530                 535                 540

Val Asn Ile Asn Ser Pro Ile Thr Gln Arg Tyr Arg Leu Arg Phe Arg
545                 550                 555                 560

Tyr Ala Ser Ser Arg Asp Ala Arg Val Ile Val Leu Thr Gly Ala Ala
                565                 570                 575

Ser Thr Gly Val Gly Gly Gln Val Ser Val Asn Met Pro Leu Gln Lys
            580                 585                 590

Thr Met Glu Ile Gly Glu Asn Leu Thr Ser Arg Thr Phe Arg Tyr Thr
        595                 600                 605
```

-continued

```
Asp Phe Ser Asn Pro Phe Ser Phe Arg Ala Asn Pro Asp Ile Ile Gly
    610                 615                 620

Ile Ser Glu Gln Pro Leu Phe Gly Ala Gly Ser Ile Ser Ser Gly Glu
625                 630                 635                 640

Leu Tyr Ile Asp Lys Ile Glu Ile Ile Leu Ala Asp Ala Thr Phe Glu
                645                 650                 655

Ala Glu Ser Asp Leu Glu Arg Ala Gln Lys Ala Val Asn Glu Leu Phe
            660                 665                 670

Thr Ser Ser Asn Gln Ile Gly Leu Lys Thr Asp Val Thr Asp Tyr His
        675                 680                 685

Ile Asp Gln Val Ser Asn Leu Val Glu Cys Leu Ser Asp Glu Phe Cys
    690                 695                 700

Leu Asp Glu Lys Lys Glu Leu Ser Glu Lys Val Lys His Ala Lys Arg
705                 710                 715                 720

Leu Ser Asp Glu Arg Asn Leu Leu Gln Asp Pro Asn Phe Arg Gly Ile
                725                 730                 735

Asn Arg Gln Leu Asp Arg Gly Trp Arg Gly Ser Thr Asp Ile Thr Ile
            740                 745                 750

Gln Gly Gly Asp Asp Val Phe Lys Glu Asn Tyr Val Thr Leu Leu Gly
        755                 760                 765

Thr Phe Asp Glu Cys Tyr Pro Thr Tyr Leu Tyr Gln Lys Ile Asp Glu
    770                 775                 780

Ser Lys Leu Lys Ala Tyr Thr Arg Tyr Gln Leu Arg Gly Tyr Ile Glu
785                 790                 795                 800

Asp Ser Gln Asp Leu Glu Ile Tyr Leu Ile Arg Tyr Asn Ala Lys His
                805                 810                 815

Glu Thr Val Asn Val Pro Gly Thr Gly Ser Leu Trp Pro Leu Ser Ala
            820                 825                 830

Pro Ser Pro Ile Gly Lys Cys Ala His His Ser His His Phe Ser Leu
        835                 840                 845

Asp Ile Asp Val Gly Cys Thr Asp Leu Asn Glu Asp Leu Gly Val Trp
    850                 855                 860

Val Ile Phe Lys Ile Lys Thr Gln Asp Gly His Ala Arg Leu Gly Asn
865                 870                 875                 880

Leu Glu Phe Leu Glu Glu Lys Pro Leu Val Gly Glu Ala Leu Ala Arg
                885                 890                 895

Val Lys Arg Ala Glu Lys Lys Trp Arg Asp Lys Arg Glu Lys Leu Glu
            900                 905                 910

Trp Glu Thr Asn Ile Val Tyr Lys Glu Ala Lys Glu Ser Val Asp Ala
        915                 920                 925

Leu Phe Val Asn Ser Gln Tyr Asp Arg Leu Gln Ala Asp Thr Asn Ile
    930                 935                 940

Ala Met Ile His Ala Ala Asp Lys Arg Val His Ser Ile Arg Glu Ala
945                 950                 955                 960

Tyr Leu Pro Glu Leu Ser Val Ile Pro Gly Val Asn Ala Ala Ile Phe
                965                 970                 975

Glu Glu Leu Glu Gly Arg Ile Phe Thr Ala Phe Ser Leu Tyr Asp Ala
            980                 985                 990

Arg Asn Val Ile Lys Asn Gly Asp  Phe Asn Asn Gly Leu  Ser Cys Trp
        995                 1000                1005

Asn Val  Lys Gly His Val Asp  Val Glu Glu Gln Asn  Asn His Arg
    1010                1015                1020

Ser Val  Leu Val Val Pro Glu  Trp Glu Ala Glu Val  Ser Gln Glu
```

```
    1025                1030                1035

Val Arg  Val Cys Pro Gly Arg  Gly Tyr Ile Leu Arg  Val Thr Ala
    1040                1045                1050

Tyr Lys  Glu Gly Tyr Gly Glu  Gly Cys Val Thr Ile  His Glu Ile
    1055                1060                1065

Glu Asn  Asn Thr Asp Glu Leu  Lys Phe Ser Asn Cys  Val Glu Glu
    1070                1075                1080

Glu Val  Tyr Pro Asn Asn Thr  Val Thr Cys Asn Asp  Tyr Thr Ala
    1085                1090                1095

Thr Gln  Glu Glu Tyr Glu Gly  Thr Tyr Thr Ser Arg  Asn Arg Gly
    1100                1105                1110

Tyr Asp  Gly Ala Tyr Glu Ser  Asn Ser Ser Val Pro  Ala Asp Tyr
    1115                1120                1125

Ala Ser  Ala Tyr Glu Glu Lys  Ala Tyr Thr Asp Gly  Arg Arg Asp
    1130                1135                1140

Asn Pro  Cys Glu Ser Asn Arg  Gly Tyr Gly Asp Tyr  Thr Pro Leu
    1145                1150                1155

Pro Ala  Gly Tyr Val Thr Lys  Glu Leu Glu Tyr Phe  Pro Glu Thr
    1160                1165                1170

Asp Lys  Val Trp Ile Glu Ile  Gly Glu Thr Glu Gly  Thr Phe Ile
    1175                1180                1185

Val Asp  Ser Val Glu Leu Leu  Leu Met Glu Glu
    1190                1195


<210> SEQ ID NO 29
<211> LENGTH: 3600
<212> TYPE: DNA
<213> ORGANISM: Artificial
<220> FEATURE:
<223> OTHER INFORMATION: Synthetic nucleotide sequence designed for
      expression in a plant cell encoding TIC868_9.

<400> SEQUENCE: 29

atgacgagca accggaagaa cgagaacgag atcatcaacg ccctctcgat ccctgctgtt     60

tcaaaccact ccgcgcagat gaacctgtcc accgacgcgc gcatcgagga ctccctctgc    120

atagccgagg gcaacaacat cgacccattc gtgtcggcca gcacggttca gaccggcatc    180

aacatcgcgg gccgtatcct cggcgtcctc ggtgtcccat tcgccggtca gatcgcgtcc    240

ttctactcgt tccttgtggg cgagctgtgg cctcgcggtc gtgacccgtg ggagatcttc    300

ctggagcatg tggagcagtt gatccggcag caagtcacgg agaacacccg cgatactgct    360

ctggccaggc tacagggcct gggaaactcc tttcgggcat accagcagtc actggaggac    420

tggttggaga acagggatga cgcgcgaaca cgctcggtac tctacaccca gtacatcgct    480

ctcgaactcg acttcctgaa cgctatgccg ctgttcgcca tcaggaacca ggaagttcca    540

ctccttatgg tgtacgccca ggccgccaac ttacatctgc tcctgctgcg ggacgccagc    600

ctgttcggct ccgagttcgg actcacatct caagaaatcc agcgttacta cgagcgccaa    660

gtggagaaga cccgtgagta cagtgactac tgcgctcgat ggtacaacac agggctcaac    720

agcctgcgcg gcaccaacgc tgagtcatgg ctccgttaca accagttccg ccgcgacttg    780

actttgggtg tcctagacct ggtggcgcta ttcccgtctt acgacacacg ggtgtaccca    840

atgaacacta gcgcgcaact cacgcgggag atctacacag acccaatcgg ccggacgaac    900

gcaccctccg gtttcgcatc cacgaattgg ttcaacaaca acgcaccctc cttctcggca    960

atcgaggccg ccgtcatccg ccctcctcac ctgctcgact ttcccgagca gctcacgatc   1020
```

ttctccgtgc tctcacgctg gtccaacaca cagtacatga actactgggt cgggcaccga 1080
ttggagagta ggacgatccg tggcagcttg agcaccagta cccacggcaa caccaacacc 1140
tccatcaacc cagttacgct acagttcacg agccgcgacg tttaccggac tgagtcgcag 1200
gcgggcatta acatccttat gacaacgccc gtcaacggcg tcccgtgggc ccggttcaac 1260
tggcgtaacc cgaagaactc cctgcgcggg tcattgctct acaccatcgg gtacacgggc 1320
gtcggcaccc agctcttcga cagtgaaact gagctgccgc ccgagaccac ggaacgcccg 1380
aactacgagt cctacagcca ccgcctgtcc aacatccggc tcatctctgg caacacgctg 1440
cgtgcgccgg tgtactcctg gacacaccgc agcgccgacc ggaccaacac gatctcttcc 1500
gactccatta accagatccc gctcgtgaag ggcttccgtg tgtggggtgg cacgagcgtc 1560
atcaccggtc cgggcttcac cggtggagac atactgcggc gcaacacttt cggcgacttc 1620
gtttcgttgc aagtgaacat caactcgccg atcacccagc gttaccgtct gaggttccgc 1680
tacgcttcaa gccgcgacgc gagggtcatt gtcctgaccg gagccgcgtc cacaggcgtg 1740
ggaggccaag tctcagtcaa catgcctctc cagaagacga tggagatagg cgagaacttg 1800
actagccgaa ccttccggta cactgatttc tcgaaccctt tctcattcag agcgaaccct 1860
gacatcattg ggatctccga gcaaccgctg ttcggtgctg gctccatcag ctctggcgaa 1920
ctgtacatcg acaagattga gatcatcctg gcggatgcga cgttcgaggc cgagtctgac 1980
ctggagcggg ctcagaaggc tgtcaacgaa ctgttcacca gcagcaacca gattgggctc 2040
aagaccgacg tcacggacta tcacattgac caagtgtcca accttgtgga gtgcctgtcc 2100
gacgagttct gcctcgacga gaagaaggag ctgtccgaga aggtcaaaca cgcgaagcgt 2160
ctgagtgacg agcggaattt gctccaggac ccgaacttcc gtggcatcaa ccgccagctc 2220
gaccgtggtt ggcgcgggag tacagacatc accatccagg gaggcgacga tgtgttcaag 2280
gagaactatg tgacgctgct cgggactttc gacgaatgct acccgacgta tctctaccag 2340
aagatagacg agagtaaatt gaaggcgtac acccgctacc agcttcgcgg gtacatcgag 2400
gatagtcagg acctggaaat ctacctgatc cgatacaacg ccaagcacga gacagtgaac 2460
gtgccaggca cgggctcact ttggccattg agcgctccct ctccaatcgg aaagtgcgct 2520
caccactcgc accacttctc tctggacatc gacgtgggct gcaccgacct caacgaggac 2580
ctgggtgtct gggttatctt caagattaag acccaggacg gacatgcccg cctcggcaac 2640
ctggagttcc ttgaggagaa gcctctcgtg ggcgaggccc tcgctcgtgt gaagcgcgcc 2700
gagaagaaat ggcgagacaa gcgggagaag ctggagtggg agaccaacat cgtgtacaag 2760
gaggccaagg agtcagtgga cgcactcttc gtcaacagcc agtacgaccg cctccaggct 2820
gacaccaaca tcgccatgat ccacgcggct gacaagcggg tccacagcat ccgtgaggcg 2880
tacctgcccg agctgtcagt gatccctggt gtgaacgcgg cgatcttcga ggaactggag 2940
ggccgcatct tcacagcatt cagcctgtac gatgccagga atgttattaa gaacggtgac 3000
ttcaacaacg ggctgagttg ctggaacgtc aagggccatg tggacgtcga ggagcagaac 3060
aaccaccggt ccgtgctggt cgtgccggag tgggaggcag aggtgagcca ggaggtccgc 3120
gtctgccctg gtcgcggcta catcctccgt gtgactgcgt acaaggaagg ctacggtgaa 3180
ggctgcgtga ctatccacga gatcgagaac aacaccgacg agctcaagtt ctcgaactgt 3240
gtggaggagg aggtgtaccc gaacaacacc gttacttgca acgactacac tgccacgcaa 3300
gaggagtacg agggcactta cacttcccgg aatcgcggct atgatggcgc gtacgagtcc 3360

-continued

```
aacagcagcg tgcctgcgga ttatgcgtcc gcttacgagg agaaggcgta caccgacgga   3420

cggagggaca acccttgcga gtccaaccgt ggctacggtg actacactcc gctgcccgcc   3480

gggtacgtca ccaaggagct ggagtacttc ccggagaccg acaaagtctg gatcgagatc   3540

ggcgagacgg agggcacttt catcgtggac tcggtcgagc tgctactgat ggaggagtga   3600


<210> SEQ ID NO 30
<211> LENGTH: 1199
<212> TYPE: PRT
<213> ORGANISM: Artificial
<220> FEATURE:
<223> OTHER INFORMATION: Amino acid sequence of the chimeric protein
      variant TIC868_9.

<400> SEQUENCE: 30

Met Thr Ser Asn Arg Lys Asn Glu Asn Glu Ile Ile Asn Ala Leu Ser
1               5                   10                  15

Ile Pro Ala Val Ser Asn His Ser Ala Gln Met Asn Leu Ser Thr Asp
            20                  25                  30

Ala Arg Ile Glu Asp Ser Leu Cys Ile Ala Glu Gly Asn Asn Ile Asp
        35                  40                  45

Pro Phe Val Ser Ala Ser Thr Val Gln Thr Gly Ile Asn Ile Ala Gly
    50                  55                  60

Arg Ile Leu Gly Val Leu Gly Val Pro Phe Ala Gly Gln Ile Ala Ser
65                  70                  75                  80

Phe Tyr Ser Phe Leu Val Gly Glu Leu Trp Pro Arg Gly Arg Asp Pro
                85                  90                  95

Trp Glu Ile Phe Leu Glu His Val Glu Gln Leu Ile Arg Gln Gln Val
            100                 105                 110

Thr Glu Asn Thr Arg Asp Thr Ala Leu Ala Arg Leu Gln Gly Leu Gly
        115                 120                 125

Asn Ser Phe Arg Ala Tyr Gln Gln Ser Leu Glu Asp Trp Leu Glu Asn
    130                 135                 140

Arg Asp Asp Ala Arg Thr Arg Ser Val Leu Tyr Thr Gln Tyr Ile Ala
145                 150                 155                 160

Leu Glu Leu Asp Phe Leu Asn Ala Met Pro Leu Phe Ala Ile Arg Asn
                165                 170                 175

Gln Glu Val Pro Leu Leu Met Val Tyr Ala Gln Ala Ala Asn Leu His
            180                 185                 190

Leu Leu Leu Leu Arg Asp Ala Ser Leu Phe Gly Ser Glu Phe Gly Leu
        195                 200                 205

Thr Ser Gln Glu Ile Gln Arg Tyr Tyr Glu Arg Gln Val Glu Lys Thr
    210                 215                 220

Arg Glu Tyr Ser Asp Tyr Cys Ala Arg Trp Tyr Asn Thr Gly Leu Asn
225                 230                 235                 240

Ser Leu Arg Gly Thr Asn Ala Glu Ser Trp Leu Arg Tyr Asn Gln Phe
                245                 250                 255

Arg Arg Asp Leu Thr Leu Gly Val Leu Asp Leu Val Ala Leu Phe Pro
            260                 265                 270

Ser Tyr Asp Thr Arg Val Tyr Pro Met Asn Thr Ser Ala Gln Leu Thr
        275                 280                 285

Arg Glu Ile Tyr Thr Asp Pro Ile Gly Arg Thr Asn Ala Pro Ser Gly
    290                 295                 300

Phe Ala Ser Thr Asn Trp Phe Asn Asn Asn Ala Pro Ser Phe Ser Ala
305                 310                 315                 320
```

-continued

```
Ile Glu Ala Ala Val Ile Arg Pro Pro His Leu Leu Asp Phe Pro Glu
                325                 330                 335

Gln Leu Thr Ile Phe Ser Val Leu Ser Arg Trp Ser Asn Thr Gln Tyr
            340                 345                 350

Met Asn Tyr Trp Val Gly His Arg Leu Glu Ser Arg Thr Ile Arg Gly
        355                 360                 365

Ser Leu Ser Thr Ser Thr His Gly Asn Thr Asn Thr Ser Ile Asn Pro
    370                 375                 380

Val Thr Leu Gln Phe Thr Ser Arg Asp Val Tyr Arg Thr Glu Ser Gln
385                 390                 395                 400

Ala Gly Ile Asn Ile Leu Met Thr Thr Pro Val Asn Gly Val Pro Trp
                405                 410                 415

Ala Arg Phe Asn Trp Arg Asn Pro Lys Asn Ser Leu Arg Gly Ser Leu
            420                 425                 430

Leu Tyr Thr Ile Gly Tyr Thr Gly Val Gly Thr Gln Leu Phe Asp Ser
        435                 440                 445

Glu Thr Glu Leu Pro Pro Glu Thr Thr Glu Arg Pro Asn Tyr Glu Ser
    450                 455                 460

Tyr Ser His Arg Leu Ser Asn Ile Arg Leu Ile Ser Gly Asn Thr Leu
465                 470                 475                 480

Arg Ala Pro Val Tyr Ser Trp Thr His Arg Ser Ala Asp Arg Thr Asn
                485                 490                 495

Thr Ile Ser Ser Asp Ser Ile Asn Gln Ile Pro Leu Val Lys Gly Phe
            500                 505                 510

Arg Val Trp Gly Gly Thr Ser Val Ile Thr Gly Pro Gly Phe Thr Gly
        515                 520                 525

Gly Asp Ile Leu Arg Arg Asn Thr Phe Gly Asp Phe Val Ser Leu Gln
    530                 535                 540

Val Asn Ile Asn Ser Pro Ile Thr Gln Arg Tyr Arg Leu Arg Phe Arg
545                 550                 555                 560

Tyr Ala Ser Ser Arg Asp Ala Arg Val Ile Val Leu Thr Gly Ala Ala
                565                 570                 575

Ser Thr Gly Val Gly Gly Gln Val Ser Val Asn Met Pro Leu Gln Lys
            580                 585                 590

Thr Met Glu Ile Gly Glu Asn Leu Thr Ser Arg Thr Phe Arg Tyr Thr
        595                 600                 605

Asp Phe Ser Asn Pro Phe Ser Phe Arg Ala Asn Pro Asp Ile Ile Gly
    610                 615                 620

Ile Ser Glu Gln Pro Leu Phe Gly Ala Gly Ser Ile Ser Ser Gly Glu
625                 630                 635                 640

Leu Tyr Ile Asp Lys Ile Glu Ile Ile Leu Ala Asp Ala Thr Phe Glu
                645                 650                 655

Ala Glu Ser Asp Leu Glu Arg Ala Gln Lys Ala Val Asn Glu Leu Phe
            660                 665                 670

Thr Ser Ser Asn Gln Ile Gly Leu Lys Thr Asp Val Thr Asp Tyr His
        675                 680                 685

Ile Asp Gln Val Ser Asn Leu Val Glu Cys Leu Ser Asp Glu Phe Cys
    690                 695                 700

Leu Asp Glu Lys Lys Glu Leu Ser Glu Lys Val Lys His Ala Lys Arg
705                 710                 715                 720

Leu Ser Asp Glu Arg Asn Leu Leu Gln Asp Pro Asn Phe Arg Gly Ile
                725                 730                 735

Asn Arg Gln Leu Asp Arg Gly Trp Arg Gly Ser Thr Asp Ile Thr Ile
```

```
            740                 745                 750

Gln Gly Gly Asp Asp Val Phe Lys Glu Asn Tyr Val Thr Leu Leu Gly
        755                 760                 765

Thr Phe Asp Glu Cys Tyr Pro Thr Tyr Leu Tyr Gln Lys Ile Asp Glu
    770                 775                 780

Ser Lys Leu Lys Ala Tyr Thr Arg Tyr Gln Leu Arg Gly Tyr Ile Glu
785                 790                 795                 800

Asp Ser Gln Asp Leu Glu Ile Tyr Leu Ile Arg Tyr Asn Ala Lys His
                805                 810                 815

Glu Thr Val Asn Val Pro Gly Thr Gly Ser Leu Trp Pro Leu Ser Ala
            820                 825                 830

Pro Ser Pro Ile Gly Lys Cys Ala His His Ser His His Phe Ser Leu
        835                 840                 845

Asp Ile Asp Val Gly Cys Thr Asp Leu Asn Glu Asp Leu Gly Val Trp
    850                 855                 860

Val Ile Phe Lys Ile Lys Thr Gln Asp Gly His Ala Arg Leu Gly Asn
865                 870                 875                 880

Leu Glu Phe Leu Glu Glu Lys Pro Leu Val Gly Glu Ala Leu Ala Arg
                885                 890                 895

Val Lys Arg Ala Glu Lys Lys Trp Arg Asp Lys Arg Glu Lys Leu Glu
            900                 905                 910

Trp Glu Thr Asn Ile Val Tyr Lys Glu Ala Lys Glu Ser Val Asp Ala
        915                 920                 925

Leu Phe Val Asn Ser Gln Tyr Asp Arg Leu Gln Ala Asp Thr Asn Ile
    930                 935                 940

Ala Met Ile His Ala Ala Asp Lys Arg Val His Ser Ile Arg Glu Ala
945                 950                 955                 960

Tyr Leu Pro Glu Leu Ser Val Ile Pro Gly Val Asn Ala Ala Ile Phe
                965                 970                 975

Glu Glu Leu Glu Gly Arg Ile Phe Thr Ala Phe Ser Leu Tyr Asp Ala
            980                 985                 990

Arg Asn Val Ile Lys Asn Gly Asp  Phe Asn Asn Gly Leu  Ser Cys Trp
        995                 1000                1005

Asn Val  Lys Gly His Val Asp  Val Glu Glu Gln Asn  Asn His Arg
    1010                1015                1020

Ser Val  Leu Val Val Pro Glu  Trp Glu Ala Glu Val  Ser Gln Glu
    1025                1030                1035

Val Arg  Val Cys Pro Gly Arg  Gly Tyr Ile Leu Arg  Val Thr Ala
    1040                1045                1050

Tyr Lys  Glu Gly Tyr Gly Glu  Gly Cys Val Thr Ile  His Glu Ile
    1055                1060                1065

Glu Asn  Asn Thr Asp Glu Leu  Lys Phe Ser Asn Cys  Val Glu Glu
    1070                1075                1080

Glu Val  Tyr Pro Asn Asn Thr  Val Thr Cys Asn Asp  Tyr Thr Ala
    1085                1090                1095

Thr Gln  Glu Glu Tyr Glu Gly  Thr Tyr Thr Ser Arg  Asn Arg Gly
    1100                1105                1110

Tyr Asp  Gly Ala Tyr Glu Ser  Asn Ser Ser Val Pro  Ala Asp Tyr
    1115                1120                1125

Ala Ser  Ala Tyr Glu Glu Lys  Ala Tyr Thr Asp Gly  Arg Arg Asp
    1130                1135                1140

Asn Pro  Cys Glu Ser Asn Arg  Gly Tyr Gly Asp Tyr  Thr Pro Leu
    1145                1150                1155
```

```
Pro Ala  Gly Tyr Val Thr Lys  Glu Leu Glu Tyr Phe  Pro Glu Thr
    1160                1165                1170

Asp Lys  Val Trp Ile Glu Ile  Gly Glu Thr Glu Gly  Thr Phe Ile
    1175                1180                1185

Val Asp  Ser Val Glu Leu Leu  Leu Met Glu Glu
    1190                1195


<210> SEQ ID NO 31
<211> LENGTH: 3678
<212> TYPE: DNA
<213> ORGANISM: Artificial
<220> FEATURE:
<223> OTHER INFORMATION: Recombinant nucleotide sequence used for
      expression in a bacterial cell encoding TIC868_10.

<400> SEQUENCE: 31

atgacttcaa ataggaaaaa tgagaatgaa attataaatg ctttatcgat tccagctgta     60

tcgaatcatt ccgcacaaat gaatctatca accgatgctc gtattgagga tagcttgtgt    120

atagccgagg ggaacaatat cgatccattt gttagcgcat caacagtcca aacgggtatt    180

aacatagctg gtagaatact aggtgtatta ggcgtaccgt ttgctggaca aatagctagt    240

ttttatagtt ttcttgttgg tgaattatgg ccccgcggca gagatccttg ggaaattttc    300

ctagaacatg tcgaacaact tataagacaa caagtaacag aaaatactag ggatacggct    360

cttgctcgat tacaaggttt aggaaattcc tttagagcct atcaacagtc acttgaagat    420

tggctagaaa accgtgatga tgcaagaacg agaagtgttc tttataccca atatatagcc    480

ttagaacttg attttcttaa tgcgatgccg cttttcgcaa ttagaaacca agaagttcca    540

ttattaatgg tatatgctca agctgcaaat ttacacctat tattattgag agatgcctct    600

ctttttggta gtgaatttgg gcttacatcc caagaaattc aacgttatta tgagcgccaa    660

gtggaaaaaa cgagagaata ttctgattat tgcgcaagat ggtataatac gggtttaaat    720

aatttgagag ggacaaatgc tgaaagttgg ttgcgatata atcaattccg tagagactta    780

acgctaggag tattagatct agtggcacta ttcccaagct atgacacgcg tgtttatcca    840

atgaatacca gtgctcaatt aacaagagaa atttatacag atccaattgg gagaacaaat    900

gcaccttcag gatttgcaag tacgaattgg tttaataata atgcaccatc gttttctgcc    960

atagaggctg ccgttattag gcctccgcat ctacttgatt ttccagaaca gcttacaatt   1020

ttcagcgtat taagtcgatg gagtaatact caatatatga attactgggt gggacataga   1080

cttgaatcgc gaacaataag gggggtcatta agtacctcga cacacggaaa taccaatact   1140

tctattaatc ctgtaacatt acagttcaca tctcgagacg tttatagaac agaatcattt   1200

gcagggataa atatacttct aactactcct gtgaatggag taccttgggc tagatttaat   1260

tggagaaatc ccctgaattc tcttagaggt agccttctct atactatagg gtatactgga   1320

gtggggacac aactatttga ttcagaaact gaattaccac cagaaacaac agaacgacca   1380

aattatgaat cttacagtca tagattatct aatataagac taatatcagg aaacactttg   1440

agagcaccag tatattcttg gacgcaccgt agtgcagatc gtacaaatac cattagttca   1500

gatagcatta atcaaatacc tttagtgaaa ggatttagag tttggggggg cacctctgtc   1560

attacaggac caggatttac aggaggggat atccttcgaa gaaatacctt tggtgatttt   1620

gtatctctac aagtcaatat taattcacca attacccaaa gataccgttt aagatttcgt   1680

tacgcttcca gtagggatgc acgagttata gtattaacag gagcggcatc cacaggagtg   1740
```

ggaggccaag ttagtgtaaa tatgcctctt cagaaaacta tggaaatagg ggagaactta 1800
acatctagaa catttagata taccgatttt agtaatcctt tttcatttag agctaatcca 1860
gatataattg ggataagtga acaacctcta tttggtgcag gttctattag tagcggtgaa 1920
ctttatatag ataaaattga aattattcta gcagatgcaa catttgaggc agaatatgat 1980
ttagaaagag cgcaaaaggt ggtgaatgcc ctgtttacgt ctacaaacca actagggcta 2040
aaaacagatg tgacggatta tcatattgat caggtatcca atctagttgc gtgtttatcg 2100
gatgaatttt gtctggatga aaagagagaa ttgtccgaga aagttaaaca tgcaaagcga 2160
ctcagtgatg agcggaattt acttcaagat ccaaacttca gagggatcaa taggcaacca 2220
gaccgtggct ggagaggaag tacggatatt actatccaag gaggagatga cgtattcaaa 2280
gagaattacg ttacgctacc gggtaccttt gatgagtgct atccaacgta tttatatcaa 2340
aaaatagatg agtcgaaatt aaaagcctat acccgttatc aattaagagg gtatatcgaa 2400
gatagtcaag acttagaaat ctatttaatt cgttacaatg caaaacacga aatagtaaat 2460
gtaccaggta caggaagttt atggcctctt tctgtagaaa atcaaattgg accttgtgga 2520
gaaccgaatc gatgcgcgcc acaccttgaa tggaatcctg atttacactg ttcctgcaga 2580
gacggggaaa aatgtgcaca tcattctcat catttctctt tggacattga tgttggatgt 2640
acagacttaa atgaggactt aggtgtatgg gtgatattca agattaagac gcaagatggc 2700
cacgcacgac tagggaatct agagtttctc gaagagaaac cattattagg agaagcacta 2760
gctcgtgtga aaagagcgga gaaaaaatgg agagacaaac gcgaaacatt acaattggaa 2820
acaactatcg tttataaaga ggcaaaagaa tctgtagatg ctttatttgt aaactctcaa 2880
tatgatagat tacaagcgga tacgaacatc gcgatgattc atgcggcaga taaacgcgtt 2940
catagaattc gagaagcgta tctgccggag ctgtctgtga ttccgggtgt caatgcggct 3000
atttttgaag aattagaaga gcgtattttc actgcatttt ccctatatga tgcgagaaat 3060
attattaaaa atggcgattt caataatggc ttattatgct ggaacgtgaa agggcatgta 3120
gaggtagaag aacaaaacaa tcaccgttca gtcctggtta tcccagaatg ggaggcagaa 3180
gtgtcacaag aggttcgtgt ctgtccaggt cgtggctata tccttcgtgt tacagcgtac 3240
aaagagggat atggagaagg ttgcgtaacg atccatgaga tcgagaacaa tacagacgaa 3300
ctgaaattca acaactgtgt agaagaggaa gtatatccaa acaacacggt aacgtgtatt 3360
aattatactg cgactcaaga agaatatgag ggtacgtaca cttctcgtaa tcgaggatat 3420
gacgaagcct atggtaataa cccttccgta ccagctgatt atgcgtcagt ctatgaagaa 3480
aaatcgtata cagatagacg aagagagaat ccttgtgaat ctaacagagg atatggagat 3540
tacacaccac taccagctgg ttatgtaaca aaggaattag agtacttccc agagaccgat 3600
aaggtatgga ttgagattgg agaaacagaa ggaacattca tcgtggacag cgtggaatta 3660
ctccttatgg aggaatag 3678

<210> SEQ ID NO 32
<211> LENGTH: 3678
<212> TYPE: DNA
<213> ORGANISM: Artificial
<220> FEATURE:
<223> OTHER INFORMATION: Synthetic nucleotide sequence designed for expression in a plant cell encoding TIC868_10.

<400> SEQUENCE: 32
atgacgagca accggaagaa cgagaacgag atcatcaacg ccctctcgat ccctgctgtt 60

-continued

```
tcaaaccact ccgcgcagat gaacctgtcc accgacgcgc gcatcgagga ctccctctgc    120
atagccgagg gcaacaacat cgacccattc gtgtcggcca gcacggttca gaccggcatc    180
aacatcgcgg gccgtatcct cggcgtcctc ggtgtcccat tcgccggtca gatcgcgtcc    240
ttctactcgt tccttgtggg cgagctgtgg cctcgcggtc gtgacccgtg ggagatcttc    300
ctggagcatg tggagcagtt gatccggcag caagtcacgg agaacacccg cgatactgct    360
ctggccaggc tacagggcct gggaaactcc tttcgggcat accagcagtc actggaggac    420
tggttggaga acagggatga cgcgcgaaca cgctcggtac tctacaccca gtacatcgct    480
ctcgaactcg acttcctgaa cgctatgccg ctgttcgcca tcaggaacca ggaagttcca    540
ctccttatgg tgtacgccca ggccgccaac ttacatctgc tcctgctgcg ggacgccagc    600
ctgttcggct ccgagttcgg actcacatct caagaaatcc agcgttacta cgagcgccaa    660
gtggagaaga cccgtgagta cagtgactac tgcgctcgat ggtacaacac agggctcaac    720
aacctgcgcg gcaccaacgc tgagtcatgg ctccgttaca accagttccg ccgcgacttg    780
actttgggtg tcctagacct ggtggcgcta ttcccgtctt acgacacacg ggtgtaccca    840
atgaacacta gcgcgcaact cacgcgggag atctacacag acccaatcgg ccggacgaac    900
gcaccctccg gtttcgcatc cacgaattgg ttcaacaaca acgcaccctc cttctcggca    960
atcgaggccg ccgtcatccg ccctcctcac ctgctcgact ttcccgagca gctcacgatc   1020
ttctccgtgc tctcacgctg gtccaacaca cagtacatga actactgggt cgggcaccga   1080
ttggagagta ggacgatccg tggcagcttg agcaccagta cccacggcaa caccaacacc   1140
tccatcaacc cagttacgct acagttcacg agccgcgacg tttaccggac tgagtcgttc   1200
gcgggcatta acatccttct gacaacgccc gtcaacggcg tcccgtgggc ccggttcaac   1260
tggcgtaacc cgttgaactc cctgcgcggg tcattgctct acaccatcgg gtacacgggc   1320
gtcggcaccc agctcttcga cagtgaaact gagctgccgc ccgagaccac ggaacgcccg   1380
aactacgagt cctacagcca ccgcctgtcc aacatccggc tcatctctgg caacacgctg   1440
cgtgcgccgg tgtactcctg gacacaccgc agcgccgacc ggaccaacac gatctcttcc   1500
gactccatta accagatccc gctcgtgaag ggcttccgtg tgtggggtgg cacgagcgtc   1560
atcaccggtc cgggcttcac cggtggagac atactgcggc gcaacacttt cggcgacttc   1620
gtttcgttgc aagtgaacat caactcgccg atcacccagc gttaccgtct gaggttccgc   1680
tacgcttcaa gccgcgacgc gagggtcatt gtcctgaccg gagccgcgtc cacaggcgtg   1740
ggaggccaag tctcagtcaa catgcctctc cagaagacga tggagatagg cgagaacttg   1800
actagccgaa ccttccggta cactgatttc tcgaaccctt tctcattcag agcgaaccct   1860
gacatcattg ggatctccga gcaaccgctg ttcggtgctg gctccatcag ctctggcgaa   1920
ctgtacatcg acaagattga gatcatcctg gcggatgcga cgttcgaggc cgagtacgac   1980
cttgagcgcg cccagaaggt ggtgaacgcc ctcttcacta gcactaacca gctaggcctg   2040
aagactgacg tgaccgacta ccacatcgac caagtgagca acctagtggc ctgcctctcc   2100
gacgagttct gcctcgacga gaagcgcgag ctgtccgaga aggtgaagca cgccaagcgc   2160
ctctccgacg agcgcaacct gctccaggac cccaacttca ggggcatcaa caggcagccc   2220
gaccgcggct ggcgcggctc caccgacatc accatccagg gcggtgacga cgtattcaag   2280
gagaactacg ttaccctccc cggcaccttc gacgagtgtt accccaccta cctctaccag   2340
aagatcgacg agtccaagct gaaggcctac acccgctacc agctccgcgg ctacatcgag   2400
gactcccagg acctggaaat ctacctcatc cgctacaacg ccaagcacga gatcgtgaac   2460
```

```
gtgcctggca ccggcagcct ctggcctctc agcgtggaga accagatcgg cccttgcggc   2520

gagcctaacc gctgcgcccc tcacctcgag tggaaccctg acctccactg ctcgtgcagg   2580

gacggcgaga agtgcgccca ccatagccac cacttctctc tggacatcga cgtgggctgc   2640

accgacctga acgaggacct gggcgtgtgg gttatcttca agatcaagac ccaggacggt   2700

cacgccaggc tgggtaacct ggagttcctt gaggaaaagc ctctgctggg tgaggccctg   2760

gccagggtca agagggctga gaagaaatgg agggataaga gggagaccct gcagctggag   2820

accactatcg tctacaagga ggctaaggag tctgtcgatg ctctgttcgt caactctcag   2880

tacgatagac tgcaagctga taccaacatc gctatgatcc acgctgcgga taagcgggtc   2940

caccggatcc gggaggctta ccttccggag ctttctgtca tcccgggtgt caacgctgcg   3000

atcttcgagg aacttgagga acggatcttc actgcgttta gtctttacga tgcgcggaac   3060

atcatcaaga acggggactt caacaatggt ctgctgtgct ggaacgtcaa gggtcatgtc   3120

gaggtcgagg aacaaaacaa tcatcgtagt gtccttgtca ttcctgagtg ggaggcggag   3180

gtctctcaag aggtccgtgt ttgcccgggg cgtgggtaca ttcttcgtgt tactgcgtac   3240

aaggaggggt acggggaggg gtgcgttact attcatgaga ttgagaacaa tactgatgag   3300

cttaagttca acaattgtgt tgaggaggag gtttacccga acaatactgt tacgtgcatc   3360

aactacacgg caacgcaaga ggaatacgag ggacgtaca cctcgcgtaa tagagggtat   3420

gatgaggcgt acggaaacaa cccgtcggtt ccagcagatt atgcctcggt ttatgaggag   3480

aagtcgtaca cggatagacg acgcgagaat ccatgtgagt caaatcgagg atacggagat   3540

tacacaccat taccagcagg atacgttaca aaggagttgg aatacttccc ggaaacagat   3600

aaagtttgga ttgaaatcgg agaaacagaa ggaacattca tcgtcgactc agtagaattg   3660

ttgttgatgg aagaatga                                                 3678
```

```
<210> SEQ ID NO 33
<211> LENGTH: 1225
<212> TYPE: PRT
<213> ORGANISM: Artificial
<220> FEATURE:
<223> OTHER INFORMATION: Amino acid sequence of the chimeric protein
      variant TIC868_10.

<400> SEQUENCE: 33

Met Thr Ser Asn Arg Lys Asn Glu Asn Glu Ile Ile Asn Ala Leu Ser
1               5                   10                  15

Ile Pro Ala Val Ser Asn His Ser Ala Gln Met Asn Leu Ser Thr Asp
            20                  25                  30

Ala Arg Ile Glu Asp Ser Leu Cys Ile Ala Glu Gly Asn Asn Ile Asp
        35                  40                  45

Pro Phe Val Ser Ala Ser Thr Val Gln Thr Gly Ile Asn Ile Ala Gly
    50                  55                  60

Arg Ile Leu Gly Val Leu Gly Val Pro Phe Ala Gly Gln Ile Ala Ser
65                  70                  75                  80

Phe Tyr Ser Phe Leu Val Gly Glu Leu Trp Pro Arg Gly Arg Asp Pro
                85                  90                  95

Trp Glu Ile Phe Leu Glu His Val Glu Gln Leu Ile Arg Gln Gln Val
            100                 105                 110

Thr Glu Asn Thr Arg Asp Thr Ala Leu Ala Arg Leu Gln Gly Leu Gly
        115                 120                 125

Asn Ser Phe Arg Ala Tyr Gln Gln Ser Leu Glu Asp Trp Leu Glu Asn
```

-continued

```
    130                 135                 140

Arg Asp Asp Ala Arg Thr Arg Ser Val Leu Tyr Thr Gln Tyr Ile Ala
145                 150                 155                 160

Leu Glu Leu Asp Phe Leu Asn Ala Met Pro Leu Phe Ala Ile Arg Asn
                165                 170                 175

Gln Glu Val Pro Leu Leu Met Val Tyr Ala Gln Ala Ala Asn Leu His
            180                 185                 190

Leu Leu Leu Leu Arg Asp Ala Ser Leu Phe Gly Ser Glu Phe Gly Leu
        195                 200                 205

Thr Ser Gln Glu Ile Gln Arg Tyr Tyr Glu Arg Gln Val Glu Lys Thr
    210                 215                 220

Arg Glu Tyr Ser Asp Tyr Cys Ala Arg Trp Tyr Asn Thr Gly Leu Asn
225                 230                 235                 240

Asn Leu Arg Gly Thr Asn Ala Glu Ser Trp Leu Arg Tyr Asn Gln Phe
                245                 250                 255

Arg Arg Asp Leu Thr Leu Gly Val Leu Asp Leu Val Ala Leu Phe Pro
            260                 265                 270

Ser Tyr Asp Thr Arg Val Tyr Pro Met Asn Thr Ser Ala Gln Leu Thr
        275                 280                 285

Arg Glu Ile Tyr Thr Asp Pro Ile Gly Arg Thr Asn Ala Pro Ser Gly
    290                 295                 300

Phe Ala Ser Thr Asn Trp Phe Asn Asn Asn Ala Pro Ser Phe Ser Ala
305                 310                 315                 320

Ile Glu Ala Ala Val Ile Arg Pro Pro His Leu Leu Asp Phe Pro Glu
                325                 330                 335

Gln Leu Thr Ile Phe Ser Val Leu Ser Arg Trp Ser Asn Thr Gln Tyr
            340                 345                 350

Met Asn Tyr Trp Val Gly His Arg Leu Glu Ser Arg Thr Ile Arg Gly
        355                 360                 365

Ser Leu Ser Thr Ser Thr His Gly Asn Thr Asn Thr Ser Ile Asn Pro
    370                 375                 380

Val Thr Leu Gln Phe Thr Ser Arg Asp Val Tyr Arg Thr Glu Ser Phe
385                 390                 395                 400

Ala Gly Ile Asn Ile Leu Leu Thr Thr Pro Val Asn Gly Val Pro Trp
                405                 410                 415

Ala Arg Phe Asn Trp Arg Asn Pro Leu Asn Ser Leu Arg Gly Ser Leu
            420                 425                 430

Leu Tyr Thr Ile Gly Tyr Thr Gly Val Gly Thr Gln Leu Phe Asp Ser
        435                 440                 445

Glu Thr Glu Leu Pro Pro Glu Thr Thr Glu Arg Pro Asn Tyr Glu Ser
    450                 455                 460

Tyr Ser His Arg Leu Ser Asn Ile Arg Leu Ile Ser Gly Asn Thr Leu
465                 470                 475                 480

Arg Ala Pro Val Tyr Ser Trp Thr His Arg Ser Ala Asp Arg Thr Asn
                485                 490                 495

Thr Ile Ser Ser Asp Ser Ile Asn Gln Ile Pro Leu Val Lys Gly Phe
            500                 505                 510

Arg Val Trp Gly Gly Thr Ser Val Ile Thr Gly Pro Gly Phe Thr Gly
        515                 520                 525

Gly Asp Ile Leu Arg Arg Asn Thr Phe Gly Asp Phe Val Ser Leu Gln
    530                 535                 540

Val Asn Ile Asn Ser Pro Ile Thr Gln Arg Tyr Arg Leu Arg Phe Arg
545                 550                 555                 560
```

-continued

```
Tyr Ala Ser Ser Arg Asp Ala Arg Val Ile Val Leu Thr Gly Ala Ala
                565                 570                 575

Ser Thr Gly Val Gly Gly Gln Val Ser Val Asn Met Pro Leu Gln Lys
            580                 585                 590

Thr Met Glu Ile Gly Glu Asn Leu Thr Ser Arg Thr Phe Arg Tyr Thr
        595                 600                 605

Asp Phe Ser Asn Pro Phe Ser Phe Arg Ala Asn Pro Asp Ile Ile Gly
    610                 615                 620

Ile Ser Glu Gln Pro Leu Phe Gly Ala Gly Ser Ile Ser Ser Gly Glu
625                 630                 635                 640

Leu Tyr Ile Asp Lys Ile Glu Ile Ile Leu Ala Asp Ala Thr Phe Glu
                645                 650                 655

Ala Glu Tyr Asp Leu Glu Arg Ala Gln Lys Val Val Asn Ala Leu Phe
            660                 665                 670

Thr Ser Thr Asn Gln Leu Gly Leu Lys Thr Asp Val Thr Asp Tyr His
        675                 680                 685

Ile Asp Gln Val Ser Asn Leu Val Ala Cys Leu Ser Asp Glu Phe Cys
    690                 695                 700

Leu Asp Glu Lys Arg Glu Leu Ser Glu Lys Val Lys His Ala Lys Arg
705                 710                 715                 720

Leu Ser Asp Glu Arg Asn Leu Leu Gln Asp Pro Asn Phe Arg Gly Ile
                725                 730                 735

Asn Arg Gln Pro Asp Arg Gly Trp Arg Gly Ser Thr Asp Ile Thr Ile
            740                 745                 750

Gln Gly Gly Asp Asp Val Phe Lys Glu Asn Tyr Val Thr Leu Pro Gly
        755                 760                 765

Thr Phe Asp Glu Cys Tyr Pro Thr Tyr Leu Tyr Gln Lys Ile Asp Glu
    770                 775                 780

Ser Lys Leu Lys Ala Tyr Thr Arg Tyr Gln Leu Arg Gly Tyr Ile Glu
785                 790                 795                 800

Asp Ser Gln Asp Leu Glu Ile Tyr Leu Ile Arg Tyr Asn Ala Lys His
                805                 810                 815

Glu Ile Val Asn Val Pro Gly Thr Gly Ser Leu Trp Pro Leu Ser Val
            820                 825                 830

Glu Asn Gln Ile Gly Pro Cys Gly Glu Pro Asn Arg Cys Ala Pro His
        835                 840                 845

Leu Glu Trp Asn Pro Asp Leu His Cys Ser Cys Arg Asp Gly Glu Lys
    850                 855                 860

Cys Ala His His Ser His His Phe Ser Leu Asp Ile Asp Val Gly Cys
865                 870                 875                 880

Thr Asp Leu Asn Glu Asp Leu Gly Val Trp Val Ile Phe Lys Ile Lys
                885                 890                 895

Thr Gln Asp Gly His Ala Arg Leu Gly Asn Leu Glu Phe Leu Glu Glu
            900                 905                 910

Lys Pro Leu Leu Gly Glu Ala Leu Ala Arg Val Lys Arg Ala Glu Lys
        915                 920                 925

Lys Trp Arg Asp Lys Arg Glu Thr Leu Gln Leu Glu Thr Thr Ile Val
    930                 935                 940

Tyr Lys Glu Ala Lys Glu Ser Val Asp Ala Leu Phe Val Asn Ser Gln
945                 950                 955                 960

Tyr Asp Arg Leu Gln Ala Asp Thr Asn Ile Ala Met Ile His Ala Ala
                965                 970                 975
```

-continued

```
Asp Lys Arg Val His Arg Ile Arg Glu Ala Tyr Leu Pro Glu Leu Ser
            980                 985                 990

Val Ile Pro Gly Val Asn Ala Ala  Ile Phe Glu Glu Leu  Glu Glu Arg
        995                 1000                 1005

Ile Phe  Thr Ala Phe Ser Leu  Tyr Asp Ala Arg Asn  Ile Ile Lys
    1010                 1015                 1020

Asn Gly  Asp Phe Asn Asn Gly  Leu Leu Cys Trp Asn  Val Lys Gly
    1025                 1030                 1035

His Val  Glu Val Glu Glu Gln  Asn Asn His Arg Ser  Val Leu Val
    1040                 1045                 1050

Ile Pro  Glu Trp Glu Ala Glu  Val Ser Gln Glu Val  Arg Val Cys
    1055                 1060                 1065

Pro Gly  Arg Gly Tyr Ile Leu  Arg Val Thr Ala Tyr  Lys Glu Gly
    1070                 1075                 1080

Tyr Gly  Glu Gly Cys Val Thr  Ile His Glu Ile Glu  Asn Asn Thr
    1085                 1090                 1095

Asp Glu  Leu Lys Phe Asn Asn  Cys Val Glu Glu Glu  Val Tyr Pro
    1100                 1105                 1110

Asn Asn  Thr Val Thr Cys Ile  Asn Tyr Thr Ala Thr  Gln Glu Glu
    1115                 1120                 1125

Tyr Glu  Gly Thr Tyr Thr Ser  Arg Asn Arg Gly Tyr  Asp Glu Ala
    1130                 1135                 1140

Tyr Gly  Asn Asn Pro Ser Val  Pro Ala Asp Tyr Ala  Ser Val Tyr
    1145                 1150                 1155

Glu Glu  Lys Ser Tyr Thr Asp  Arg Arg Arg Glu Asn  Pro Cys Glu
    1160                 1165                 1170

Ser Asn  Arg Gly Tyr Gly Asp  Tyr Thr Pro Leu Pro  Ala Gly Tyr
    1175                 1180                 1185

Val Thr  Lys Glu Leu Glu Tyr  Phe Pro Glu Thr Asp  Lys Val Trp
    1190                 1195                 1200

Ile Glu  Ile Gly Glu Thr Glu  Gly Thr Phe Ile Val  Asp Ser Val
    1205                 1210                 1215

Glu Leu  Leu Leu Met Glu Glu
    1220                 1225


<210> SEQ ID NO 34
<211> LENGTH: 3726
<212> TYPE: DNA
<213> ORGANISM: Artificial
<220> FEATURE:
<223> OTHER INFORMATION: Recombinant nucleotide sequence used for
      expression in a bacterial cell encoding TIC868_11.

<400> SEQUENCE: 34

atgacttcaa ataggaaaaa tgagaatgaa attataaatg ctttatcgat tccagctgta      60

tcgaatcatt ccgcacaaat gaatctatca accgatgctc gtattgagga tagcttgtgt     120

atagccgagg ggaacaatat cgatccattt gttagcgcat caacagtcca aacgggtatt     180

aacatagctg gtagaatact aggtgtatta ggcgtaccgt ttgctggaca aatagctagt     240

ttttatagtt ttcttgttgg tgaattatgg ccccgcggca gagatccttg ggaaattttc     300

ctagaacatg tcgaacaact tataagacaa caagtaacag aaaatactag ggatacggct     360

cttgctcgat tacaaggttt aggaaattcc tttagagcct atcaacagtc acttgaagat     420

tggctagaaa accgtgatga tgcaagaacg agaagtgttc tttataccca atatatagcc     480

ttagaacttg atttcttaa tgcgatgccg cttttcgcaa ttagaaacca agaagttcca      540
```

-continued

```
ttattaatgg tatatgctca agctgcaaat ttacacctat tattattgag agatgcctct    600
ctttttggta gtgaatttgg gcttacatcc caagaaattc aacgttatta tgagcgccaa    660
gtggaaaaaa cgagagaata ttctgattat tgcgcaagat ggtataatac gggtttaaat    720
aatttgagag ggacaaatgc tgaaagttgg ttgcgatata atcaattccg tagagactta    780
acgctaggag tattagatct agtggcacta ttcccaagct atgacacgcg tgtttatcca    840
atgaatacca gtgctcaatt aacaagagaa atttatacag atccaattgg gagaacaaat    900
gcaccttcag gatttgcaag tacgaattgg tttaataata atgcaccatc gttttctgcc    960
atagaggctg ccgttattag gcctccgcat ctacttgatt ttccagaaca gcttacaatt   1020
ttcagcgtat taagtcgatg gagtaatact caatatatga attactgggt gggacataga   1080
cttgaatcgc gaacaataag gggtcatta agtacctcga cacacggaaa taccaatact    1140
tctattaatc ctgtaacatt acagttcaca tctcgagacg tttatagaac agaatcattt   1200
gcagggataa atatacttct aactactcct gtgaatggag taccttgggc tagatttaat   1260
tggagaaatc ccctgaattc tcttagaggt agccttctct atactatagg gtatactgga   1320
gtggggacac aactatttga ttcagaaact gaattaccac cagaaacaac agaacgacca   1380
aattatgaat cttacagtca tagattatct aatataagac taatatcagg aaacactttg   1440
agagcaccag tatattcttg gacgcaccgt agtgcagatc gtacaaatac cattagttca   1500
gatagcatta atcaaatacc tttagtgaaa ggatttagag tttggggggg cacctctgtc   1560
attacaggac caggatttac aggaggggat atccttcgaa gaaatacctt tggtgatttt   1620
gtatctctac aagtcaatat taattcacca attacccaaa gataccgttt aagatttcgt   1680
tacgcttcca gtagggatgc acgagttata gtattaacag gagcggcatc cacaggagtg   1740
ggaggccaag ttagtgtaaa tatgcctctt cagaaaacta tggaaatagg ggagaactta   1800
acatctagaa catttagata taccgatttt agtaatcctt tttcatttag agctaatcca   1860
gatataattg ggataagtga acaacctcta tttggtgcag gttctattag tagcggtgaa   1920
ctttatatag ataaaattga aattattcta gcagatgcaa caggaacgac aacctatgag   1980
tatgaagaga agcagaatct agaaaaagcg cagaaagcgt tgaacgcttt gtttacggat   2040
ggcacgaatg gctatctaca aatggatgcc actgattatg atatcaatca aactgcaaac   2100
ttaatagaat gtgtatcaga tgaattgtat gcaaaagaaa agatagtttt attagatgaa   2160
gtcaaatatg cgaagcggct tagcatatca cgtaacctac ttttgaacga tgatttagaa   2220
ttttcagatg gatttggaga aaacggatgg acgacaagtg ataatatttc aatccaggcg   2280
gataatcccc tttttaaggg gaattattta aaaatgtttg gggcaagaga tattgatgga   2340
accctatttc caacttatct ctatcaaaaa atagatgagt ccaggttaaa accatataca   2400
cgttatcgag taagagggtt tgtgggaagt agtaaaaatc taaaattagt ggtaacacgc   2460
tatgagaaag aaattgatgc cattatgaat gttccaaatg atttggcaca tatgcagctt   2520
aacccttcat gtggagatta tcgctgtgaa tcatcgtccc agtttttggt gaaccaagtg   2580
catcctacac caacagctgg atatgctctt gatatgtatg catgcccgtc aagttcagat   2640
aaaaaacata ttatgtgtca cgatcgtcat ccatttgatt ttcatattga caccggagaa   2700
ttaaatccaa acacaaacct gggtattgat gtcttgttta aaatttctaa tccaaatgga   2760
tacgctacat tagggaatct agaagtcatt gaagaaggac cactaacaga tgaagcattg   2820
gtacatgtaa aacaaaagga aaagaaatgg cgtcagcaca tggagaaaaa acgaatggaa   2880
```

-continued acacaacaag cctatgatcc agcaaaacaa gctgtagatg cattatttac aaatgaacaa 2940
gagttagact atcatactac tttagatcat attcagaacg ccgatcagct ggtacaggcg 3000
attccctatg tacaccatgc ttggttaccg gatgctccag gtatgaacta tgatgtatat 3060
caagggttaa acgcacgtat catgcaggcg tacaatttat atgatgcacg aaatgtcata 3120
ataaatggtg actttacaca aggactacaa ggatggcacg caacaggaaa agcagcggta 3180
caacaaatag atggagcttc agtattagtt ctatcaaact ggagtgccga ggtatctcag 3240
aatctgcatg cccaagatca tcatggatat atgttacgtg tgattgccaa aaaagaaggt 3300
cctggaaaag ggtatgtaat gatgatggat tttaatggaa agcaggaaac acttacgttc 3360
acttcttgtg aagaaggata tataacaaaa acaatagagg tattcccgga aagtgatcga 3420
atacgaattg aaatgggaga aacagagggt acgttttatg tagatagcat cgagttgctt 3480
tgtatgcaag gatatgctag cgataataac ccgcacacgg gtaatatgta tgagcaaagt 3540
tataatggaa attataatca aaatactagc gatgtgtatc accaaggata tataaacaac 3600
tataaccaaa attctagtag tatgtataat caaaattata ttaacaatga tgacctgcat 3660
tccggttgca catgtaacca agggcataac tctggctgta catgtaatca aggatataac 3720
cgttag 3726

<210> SEQ ID NO 35
<211> LENGTH: 3726
<212> TYPE: DNA
<213> ORGANISM: Artificial
<220> FEATURE:
<223> OTHER INFORMATION: Synthetic nucleotide sequence designed for
      expression in a plant cell encoding TIC868_11.

<400> SEQUENCE: 35
atgacgagca accggaagaa cgagaacgag atcatcaacg ccctctcgat ccctgctgtt 60
tcaaaccact ccgcgcagat gaacctgtcc accgacgcgc gcatcgagga ctccctctgc 120
atagccgagg gcaacaacat cgacccattc gtgtcggcca gcacggttca gaccggcatc 180
aacatcgcgg gccgtatcct cggcgtcctc ggtgtcccat tcgccggtca gatcgcgtcc 240
ttctactcgt tccttgtggg cgagctgtgg cctcgcggtc gtgacccgtg ggagatcttc 300
ctggagcatg tggagcagtt gatccggcag caagtcacgg agaacacccg cgatactgct 360
ctggccaggc tacagggcct gggaaactcc tttcgggcat accagcagtc actggaggac 420
tggttggaga acagggatga cgcgcgaaca cgctcggtac tctacaccca gtacatcgct 480
ctcgaactcg acttcctgaa cgctatgccg ctgttcgcca tcaggaacca ggaagttcca 540
ctccttatgg tgtacgccca ggccgccaac ttacatctgc tcctgctgcg ggacgccagc 600
ctgttcggct ccgagttcgg actcacatct caagaaatcc agcgttacta cgagcgccaa 660
gtggagaaga cccgtgagta cagtgactac tgcgctcgat ggtacaacac agggctcaac 720
aacctgcgcg gcaccaacgc tgagtcatgg ctccgttaca accagttccg ccgcgacttg 780
actttgggtg tcctagacct ggtggcgcta ttcccgtctt acgacacacg ggtgtaccca 840
atgaacacta gcgcgcaact cacgcgggag atctacacag acccaatcgg ccggacgaac 900
gcaccctccg gtttcgcatc cacgaattgg ttcaacaaca acgcaccctc cttctcggca 960
atcgaggccg ccgtcatccg ccctcctcac ctgctcgact ttcccgagca gctcacgatc 1020
ttctccgtgc tctcacgctg gtccaacaca cagtacatga actactgggt cgggcaccga 1080
ttggagagta ggacgatccg tggcagcttg agcaccagta cccacggcaa caccaacacc 1140

-continued

```
tccatcaacc cagttacgct acagttcacg agccgcgacg tttaccggac tgagtcgttc   1200
gcgggcatta acatccttct gacaacgccc gtcaacggcg tcccgtgggc ccggttcaac   1260
tggcgtaacc cgttgaactc cctgcgcggg tcattgctct acaccatcgg gtacacgggc   1320
gtcggcaccc agctcttcga cagtgaaact gagctgccgc ccgagaccac ggaacgcccg   1380
aactacgagt cctacagcca ccgcctgtcc aacatccggc tcatctctgg caacacgctg   1440
cgtgcgccgg tgtactcctg gacacaccgc agcgccgacc ggaccaacac gatctcttcc   1500
gactccatta accagatccc gctcgtgaag ggcttccgtg tgtggggtgg cacgagcgtc   1560
atcaccggtc cgggcttcac cggtggagac atactgcggc gcaacacttt cggcgacttc   1620
gtttcgttgc aagtgaacat caactcgccg atcacccagc gttaccgtct gaggttccgc   1680
tacgcttcaa gccgcgacgc gagggtcatt gtcctgaccg gagccgcgtc cacaggcgtg   1740
ggaggccaag tctcagtcaa catgcctctc cagaagacga tggagatagg cgagaacttg   1800
actagccgaa ccttccggta cactgatttc tcgaaccctt tctcattcag agcgaaccct   1860
gacatcattg ggatctccga gcaaccgctg ttcggtgctg gctccatcag ctctggcgaa   1920
ctgtacatcg acaagattga gatcatcctg gcggatgcga cggggactac cacctacgag   1980
tacgaggaga agcagaatct cgagaaggct cagaaggctc tgaacgctct gttcactgac   2040
gggaccaacg gctacctcca gatggacgcc actgactacg acatcaacca gacagctaac   2100
ctgattgagt gtgtgagtga cgaactgtac gctaaggaga agatcgtact cctggacgag   2160
gtgaagtacg ctaagcgcct gagcattagc cgtaacctgc tgctgaacga cgatctggag   2220
ttcagcgacg gctttggcga gaacggctgg accaccagcg acaacatctc catccaggcc   2280
gacaatccac tcttcaaagg caactacctc aagatgttcg gagccaggga catcgacggc   2340
accctctttc cgacctacct ctaccagaag atcgacgagt cccgcctcaa accctacacc   2400
cgctacaggg tgcgcggctt cgtgggcagc agcaagaacc tcaagctcgt ggtcacacgg   2460
tatgagaagg agatcgacgc catcatgaac gtgcccaacg atctcgccca catgcagctc   2520
aatccatcct gcggcgacta ccggtgcgag tccagctccc agttcctcgt gaaccaggtg   2580
caccctactc cgaccgctgg ctatgccctg gacatgtacg cctgccctag ttcctccgac   2640
aagaagcaca tcatgtgcca cgaccgtcat ccgttcgact tccacatcga caccggcgaa   2700
ctgaacccga acaccaacct gggcatcgac gtactgttca agatttccaa cccgaacggg   2760
tacgccacct tgggcaacct ggaggtcatc gaagaaggcc cgctgaccga cgaggccctg   2820
gtccacgtca aacagaagga gaagaagtgg cggcagcaca tggagaagaa gcggatggag   2880
actcaacaag cctacgaccc ggccaagcaa gctgtggacg ctctgttcac caacgagcaa   2940
gagcttgact accacactac tcttgaccac atccagaatg ctgaccagct tgtccaggct   3000
attccgtacg tccaccacgc ttggctaccg gacgctccag ggatgaacta cgatgtgtac   3060
cagggtctga acgcgcggat catgcaagcg tacaacctgt acgacgcgcg taacgtcatc   3120
atcaacggtg acttcactca gggtcttcaa ggttggcacg cgactggcaa agcggcagtc   3180
cagcagattg atggtgcgtc tgttcttgtg ttgagcaact ggtctgcgga ggtttctcag   3240
aacctgcacg cacaggatca ccacggctac atgctgaggg tgattgctaa gaaggagggc   3300
cctggcaaag gctacgtcat gatgatggac ttcaacggaa agcaagaaac cctgaccttc   3360
actagctgtg aggagggcta catcactaag accattgagg tctttccgga gtctgaccgc   3420
atccggatcg agatgggcga gaccgaaggc acgttctacg tggactccat cgaactcctc   3480
tgcatgcaag gctacgcctc cgacaacaac ccacacacgg gcaacatgta cgagcagtcc   3540
```

```
tacaacggga actacaacca gaacacctcc gatgtgtacc atcagggcta catcaacaac   3600

tacaaccaga acagcagcag catgtacaac cagaactaca tcaacaacga tgacttgcac   3660

tcgggttgca cctgcaacca gggtcacaac agtgggtgca cgtgcaacca gggatacaac   3720

cgttga                                                              3726


<210> SEQ ID NO 36
<211> LENGTH: 1241
<212> TYPE: PRT
<213> ORGANISM: Artificial
<220> FEATURE:
<223> OTHER INFORMATION: Amino acid sequence of the chimeric protein
      variant TIC868_11.

<400> SEQUENCE: 36

Met Thr Ser Asn Arg Lys Asn Glu Asn Glu Ile Ile Asn Ala Leu Ser
1               5                   10                  15

Ile Pro Ala Val Ser Asn His Ser Ala Gln Met Asn Leu Ser Thr Asp
            20                  25                  30

Ala Arg Ile Glu Asp Ser Leu Cys Ile Ala Glu Gly Asn Asn Ile Asp
        35                  40                  45

Pro Phe Val Ser Ala Ser Thr Val Gln Thr Gly Ile Asn Ile Ala Gly
    50                  55                  60

Arg Ile Leu Gly Val Leu Gly Val Pro Phe Ala Gly Gln Ile Ala Ser
65                  70                  75                  80

Phe Tyr Ser Phe Leu Val Gly Glu Leu Trp Pro Arg Gly Arg Asp Pro
                85                  90                  95

Trp Glu Ile Phe Leu Glu His Val Glu Gln Leu Ile Arg Gln Gln Val
            100                 105                 110

Thr Glu Asn Thr Arg Asp Thr Ala Leu Ala Arg Leu Gln Gly Leu Gly
        115                 120                 125

Asn Ser Phe Arg Ala Tyr Gln Gln Ser Leu Glu Asp Trp Leu Glu Asn
    130                 135                 140

Arg Asp Asp Ala Arg Thr Arg Ser Val Leu Tyr Thr Gln Tyr Ile Ala
145                 150                 155                 160

Leu Glu Leu Asp Phe Leu Asn Ala Met Pro Leu Phe Ala Ile Arg Asn
                165                 170                 175

Gln Glu Val Pro Leu Leu Met Val Tyr Ala Gln Ala Ala Asn Leu His
            180                 185                 190

Leu Leu Leu Leu Arg Asp Ala Ser Leu Phe Gly Ser Glu Phe Gly Leu
        195                 200                 205

Thr Ser Gln Glu Ile Gln Arg Tyr Tyr Glu Arg Gln Val Glu Lys Thr
    210                 215                 220

Arg Glu Tyr Ser Asp Tyr Cys Ala Arg Trp Tyr Asn Thr Gly Leu Asn
225                 230                 235                 240

Asn Leu Arg Gly Thr Asn Ala Glu Ser Trp Leu Arg Tyr Asn Gln Phe
                245                 250                 255

Arg Arg Asp Leu Thr Leu Gly Val Leu Asp Leu Val Ala Leu Phe Pro
            260                 265                 270

Ser Tyr Asp Thr Arg Val Tyr Pro Met Asn Thr Ser Ala Gln Leu Thr
        275                 280                 285

Arg Glu Ile Tyr Thr Asp Pro Ile Gly Arg Thr Asn Ala Pro Ser Gly
    290                 295                 300

Phe Ala Ser Thr Asn Trp Phe Asn Asn Asn Ala Pro Ser Phe Ser Ala
305                 310                 315                 320
```

-continued

```
Ile Glu Ala Ala Val Ile Arg Pro Pro His Leu Leu Asp Phe Pro Glu
                325                 330                 335

Gln Leu Thr Ile Phe Ser Val Leu Ser Arg Trp Ser Asn Thr Gln Tyr
            340                 345                 350

Met Asn Tyr Trp Val Gly His Arg Leu Glu Ser Arg Thr Ile Arg Gly
        355                 360                 365

Ser Leu Ser Thr Ser Thr His Gly Asn Thr Asn Thr Ser Ile Asn Pro
    370                 375                 380

Val Thr Leu Gln Phe Thr Ser Arg Asp Val Tyr Arg Thr Glu Ser Phe
385                 390                 395                 400

Ala Gly Ile Asn Ile Leu Leu Thr Thr Pro Val Asn Gly Val Pro Trp
                405                 410                 415

Ala Arg Phe Asn Trp Arg Asn Pro Leu Asn Ser Leu Arg Gly Ser Leu
            420                 425                 430

Leu Tyr Thr Ile Gly Tyr Thr Gly Val Gly Thr Gln Leu Phe Asp Ser
        435                 440                 445

Glu Thr Glu Leu Pro Pro Glu Thr Thr Glu Arg Pro Asn Tyr Glu Ser
    450                 455                 460

Tyr Ser His Arg Leu Ser Asn Ile Arg Leu Ile Ser Gly Asn Thr Leu
465                 470                 475                 480

Arg Ala Pro Val Tyr Ser Trp Thr His Arg Ser Ala Asp Arg Thr Asn
                485                 490                 495

Thr Ile Ser Ser Asp Ser Ile Asn Gln Ile Pro Leu Val Lys Gly Phe
            500                 505                 510

Arg Val Trp Gly Gly Thr Ser Val Ile Thr Gly Pro Gly Phe Thr Gly
        515                 520                 525

Gly Asp Ile Leu Arg Arg Asn Thr Phe Gly Asp Phe Val Ser Leu Gln
    530                 535                 540

Val Asn Ile Asn Ser Pro Ile Thr Gln Arg Tyr Arg Leu Arg Phe Arg
545                 550                 555                 560

Tyr Ala Ser Ser Arg Asp Ala Arg Val Ile Val Leu Thr Gly Ala Ala
                565                 570                 575

Ser Thr Gly Val Gly Gly Gln Val Ser Val Asn Met Pro Leu Gln Lys
            580                 585                 590

Thr Met Glu Ile Gly Glu Asn Leu Thr Ser Arg Thr Phe Arg Tyr Thr
        595                 600                 605

Asp Phe Ser Asn Pro Phe Ser Phe Arg Ala Asn Pro Asp Ile Ile Gly
    610                 615                 620

Ile Ser Glu Gln Pro Leu Phe Gly Ala Gly Ser Ile Ser Ser Gly Glu
625                 630                 635                 640

Leu Tyr Ile Asp Lys Ile Glu Ile Ile Leu Ala Asp Ala Thr Gly Thr
                645                 650                 655

Thr Thr Tyr Glu Tyr Glu Glu Lys Gln Asn Leu Glu Lys Ala Gln Lys
            660                 665                 670

Ala Leu Asn Ala Leu Phe Thr Asp Gly Thr Asn Gly Tyr Leu Gln Met
        675                 680                 685

Asp Ala Thr Asp Tyr Asp Ile Asn Gln Thr Ala Asn Leu Ile Glu Cys
    690                 695                 700

Val Ser Asp Glu Leu Tyr Ala Lys Glu Lys Ile Val Leu Leu Asp Glu
705                 710                 715                 720

Val Lys Tyr Ala Lys Arg Leu Ser Ile Ser Arg Asn Leu Leu Leu Asn
                725                 730                 735
```

-continued

```
Asp Asp Leu Glu Phe Ser Asp Gly Phe Gly Glu Asn Gly Trp Thr Thr
            740                 745                 750

Ser Asp Asn Ile Ser Ile Gln Ala Asp Asn Pro Leu Phe Lys Gly Asn
        755                 760                 765

Tyr Leu Lys Met Phe Gly Ala Arg Asp Ile Asp Gly Thr Leu Phe Pro
    770                 775                 780

Thr Tyr Leu Tyr Gln Lys Ile Asp Glu Ser Arg Leu Lys Pro Tyr Thr
785                 790                 795                 800

Arg Tyr Arg Val Arg Gly Phe Val Gly Ser Ser Lys Asn Leu Lys Leu
                805                 810                 815

Val Val Thr Arg Tyr Glu Lys Glu Ile Asp Ala Ile Met Asn Val Pro
            820                 825                 830

Asn Asp Leu Ala His Met Gln Leu Asn Pro Ser Cys Gly Asp Tyr Arg
        835                 840                 845

Cys Glu Ser Ser Ser Gln Phe Leu Val Asn Gln Val His Pro Thr Pro
    850                 855                 860

Thr Ala Gly Tyr Ala Leu Asp Met Tyr Ala Cys Pro Ser Ser Ser Asp
865                 870                 875                 880

Lys Lys His Ile Met Cys His Asp Arg His Pro Phe Asp Phe His Ile
                885                 890                 895

Asp Thr Gly Glu Leu Asn Pro Asn Thr Asn Leu Gly Ile Asp Val Leu
            900                 905                 910

Phe Lys Ile Ser Asn Pro Asn Gly Tyr Ala Thr Leu Gly Asn Leu Glu
        915                 920                 925

Val Ile Glu Glu Gly Pro Leu Thr Asp Glu Ala Leu Val His Val Lys
    930                 935                 940

Gln Lys Glu Lys Lys Trp Arg Gln His Met Glu Lys Lys Arg Met Glu
945                 950                 955                 960

Thr Gln Gln Ala Tyr Asp Pro Ala Lys Gln Ala Val Asp Ala Leu Phe
                965                 970                 975

Thr Asn Glu Gln Glu Leu Asp Tyr His Thr Thr Leu Asp His Ile Gln
            980                 985                 990

Asn Ala Asp Gln Leu Val Gln Ala  Ile Pro Tyr Val His  His Ala Trp
        995                 1000                1005

Leu Pro  Asp Ala Pro Gly Met  Asn Tyr Asp Val Tyr  Gln Gly Leu
    1010                1015                1020

Asn Ala  Arg Ile Met Gln Ala  Tyr Asn Leu Tyr Asp  Ala Arg Asn
    1025                1030                1035

Val Ile  Ile Asn Gly Asp Phe  Thr Gln Gly Leu Gln  Gly Trp His
    1040                1045                1050

Ala Thr  Gly Lys Ala Ala Val  Gln Gln Ile Asp Gly  Ala Ser Val
    1055                1060                1065

Leu Val  Leu Ser Asn Trp Ser  Ala Glu Val Ser Gln  Asn Leu His
    1070                1075                1080

Ala Gln  Asp His His Gly Tyr  Met Leu Arg Val Ile  Ala Lys Lys
    1085                1090                1095

Glu Gly  Pro Gly Lys Gly Tyr  Val Met Met Met Asp  Phe Asn Gly
    1100                1105                1110

Lys Gln  Glu Thr Leu Thr Phe  Thr Ser Cys Glu Glu  Gly Tyr Ile
    1115                1120                1125

Thr Lys  Thr Ile Glu Val Phe  Pro Glu Ser Asp Arg  Ile Arg Ile
    1130                1135                1140

Glu Met  Gly Glu Thr Glu Gly  Thr Phe Tyr Val Asp  Ser Ile Glu
```

```
    1145                1150                1155

Leu Leu  Cys Met Gln Gly Tyr  Ala Ser Asp Asn Asn  Pro His Thr
    1160                1165                1170

Gly Asn  Met Tyr Glu Gln Ser  Tyr Asn Gly Asn Tyr  Asn Gln Asn
    1175                1180                1185

Thr Ser  Asp Val Tyr His Gln  Gly Tyr Ile Asn Asn  Tyr Asn Gln
    1190                1195                1200

Asn Ser  Ser Ser Met Tyr Asn  Gln Asn Tyr Ile Asn  Asn Asp Asp
    1205                1210                1215

Leu His  Ser Gly Cys Thr Cys  Asn Gln Gly His Asn  Ser Gly Cys
    1220                1225                1230

Thr Cys  Asn Gln Gly Tyr Asn  Arg
    1235                1240
```

```
<210> SEQ ID NO 37
<211> LENGTH: 3468
<212> TYPE: DNA
<213> ORGANISM: Artificial
<220> FEATURE:
<223> OTHER INFORMATION: Recombinant nucleotide sequence used for
      expression in a bacterial cell encoding TIC868_12.

<400> SEQUENCE: 37

atgacttcaa ataggaaaaa tgagaatgaa attataaatg ctttatcgat tccagctgta     60

tcgaatcatt ccgcacaaat gaatctatca accgatgctc gtattgagga tagcttgtgt    120

atagccgagg ggaacaatat cgatccattt gttagcgcat caacagtcca aacgggtatt    180

aacatagctg gtagaatact aggtgtatta ggcgtaccgt ttgctggaca aatagctagt    240

ttttatagtt ttcttgttgg tgaattatgg ccccgcggca gagatccttg ggaaattttc    300

ctagaacatg tcgaacaact tataagacaa caagtaacag aaaatactag ggatacggct    360

cttgctcgat tacaaggttt aggaaattcc tttagagcct atcaacagtc acttgaagat    420

tggctagaaa accgtgatga tgcaagaacg agaagtgttc tttataccca atatatagcc    480

ttagaacttg attttcttaa tgcgatgccg cttttcgcaa ttagaaacca agaagttcca    540

ttattaatgg tatatgctca agctgcaaat ttacacctat tattattgag agatgcctct    600

ctttttggta gtgaatttgg gcttacatcc caagaaattc aacgttatta tgagcgccaa    660

gtggaaaaaa cgagagaata ttctgattat tgcgcaagat ggtataatac gggtttaaat    720

aatttgagag ggacaaatgc tgaaagttgg ttgcgatata atcaattccg tagagactta    780

acgctaggag tattagatct agtggcacta ttcccaagct atgacacgcg tgtttatcca    840

atgaatacca gtgctcaatt aacaagagaa atttatacag atccaattgg gagaacaaat    900

gcaccttcag gatttgcaag tacgaattgg tttaataata atgcaccatc gttttctgcc    960

atagaggctg ccgttattag gcctccgcat ctacttgatt ttccagaaca gcttacaatt   1020

ttcagcgtat taagtcgatg gagtaatact caatatatga attactgggt gggacataga   1080

cttgaatcgc gaacaataag gggtcatta agtacctcga cacacggaaa taccaatact   1140

tctattaatc ctgtaacatt acagttcaca tctcgagacg tttatagaac agaatcattt   1200

gcagggataa atatacttct aactactcct gtgaatggag taccttgggc tagatttaat   1260

tggagaaatc ccctgaattc tcttagaggt agccttctct atactatagg gtatactgga   1320

gtggggacac aactatttga ttcagaaact gaattaccac cagaaacaac agaacgacca   1380

aattatgaat cttacagtca tagattatct aatataagac taatatcagg aaacactttg   1440
```

```
agagcaccag tatattcttg gacgcaccgt agtgcagatc gtacaaatac cattagttca   1500

gatagcatta atcaaatacc tttagtgaaa ggatttagag tttggggggg cacctctgtc   1560

attacaggac caggatttac aggaggggat atccttcgaa gaaatacctt tggtgatttt   1620

gtatctctac aagtcaatat taattcacca attacccaaa gataccgttt aagatttcgt   1680

tacgcttcca gtagggatgc acgagttata gtattaacag gagcggcatc cacaggagtg   1740

ggaggccaag ttagtgtaaa tatgcctctt cagaaaacta tggaaatagg ggagaactta   1800

acatctagaa catttagata taccgatttt agtaatcctt tttcatttag agctaatcca   1860

gatataattg ggataagtga acaacctcta tttggtgcag gttctattag tagcggtgaa   1920

ctttatatag ataaaattga aattattcta gcagatgcaa caaatccgac gcgagaggcg   1980

gaagaggatc tagaagcagc gaagaaagcg gtggcgagct tgtttacacg tacaagggac   2040

ggattacaag taaatgtgac agattatcaa gtcgatcaag cggcaaattt agtgtcatgc   2100

ttatcagatg aacaatatgg gcatgacaaa aagatgttat tggaagcggt aagagcggca   2160

aaacgcctca gccgagaacg caacttactt caggatccag attttaatac aatcaatagt   2220

acagaagaaa atggatggaa agcaagtaac ggcgttacta ttagcgaggg cggtccattc   2280

tataaaggcc gtgcgcttca gctagcaagc gcaagagaaa attacccaac atacatttat   2340

caaaaagtaa atgcatcaga gttaaagccg tatacacgtt atagactgga tgggttcgtg   2400

aagagtagtc aagatttaga aattgatctc attcaccatc ataaagtcca tctcgtgaaa   2460

aatgtaccag ataatttagt atccgatact tactcggatg gttcttgcag tggaatgaat   2520

cgatgtgagg aacaacagat ggtaaatgcg caactggaaa cagaacatca tcatccgatg   2580

gattgctgtg aagcggctca aacacatgag ttttcttcct atattaatac aggcgatcta   2640

aattcaagtg tagatcaagg catttgggtt gtattgaaag ttcgaacaac cgatggttat   2700

gcgacgctag gaaatcttga attggtagag gtcggaccgt tatcgggtga atctctagaa   2760

cgtgaacaaa gggataatgc gaaatggagt gcagagctag gaagaaagcg tgcagaaaca   2820

gatcgcgtgt atcaagatgc caaacaatcc atcaatcatt tatttgtgga ttatcaagat   2880

caacaattaa atccagaaat agggatggca gatattattg acgctcaaaa tcttgtcgca   2940

tcaatttcag atgtgtatag cgatgcagta ctgcaaatcc ctggaattaa ctatgagatt   3000

tacacagagc tatccaatcg cttacaacaa gcatcgtatc tgtatacgtc tcgaaatgcg   3060

gtgcaaaatg gggactttaa cagcggtcta gatagttgga atgcaacagg gggggctacg   3120

gtacaacagg atggcaatac gcatttctta gttctttctc attgggatgc acaagtttct   3180

caacaattta gagtgcagcc gaattgtaaa tatgtattac gtgtaacagc agagaaagta   3240

ggcggcggag acggatacgt gacaatccgg gatggtgctc atcatacaga aaagcttaca   3300

tttaatgcat gtgattatga tataaatggc acgtacgtga ctgataatac gtatctaaca   3360

aaagaagtgg tattctattc acatacagaa cacatgtggg tagaggtaag tgaaacagaa   3420

ggtgcatttc atatagatag tattgaattc gttgaaacag aaaagtag                3468
```

<210> SEQ ID NO 38
<211> LENGTH: 3468
<212> TYPE: DNA
<213> ORGANISM: Artificial
<220> FEATURE:
<223> OTHER INFORMATION: Synthetic nucleotide sequence designed for expression in a plant cell encoding TIC868_12.

<400> SEQUENCE: 38

-continued

```
atgacgagca accggaagaa cgagaacgag atcatcaacg ccctctcgat ccctgctgtt      60
tcaaaccact ccgcgcagat gaacctgtcc accgacgcgc gcatcgagga ctccctctgc     120
atagccgagg gcaacaacat cgacccattc gtgtcggcca gcacggttca gaccggcatc     180
aacatcgcgg gccgtatcct cggcgtcctc ggtgtcccat tcgccggtca gatcgcgtcc     240
ttctactcgt tccttgtggg cgagctgtgg cctcgcggtc gtgacccgtg ggagatcttc     300
ctggagcatg tggagcagtt gatccggcag caagtcacgg agaacacccg cgatactgct     360
ctggccaggc tacagggcct gggaaactcc tttcgggcat accagcagtc actggaggac     420
tggttggaga acagggatga cgcgcgaaca cgctcggtac tctacaccca gtacatcgct     480
ctcgaactcg acttcctgaa cgctatgccg ctgttcgcca tcaggaacca ggaagttcca     540
ctccttatgg tgtacgccca ggccgccaac ttacatctgc tcctgctgcg ggacgccagc     600
ctgttcggct ccgagttcgg actcacatct caagaaatcc agcgttacta cgagcgccaa     660
gtggagaaga cccgtgagta cagtgactac tgcgctcgat ggtacaacac agggctcaac     720
aacctgcgcg gcaccaacgc tgagtcatgg ctccgttaca accagttccg ccgcgacttg     780
actttgggtg tcctagacct ggtggcgcta ttcccgtctt acgacacacg ggtgtaccca     840
atgaacacta gcgcgcaact cacgcgggag atctacacag acccaatcgg ccggacgaac     900
gcaccctccg gtttcgcatc cacgaattgg ttcaacaaca acgcaccctc cttctcggca     960
atcgaggccg ccgtcatccg ccctcctcac ctgctcgact ttcccgagca gctcacgatc    1020
ttctccgtgc tctcacgctg gtccaacaca cagtacatga actactgggt cgggcaccga    1080
ttggagagta ggacgatccg tggcagcttg agcaccagta cccacggcaa caccaacacc    1140
tccatcaacc cagttacgct acagttcacg agccgcgacg tttaccggac tgagtcgttc    1200
gcgggcatta acatccttct gacaacgccc gtcaacggcg tcccgtgggc ccggttcaac    1260
tggcgtaacc cgttgaactc cctgcgcggg tcattgctct acaccatcgg gtacacgggc    1320
gtcggcaccc agctcttcga cagtgaaact gagctgccgc ccgagaccac ggaacgcccg    1380
aactacgagt cctacagcca ccgcctgtcc aacatccggc tcatctctgg caacacgctg    1440
cgtgcgccgg tgtactcctg gacacaccgc agcgccgacc ggaccaacac gatctcttcc    1500
gactccatta accagatccc gctcgtgaag ggcttccgtg tgtggggtgg cacgagcgtc    1560
atcaccggtc cgggcttcac cggtggagac atactgcggc gcaacacttt cggcgacttc    1620
gtttcgttgc aagtgaacat caactcgccg atcacccagc gttaccgtct gaggttccgc    1680
tacgcttcaa gccgcgacgc gagggtcatt gtcctgaccg gagccgcgtc cacaggcgtg    1740
ggaggccaag tctcagtcaa catgcctctc cagaagacga tggagatagg cgagaacttg    1800
actagccgaa ccttccggta cactgatttc tcgaaccctt tctcattcag agcgaaccct    1860
gacatcattg ggatctccga gcaaccgctg ttcggtgctg gctccatcag ctctggcgaa    1920
ctgtacatcg acaagattga gatcatcctg gcggatgcga cgaacccgac gcgggaagct    1980
gaggaagact tggaagccgc caagaaagcg gtcgccagcc tgtttactcg gacgcgggac    2040
gggctccaag tgaatgtgac ggactatcaa gtggatcagg ccgctaacct cgtgtcatgc    2100
ctgagcgacg agcagtacgg tcacgacaag aaaatgctgc tggaggccgt ccgggccgcc    2160
aagcggctgt ccagggagcg taacctgcta caagatcccg actttaacac gatcaacagc    2220
acagaggaga atggctggaa ggccagcaac ggagttacga taagcgaggg cggtccgttc    2280
tacaagggtc gtgccctcca gctcgcctct gcaagggaga actatccaac ctacatctat    2340
cagaaggtga acgcatccga gcttaagccc tacacacgct accgcctgga cgggttcgtt    2400
```

aagtccagtc aagacctaga gatagacctc atccaccacc acaaagtgca tctggtcaag 2460
aacgttcccg ataatctcgt gagcgatacc tactcagacg gctcatgctc tggcatgaac 2520
agatgtgagg agcaacagat ggttaatgct caactcgaaa ccgagcatca tcatcctatg 2580
gattgctgcg aggccgcgca gacccatgag ttcagctctt acatcaacac cggagacctc 2640
aacagtagcg tggatcaggg aatttgggtg gtgcttaaag tgcgtacaac cgacggctac 2700
gccaccctcg gcaaccttga gcttgtcgag gtcggaccac ttagcggcga gtccctggaa 2760
cgtgagcagc gggacaacgc caaatggagc gcagagctag ggcgcaaacg cgcggagacg 2820
gaccgggttt atcaggacgc gaagcagtcc atcaatcacc tcttcgtgga ttatcaggac 2880
cagcagctta atccagagat cggcatggcc gacatcatcg acgcccagaa cctagtagcg 2940
tcgatttccg atgtctattc cgacgccgtg cttcaaatac ctggcatcaa ctacgagatc 3000
tacacagagt tgtccaacag gctccagcaa gcgtcatacc tctacaccag ccgcaacgcc 3060
gtccagaatg gcgacttcaa ttccggacta gactcctgga acgccacggg cggagctacg 3120
gtgcaacaag acggcaacac ccacttcctc gtacttagcc actgggacgc tcaagtgagt 3180
cagcaattcc gggttcagcc gaactgcaag tacgtcctgc gcgtaacggc cgagaaggtt 3240
ggaggcggag acggctacgt taccatccgc gacggcgctc accacaccga gaaactgacg 3300
ttcaacgctt gtgactacga catcaacggc acttacgtga cggacaacac ctacctgacg 3360
aaggaggtgg tgttctattc tcacaccgag cacatgtggg ttgaggtcag cgagaccgag 3420
ggagccttcc acattgacag catcgagttc gtggagactg agaagtga 3468

<210> SEQ ID NO 39
<211> LENGTH: 1155
<212> TYPE: PRT
<213> ORGANISM: Artificial
<220> FEATURE:
<223> OTHER INFORMATION: Amino acid sequence of the chimeric protein variant TIC868_12.

<400> SEQUENCE: 39

Met Thr Ser Asn Arg Lys Asn Glu Asn Glu Ile Ile Asn Ala Leu Ser
1 5 10 15

Ile Pro Ala Val Ser Asn His Ser Ala Gln Met Asn Leu Ser Thr Asp
20 25 30

Ala Arg Ile Glu Asp Ser Leu Cys Ile Ala Glu Gly Asn Asn Ile Asp
35 40 45

Pro Phe Val Ser Ala Ser Thr Val Gln Thr Gly Ile Asn Ile Ala Gly
50 55 60

Arg Ile Leu Gly Val Leu Gly Val Pro Phe Ala Gly Gln Ile Ala Ser
65 70 75 80

Phe Tyr Ser Phe Leu Val Gly Glu Leu Trp Pro Arg Gly Arg Asp Pro
85 90 95

Trp Glu Ile Phe Leu Glu His Val Glu Gln Leu Ile Arg Gln Gln Val
100 105 110

Thr Glu Asn Thr Arg Asp Thr Ala Leu Ala Arg Leu Gln Gly Leu Gly
115 120 125

Asn Ser Phe Arg Ala Tyr Gln Gln Ser Leu Glu Asp Trp Leu Glu Asn
130 135 140

Arg Asp Asp Ala Arg Thr Arg Ser Val Leu Tyr Thr Gln Tyr Ile Ala
145 150 155 160

Leu Glu Leu Asp Phe Leu Asn Ala Met Pro Leu Phe Ala Ile Arg Asn

-continued

```
                165                 170                 175

Gln Glu Val Pro Leu Leu Met Val Tyr Ala Gln Ala Ala Asn Leu His
            180                 185                 190

Leu Leu Leu Leu Arg Asp Ala Ser Leu Phe Gly Ser Glu Phe Gly Leu
        195                 200                 205

Thr Ser Gln Glu Ile Gln Arg Tyr Tyr Glu Arg Gln Val Glu Lys Thr
    210                 215                 220

Arg Glu Tyr Ser Asp Tyr Cys Ala Arg Trp Tyr Asn Thr Gly Leu Asn
225                 230                 235                 240

Asn Leu Arg Gly Thr Asn Ala Glu Ser Trp Leu Arg Tyr Asn Gln Phe
                245                 250                 255

Arg Arg Asp Leu Thr Leu Gly Val Leu Asp Leu Val Ala Leu Phe Pro
            260                 265                 270

Ser Tyr Asp Thr Arg Val Tyr Pro Met Asn Thr Ser Ala Gln Leu Thr
        275                 280                 285

Arg Glu Ile Tyr Thr Asp Pro Ile Gly Arg Thr Asn Ala Pro Ser Gly
    290                 295                 300

Phe Ala Ser Thr Asn Trp Phe Asn Asn Asn Ala Pro Ser Phe Ser Ala
305                 310                 315                 320

Ile Glu Ala Ala Val Ile Arg Pro Pro His Leu Leu Asp Phe Pro Glu
                325                 330                 335

Gln Leu Thr Ile Phe Ser Val Leu Ser Arg Trp Ser Asn Thr Gln Tyr
            340                 345                 350

Met Asn Tyr Trp Val Gly His Arg Leu Glu Ser Arg Thr Ile Arg Gly
        355                 360                 365

Ser Leu Ser Thr Ser Thr His Gly Asn Thr Asn Thr Ser Ile Asn Pro
    370                 375                 380

Val Thr Leu Gln Phe Thr Ser Arg Asp Val Tyr Arg Thr Glu Ser Phe
385                 390                 395                 400

Ala Gly Ile Asn Ile Leu Leu Thr Thr Pro Val Asn Gly Val Pro Trp
                405                 410                 415

Ala Arg Phe Asn Trp Arg Asn Pro Leu Asn Ser Leu Arg Gly Ser Leu
            420                 425                 430

Leu Tyr Thr Ile Gly Tyr Thr Gly Val Gly Thr Gln Leu Phe Asp Ser
        435                 440                 445

Glu Thr Glu Leu Pro Pro Glu Thr Thr Glu Arg Pro Asn Tyr Glu Ser
    450                 455                 460

Tyr Ser His Arg Leu Ser Asn Ile Arg Leu Ile Ser Gly Asn Thr Leu
465                 470                 475                 480

Arg Ala Pro Val Tyr Ser Trp Thr His Arg Ser Ala Asp Arg Thr Asn
                485                 490                 495

Thr Ile Ser Ser Asp Ser Ile Asn Gln Ile Pro Leu Val Lys Gly Phe
            500                 505                 510

Arg Val Trp Gly Gly Thr Ser Val Ile Thr Gly Pro Gly Phe Thr Gly
        515                 520                 525

Gly Asp Ile Leu Arg Arg Asn Thr Phe Gly Asp Phe Val Ser Leu Gln
    530                 535                 540

Val Asn Ile Asn Ser Pro Ile Thr Gln Arg Tyr Arg Leu Arg Phe Arg
545                 550                 555                 560

Tyr Ala Ser Ser Arg Asp Ala Arg Val Ile Val Leu Thr Gly Ala Ala
                565                 570                 575

Ser Thr Gly Val Gly Gly Gln Val Ser Val Asn Met Pro Leu Gln Lys
            580                 585                 590
```

-continued

```
Thr Met Glu Ile Gly Glu Asn Leu Thr Ser Arg Thr Phe Arg Tyr Thr
        595                 600                 605

Asp Phe Ser Asn Pro Phe Ser Phe Arg Ala Asn Pro Asp Ile Ile Gly
    610                 615                 620

Ile Ser Glu Gln Pro Leu Phe Gly Ala Gly Ser Ile Ser Ser Gly Glu
625                 630                 635                 640

Leu Tyr Ile Asp Lys Ile Glu Ile Ile Leu Ala Asp Ala Thr Asn Pro
                645                 650                 655

Thr Arg Glu Ala Glu Glu Asp Leu Glu Ala Ala Lys Lys Ala Val Ala
            660                 665                 670

Ser Leu Phe Thr Arg Thr Arg Asp Gly Leu Gln Val Asn Val Thr Asp
        675                 680                 685

Tyr Gln Val Asp Gln Ala Ala Asn Leu Val Ser Cys Leu Ser Asp Glu
    690                 695                 700

Gln Tyr Gly His Asp Lys Lys Met Leu Leu Glu Ala Val Arg Ala Ala
705                 710                 715                 720

Lys Arg Leu Ser Arg Glu Arg Asn Leu Leu Gln Asp Pro Asp Phe Asn
                725                 730                 735

Thr Ile Asn Ser Thr Glu Glu Asn Gly Trp Lys Ala Ser Asn Gly Val
            740                 745                 750

Thr Ile Ser Glu Gly Gly Pro Phe Tyr Lys Gly Arg Ala Leu Gln Leu
        755                 760                 765

Ala Ser Ala Arg Glu Asn Tyr Pro Thr Tyr Ile Tyr Gln Lys Val Asn
    770                 775                 780

Ala Ser Glu Leu Lys Pro Tyr Thr Arg Tyr Arg Leu Asp Gly Phe Val
785                 790                 795                 800

Lys Ser Ser Gln Asp Leu Glu Ile Asp Leu Ile His His His Lys Val
                805                 810                 815

His Leu Val Lys Asn Val Pro Asp Asn Leu Val Ser Asp Thr Tyr Ser
            820                 825                 830

Asp Gly Ser Cys Ser Gly Met Asn Arg Cys Glu Glu Gln Gln Met Val
        835                 840                 845

Asn Ala Gln Leu Glu Thr Glu His His His Pro Met Asp Cys Cys Glu
    850                 855                 860

Ala Ala Gln Thr His Glu Phe Ser Ser Tyr Ile Asn Thr Gly Asp Leu
865                 870                 875                 880

Asn Ser Ser Val Asp Gln Gly Ile Trp Val Val Leu Lys Val Arg Thr
                885                 890                 895

Thr Asp Gly Tyr Ala Thr Leu Gly Asn Leu Glu Leu Val Glu Val Gly
            900                 905                 910

Pro Leu Ser Gly Glu Ser Leu Glu Arg Glu Gln Arg Asp Asn Ala Lys
        915                 920                 925

Trp Ser Ala Glu Leu Gly Arg Lys Arg Ala Glu Thr Asp Arg Val Tyr
    930                 935                 940

Gln Asp Ala Lys Gln Ser Ile Asn His Leu Phe Val Asp Tyr Gln Asp
945                 950                 955                 960

Gln Gln Leu Asn Pro Glu Ile Gly Met Ala Asp Ile Ile Asp Ala Gln
                965                 970                 975

Asn Leu Val Ala Ser Ile Ser Asp Val Tyr Ser Asp Ala Val Leu Gln
            980                 985                 990

Ile Pro Gly Ile Asn Tyr Glu Ile  Tyr Thr Glu Leu Ser  Asn Arg Leu
        995                 1000                1005
```

```
Gln Gln  Ala Ser Tyr Leu Tyr  Thr Ser Arg Asn Ala  Val Gln Asn
    1010                 1015                 1020

Gly Asp  Phe Asn Ser Gly Leu  Asp Ser Trp Asn Ala  Thr Gly Gly
    1025                 1030                 1035

Ala Thr  Val Gln Gln Asp Gly  Asn Thr His Phe Leu  Val Leu Ser
    1040                 1045                 1050

His Trp  Asp Ala Gln Val Ser  Gln Gln Phe Arg Val  Gln Pro Asn
    1055                 1060                 1065

Cys Lys  Tyr Val Leu Arg Val  Thr Ala Glu Lys Val  Gly Gly Gly
    1070                 1075                 1080

Asp Gly  Tyr Val Thr Ile Arg  Asp Gly Ala His His  Thr Glu Lys
    1085                 1090                 1095

Leu Thr  Phe Asn Ala Cys Asp  Tyr Asp Ile Asn Gly  Thr Tyr Val
    1100                 1105                 1110

Thr Asp  Asn Thr Tyr Leu Thr  Lys Glu Val Val Phe  Tyr Ser His
    1115                 1120                 1125

Thr Glu  His Met Trp Val Glu  Val Ser Glu Thr Glu  Gly Ala Phe
    1130                 1135                 1140

His Ile  Asp Ser Ile Glu Phe  Val Glu Thr Glu Lys
    1145                 1150                 1155


<210> SEQ ID NO 40
<211> LENGTH: 3732
<212> TYPE: DNA
<213> ORGANISM: Artificial
<220> FEATURE:
<223> OTHER INFORMATION: Synthetic nucleotide sequence designed for
      expression in a plant cell encoding TIC868_13.

<400> SEQUENCE: 40

atgacgagca accggaagaa cgagaacgag atcatcaacg ccctctcgat ccctgctgtt     60

tcaaaccact ccgcgcagat gaacctgtcc accgacgcgc gcatcgagga ctccctctgc    120

atagccgagg gcaacaacat cgacccattc gtgtcggcca gcacggttca gaccggcatc    180

aacatcgcgg gccgtatcct cggcgtcctc ggtgtcccat tcgccggtca gatcgcgtcc    240

ttctactcgt tccttgtggg cgagctgtgg cctcgcggtc gtgacccgtg ggagatcttc    300

ctggagcatg tggagcagtt gatccggcag caagtcacgg agaacacccg cgatactgct    360

ctggccaggc tacagggcct gggaaactcc tttcgggcat accagcagtc actggaggac    420

tggttggaga acagggatga cgcgcgaaca cgctcggtac tctacaccca gtacatcgct    480

ctcgaactcg acttcctgaa cgctatgccg ctgttcgcca tcaggaacca ggaagttcca    540

ctccttatgg tgtacgccca ggccgccaac ttacatctgc tcctgctgcg ggacgccagc    600

ctgttcggct ccgagttcgg actcacatct caagaaatcc agcgttacta cgagcgccaa    660

gtggagaaga cccgtgagta cagtgactac tgcgctcgat ggtacaacac agggctcaac    720

aacctgcgcg gcaccaacgc tgagtcatgg ctccgttaca accagttccg ccgcgacttg    780

actttgggtg tcctagacct ggtggcgcta ttcccgtctt acgacacacg ggtgtaccca    840

atgaacacta gcgcgcaact cacgcgggag atctacacag acccaatcgg ccggacgaac    900

gcaccctccg gtttcgcatc cacgaattgg ttcaacaaca acgcaccctc cttctcggca    960

atcgaggccg ccgtcatccg ccctcctcac ctgctcgact ttcccgagca gctcacgatc   1020

ttctccgtgc tctcacgctg gtccaacaca cagtacatga actactgggt cgggcaccga   1080

ttggagagta ggacgatccg tggcagcttg agcaccagta cccacggcaa caccaacacc   1140
```

-continued tccatcaacc cagttacgct acagttcacg agccgcgacg tttaccggac tgagtcgttc 1200
gcgggcatta acatccttct gacaacgccc gtcaacggcg tcccgtgggc ccggttcaac 1260
tggcgtaacc cgttgaactc cctgcgcggg tcattgctct acaccatcgg gtacacgggc 1320
gtcggcaccc agctcttcga cagtgaaact gagctgccgc ccgagaccac ggaacgcccg 1380
aactacgagt cctacagcca ccgcctgtcc aacatccggc tcatctctgg caacacgctg 1440
cgtgcgccgg tgtactcctg gacacaccgc agcgccgacc ggaccaacac gatctcttcc 1500
gactccatta accagatccc gctcgtgaag ggcttccgtg tgtggggtgg cacgagcgtc 1560
atcaccggtc cgggcttcac cggtggagac atactgcggc gcaacacttt cggcgacttc 1620
gtttcgttgc aagtgaacat caactcgccg atcacccagc gttaccgtct gaggttccgc 1680
tacgcttcaa gccgcgacgc gagggtcatt gtcctgaccg gagccgcgtc cacaggcgtg 1740
ggaggccaag tctcagtcaa catgcctctc cagaagacga tggagatagg cgagaacttg 1800
actagccgaa ccttccggta cactgatttc tcgaaccctt tctcattcag agcgaaccct 1860
gacatcattg ggatctccga gcaaccgctg ttcggtgctg gctccatcag ctctggcgaa 1920
ctgtacatcg acaagattga gatcatcctg gcggatgcga cgacggcgac cttcgaggcg 1980
gagtatgact tggagcgggc tcaggaggcc gtcaacgcgc tgttcacaaa caccaatcct 2040
cgccgcctca agacgggtgt gactgattac cacattgacg aggtctccaa cttggtcgcg 2100
tgtctgtccg atgagttctg cctggacgag aagcgggaac tgctggagaa ggtcaagtac 2160
gccaagcgcc tctccgacga aaggaacctc ctccaagatc ccaactttac ttccattaac 2220
aagcagccgg acttcatctc caccaacgag cagtccaact tcacctcaat ccacgagcag 2280
tcggagcacg ggtggtgggg cagcgagaac atcaccatcc aagagggcaa cgacgtcttc 2340
aaggagaact acgtgatcct gcccggcacc ttcaacgagt gttacccgac ctatctctac 2400
cagaagattg gcgaagcgga actcaaggct tacacccgtt accaactgag tggctacatt 2460
gaggactcac aagacctgga aatctacctg atccgctaca acgccaagca cgagaccctc 2520
gacgtgcctg gcacggagtc cgtctggccc ttgagcgtgg agtctcctat cggtcgttgc 2580
ggcgagccca atcgctgcgc tccgcacttt gagtggaatc ctgatttgga ttgctcctgc 2640
cgagacggtg agaaatgcgc ccaccactcg caccacttca gcctagacat cgacgtgggc 2700
tgcatcgacc tgcacgagaa cttgggcgtc tgggtcgtgt tcaagatcaa gacacaggag 2760
ggccatgctc ggcttgggaa cctggagttc atcgaggaga agccactgct gggtgaagcc 2820
ttgtcacggg tgaaacgcgc cgagaagaag tggcgggaca aacgggagaa gctccagttg 2880
gagacaaagc gtgtgtacac agaggccaag gaggccgtgg atgccttgtt cgtggacagt 2940
cagtacgaca ggctgcaagc ggacaccaac atcgggatga tccacgcggc tgataagctt 3000
gttcacagaa tccgcgaggc gtacctgtca gagcttagcg tgatcccagg cgtcaacgcc 3060
gaaatcttcg aggaactgga gggccgcatt atcacggcaa tctcacttta tgacgcgagg 3120
aatgtggtca agaacggtga cttcaacaac ggcttggcgt gttggaacgt taaagggcac 3180
gtggatgtac aacagtcaca ccacagaagt gtcttggtca tcccggagtg ggaggcggaa 3240
gtgagccagg ccgtccgggt ctgccctggg cgcggttaca tcctccgcgt gacagcgtac 3300
aaggagggct acggtgaggg ctgcgtgacg atccacgaga ttgagaacaa cacggacgag 3360
cttaagttca agaactgcga ggaggaggaa gtgtacccga cagacaccgg cacctgcaac 3420
gactacaccg cccaccaagg gaccgccgcc tgcaacagcc gcaacgcggg ctatgaagat 3480
gcgtacgagg ttgataccac cgcctcagtg aactacaaac cgacttatga ggaggagaca 3540

```
tacacggacg tcaggcgcga caaccattgt gagtacgacc gtggctacgt gaactatccg   3600

ccggtgccag cgggctacat gacgaaggag ctagaatact tccctgagac ggacaaggtg   3660

tggattgaaa tcggcgagac cgagggcaag tttatcgtgg attctgtcga gctgctgcta   3720

atggaggagt ag                                                       3732


<210> SEQ ID NO 41
<211> LENGTH: 1243
<212> TYPE: PRT
<213> ORGANISM: Artificial
<220> FEATURE:
<223> OTHER INFORMATION: Amino acid sequence of the chimeric protein
      variant TIC868_13.

<400> SEQUENCE: 41

Met Thr Ser Asn Arg Lys Asn Glu Asn Glu Ile Ile Asn Ala Leu Ser
1               5                   10                  15

Ile Pro Ala Val Ser Asn His Ser Ala Gln Met Asn Leu Ser Thr Asp
            20                  25                  30

Ala Arg Ile Glu Asp Ser Leu Cys Ile Ala Glu Gly Asn Asn Ile Asp
        35                  40                  45

Pro Phe Val Ser Ala Ser Thr Val Gln Thr Gly Ile Asn Ile Ala Gly
    50                  55                  60

Arg Ile Leu Gly Val Leu Gly Val Pro Phe Ala Gly Gln Ile Ala Ser
65                  70                  75                  80

Phe Tyr Ser Phe Leu Val Gly Glu Leu Trp Pro Arg Gly Arg Asp Pro
                85                  90                  95

Trp Glu Ile Phe Leu Glu His Val Glu Gln Leu Ile Arg Gln Gln Val
            100                 105                 110

Thr Glu Asn Thr Arg Asp Thr Ala Leu Ala Arg Leu Gln Gly Leu Gly
        115                 120                 125

Asn Ser Phe Arg Ala Tyr Gln Gln Ser Leu Glu Asp Trp Leu Glu Asn
    130                 135                 140

Arg Asp Asp Ala Arg Thr Arg Ser Val Leu Tyr Thr Gln Tyr Ile Ala
145                 150                 155                 160

Leu Glu Leu Asp Phe Leu Asn Ala Met Pro Leu Phe Ala Ile Arg Asn
                165                 170                 175

Gln Glu Val Pro Leu Leu Met Val Tyr Ala Gln Ala Ala Asn Leu His
            180                 185                 190

Leu Leu Leu Leu Arg Asp Ala Ser Leu Phe Gly Ser Glu Phe Gly Leu
        195                 200                 205

Thr Ser Gln Glu Ile Gln Arg Tyr Tyr Glu Arg Gln Val Glu Lys Thr
    210                 215                 220

Arg Glu Tyr Ser Asp Tyr Cys Ala Arg Trp Tyr Asn Thr Gly Leu Asn
225                 230                 235                 240

Asn Leu Arg Gly Thr Asn Ala Glu Ser Trp Leu Arg Tyr Asn Gln Phe
                245                 250                 255

Arg Arg Asp Leu Thr Leu Gly Val Leu Asp Leu Val Ala Leu Phe Pro
            260                 265                 270

Ser Tyr Asp Thr Arg Val Tyr Pro Met Asn Thr Ser Ala Gln Leu Thr
        275                 280                 285

Arg Glu Ile Tyr Thr Asp Pro Ile Gly Arg Thr Asn Ala Pro Ser Gly
    290                 295                 300

Phe Ala Ser Thr Asn Trp Phe Asn Asn Asn Ala Pro Ser Phe Ser Ala
305                 310                 315                 320
```

```
Ile Glu Ala Ala Val Ile Arg Pro Pro His Leu Leu Asp Phe Pro Glu
                325                 330                 335

Gln Leu Thr Ile Phe Ser Val Leu Ser Arg Trp Ser Asn Thr Gln Tyr
            340                 345                 350

Met Asn Tyr Trp Val Gly His Arg Leu Glu Ser Arg Thr Ile Arg Gly
        355                 360                 365

Ser Leu Ser Thr Ser Thr His Gly Asn Thr Asn Thr Ser Ile Asn Pro
    370                 375                 380

Val Thr Leu Gln Phe Thr Ser Arg Asp Val Tyr Arg Thr Glu Ser Phe
385                 390                 395                 400

Ala Gly Ile Asn Ile Leu Leu Thr Thr Pro Val Asn Gly Val Pro Trp
                405                 410                 415

Ala Arg Phe Asn Trp Arg Asn Pro Leu Asn Ser Leu Arg Gly Ser Leu
            420                 425                 430

Leu Tyr Thr Ile Gly Tyr Thr Gly Val Gly Thr Gln Leu Phe Asp Ser
        435                 440                 445

Glu Thr Glu Leu Pro Pro Glu Thr Thr Glu Arg Pro Asn Tyr Glu Ser
    450                 455                 460

Tyr Ser His Arg Leu Ser Asn Ile Arg Leu Ile Ser Gly Asn Thr Leu
465                 470                 475                 480

Arg Ala Pro Val Tyr Ser Trp Thr His Arg Ser Ala Asp Arg Thr Asn
                485                 490                 495

Thr Ile Ser Ser Asp Ser Ile Asn Gln Ile Pro Leu Val Lys Gly Phe
            500                 505                 510

Arg Val Trp Gly Gly Thr Ser Val Ile Thr Gly Pro Gly Phe Thr Gly
        515                 520                 525

Gly Asp Ile Leu Arg Arg Asn Thr Phe Gly Asp Phe Val Ser Leu Gln
    530                 535                 540

Val Asn Ile Asn Ser Pro Ile Thr Gln Arg Tyr Arg Leu Arg Phe Arg
545                 550                 555                 560

Tyr Ala Ser Ser Arg Asp Ala Arg Val Ile Val Leu Thr Gly Ala Ala
                565                 570                 575

Ser Thr Gly Val Gly Gly Gln Val Ser Val Asn Met Pro Leu Gln Lys
            580                 585                 590

Thr Met Glu Ile Gly Glu Asn Leu Thr Ser Arg Thr Phe Arg Tyr Thr
        595                 600                 605

Asp Phe Ser Asn Pro Phe Ser Phe Arg Ala Asn Pro Asp Ile Ile Gly
    610                 615                 620

Ile Ser Glu Gln Pro Leu Phe Gly Ala Gly Ser Ile Ser Ser Gly Glu
625                 630                 635                 640

Leu Tyr Ile Asp Lys Ile Glu Ile Ile Leu Ala Asp Ala Thr Thr Ala
                645                 650                 655

Thr Phe Glu Ala Glu Tyr Asp Leu Glu Arg Ala Gln Glu Ala Val Asn
            660                 665                 670

Ala Leu Phe Thr Asn Thr Asn Pro Arg Arg Leu Lys Thr Gly Val Thr
        675                 680                 685

Asp Tyr His Ile Asp Glu Val Ser Asn Leu Val Ala Cys Leu Ser Asp
    690                 695                 700

Glu Phe Cys Leu Asp Glu Lys Arg Glu Leu Leu Glu Lys Val Lys Tyr
705                 710                 715                 720

Ala Lys Arg Leu Ser Asp Glu Arg Asn Leu Leu Gln Asp Pro Asn Phe
                725                 730                 735
```

-continued

```
Thr Ser Ile Asn Lys Gln Pro Asp Phe Ile Ser Thr Asn Glu Gln Ser
            740                 745                 750

Asn Phe Thr Ser Ile His Glu Gln Ser Glu His Gly Trp Trp Gly Ser
        755                 760                 765

Glu Asn Ile Thr Ile Gln Glu Gly Asn Asp Val Phe Lys Glu Asn Tyr
    770                 775                 780

Val Ile Leu Pro Gly Thr Phe Asn Glu Cys Tyr Pro Thr Tyr Leu Tyr
785                 790                 795                 800

Gln Lys Ile Gly Glu Ala Glu Leu Lys Ala Tyr Thr Arg Tyr Gln Leu
                805                 810                 815

Ser Gly Tyr Ile Glu Asp Ser Gln Asp Leu Glu Ile Tyr Leu Ile Arg
            820                 825                 830

Tyr Asn Ala Lys His Glu Thr Leu Asp Val Pro Gly Thr Glu Ser Val
        835                 840                 845

Trp Pro Leu Ser Val Glu Ser Pro Ile Gly Arg Cys Gly Glu Pro Asn
    850                 855                 860

Arg Cys Ala Pro His Phe Glu Trp Asn Pro Asp Leu Asp Cys Ser Cys
865                 870                 875                 880

Arg Asp Gly Glu Lys Cys Ala His His Ser His His Phe Ser Leu Asp
                885                 890                 895

Ile Asp Val Gly Cys Ile Asp Leu His Glu Asn Leu Gly Val Trp Val
            900                 905                 910

Val Phe Lys Ile Lys Thr Gln Glu Gly His Ala Arg Leu Gly Asn Leu
        915                 920                 925

Glu Phe Ile Glu Glu Lys Pro Leu Leu Gly Glu Ala Leu Ser Arg Val
    930                 935                 940

Lys Arg Ala Glu Lys Lys Trp Arg Asp Lys Arg Glu Lys Leu Gln Leu
945                 950                 955                 960

Glu Thr Lys Arg Val Tyr Thr Glu Ala Lys Glu Ala Val Asp Ala Leu
                965                 970                 975

Phe Val Asp Ser Gln Tyr Asp Arg Leu Gln Ala Asp Thr Asn Ile Gly
            980                 985                 990

Met Ile His Ala Ala Asp Lys Leu  Val His Arg Ile Arg  Glu Ala Tyr
        995                 1000                 1005

Leu Ser  Glu Leu Ser Val Ile  Pro Gly Val Asn Ala  Glu Ile Phe
    1010                 1015                 1020

Glu Glu  Leu Glu Gly Arg Ile  Ile Thr Ala Ile Ser  Leu Tyr Asp
    1025                 1030                 1035

Ala Arg  Asn Val Val Lys Asn  Gly Asp Phe Asn Asn  Gly Leu Ala
    1040                 1045                 1050

Cys Trp  Asn Val Lys Gly His  Val Asp Val Gln Gln  Ser His His
    1055                 1060                 1065

Arg Ser  Val Leu Val Ile Pro  Glu Trp Glu Ala Glu  Val Ser Gln
    1070                 1075                 1080

Ala Val  Arg Val Cys Pro Gly  Arg Gly Tyr Ile Leu  Arg Val Thr
    1085                 1090                 1095

Ala Tyr  Lys Glu Gly Tyr Gly  Glu Gly Cys Val Thr  Ile His Glu
    1100                 1105                 1110

Ile Glu  Asn Asn Thr Asp Glu  Leu Lys Phe Lys Asn  Cys Glu Glu
    1115                 1120                 1125

Glu Glu  Val Tyr Pro Thr Asp  Thr Gly Thr Cys Asn  Asp Tyr Thr
    1130                 1135                 1140

Ala His  Gln Gly Thr Ala Ala  Cys Asn Ser Arg Asn  Ala Gly Tyr
```

```
    1145                1150                1155

Glu Asp  Ala Tyr Glu Val Asp  Thr Thr Ala Ser Val  Asn Tyr Lys
    1160                1165                1170

Pro Thr  Tyr Glu Glu Glu Thr  Tyr Thr Asp Val Arg  Arg Asp Asn
    1175                1180                1185

His Cys  Glu Tyr Asp Arg Gly  Tyr Val Asn Tyr Pro  Pro Val Pro
    1190                1195                1200

Ala Gly  Tyr Met Thr Lys Glu  Leu Glu Tyr Phe Pro  Glu Thr Asp
    1205                1210                1215

Lys Val  Trp Ile Glu Ile Gly  Glu Thr Glu Gly Lys  Phe Ile Val
    1220                1225                1230

Asp Ser  Val Glu Leu Leu Leu  Met Glu Glu
    1235                1240
```

<210> SEQ ID NO 42
<211> LENGTH: 3702
<212> TYPE: DNA
<213> ORGANISM: Artificial
<220> FEATURE:
<223> OTHER INFORMATION: Synthetic nucleotide sequence designed for expression in a plant cell encoding TIC868_14.

<400> SEQUENCE: 42

```
atgacgagca accggaagaa cgagaacgag atcatcaacg ccctctcgat ccctgctgtt     60

tcaaaccact ccgcgcagat gaacctgtcc accgacgcgc gcatcgagga ctccctctgc    120

atagccgagg gcaacaacat cgacccattc gtgtcggcca gcacggttca gaccggcatc    180

aacatcgcgg gccgtatcct cggcgtcctc ggtgtcccat tcgccggtca gatcgcgtcc    240

ttctactcgt tccttgtggg cgagctgtgg cctcgcggtc gtgacccgtg ggagatcttc    300

ctggagcatg tggagcagtt gatccggcag caagtcacgg agaacacccg cgatactgct    360

ctggccaggc tacagggcct gggaaactcc tttcgggcat accagcagtc actggaggac    420

tggttggaga acagggatga cgcgcgaaca cgctcggtac tctacaccca gtacatcgct    480

ctcgaactcg acttcctgaa cgctatgccg ctgttcgcca tcaggaacca ggaagttcca    540

ctccttatgg tgtacgccca ggccgccaac ttacatctgc tcctgctgcg ggacgccagc    600

ctgttcggct ccgagttcgg actcacatct caagaaatcc agcgttacta cgagcgccaa    660

gtggagaaga cccgtgagta cagtgactac tgcgctcgat ggtacaacac agggctcaac    720

aacctgcgcg gcaccaacgc tgagtcatgg ctccgttaca accagttccg ccgcgacttg    780

actttgggtg tcctagacct ggtggcgcta ttcccgtctt acgacacacg ggtgtaccca    840

atgaacacta gcgcgcaact cacgcgggag atctacacag acccaatcgg ccggacgaac    900

gcaccctccg gtttcgcatc cacgaattgg ttcaacaaca acgcaccctc cttctcggca    960

atcgaggccg ccgtcatccg ccctcctcac ctgctcgact ttcccgagca gctcacgatc   1020

ttctccgtgc tctcacgctg gtccaacaca cagtacatga actactgggt cgggcaccga   1080

ttggagagta ggacgatccg tggcagcttg agcaccagta cccacggcaa caccaacacc   1140

tccatcaacc cagttacgct acagttcacg agccgcgacg tttaccggac tgagtcgttc   1200

gcgggcatta acatccttct gacaacgccc gtcaacggcg tcccgtgggc ccggttcaac   1260

tggcgtaacc cgttgaactc cctgcgcggg tcattgctct acaccatcgg gtacacgggc   1320

gtcggcaccc agctcttcga cagtgaaact gagctgccgc ccgagaccac ggaacgcccg   1380

aactacgagt cctacagcca ccgcctgtcc aacatccggc tcatctctgg caacacgctg   1440
```

cgtgcgccgg tgtactcctg gacacaccgc agcgccgacc ggaccaacac gatctcttcc 1500
gactccatta accagatccc gctcgtgaag ggcttccgtg tgtggggtgg cacgagcgtc 1560
atcaccggtc cgggcttcac cggtggagac atactgcggc gcaacacttt cggcgacttc 1620
gtttcgttgc aagtgaacat caactcgccg atcacccagc gttaccgtct gaggttccgc 1680
tacgcttcaa gccgcgacgc gagggtcatt gtcctgaccg gagccgcgtc cacaggcgtg 1740
ggaggccaag tctcagtcaa catgcctctc cagaagacga tggagatagg cgagaacttg 1800
actagccgaa ccttccggta cactgatttc tcgaaccctt tctcattcag agcgaaccct 1860
gacatcattg ggatctccga gcaaccgctg ttcggtgctg gctccatcag ctctggcgaa 1920
ctgtacatcg acaagattga gatcatcctg gcggatgcga cgaccgcgac gtttgaagct 1980
gaatccgacc tcgagcgtgc gcgcaaggcg gtgaacgctc tgttcacgag caccaaccct 2040
cgtggcttga agacggatgt gacggactac cacatcgacc aagtctcgaa cctcgtggag 2100
tgcctgagcg acgagttctg tcttgacaag aagcgcgagc tgctggagga ggtgaagtac 2160
gccaagcgcc tctccgatga gcgcaacctg ctccaagatc ctaccttcac gtcgatttcc 2220
ggccaaaccg accgtggatg gatcggctcg actggcatct ccatccaggg cggcgacgac 2280
atcttcaagg agaactatgt tcggctgccg ggcacggtgg acgagtgtta cccgacgtac 2340
ctctaccaga agatagacga gagtcaactc aagtcctaca cgcggtatca gttacgtggc 2400
tacattgaag actcccagga cttggaaatc tatctcatac ggtacaacgc caagcacgag 2460
accttaagcg tgccgggaac ggagtcgccc tggccaagct ctggcgtgta cccttccggt 2520
aggtgcggcg agcccaaccg ctgtgcacct cgaatcgaat ggaacccgga ccttgactgc 2580
tcttgccggt acggcgagaa gtgcgtccat cattctcacc acttcagctt ggacattgac 2640
gtcggctgca ccgacctcaa tgaagacctc ggagtgtggg tcatcttcaa gatcaagaca 2700
caggacgggc acgcgaaact aggaaacctg gagttcatcg aggagaagcc actcctcggc 2760
aaggcacttt ccagggtcaa gcgggccgag aagaaatgga gggacaagta cgagaaactc 2820
cagctcgaaa caaagcgggt gtacacggag gcaaaggaat ccgtggacgc cctgttcgtg 2880
gactctcagt acgacaagct ccaggcgaac acaaacattg gcatcatcca cggtgcggac 2940
aagcaagtgc acaggatacg ggagccttac ctctcggagc tgccggtgat tccctcgatc 3000
aacgcggcga tcttcgagga actggagggc cacatcttca aggcgtattc tctgtacgac 3060
gcgcgtaacg tcatcaagaa cggcgacttc aacaatgggc tgtcctgctg gaacgttaaa 3120
ggccacgtcg atgtccagca gaaccaccat aggtcagtcc tggtgctgag cgagtgggag 3180
gcggaggtgt cccagaaggt gcgcgtgtgc ccggatcgcg gctacatctt gagggtgaca 3240
gcctacaagg agggctacgg cgagggctgt gtcacgatcc atgagttcga ggacaacacg 3300
gatgtcctga aattccgtaa cttcgtcgag gaggaggtct atcccaacaa caccgtgacc 3360
tgcaacgact acacgaccaa tcagtcggct gagggcagta ccgatgcctg caacagctac 3420
aaccgtggtt acgaagatgg atacgagaac cgctacgagc ccaatccttc ggctcccgtg 3480
aattacactc ccacgtacga ggagggcatg tacactgaca ctcagggcta caaccattgc 3540
gtcagcgacc gtggctaccg caaccacacg ccgctcccag cgggctacgt gacgctggag 3600
ctggaatact ttcccgagac agaacaagtg tggatagaga tcggcgagac cgagggcaca 3660
ttcatcgtgg gctctgtgga attgctcctc atggaggagt aa 3702

<210> SEQ ID NO 43
<211> LENGTH: 1200

```
<212> TYPE: PRT
<213> ORGANISM: Artificial
<220> FEATURE:
<223> OTHER INFORMATION: Amino acid sequence of the chimeric protein
      variant TIC868_14.

<400> SEQUENCE: 43

Met Thr Ser Asn Arg Lys Asn Glu Asn Glu Ile Ile Asn Ala Leu Ser
1               5                   10                  15

Ile Pro Ala Val Ser Asn His Ser Ala Gln Met Asn Leu Ser Thr Asp
            20                  25                  30

Ala Arg Ile Glu Asp Ser Leu Cys Ile Ala Glu Gly Asn Asn Ile Asp
        35                  40                  45

Pro Phe Val Ser Ala Ser Thr Val Gln Thr Gly Ile Asn Ile Ala Gly
    50                  55                  60

Arg Ile Leu Gly Val Leu Gly Val Pro Phe Ala Gly Gln Ile Ala Ser
65                  70                  75                  80

Phe Tyr Ser Phe Leu Val Gly Glu Leu Trp Pro Arg Gly Arg Asp Pro
                85                  90                  95

Trp Glu Ile Phe Leu Glu His Val Glu Gln Leu Ile Arg Gln Gln Val
            100                 105                 110

Thr Glu Asn Thr Arg Asp Thr Ala Leu Ala Arg Leu Gln Gly Leu Gly
        115                 120                 125

Asn Ser Phe Arg Ala Tyr Gln Gln Ser Leu Glu Asp Trp Leu Glu Asn
    130                 135                 140

Arg Asp Asp Ala Arg Thr Arg Ser Val Leu Tyr Thr Gln Tyr Ile Ala
145                 150                 155                 160

Leu Glu Leu Asp Phe Leu Asn Ala Met Pro Leu Phe Ala Ile Arg Asn
                165                 170                 175

Gln Glu Val Pro Leu Leu Met Val Tyr Ala Gln Ala Ala Asn Leu His
            180                 185                 190

Leu Leu Leu Leu Arg Asp Ala Ser Leu Phe Gly Ser Glu Phe Gly Leu
        195                 200                 205

Thr Ser Gln Glu Ile Gln Arg Tyr Tyr Glu Arg Gln Val Glu Lys Thr
    210                 215                 220

Arg Glu Tyr Ser Asp Tyr Cys Ala Arg Trp Tyr Asn Thr Gly Leu Asn
225                 230                 235                 240

Asn Leu Arg Gly Thr Asn Ala Glu Ser Trp Leu Arg Tyr Asn Gln Phe
                245                 250                 255

Arg Arg Asp Leu Thr Leu Gly Val Leu Asp Leu Val Ala Leu Phe Pro
            260                 265                 270

Ser Tyr Asp Thr Arg Val Tyr Pro Met Asn Thr Ser Ala Gln Leu Thr
        275                 280                 285

Arg Glu Ile Tyr Thr Asp Pro Ile Gly Arg Thr Asn Ala Pro Ser Gly
    290                 295                 300

Phe Ala Ser Thr Asn Trp Phe Asn Asn Asn Ala Pro Ser Phe Ser Ala
305                 310                 315                 320

Ile Glu Ala Ala Val Ile Arg Pro Pro His Leu Leu Asp Phe Pro Glu
                325                 330                 335

Gln Leu Thr Ile Phe Ser Val Leu Ser Arg Trp Ser Asn Thr Gln Tyr
            340                 345                 350

Met Asn Tyr Trp Val Gly His Arg Leu Glu Ser Arg Thr Ile Arg Gly
        355                 360                 365

Ser Leu Ser Thr Ser Thr His Gly Asn Thr Asn Thr Ser Ile Asn Pro
    370                 375                 380
```

-continued

Val Thr Leu Gln Phe Thr Ser Arg Asp Val Tyr Arg Thr Glu Ser Phe
385 390 395 400

Ala Gly Ile Asn Ile Leu Leu Thr Thr Pro Val Asn Gly Val Pro Trp
405 410 415

Ala Arg Phe Asn Trp Arg Asn Pro Leu Asn Ser Leu Arg Gly Ser Leu
420 425 430

Leu Tyr Thr Ile Gly Tyr Thr Gly Val Gly Thr Gln Leu Phe Asp Ser
435 440 445

Glu Thr Glu Leu Pro Pro Glu Thr Thr Glu Arg Pro Asn Tyr Glu Ser
450 455 460

Tyr Ser His Arg Leu Ser Asn Ile Arg Leu Ile Ser Gly Asn Thr Leu
465 470 475 480

Arg Ala Pro Val Tyr Ser Trp Thr His Arg Ser Ala Asp Arg Thr Asn
485 490 495

Thr Ile Ser Ser Asp Ser Ile Asn Gln Ile Pro Leu Val Lys Gly Phe
500 505 510

Arg Val Trp Gly Gly Thr Ser Val Ile Thr Gly Pro Gly Phe Thr Gly
515 520 525

Gly Asp Ile Leu Arg Arg Asn Thr Phe Gly Asp Phe Val Ser Leu Gln
530 535 540

Val Asn Ile Asn Ser Pro Ile Thr Gln Arg Tyr Arg Leu Arg Phe Arg
545 550 555 560

Tyr Ala Ser Ser Arg Asp Ala Arg Val Ile Val Leu Thr Gly Ala Ala
565 570 575

Ser Thr Gly Val Gly Gly Gln Val Ser Val Asn Met Pro Leu Gln Lys
580 585 590

Thr Met Glu Ile Gly Glu Asn Leu Thr Ser Arg Thr Phe Arg Tyr Thr
595 600 605

Asp Phe Ser Asn Pro Phe Ser Phe Arg Ala Asn Pro Asp Ile Ile Gly
610 615 620

Ile Ser Glu Gln Pro Leu Phe Gly Ala Gly Ser Ile Ser Ser Gly Glu
625 630 635 640

Leu Tyr Ile Asp Lys Ile Glu Ile Ile Leu Ala Asp Ala Thr Thr Ala
645 650 655

Thr Phe Glu Ala Glu Ser Asp Leu Glu Arg Ala Arg Lys Ala Val Asn
660 665 670

Ala Leu Phe Thr Ser Thr Asn Pro Arg Gly Leu Lys Thr Asp Val Thr
675 680 685

Asp Tyr His Ile Asp Gln Val Ser Asn Leu Val Glu Cys Leu Ser Asp
690 695 700

Glu Phe Cys Leu Asp Lys Lys Arg Glu Leu Leu Glu Glu Val Lys Tyr
705 710 715 720

Ala Lys Arg Leu Ser Asp Glu Arg Asn Leu Leu Gln Asp Pro Thr Phe
725 730 735

Thr Ser Ile Ser Gly Gln Thr Asp Arg Gly Trp Ile Gly Ser Thr Gly
740 745 750

Ile Ser Ile Gln Gly Gly Asp Asp Ile Phe Lys Glu Asn Tyr Val Arg
755 760 765

Leu Pro Gly Thr Val Asp Glu Cys Tyr Pro Thr Tyr Leu Tyr Gln Lys
770 775 780

Ile Asp Glu Ser Gln Leu Lys Ser Tyr Thr Arg Tyr Gln Leu Arg Gly
785 790 795 800

-continued

Tyr Ile Glu Asp Ser Gln Asp Leu Glu Ile Tyr Leu Ile Arg Tyr Asn
805 810 815

Ala Lys His Glu Thr Leu Ser Val Pro Gly Thr Glu Ser Pro Trp Pro
820 825 830

Ser Ser Gly Val Tyr Pro Ser Gly Arg Cys Gly Glu Pro Asn Arg Cys
835 840 845

Ala Pro Arg Ile Glu Trp Asn Pro Asp Leu Asp Cys Ser Cys Arg Tyr
850 855 860

Gly Glu Lys Cys Val His His Ser His His Phe Ser Leu Asp Ile Asp
865 870 875 880

Val Gly Cys Thr Asp Leu Asn Glu Asp Leu Gly Val Trp Val Ile Phe
885 890 895

Lys Ile Lys Thr Gln Asp Gly His Ala Lys Leu Gly Asn Leu Glu Phe
900 905 910

Ile Glu Glu Lys Pro Leu Leu Gly Lys Ala Leu Ser Arg Val Lys Arg
915 920 925

Ala Glu Lys Lys Trp Arg Asp Lys Tyr Glu Lys Leu Gln Leu Glu Thr
930 935 940

Lys Arg Val Tyr Thr Glu Ala Lys Glu Ser Val Asp Ala Leu Phe Val
945 950 955 960

Asp Ser Gln Tyr Asp Lys Leu Gln Ala Asn Thr Asn Ile Gly Ile Ile
965 970 975

His Gly Ala Asp Lys Gln Val His Arg Ile Arg Glu Pro Tyr Leu Ser
980 985 990

Glu Leu Pro Val Ile Pro Ser Ile Asn Ala Ala Ile Phe Glu Glu Leu
995 1000 1005

Glu Gly His Ile Phe Lys Ala Tyr Ser Leu Tyr Asp Ala Arg Asn
1010 1015 1020

Val Ile Lys Asn Gly Asp Phe Asn Asn Gly Leu Ser Cys Trp Asn
1025 1030 1035

Val Lys Gly His Val Asp Val Gln Gln Asn His His Arg Ser Val
1040 1045 1050

Leu Val Leu Ser Glu Trp Glu Ala Glu Val Ser Gln Lys Val Arg
1055 1060 1065

Val Cys Pro Asp Arg Gly Tyr Ile Leu Arg Val Thr Ala Tyr Lys
1070 1075 1080

Glu Gly Tyr Gly Glu Gly Cys Val Thr Ile His Glu Phe Glu Asp
1085 1090 1095

Asn Thr Asp Val Leu Lys Phe Arg Asn Phe Val Glu Glu Glu Val
1100 1105 1110

Tyr Pro Asn Asn Thr Val Thr Cys Asn Asp Tyr Thr Thr Asn Gln
1115 1120 1125

Ser Ala Glu Gly Ser Thr Asp Ala Cys Asn Ser Tyr Asn Arg Gly
1130 1135 1140

Tyr Glu Asp Gly Tyr Glu Asn Arg Tyr Glu Pro Asn Pro Ser Ala
1145 1150 1155

Pro Val Asn Tyr Thr Pro Thr Tyr Glu Glu Gly Met Tyr Thr Asp
1160 1165 1170

Thr Gln Gly Tyr Asn His Cys Val Ser Asp Arg Gly Tyr Arg Asn
1175 1180 1185

His Thr Pro Leu Pro Ala Gly Tyr Val Thr Leu Glu
1190 1195 1200

```
<210> SEQ ID NO 44
<211> LENGTH: 3687
<212> TYPE: DNA
<213> ORGANISM: Artificial
<220> FEATURE:
<223> OTHER INFORMATION: Synthetic nucleotide sequence designed for
      expression in a plant cell encoding TIC868_15.

<400> SEQUENCE: 44

atgacgagca accggaagaa cgagaacgag atcatcaacg ccctctcgat ccctgctgtt     60

tcaaaccact ccgcgcagat gaacctgtcc accgacgcgc gcatcgagga ctccctctgc    120

atagccgagg gcaacaacat cgacccattc gtgtcggcca gcacggttca gaccggcatc    180

aacatcgcgg gccgtatcct cggcgtcctc ggtgtcccat tcgccggtca gatcgcgtcc    240

ttctactcgt tccttgtggg cgagctgtgg cctcgcggtc gtgacccgtg ggagatcttc    300

ctggagcatg tggagcagtt gatccggcag caagtcacgg agaacacccg cgatactgct    360

ctggccaggc tacagggcct gggaaactcc tttcgggcat accagcagtc actggaggac    420

tggttggaga acagggatga cgcgcgaaca cgctcggtac tctacaccca gtacatcgct    480

ctcgaactcg acttcctgaa cgctatgccg ctgttcgcca tcaggaacca ggaagttcca    540

ctccttatgg tgtacgccca ggccgccaac ttacatctgc tcctgctgcg ggacgccagc    600

ctgttcggct ccgagttcgg actcacatct caagaaatcc agcgttacta cgagcgccaa    660

gtggagaaga cccgtgagta cagtgactac tgcgctcgat ggtacaacac agggctcaac    720

aacctgcgcg gcaccaacgc tgagtcatgg ctccgttaca accagttccg ccgcgacttg    780

actttgggtg tcctagacct ggtggcgcta ttcccgtctt acgacacacg ggtgtaccca    840

atgaacacta gcgcgcaact cacgcgggag atctacacag acccaatcgg ccggacgaac    900

gcaccctccg gtttcgcatc cacgaattgg ttcaacaaca acgcaccctc cttctcggca    960

atcgaggccg ccgtcatccg ccctcctcac ctgctcgact ttcccgagca gctcacgatc   1020

ttctccgtgc tctcacgctg gtccaacaca cagtacatga actactgggt cgggcaccga   1080

ttggagagta ggacgatccg tggcagcttg agcaccagta cccacggcaa caccaacacc   1140

tccatcaacc cagttacgct acagttcacg agccgcgacg tttaccggac tgagtcgttc   1200

gcgggcatta acatccttct gacaacgccc gtcaacggcg tcccgtgggc ccggttcaac   1260

tggcgtaacc cgttgaactc cctgcgcggg tcattgctct acaccatcgg gtacacgggc   1320

gtcggcaccc agctcttcga cagtgaaact gagctgccgc ccgagaccac ggaacgcccg   1380

aactacgagt cctacagcca ccgcctgtcc aacatccggc tcatctctgg caacacgctg   1440

cgtgcgccgg tgtactcctg gacacaccgc agcgccgacc ggaccaacac gatctcttcc   1500

gactccatta accagatccc gctcgtgaag ggcttccgtg tgtggggtgg cacgagcgtc   1560

atcaccggtc cgggcttcac cggtggagac atactgcggc gcaacacttt cggcgacttc   1620

gtttcgttgc aagtgaacat caactcgccg atcacccagc gttaccgtct gaggttccgc   1680

tacgcttcaa gccgcgacgc gagggtcatt gtcctgaccg gagccgcgtc cacaggcgtg   1740

ggaggccaag tctcagtcaa catgcctctc cagaagacga tggagatagg cgagaacttg   1800

actagccgaa ccttccggta cactgatttc tcgaaccctt tctcattcag agcgaaccct   1860

gacatcattg ggatctccga gcaaccgctg ttcggtgctg gctccatcag ctctggcgaa   1920

ctgtacatcg acaagattga gatcatcctg gcggatgcga cggatgctac ctttgaagca   1980

gagtccgact tggaacgtgc acagaaggca gtgaacgcac tcttcacctc aagcaaccag   2040

atcggattga agacagatgt gacagattac cacatcgacc aagtgagcaa cttggtggat   2100
```

```
tgcttgtcag atgagttctg cttggatgag aagcgtgaac tctccgagaa ggtgaagcac   2160
gcaaagcgtc tctcagatga acgtaatctc cttcaagacc ctaactttcg tggtatcaat   2220
cgtcagccag atcgtggatg gcgtggatca acagacatca ccatccaggg aggcgatgat   2280
gtgttcaagg agaactacgt gaccctccca ggaaccgtgg atgaatgcta cccaacctac   2340
ctctaccaga agatcgacga gtcaaagctc aaggcttaca cccgttatga actccgtggc   2400
tacatcgaag atagccagga tctcgaaatc tatctcatcc gttacaatgc taagcacgaa   2460
atcgtgaatg tgccaggaac cggctcactc tggccactct cagcacagtc accaatcggc   2520
aagtgcggcg aacccaatcg ctgcgctcct catctcgaat ggaatcccga tctcgactgc   2580
tcctgccgag acggcgagaa gtgtgcacat cactcacacc acttcaccct cgacatcgac   2640
gtgggctgca ccgacctcaa tgaagacctg ggcgtgtggg tgatcttcaa gatcaagacc   2700
caggacggcc acgcacgact gggcaatctg gagtttctgg aggagaagcc actgcttggc   2760
gaggcactgg cacgagtgaa acgagccgag aagaaatggc gagacaaacg tgagaagctg   2820
caactggaga ccaacatcgt gtacaaagag gccaaagagt cagttgacgc cctgtttgtc   2880
aatagccagt atgaccgact gcaagttgac accaacatcg ccatgatcca cgctgcggac   2940
aagcgcgtcc accgcatccg cgaggcttat ctgcccgagc tgagcgtcat tcccggcgtc   3000
aatgccgcga tcttcgagga gttagagggc cgcatcttca ccgcctacag cctctatgac   3060
gcccgcaatg tcattaagaa tggcgacttc aacaatggct tactatgctg gaatgtcaaa   3120
gggcacgttg acgtcgagga gcagaacaat caccgcagcg tcttagtcat acccgagtgg   3180
gaggccgaag tcagccagga agtccgcgtc tgtccagggc gcgggtacat cctgcgggtc   3240
accgcctaca aagagggata cggcgagggt tgtgtcacca tacacgagat agaggacaat   3300
accgacgaac tcaagttcag caattgtgtc gaggaggaag tctatcccaa caataccgta   3360
acctgcaaca actacaccgg aacccaggag gagtatgaag ggacgtacac ctcgcggaac   3420
cagggctatg acgaagccta tgggaacaac ccgtcggtgc ctgctgacta tgcgtcggtc   3480
tatgaggaga aatcgtacac ggacgggcgg cgggagaatc cgtgtgagtc gaatcgcggg   3540
tatggtgact acacgccgct accggcgggc tatgtaacga aagacctgga atacttcccg   3600
gagacggaca aagtatggat agagataggc gagacggagg gaacgttcat cgtggactcg   3660
gtagagctgc tgctcatgga ggagtga                                      3687
```

<210> SEQ ID NO 45
<211> LENGTH: 1228
<212> TYPE: PRT
<213> ORGANISM: Artificial
<220> FEATURE:
<223> OTHER INFORMATION: Amino acid sequence of the chimeric protein variant TIC868_15.

<400> SEQUENCE: 45

```
Met Thr Ser Asn Arg Lys Asn Glu Asn Glu Ile Ile Asn Ala Leu Ser
1               5                   10                  15

Ile Pro Ala Val Ser Asn His Ser Ala Gln Met Asn Leu Ser Thr Asp
            20                  25                  30

Ala Arg Ile Glu Asp Ser Leu Cys Ile Ala Glu Gly Asn Asn Ile Asp
        35                  40                  45

Pro Phe Val Ser Ala Ser Thr Val Gln Thr Gly Ile Asn Ile Ala Gly
    50                  55                  60

Arg Ile Leu Gly Val Leu Gly Val Pro Phe Ala Gly Gln Ile Ala Ser
```

-continued

```
65                  70                  75                  80

Phe Tyr Ser Phe Leu Val Gly Glu Leu Trp Pro Arg Gly Arg Asp Pro
                85                  90                  95

Trp Glu Ile Phe Leu Glu His Val Glu Gln Leu Ile Arg Gln Gln Val
            100                 105                 110

Thr Glu Asn Thr Arg Asp Thr Ala Leu Ala Arg Leu Gln Gly Leu Gly
        115                 120                 125

Asn Ser Phe Arg Ala Tyr Gln Gln Ser Leu Glu Asp Trp Leu Glu Asn
    130                 135                 140

Arg Asp Asp Ala Arg Thr Arg Ser Val Leu Tyr Thr Gln Tyr Ile Ala
145                 150                 155                 160

Leu Glu Leu Asp Phe Leu Asn Ala Met Pro Leu Phe Ala Ile Arg Asn
                165                 170                 175

Gln Glu Val Pro Leu Leu Met Val Tyr Ala Gln Ala Ala Asn Leu His
            180                 185                 190

Leu Leu Leu Leu Arg Asp Ala Ser Leu Phe Gly Ser Glu Phe Gly Leu
        195                 200                 205

Thr Ser Gln Glu Ile Gln Arg Tyr Tyr Glu Arg Gln Val Glu Lys Thr
    210                 215                 220

Arg Glu Tyr Ser Asp Tyr Cys Ala Arg Trp Tyr Asn Thr Gly Leu Asn
225                 230                 235                 240

Asn Leu Arg Gly Thr Asn Ala Glu Ser Trp Leu Arg Tyr Asn Gln Phe
                245                 250                 255

Arg Arg Asp Leu Thr Leu Gly Val Leu Asp Leu Val Ala Leu Phe Pro
            260                 265                 270

Ser Tyr Asp Thr Arg Val Tyr Pro Met Asn Thr Ser Ala Gln Leu Thr
        275                 280                 285

Arg Glu Ile Tyr Thr Asp Pro Ile Gly Arg Thr Asn Ala Pro Ser Gly
    290                 295                 300

Phe Ala Ser Thr Asn Trp Phe Asn Asn Asn Ala Pro Ser Phe Ser Ala
305                 310                 315                 320

Ile Glu Ala Ala Val Ile Arg Pro Pro His Leu Leu Asp Phe Pro Glu
                325                 330                 335

Gln Leu Thr Ile Phe Ser Val Leu Ser Arg Trp Ser Asn Thr Gln Tyr
            340                 345                 350

Met Asn Tyr Trp Val Gly His Arg Leu Glu Ser Arg Thr Ile Arg Gly
        355                 360                 365

Ser Leu Ser Thr Ser Thr His Gly Asn Thr Asn Thr Ser Ile Asn Pro
    370                 375                 380

Val Thr Leu Gln Phe Thr Ser Arg Asp Val Tyr Arg Thr Glu Ser Phe
385                 390                 395                 400

Ala Gly Ile Asn Ile Leu Leu Thr Thr Pro Val Asn Gly Val Pro Trp
                405                 410                 415

Ala Arg Phe Asn Trp Arg Asn Pro Leu Asn Ser Leu Arg Gly Ser Leu
            420                 425                 430

Leu Tyr Thr Ile Gly Tyr Thr Gly Val Gly Thr Gln Leu Phe Asp Ser
        435                 440                 445

Glu Thr Glu Leu Pro Pro Glu Thr Thr Glu Arg Pro Asn Tyr Glu Ser
    450                 455                 460

Tyr Ser His Arg Leu Ser Asn Ile Arg Leu Ile Ser Gly Asn Thr Leu
465                 470                 475                 480

Arg Ala Pro Val Tyr Ser Trp Thr His Arg Ser Ala Asp Arg Thr Asn
                485                 490                 495
```

```
Thr Ile Ser Ser Asp Ser Ile Asn Gln Ile Pro Leu Val Lys Gly Phe
            500                 505                 510

Arg Val Trp Gly Gly Thr Ser Val Ile Thr Gly Pro Gly Phe Thr Gly
        515                 520                 525

Gly Asp Ile Leu Arg Arg Asn Thr Phe Gly Asp Phe Val Ser Leu Gln
    530                 535                 540

Val Asn Ile Asn Ser Pro Ile Thr Gln Arg Tyr Arg Leu Arg Phe Arg
545                 550                 555                 560

Tyr Ala Ser Ser Arg Asp Ala Arg Val Ile Val Leu Thr Gly Ala Ala
                565                 570                 575

Ser Thr Gly Val Gly Gly Gln Val Ser Val Asn Met Pro Leu Gln Lys
            580                 585                 590

Thr Met Glu Ile Gly Glu Asn Leu Thr Ser Arg Thr Phe Arg Tyr Thr
        595                 600                 605

Asp Phe Ser Asn Pro Phe Ser Phe Arg Ala Asn Pro Asp Ile Ile Gly
    610                 615                 620

Ile Ser Glu Gln Pro Leu Phe Gly Ala Gly Ser Ile Ser Ser Gly Glu
625                 630                 635                 640

Leu Tyr Ile Asp Lys Ile Glu Ile Ile Leu Ala Asp Ala Thr Asp Ala
                645                 650                 655

Thr Phe Glu Ala Glu Ser Asp Leu Glu Arg Ala Gln Lys Ala Val Asn
            660                 665                 670

Ala Leu Phe Thr Ser Ser Asn Gln Ile Gly Leu Lys Thr Asp Val Thr
        675                 680                 685

Asp Tyr His Ile Asp Gln Val Ser Asn Leu Val Asp Cys Leu Ser Asp
    690                 695                 700

Glu Phe Cys Leu Asp Glu Lys Arg Glu Leu Ser Glu Lys Val Lys His
705                 710                 715                 720

Ala Lys Arg Leu Ser Asp Glu Arg Asn Leu Leu Gln Asp Pro Asn Phe
                725                 730                 735

Arg Gly Ile Asn Arg Gln Pro Asp Arg Gly Trp Arg Gly Ser Thr Asp
            740                 745                 750

Ile Thr Ile Gln Gly Gly Asp Asp Val Phe Lys Glu Asn Tyr Val Thr
        755                 760                 765

Leu Pro Gly Thr Val Asp Glu Cys Tyr Pro Thr Tyr Leu Tyr Gln Lys
    770                 775                 780

Ile Asp Glu Ser Lys Leu Lys Ala Tyr Thr Arg Tyr Glu Leu Arg Gly
785                 790                 795                 800

Tyr Ile Glu Asp Ser Gln Asp Leu Glu Ile Tyr Leu Ile Arg Tyr Asn
                805                 810                 815

Ala Lys His Glu Ile Val Asn Val Pro Gly Thr Gly Ser Leu Trp Pro
            820                 825                 830

Leu Ser Ala Gln Ser Pro Ile Gly Lys Cys Gly Glu Pro Asn Arg Cys
        835                 840                 845

Ala Pro His Leu Glu Trp Asn Pro Asp Leu Asp Cys Ser Cys Arg Asp
    850                 855                 860

Gly Glu Lys Cys Ala His His Ser His His Phe Thr Leu Asp Ile Asp
865                 870                 875                 880

Val Gly Cys Thr Asp Leu Asn Glu Asp Leu Gly Val Trp Val Ile Phe
                885                 890                 895

Lys Ile Lys Thr Gln Asp Gly His Ala Arg Leu Gly Asn Leu Glu Phe
            900                 905                 910
```

```
Leu Glu Glu Lys Pro Leu Leu Gly Glu Ala Leu Ala Arg Val Lys Arg
        915                 920                 925

Ala Glu Lys Lys Trp Arg Asp Lys Arg Glu Lys Leu Gln Leu Glu Thr
    930                 935                 940

Asn Ile Val Tyr Lys Glu Ala Lys Glu Ser Val Asp Ala Leu Phe Val
945                 950                 955                 960

Asn Ser Gln Tyr Asp Arg Leu Gln Val Asp Thr Asn Ile Ala Met Ile
                965                 970                 975

His Ala Ala Asp Lys Arg Val His Arg Ile Arg Glu Ala Tyr Leu Pro
            980                 985                 990

Glu Leu Ser Val Ile Pro Gly Val  Asn Ala Ala Ile Phe  Glu Glu Leu
        995                 1000                 1005

Glu Gly  Arg Ile Phe Thr Ala  Tyr Ser Leu Tyr Asp  Ala Arg Asn
    1010                 1015                 1020

Val Ile  Lys Asn Gly Asp Phe  Asn Asn Gly Leu Leu  Cys Trp Asn
    1025                 1030                 1035

Val Lys  Gly His Val Asp Val  Glu Glu Gln Asn Asn  His Arg Ser
    1040                 1045                 1050

Val Leu  Val Ile Pro Glu Trp  Glu Ala Glu Val Ser  Gln Glu Val
    1055                 1060                 1065

Arg Val  Cys Pro Gly Arg Gly  Tyr Ile Leu Arg Val  Thr Ala Tyr
    1070                 1075                 1080

Lys Glu  Gly Tyr Gly Glu Gly  Cys Val Thr Ile His  Glu Ile Glu
    1085                 1090                 1095

Asp Asn  Thr Asp Glu Leu Lys  Phe Ser Asn Cys Val  Glu Glu Glu
    1100                 1105                 1110

Val Tyr  Pro Asn Asn Thr Val  Thr Cys Asn Asn Tyr  Thr Gly Thr
    1115                 1120                 1125

Gln Glu  Glu Tyr Glu Gly Thr  Tyr Thr Ser Arg Asn  Gln Gly Tyr
    1130                 1135                 1140

Asp Glu  Ala Tyr Gly Asn Asn  Pro Ser Val Pro Ala  Asp Tyr Ala
    1145                 1150                 1155

Ser Val  Tyr Glu Glu Lys Ser  Tyr Thr Asp Gly Arg  Arg Glu Asn
    1160                 1165                 1170

Pro Cys  Glu Ser Asn Arg Gly  Tyr Gly Asp Tyr Thr  Pro Leu Pro
    1175                 1180                 1185

Ala Gly  Tyr Val Thr Lys Asp  Leu Glu Tyr Phe Pro  Glu Thr Asp
    1190                 1195                 1200

Lys Val  Trp Ile Glu Ile Gly  Glu Thr Glu Gly Thr  Phe Ile Val
    1205                 1210                 1215

Asp Ser  Val Glu Leu Leu Leu  Met Glu Glu
    1220                 1225
```

<210> SEQ ID NO 46
<211> LENGTH: 3600
<212> TYPE: DNA
<213> ORGANISM: Artificial
<220> FEATURE:
<223> OTHER INFORMATION: Synthetic nucleotide sequence designed for expression in a plant cell encoding TIC868_29.

<400> SEQUENCE: 46

```
atgacgagca accggaagaa cgagaacgag atcatcaacg ccctctcgat ccctgctgtt      60

tcaaaccact ccgcgcagat gaacctgtcc accgacgcgc gcatcgagga ctccctctgc     120

atagccgagg gcaacaacat cgacccattc gtgtcggcca gcacggttca gaccggcatc     180
```

```
aacatcgcgg gccgtatcct cggcgtcctc ggtgtcccat tcgccggtca gatcgcgtcc    240
ttctactcgt tccttgtggg cgagctgtgg cctcgcggtc gtgacccgtg ggagatcttc    300
ctggagcatg tggagcagtt gatccggcag caagtcacgg agaacacccg cgatactgct    360
ctggccaggc tacagggcct gggaaactcc tttcgggcat accagtactc actggaggac    420
tggttggaga acagggatga cgcgcgaaca cgctcggtac tctacaccca gtacatcgct    480
ctcgaactcg acttcctgaa cgctatgccg ctgttcgcca tcaggaacca ggaagttcca    540
ctccttatgg tgtacgccca ggccgccaac ttacatctgc tcctgctgcg ggacgccagc    600
ctgttcggct ccgagttcgg actcacatct caagaaatcc agcgttacta cgagcgccaa    660
gtggagaaga cccgtgagta cagtgactac tgcgctcgat ggtacaacac agggctcaac    720
aacctgcgcg gcaccaacgc tgagtcatgg ctccgttaca accagttccg ccgcgacttg    780
actttgggtg tcctagacct ggtggcgcta ttcccgtctt acgacacacg ggtgtaccca    840
atgaacacta gcgcgcaact cacgcgggag atctacacag acccaatcgg ccggacgaac    900
gcaccctccg gtttcgcatc cacgaattgg ttcaacaaca acgcaccctc cttctcggca    960
atcgaggccg ccgtcatccg ccctcctcac ctgctcgact ttcccgagca gctcacgatc   1020
ttctcccagc tctcacgctg gtcccacaca cagtacatga actactgggt cgggcaccga   1080
ttggagagta ggacgatccg tggcagcttg agcaccagta cccacggcaa caccaacacc   1140
tccatcaacc cagttacgct acagttcacg agccgcgacg tttaccggac tgagtcgttc   1200
gcgggcatta acatccttct gacaacgccc gtcaacggcg tcccgtgggc ccggttcaac   1260
tggcgtaacc cgttgaactc cctgcgcggg tcattgctct acaccatcgg gtacacgggc   1320
gtcggcaccc agctcttcga cagtgaaact gagctgccgc ccgagaccac ggaacgcccg   1380
aactacgagt cctacagcca ccgcctgtcc aacatccggc tcatctctgg caacacgctg   1440
cgtgcgccgg tgtactcctg gacacaccgc agcgccgacc ggaccaacac gatctcttcc   1500
gactccatta accagatccc gctcgtgaag ggcttccgtg tgtggggtgg cacgagcgtc   1560
atcaccggtc cgggcttcac cggtggagac atactgcggc gcaacacttt cggcgacttc   1620
gtttcgttgc aagtgaacat caactcgccg atcacccagc gttaccgtct gaggttccgc   1680
tacgcttcaa gccgcgacgc gagggtcatt gtcctgaccg gagccgcgtc cacaggcgtg   1740
ggaggccaag tctcagtcaa catgcctctc cagaagacga tggagatagg cgagaacttg   1800
actagccgaa ccttccggta cactgatttc tcgaaccctt tctcattcag agcgaaccct   1860
gacatcattg ggatctccga gcaaccgctg ttcggtgctg gctccatcag ctctggcgaa   1920
ctgtacatcg acaagattga gatcatcctg gcggatgcga cgttcgaggc cgagtctgac   1980
ctggagcggg ctcagaaggc tgtcaacgaa ctgttcacca gcagcaacca gattgggctc   2040
aagaccgacg tcacggacta tcacattgac caagtgtcca accttgtgga gtgcctgtcc   2100
gacgagttct gcctcgacga gaagaaggag ctgtccgaga aggtcaaaca cgcgaagcgt   2160
ctgagtgacg agcggaattt gctccaggac ccgaacttcc gtggcatcaa ccgccagctc   2220
gaccgtggtt ggcgcgggag tacagacatc accatccagg gaggcgacga tgtgttcaag   2280
gagaactatg tgacgctgct cgggactttc gacgaatgct acccgacgta tctctaccag   2340
aagatagacg agagtaaatt gaaggcgtac acccgctacc agcttcgcgg gtacatcgag   2400
gatagtcagg acctggaaat ctacctgatc cgatacaacg ccaagcacga gacagtgaac   2460
gtgccaggca cgggctcact ttggccattg agcgctccct ctccaatcgg aaagtgcgct   2520
```

```
caccactcgc accacttctc tctggacatc gacgtgggct gcaccgacct caacgaggac   2580

ctgggtgtct gggttatctt caagattaag acccaggacg gacatgcccg cctcggcaac   2640

ctggagttcc ttgaggagaa gcctctcgtg ggcgaggccc tcgctcgtgt gaagcgcgcc   2700

gagaagaaat ggcgagacaa gcgggagaag ctggagtggg agaccaacat cgtgtacaag   2760

gaggccaagg agtcagtgga cgcactcttc gtcaacagcc agtacgaccg cctccaggct   2820

gacaccaaca tcgccatgat ccacgcggct gacaagcggg tccacagcat ccgtgaggcg   2880

tacctgcccg agctgtcagt gatccctggt gtgaacgcgg cgatcttcga ggaactggag   2940

ggccgcatct tcacagcatt cagcctgtac gatgccagga atgttattaa gaacggtgac   3000

ttcaacaacg ggctgagttg ctggaacgtc aagggccatg tggacgtcga ggagcagaac   3060

aaccaccggt ccgtgctggt cgtgccggag tgggaggcag aggtgagcca ggaggtccgc   3120

gtctgccctg gtcgcggcta catcctccgt gtgactgcgt acaaggaagg ctacggtgaa   3180

ggctgcgtga ctatccacga gatcgagaac aacaccgacg agctcaagtt ctcgaactgt   3240

gtggaggagg aggtgtaccc gaacaacacc gttacttgca acgactacac tgccacgcaa   3300

gaggagtacg agggcactta cacttcccgg aatcgcggct atgatggcgc gtacgagtcc   3360

aacagcagcg tgcctgcgga ttatgcgtcc gcttacgagg agaaggcgta caccgacgga   3420

cggagggaca acccttgcga gtccaaccgt ggctacggtg actacactcc gctgcccgcc   3480

gggtacgtca ccaaggagct ggagtacttc ccggagaccg acaaagtctg gatcgagatc   3540

ggcgagacgg agggcacttt catcgtggac tcggtcgagc tgctactgat ggaggagtga   3600
```

<210> SEQ ID NO 47
<211> LENGTH: 1199
<212> TYPE: PRT
<213> ORGANISM: Artificial
<220> FEATURE:
<223> OTHER INFORMATION: Amino acid sequence of the chimeric protein variant TIC868_29.

<400> SEQUENCE: 47

```
Met Thr Ser Asn Arg Lys Asn Glu Asn Glu Ile Ile Asn Ala Leu Ser
1               5                   10                  15

Ile Pro Ala Val Ser Asn His Ser Ala Gln Met Asn Leu Ser Thr Asp
            20                  25                  30

Ala Arg Ile Glu Asp Ser Leu Cys Ile Ala Glu Gly Asn Asn Ile Asp
        35                  40                  45

Pro Phe Val Ser Ala Ser Thr Val Gln Thr Gly Ile Asn Ile Ala Gly
    50                  55                  60

Arg Ile Leu Gly Val Leu Gly Val Pro Phe Ala Gly Gln Ile Ala Ser
65                  70                  75                  80

Phe Tyr Ser Phe Leu Val Gly Glu Leu Trp Pro Arg Gly Arg Asp Pro
                85                  90                  95

Trp Glu Ile Phe Leu Glu His Val Glu Gln Leu Ile Arg Gln Gln Val
            100                 105                 110

Thr Glu Asn Thr Arg Asp Thr Ala Leu Ala Arg Leu Gln Gly Leu Gly
        115                 120                 125

Asn Ser Phe Arg Ala Tyr Gln Tyr Ser Leu Glu Asp Trp Leu Glu Asn
    130                 135                 140

Arg Asp Asp Ala Arg Thr Arg Ser Val Leu Tyr Thr Gln Tyr Ile Ala
145                 150                 155                 160

Leu Glu Leu Asp Phe Leu Asn Ala Met Pro Leu Phe Ala Ile Arg Asn
                165                 170                 175
```

-continued

```
Gln Glu Val Pro Leu Leu Met Val Tyr Ala Gln Ala Ala Asn Leu His
            180                 185                 190

Leu Leu Leu Leu Arg Asp Ala Ser Leu Phe Gly Ser Glu Phe Gly Leu
        195                 200                 205

Thr Ser Gln Glu Ile Gln Arg Tyr Tyr Glu Arg Gln Val Glu Lys Thr
    210                 215                 220

Arg Glu Tyr Ser Asp Tyr Cys Ala Arg Trp Tyr Asn Thr Gly Leu Asn
225                 230                 235                 240

Asn Leu Arg Gly Thr Asn Ala Glu Ser Trp Leu Arg Tyr Asn Gln Phe
                245                 250                 255

Arg Arg Asp Leu Thr Leu Gly Val Leu Asp Leu Val Ala Leu Phe Pro
            260                 265                 270

Ser Tyr Asp Thr Arg Val Tyr Pro Met Asn Thr Ser Ala Gln Leu Thr
        275                 280                 285

Arg Glu Ile Tyr Thr Asp Pro Ile Gly Arg Thr Asn Ala Pro Ser Gly
    290                 295                 300

Phe Ala Ser Thr Asn Trp Phe Asn Asn Asn Ala Pro Ser Phe Ser Ala
305                 310                 315                 320

Ile Glu Ala Ala Val Ile Arg Pro Pro His Leu Leu Asp Phe Pro Glu
                325                 330                 335

Gln Leu Thr Ile Phe Ser Gln Leu Ser Arg Trp Ser His Thr Gln Tyr
            340                 345                 350

Met Asn Tyr Trp Val Gly His Arg Leu Glu Ser Arg Thr Ile Arg Gly
        355                 360                 365

Ser Leu Ser Thr Ser Thr His Gly Asn Thr Asn Thr Ser Ile Asn Pro
    370                 375                 380

Val Thr Leu Gln Phe Thr Ser Arg Asp Val Tyr Arg Thr Glu Ser Phe
385                 390                 395                 400

Ala Gly Ile Asn Ile Leu Leu Thr Thr Pro Val Asn Gly Val Pro Trp
                405                 410                 415

Ala Arg Phe Asn Trp Arg Asn Pro Leu Asn Ser Leu Arg Gly Ser Leu
            420                 425                 430

Leu Tyr Thr Ile Gly Tyr Thr Gly Val Gly Thr Gln Leu Phe Asp Ser
        435                 440                 445

Glu Thr Glu Leu Pro Pro Glu Thr Thr Glu Arg Pro Asn Tyr Glu Ser
    450                 455                 460

Tyr Ser His Arg Leu Ser Asn Ile Arg Leu Ile Ser Gly Asn Thr Leu
465                 470                 475                 480

Arg Ala Pro Val Tyr Ser Trp Thr His Arg Ser Ala Asp Arg Thr Asn
                485                 490                 495

Thr Ile Ser Ser Asp Ser Ile Asn Gln Ile Pro Leu Val Lys Gly Phe
            500                 505                 510

Arg Val Trp Gly Gly Thr Ser Val Ile Thr Gly Pro Gly Phe Thr Gly
        515                 520                 525

Gly Asp Ile Leu Arg Arg Asn Thr Phe Gly Asp Phe Val Ser Leu Gln
    530                 535                 540

Val Asn Ile Asn Ser Pro Ile Thr Gln Arg Tyr Arg Leu Arg Phe Arg
545                 550                 555                 560

Tyr Ala Ser Ser Arg Asp Ala Arg Val Ile Val Leu Thr Gly Ala Ala
                565                 570                 575

Ser Thr Gly Val Gly Gly Gln Val Ser Val Asn Met Pro Leu Gln Lys
            580                 585                 590
```

-continued

```
Thr Met Glu Ile Gly Glu Asn Leu Thr Ser Arg Thr Phe Arg Tyr Thr
        595                 600                 605

Asp Phe Ser Asn Pro Phe Ser Phe Arg Ala Asn Pro Asp Ile Ile Gly
    610                 615                 620

Ile Ser Glu Gln Pro Leu Phe Gly Ala Gly Ser Ile Ser Ser Gly Glu
625                 630                 635                 640

Leu Tyr Ile Asp Lys Ile Glu Ile Ile Leu Ala Asp Ala Thr Phe Glu
                645                 650                 655

Ala Glu Ser Asp Leu Glu Arg Ala Gln Lys Ala Val Asn Glu Leu Phe
            660                 665                 670

Thr Ser Ser Asn Gln Ile Gly Leu Lys Thr Asp Val Thr Asp Tyr His
        675                 680                 685

Ile Asp Gln Val Ser Asn Leu Val Glu Cys Leu Ser Asp Glu Phe Cys
    690                 695                 700

Leu Asp Glu Lys Lys Glu Leu Ser Glu Lys Val Lys His Ala Lys Arg
705                 710                 715                 720

Leu Ser Asp Glu Arg Asn Leu Leu Gln Asp Pro Asn Phe Arg Gly Ile
                725                 730                 735

Asn Arg Gln Leu Asp Arg Gly Trp Arg Gly Ser Thr Asp Ile Thr Ile
            740                 745                 750

Gln Gly Gly Asp Asp Val Phe Lys Glu Asn Tyr Val Thr Leu Leu Gly
        755                 760                 765

Thr Phe Asp Glu Cys Tyr Pro Thr Tyr Leu Tyr Gln Lys Ile Asp Glu
    770                 775                 780

Ser Lys Leu Lys Ala Tyr Thr Arg Tyr Gln Leu Arg Gly Tyr Ile Glu
785                 790                 795                 800

Asp Ser Gln Asp Leu Glu Ile Tyr Leu Ile Arg Tyr Asn Ala Lys His
                805                 810                 815

Glu Thr Val Asn Val Pro Gly Thr Gly Ser Leu Trp Pro Leu Ser Ala
            820                 825                 830

Pro Ser Pro Ile Gly Lys Cys Ala His His Ser His His Phe Ser Leu
        835                 840                 845

Asp Ile Asp Val Gly Cys Thr Asp Leu Asn Glu Asp Leu Gly Val Trp
    850                 855                 860

Val Ile Phe Lys Ile Lys Thr Gln Asp Gly His Ala Arg Leu Gly Asn
865                 870                 875                 880

Leu Glu Phe Leu Glu Glu Lys Pro Leu Val Gly Glu Ala Leu Ala Arg
                885                 890                 895

Val Lys Arg Ala Glu Lys Lys Trp Arg Asp Lys Arg Glu Lys Leu Glu
            900                 905                 910

Trp Glu Thr Asn Ile Val Tyr Lys Glu Ala Lys Glu Ser Val Asp Ala
        915                 920                 925

Leu Phe Val Asn Ser Gln Tyr Asp Arg Leu Gln Ala Asp Thr Asn Ile
    930                 935                 940

Ala Met Ile His Ala Ala Asp Lys Arg Val His Ser Ile Arg Glu Ala
945                 950                 955                 960

Tyr Leu Pro Glu Leu Ser Val Ile Pro Gly Val Asn Ala Ala Ile Phe
                965                 970                 975

Glu Glu Leu Glu Gly Arg Ile Phe Thr Ala Phe Ser Leu Tyr Asp Ala
            980                 985                 990

Arg Asn Val Ile Lys Asn Gly Asp  Phe Asn Asn Gly Leu  Ser Cys Trp
        995                 1000                1005

Asn Val  Lys Gly His Val Asp  Val Glu Glu Gln Asn  Asn His Arg
```

```
    1010                1015                1020

Ser Val  Leu Val Val Pro Glu  Trp Glu Ala Glu Val  Ser Gln Glu
    1025                1030                1035

Val Arg  Val Cys Pro Gly Arg  Gly Tyr Ile Leu Arg  Val Thr Ala
    1040                1045                1050

Tyr Lys  Glu Gly Tyr Gly Glu  Gly Cys Val Thr Ile  His Glu Ile
    1055                1060                1065

Glu Asn  Asn Thr Asp Glu Leu  Lys Phe Ser Asn Cys  Val Glu Glu
    1070                1075                1080

Glu Val  Tyr Pro Asn Asn Thr  Val Thr Cys Asn Asp  Tyr Thr Ala
    1085                1090                1095

Thr Gln  Glu Glu Tyr Glu Gly  Thr Tyr Thr Ser Arg  Asn Arg Gly
    1100                1105                1110

Tyr Asp  Gly Ala Tyr Glu Ser  Asn Ser Ser Val Pro  Ala Asp Tyr
    1115                1120                1125

Ala Ser  Ala Tyr Glu Glu Lys  Ala Tyr Thr Asp Gly  Arg Arg Asp
    1130                1135                1140

Asn Pro  Cys Glu Ser Asn Arg  Gly Tyr Gly Asp Tyr  Thr Pro Leu
    1145                1150                1155

Pro Ala  Gly Tyr Val Thr Lys  Glu Leu Glu Tyr Phe  Pro Glu Thr
    1160                1165                1170

Asp Lys  Val Trp Ile Glu Ile  Gly Glu Thr Glu Gly  Thr Phe Ile
    1175                1180                1185

Val Asp  Ser Val Glu Leu Leu  Leu Met Glu Glu
    1190                1195
```

<210> SEQ ID NO 48
<211> LENGTH: 3432
<212> TYPE: DNA
<213> ORGANISM: Artificial
<220> FEATURE:
<223> OTHER INFORMATION: Recombinant nucleotide sequence used for expression in a bacterial cell encoding TIC869.

<400> SEQUENCE: 48

```
atggagataa ataatcagaa gcaatgcata ccatataatt gcttaagtaa tcctgaggaa     60

gtacttttgg atggggagag gatattacct gatatcgatc cactcgaagt ttctttgtcg    120

cttttgcaat ttcttttgaa taactttgtt ccagggggag gctttatttc aggattagtt    180

gataaaatat ggggggcttt gagaccatct gaatgggact tatttcttgc acagattgaa    240

cggttgattg atcaaagaat agaagcaaca gtaagagcaa aagcaatcac tgaattagaa    300

ggattaggga gaaattatca aatatacgct gaagcattta aagaatggga atcagatcct    360

gataacgaag cggctaaaag tagagtaatt gatcgctttc gtatacttga tggtctaatt    420

gaagcaaata tcccttcatt tcggataatt ggatttgaag tgccactttt atcggtttat    480

gttcaagcag ctaatctaca tctcgctcta ttgagagatt ctgttatttt tggagagaga    540

tggggattga cgacaaaaaa tgtcaatgat atctataata gacaaattag agaaattcat    600

gaatatagca atcattgcgt agatacgtat aacacagaac tagaacgtct agggtttaga    660

tctatagcgc agtggagaat atataatcag tttagaagag aactaacact aactgtatta    720

gatattgtcg ctcttttccc gaactatgac agtagactgt atccgatcca aacttttttct    780

caattgacaa gagaaattgt tacatcccca gtaagcgaat tttattatgg tgttattaat    840

agtggtaata taattggtac tcttactgaa cagcagataa ggcgaccaca tcttatggac    900
```

-continued

```
ttctttaact ccatgatcat gtatacatca gataatagac gggaacatta ttggtcagga    960
cttgaaatga cggcttattt tacaggattt gcaggagctc aagtgtcatt ccctttagtc   1020
gggactagag gggagtcagc tccaccatta actgttagaa gtgttaatga tggaatttat   1080
agaatattat cggcaccgtt ttattcagcg ccttttctag gcaccattgt attgggaagt   1140
cgtggagaaa aatttgattt tgcgcttaat aatatttcac ctccgccatc tacaatatac   1200
agacatcctg gaacagtaga ttcactagtc agtataccgc cacaggataa tagcgtacca   1260
ccgcacaggg gatctagtca tcgattaagt catgttacaa tgcgcgcaag ttcccctata   1320
ttccattgga cgcatcgcag cgcaaccact acaaatacaa ttaatccaaa tgctattatc   1380
caaataccac tagtaaaagc atttaacctt cattcaggtg ccactgttgt tagaggacca   1440
gggtttacag gtggagatct cttacgaaga acgaatactg gtacatttgc agacataaga   1500
gtcaatgttc cttcatcact attttcccaa agatatcgcg taaggattcg ttatgcttct   1560
actaccgatt tacaattttt cacgagaatt aatggaactt ctgttaatca aggtaatttc   1620
tcaaaaacga tggatagagg ggataaactg aaatctgaaa actttagaac tgccggattt   1680
agtactcctt ttagattttc aaattttcaa agtacattca cgttgggtac tcaggctttt   1740
tcaaatcagg aagtttatat agatagaatt gaatttgtcc cggcagaagt aacattcgag   1800
gcagaatctg atttagaaag agcacaaaag gcggtgaatg agctgtttac ttcttccaat   1860
caaatcgggt taaaaacaga tgtgacggat tatcatattg atcaagtatc caatttagtt   1920
gagtgtttat ctgatgaatt ttgtctggat gaaaaaaaag aattgtccga gaaagtcaaa   1980
catgcgaagc gacttagtga tgagcggaat ttacttcaag atccaaactt tagagggatc   2040
aatagacaac tagaccgtgg ctggagagga agtacggata ttaccatcca aggaggcgat   2100
gacgtattca aagagaatta cgttacgcta ttgggtacct ttgatgagtg ctatccaacg   2160
tatttatatc aaaaaataga tgagtcgaaa ttaaaagcct atacccgtta ccaattaaga   2220
gggtatatcg aagatagtca agacttagaa atctatttaa ttcgctacaa tgccaaacac   2280
gaaacagtaa atgtgccagg tacgggttcc ttatggccgc tttcagcccc aagtccaatc   2340
ggaaaatgtg cccatcattc ccatcatttc tccttggaca ttgatgttgg atgtacagac   2400
ttaaatgagg acttaggtgt atgggtgata ttcaagatta agacgcaaga tggccatgca   2460
agactaggaa atctagaatt tctcgaagag aaaccattag taggagaagc actagctcgt   2520
gtgaaaagag cggagaaaaa atggagagac aaacgtgaaa aattggaatg ggaaacaaat   2580
attgtttata aagaggcaaa agaatctgta gatgctttat ttgtaaactc tcaatatgat   2640
agattacaag cggataccaa catcgcgatg attcatgcgg cagataaacg cgttcatagc   2700
attcgagaag cttatctgcc tgagctgtct gtgattccgg gtgtcaatgc ggctattttt   2760
gaagaattag aagggcgtat tttcactgca ttctccctat atgatgcgag aaatgtcatt   2820
aaaaatggtg attttaataa tggcttatcc tgctggaacg tgaaagggca tgtagatgta   2880
gaagaacaaa acaaccaccg ttcggtcctt gttgttccgg aatgggaagc agaagtgtca   2940
caagaagttc gtgtctgtcc gggtcgtggc tatatccttc gtgtcacagc gtacaaggag   3000
ggatatggag aaggttgcgt aaccattcat gagatcgaga acaatacaga cgaactgaag   3060
tttagcaact gtgtagaaga ggaagtatat ccaaacaaca cggtaacgtg taatgattat   3120
actgcgactc aagaagaata tgagggtacg tacacttctc gtaatcgagg atatgacgga   3180
gcctatgaaa gcaattcttc tgtaccagct gattatgcat cagcctatga agaaaaagca   3240
tatacagatg gacgaagaga caatccttgt gaatctaaca gaggatatgg ggattacaca   3300
```

ccactaccag ctggctatgt gacaaaagaa ttagagtact tcccagaaac cgataaggta 3360
tggattgaga tcggagaaac ggaaggaaca ttcatcgtgg acagcgtgga attacttctt 3420
atggaggaat ag 3432

<210> SEQ ID NO 49
<211> LENGTH: 3432
<212> TYPE: DNA
<213> ORGANISM: Artificial
<220> FEATURE:
<223> OTHER INFORMATION: Synthetic nucleotide sequence designed for expression in a plant cell encoding TIC869.

<400> SEQUENCE: 49
atggagataa acaaccagaa gcagtgcatt ccgtacaact gcctcagcaa cccggaggag 60
gtgctgctgg acggcgagcg tatcctccca gacatcgacc cactggaggt cagcctgagc 120
ctcctccagt tcctcctcaa taacttcgtg ccaggcggcg gcttcatctc cggcctggtg 180
gacaagatct ggggcgcact ccggccaagt gagtgggatc tgttcctggc ccaaatcgag 240
cgcctgatcg accagaggat cgaggcgacg gtccgcgcca aggcgataac cgagctggag 300
ggcctcggtc gcaactacca gatctacgca gaggcgttca aggagtggga gagcgacccg 360
gacaacgagg cggccaagtc tcgggtgatt gaccgcttcc gcatcctcga cggcctcatc 420
gaagccaaca tcccttcctt ccggatcata ggcttcgaag tcccgctcct cagcgtgtac 480
gtgcaagcgg ccaatctcca cctcgcgttg ctccgtgaca gcgtcatctt tggcgagaga 540
tggggcctga cgacgaagaa cgtgaacgac atctacaaca ggcagatccg agagattcac 600
gagtacagca accactgcgt ggacacatac aacacggagc tggagcggct cggcttccgc 660
tcaatcgctc agtggcggat ctacaaccag ttccgccgcg agctgaccct caccgtgctc 720
gacatcgtcg cattgtttcc caattacgac tcacgcctct acccaatcca gactttcagc 780
cagctcacac gcgagattgt gaccagcccg gtgtcagagt tctactacgg cgtcatcaac 840
tcaggcaaca tcatcgggac actgactgaa cagcagatca gacgtccgca cttgatggac 900
ttcttcaact ccatgattat gtacacatca gacaacagga gagagcacta ctggtccggg 960
ttggagatga ctgcttactt caccggcttc gccggtgccc aagtgagctt cccactggtc 1020
ggaactcgtg gcgagtcagc tcctccgcta actgtgcgat ctgtcaacga cgggatctac 1080
agaatactgt cggctccctt ctacagtgcg ccgttcctcg gcaccatcgt cctcggctca 1140
cgtggtgaga agttcgactt cgcactgaac aacattagcc cgccgcctag tacaatctac 1200
aggcaccctg gcaccgtgga ctcactggtt tcgatcccgc cacaagacaa cagtgtgccg 1260
ccacatcgtg gttctagcca caggctctcc catgtgacca tgcgcgcctc ttcaccgatc 1320
tttcactgga cccatcggtc cgctacaacc acaaacacca tcaaccctaa cgccatcatc 1380
caaatcccgc tggtgaaggc gtttaacctc cacagcggcg caactgtcgt gcgcggccct 1440
ggattcaccg gtggtgacct gctccgtcgg accaatactg gcacgttcgc agacatccga 1500
gtgaacgtcc cgtcctcgct gttcagtcag cgctaccgtg tccgcattcg gtacgcttcc 1560
accacggatc tccagttctt tactcgcatc aatgggacga gcgtcaacca gggcaacttc 1620
agcaagacga tggaccgtgg agataagctc aagtccgaga acttccgcac ggctggcttc 1680
tcgacaccgt tcagattcag caacttccag agcactttca cgctgggcac acaggcgttc 1740
tccaaccagg aggtgtacat cgaccgcatc gagttcgtgc ctgctgaggt taccttcgag 1800
gcggaaagcg acctcgaaag ggcccagaag gccgtcaacg agctgttcac ctccagcaac 1860

```
cagatcggtc tcaagaccga cgtcactgac tatcacattg accaagtcag caacctggtg   1920
gagtgcctca gtgatgagtt ctgcctggat gagaagaagg agcttagcga gaaggtcaag   1980
cacgcaaagc gcttgagcga cgagcgcaac cttctccagg acccgaattt ccgtggtatc   2040
aatagacagc ttgaccgtgg gtggcgcggt agtaccgaca taaccatcca gggtggcgac   2100
gatgtgttca aggagaatta tgttacgctg ctcggtacgt tcgacgagtg ctatcccacg   2160
tacttgtacc agaagattga cgagagcaag ctcaaggcgt acacccgtta ccagctccgt   2220
ggctacatcg aggacagcca ggatctggaa atctacctta tccgatacaa tgctaagcac   2280
gagacagtca acgtgcccgg aacagggtcg ctctggccgc tcagtgctcc gtcgcccatt   2340
ggcaagtgcg cgcaccattc gcatcacttc tcacttgaca ttgacgtggg ctgcaccgac   2400
ctgaacgagg atctgggtgt ctgggtcatc ttcaagatca agacccaaga cggccacgcg   2460
cgcctcggga acctggagtt cctggaggag aagcctttgg taggtgaagc cctggcccgc   2520
gtcaagcgcg cggagaagaa gtggcgcgac aagagggaga agctggaatg ggagaccaac   2580
atcgtgtaca aggaggcgaa ggagtcggtg gacgcactat tcgtgaactc ccagtacgac   2640
cgtctccagg ccgacaccaa catcgccatg atccacgccg ctgacaaacg agttcattcc   2700
attcgtgaag cctatcttcc cgagctgtct gtcataccgg gcgtcaacgc ggccatcttc   2760
gaggagttag agggtcggat ctttacagct ttctcactgt acgatgcccg caacgtcatc   2820
aagaacggcg acttcaacaa cggtctctcc tgttggaacg tgaagggcca cgtggatgtc   2880
gaggagcaga acaaccaccg ctctgtgctt gtggtgcccg agtgggaggc cgaggtgagc   2940
caggaggtcc gcgtctgtcc gggtcgcggc tacatcctgc gggtcaccgc ctacaaggag   3000
ggctacggcg aaggctgcgt tactattcac gagattgaga acaataccga cgaactcaag   3060
ttctccaact gtgtcgagga ggaggtgtac ccgaacaaca ccgtgacgtg caacgactac   3120
accgcgacac aggaggaata cgagggcacc tacaccagcc gcaaccgagg ctacgacgga   3180
gcgtacgaga gcaactcgtc cgtgcccgct gattacgcga gtgcgtacga ggagaaggct   3240
tacaccgacg gacggcgcga caatccctgc gagagtaacc gtggatacgg agattacacg   3300
ccgctacccg ctggctacgt cactaaggaa ctggagtact tcccagagac ggacaaggtg   3360
tggatcgaaa tcggcgagac agagggcacg ttcatcgtgg actccgtgga gctgctgctg   3420
atggaggagt ga                                                       3432
```

```
<210> SEQ ID NO 50
<211> LENGTH: 1143
<212> TYPE: PRT
<213> ORGANISM: Artificial
<220> FEATURE:
<223> OTHER INFORMATION: Amino acid sequence of the chimeric protein
      TIC869.

<400> SEQUENCE: 50

Met Glu Ile Asn Asn Gln Lys Gln Cys Ile Pro Tyr Asn Cys Leu Ser
1               5                   10                  15

Asn Pro Glu Glu Val Leu Leu Asp Gly Glu Arg Ile Leu Pro Asp Ile
            20                  25                  30

Asp Pro Leu Glu Val Ser Leu Ser Leu Leu Gln Phe Leu Leu Asn Asn
        35                  40                  45

Phe Val Pro Gly Gly Gly Phe Ile Ser Gly Leu Val Asp Lys Ile Trp
    50                  55                  60

Gly Ala Leu Arg Pro Ser Glu Trp Asp Leu Phe Leu Ala Gln Ile Glu
```

-continued

```
65                  70                  75                  80

Arg Leu Ile Asp Gln Arg Ile Glu Ala Thr Val Arg Ala Lys Ala Ile
                85                  90                  95

Thr Glu Leu Glu Gly Leu Gly Arg Asn Tyr Gln Ile Tyr Ala Glu Ala
            100                 105                 110

Phe Lys Glu Trp Glu Ser Asp Pro Asp Asn Glu Ala Ala Lys Ser Arg
        115                 120                 125

Val Ile Asp Arg Phe Arg Ile Leu Asp Gly Leu Ile Glu Ala Asn Ile
    130                 135                 140

Pro Ser Phe Arg Ile Ile Gly Phe Glu Val Pro Leu Leu Ser Val Tyr
145                 150                 155                 160

Val Gln Ala Ala Asn Leu His Leu Ala Leu Leu Arg Asp Ser Val Ile
                165                 170                 175

Phe Gly Glu Arg Trp Gly Leu Thr Thr Lys Asn Val Asn Asp Ile Tyr
            180                 185                 190

Asn Arg Gln Ile Arg Glu Ile His Glu Tyr Ser Asn His Cys Val Asp
        195                 200                 205

Thr Tyr Asn Thr Glu Leu Glu Arg Leu Gly Phe Arg Ser Ile Ala Gln
    210                 215                 220

Trp Arg Ile Tyr Asn Gln Phe Arg Arg Glu Leu Thr Leu Thr Val Leu
225                 230                 235                 240

Asp Ile Val Ala Leu Phe Pro Asn Tyr Asp Ser Arg Leu Tyr Pro Ile
                245                 250                 255

Gln Thr Phe Ser Gln Leu Thr Arg Glu Ile Val Thr Ser Pro Val Ser
            260                 265                 270

Glu Phe Tyr Tyr Gly Val Ile Asn Ser Gly Asn Ile Ile Gly Thr Leu
        275                 280                 285

Thr Glu Gln Gln Ile Arg Arg Pro His Leu Met Asp Phe Phe Asn Ser
    290                 295                 300

Met Ile Met Tyr Thr Ser Asp Asn Arg Arg Glu His Tyr Trp Ser Gly
305                 310                 315                 320

Leu Glu Met Thr Ala Tyr Phe Thr Gly Phe Ala Gly Ala Gln Val Ser
                325                 330                 335

Phe Pro Leu Val Gly Thr Arg Gly Glu Ser Ala Pro Pro Leu Thr Val
            340                 345                 350

Arg Ser Val Asn Asp Gly Ile Tyr Arg Ile Leu Ser Ala Pro Phe Tyr
        355                 360                 365

Ser Ala Pro Phe Leu Gly Thr Ile Val Leu Gly Ser Arg Gly Glu Lys
    370                 375                 380

Phe Asp Phe Ala Leu Asn Asn Ile Ser Pro Pro Pro Ser Thr Ile Tyr
385                 390                 395                 400

Arg His Pro Gly Thr Val Asp Ser Leu Val Ser Ile Pro Pro Gln Asp
                405                 410                 415

Asn Ser Val Pro Pro His Arg Gly Ser Ser His Arg Leu Ser His Val
            420                 425                 430

Thr Met Arg Ala Ser Ser Pro Ile Phe His Trp Thr His Arg Ser Ala
        435                 440                 445

Thr Thr Thr Asn Thr Ile Asn Pro Asn Ala Ile Ile Gln Ile Pro Leu
    450                 455                 460

Val Lys Ala Phe Asn Leu His Ser Gly Ala Thr Val Val Arg Gly Pro
465                 470                 475                 480

Gly Phe Thr Gly Gly Asp Leu Leu Arg Arg Thr Asn Thr Gly Thr Phe
                485                 490                 495
```

```
Ala Asp Ile Arg Val Asn Val Pro Ser Ser Leu Phe Ser Gln Arg Tyr
            500                 505                 510

Arg Val Arg Ile Arg Tyr Ala Ser Thr Thr Asp Leu Gln Phe Phe Thr
        515                 520                 525

Arg Ile Asn Gly Thr Ser Val Asn Gln Gly Asn Phe Ser Lys Thr Met
    530                 535                 540

Asp Arg Gly Asp Lys Leu Lys Ser Glu Asn Phe Arg Thr Ala Gly Phe
545                 550                 555                 560

Ser Thr Pro Phe Arg Phe Ser Asn Phe Gln Ser Thr Phe Thr Leu Gly
                565                 570                 575

Thr Gln Ala Phe Ser Asn Gln Glu Val Tyr Ile Asp Arg Ile Glu Phe
            580                 585                 590

Val Pro Ala Glu Val Thr Phe Glu Ala Glu Ser Asp Leu Glu Arg Ala
        595                 600                 605

Gln Lys Ala Val Asn Glu Leu Phe Thr Ser Ser Asn Gln Ile Gly Leu
    610                 615                 620

Lys Thr Asp Val Thr Asp Tyr His Ile Asp Gln Val Ser Asn Leu Val
625                 630                 635                 640

Glu Cys Leu Ser Asp Glu Phe Cys Leu Asp Glu Lys Lys Glu Leu Ser
                645                 650                 655

Glu Lys Val Lys His Ala Lys Arg Leu Ser Asp Glu Arg Asn Leu Leu
            660                 665                 670

Gln Asp Pro Asn Phe Arg Gly Ile Asn Arg Gln Leu Asp Arg Gly Trp
        675                 680                 685

Arg Gly Ser Thr Asp Ile Thr Ile Gln Gly Gly Asp Asp Val Phe Lys
    690                 695                 700

Glu Asn Tyr Val Thr Leu Leu Gly Thr Phe Asp Glu Cys Tyr Pro Thr
705                 710                 715                 720

Tyr Leu Tyr Gln Lys Ile Asp Glu Ser Lys Leu Lys Ala Tyr Thr Arg
                725                 730                 735

Tyr Gln Leu Arg Gly Tyr Ile Glu Asp Ser Gln Asp Leu Glu Ile Tyr
            740                 745                 750

Leu Ile Arg Tyr Asn Ala Lys His Glu Thr Val Asn Val Pro Gly Thr
        755                 760                 765

Gly Ser Leu Trp Pro Leu Ser Ala Pro Ser Pro Ile Gly Lys Cys Ala
    770                 775                 780

His His Ser His His Phe Ser Leu Asp Ile Asp Val Gly Cys Thr Asp
785                 790                 795                 800

Leu Asn Glu Asp Leu Gly Val Trp Val Ile Phe Lys Ile Lys Thr Gln
                805                 810                 815

Asp Gly His Ala Arg Leu Gly Asn Leu Glu Phe Leu Glu Glu Lys Pro
            820                 825                 830

Leu Val Gly Glu Ala Leu Ala Arg Val Lys Arg Ala Glu Lys Lys Trp
        835                 840                 845

Arg Asp Lys Arg Glu Lys Leu Glu Trp Glu Thr Asn Ile Val Tyr Lys
    850                 855                 860

Glu Ala Lys Glu Ser Val Asp Ala Leu Phe Val Asn Ser Gln Tyr Asp
865                 870                 875                 880

Arg Leu Gln Ala Asp Thr Asn Ile Ala Met Ile His Ala Ala Asp Lys
                885                 890                 895

Arg Val His Ser Ile Arg Glu Ala Tyr Leu Pro Glu Leu Ser Val Ile
            900                 905                 910
```

```
Pro Gly Val Asn Ala Ala Ile Phe Glu Glu Leu Glu Gly Arg Ile Phe
        915                 920                 925

Thr Ala Phe Ser Leu Tyr Asp Ala Arg Asn Val Ile Lys Asn Gly Asp
    930                 935                 940

Phe Asn Asn Gly Leu Ser Cys Trp Asn Val Lys Gly His Val Asp Val
945                 950                 955                 960

Glu Glu Gln Asn Asn His Arg Ser Val Leu Val Val Pro Glu Trp Glu
                965                 970                 975

Ala Glu Val Ser Gln Glu Val Arg Val Cys Pro Gly Arg Gly Tyr Ile
            980                 985                 990

Leu Arg Val Thr Ala Tyr Lys Glu  Gly Tyr Gly Glu Gly  Cys Val Thr
        995                 1000                 1005

Ile His  Glu Ile Glu Asn Asn  Thr Asp Glu Leu Lys  Phe Ser Asn
    1010                 1015                 1020

Cys Val  Glu Glu Glu Val Tyr  Pro Asn Asn Thr Val  Thr Cys Asn
    1025                 1030                 1035

Asp Tyr  Thr Ala Thr Gln Glu  Glu Tyr Glu Gly Thr  Tyr Thr Ser
    1040                 1045                 1050

Arg Asn  Arg Gly Tyr Asp Gly  Ala Tyr Glu Ser Asn  Ser Ser Val
    1055                 1060                 1065

Pro Ala  Asp Tyr Ala Ser Ala  Tyr Glu Glu Lys Ala  Tyr Thr Asp
    1070                 1075                 1080

Gly Arg  Arg Asp Asn Pro Cys  Glu Ser Asn Arg Gly  Tyr Gly Asp
    1085                 1090                 1095

Tyr Thr  Pro Leu Pro Ala Gly  Tyr Val Thr Lys Glu  Leu Glu Tyr
    1100                 1105                 1110

Phe Pro  Glu Thr Asp Lys Val  Trp Ile Glu Ile Gly  Glu Thr Glu
    1115                 1120                 1125

Gly Thr  Phe Ile Val Asp Ser  Val Glu Leu Leu Leu  Met Glu Glu
    1130                 1135                 1140
```

<210> SEQ ID NO 51
<211> LENGTH: 3513
<212> TYPE: DNA
<213> ORGANISM: Artificial
<220> FEATURE:
<223> OTHER INFORMATION: Recombinant nucleotide sequence used for expression in a bacterial cell encoding TIC836.

<400> SEQUENCE: 51

```
atggagaata atattcaaaa tcaatgcgta ccttacaatt gtttaaataa tcctgaagta     60

gaaatattaa atgaagaaag aagtactggc agattaccgt tagatatatc cttatcgctt    120

acacgtttcc ttttgagtga atttgttcca ggtgtgggag ttgcgtttgg attatttgat    180

ttaatatggg gttttataac tccttctgat tggagcttat ttcttttaca gattgaacaa    240

ttgattgagc aaagaataga aacattggaa aggaaccggg caattactac attacgaggg    300

ttagcagata gctatgaaat ttatattgaa gcactaagag agtgggaagc aaatcctaat    360

aatgcacaat taagggaaga tgtgcgtatt cgatttgcta atacagacga cgctttaata    420

acagcaataa ataattttac acttacaagt tttgaaatcc ctcttttatc ggtctatgtt    480

caagcggcga atttacattt atcactatta agagacgctg tatcgtttgg gcagggttgg    540

ggactggata tagctactgt taataatcat tataatagat taataaatct tattcataga    600

tatacgaaac attgtttgga cacatacaat caaggattag aaaacttaag aggtactaat    660

actcgacaat gggcaagatt caatcagttt aggagagatt taacacttac tgtattagat    720
```

```
atcgttgctc tttttccgaa ctacgatgtt agaacatatc caattcaaac gtcatcccaa     780
ttaacaaggg aaatttatac aagttcagta attgaggatt ctccagtttc tgctaatata     840
cctaatggtt ttaatagggc ggaatttgga gttagaccgc cccatcttat ggactttatg     900
aattctttgt ttgtaactgc agagactgtt agaagtcaaa ctgtgtgggg aggacactta     960
gttagttcac gaaatacggc tggtaaccgt ataaatttcc ctagttacgg ggtcttcaat    1020
cctggtggcg ccatttggat tgcagatgag gatccacgtc ctttttatcg gacattatca    1080
gatcctgttt ttgtccgagg aggatttggg aatcctcatt atgtactggg gcttagggga    1140
gtagcatttc aacaaactgg tacgaaccac acccgaacat ttagaaatag tgggaccata    1200
gattctctag atgaaatccc acctcaggat aatagtgggg caccttggaa tgattatagt    1260
catgtattaa atcatgttac atttgtacga tggccaggtg agatttcagg aagtgattca    1320
tggagagctc caatgttttc ttggacgcac cgtagtgcaa cccctacaaa tacaattgat    1380
ccggagagga ttacacaaat acctttaaca aaatctacta atcttggctc tggaacttct    1440
gtcgttaaag gaccaggatt tacaggagga gatattcttc gaagaacttc acctggccag    1500
atttcaacct taagagtaaa tattactgca ccattatcac aaagatatcg ggtaagaatt    1560
cgctacgctt ctaccacaaa tttacaattc catacatcaa ttgacggaag acctattaat    1620
caggggaatt tttcagcaac tatgagtagt gggagtaatt tacagtccgg aagctttagg    1680
actgtaggtt ttactactcc gtttaacttt tcaaatggat caagtgtatt tacgttaagt    1740
gctcatgtct tcaattcagg caatgaagtt tatatagatc gaattgaatt tgttccggca    1800
gaagtaacct ttgaggcaga atatgattta gaaagagcgc agaaggcggt gaatgcgctg    1860
tttacgtcta caaaccaact agggctaaaa acaaatgtaa cggattatca tattgatcaa    1920
gtgtccaatt tagttacgta tttatcggat gaattttgtc tggatgaaaa gcgagaattg    1980
tccgagaaag tcaaacatgc gaagcgactc agtgatgaac gcaatttact ccaagattca    2040
aatttcaaag acattaatag gcaaccagaa cgtgggtggg gcggaagtac agggattacc    2100
atccaaggag gggatgacgt atttaaagaa aattacgtca cactatcagg tacctttgat    2160
gagtgctatc caacatattt gtatcaaaaa atcgatgaat caaaattaaa agcctttacc    2220
cgttatcaat taagagggta tatcgaagat agtcaagact tagaaatcta tttaattcgc    2280
tacaatgcaa aacatgaaac agtaaatgtg ccaggtacgg gttccttatg gccgctttca    2340
gcccaaagtc caatcggaaa gtgtggagag ccgaatcgat gcgcgccaca ccttgaatgg    2400
aatcctgact tagattgttc gtgtagggat ggagaaaagt gtgcccatca ttcgcatcat    2460
ttctccttag acattgatgt aggatgtaca gacttaaatg aggacctagg tgtatgggtg    2520
atctttaaga ttaagacgca agatgggcac gcaagactag ggaatctaga gtttctcgaa    2580
gaaaaaccat tagtaggaga agcgctagct cgtgtgaaaa gagcggagaa aaaatggaga    2640
gacaaacgtg aaaaattgga atgggaaaca aatatcgttt ataaagaggc aaaagaatct    2700
gtagatgctt tatttgtaaa ctctcaatat gatcaattac aagcggatac gaatattgcc    2760
atgattcatg cggcagataa acgtgttcat agcattcgag aagcttatct gcctgagctg    2820
tctgtgattc cgggtgtcaa tgcggctatt tttgaagaat tagaagggcg tattttcact    2880
gcattctccc tatatgatgc gagaaatgtc attaaaaatg gtgattttaa taatggctta    2940
tcctgctgga acgtgaaagg gcatgtagat gtagaagaac aaaacaacca acgttcggtc    3000
cttgttgttc cggaatggga agcagaagtg tcacaagaag ttcgtgtctg tccgggtcgt    3060
```

```
ggctatatcc ttcgtgtcac agcgtacaag gagggatatg gagaaggttg cgtaaccatt   3120

catgagatcg agaacaatac agacgaactg aagtttagca actgcgtaga ggaggaaatc   3180

tatccaaata acacggtaac gtgtaatgat tatactgtaa atcaagaaga atacggaggt   3240

gcgtacactt ctcgtaatcg aggatataac gaagctcctt ccgtaccagc tgattatgcg   3300

tcagtctatg aagaaaaatc gtatacagat ggacgtagag agaatccttg tgaatttaac   3360

agagggtata gggattacac gccactacca gttggttatg tgacaaaaga attagaatac   3420

ttcccagaaa ccgataaggt atggattgag attggagaaa cggaaggaac atttatcgtg   3480

gacagcgtgg aattactcct tatggaggaa taa                                3513
```

<210> SEQ ID NO 52
<211> LENGTH: 3513
<212> TYPE: DNA
<213> ORGANISM: Artificial
<220> FEATURE:
<223> OTHER INFORMATION: Synthetic nucleotide sequence designed for expression in a plant cell encoding TIC836.

<400> SEQUENCE: 52

```
atggagaaca acatccagaa ccagtgcgtg ccctacaact gcctgaacaa ccctgaggtt     60

gagatcctga acgaggagcg tagcaccggt aggctcccgc tagacatctc cctgagcctg    120

acccgcttcc tccttagtga gttcgtgccc ggcgtgggcg tggccttcgg cctcttcgac    180

ctcatctggg gcttcatcac tccttccgac tggtccctct tcctccttca gattgagcaa    240

ctgatcgagc agcgcatcga gacccttgag cgcaaccgcg ccatcaccac tctcagaggt    300

ctcgccgact cctacgaaat ctacatcgag gcactccgtg agtgggaggc caacccgaac    360

aatgcccagc tccgcgagga cgtgaggatc agattcgcca acaccgacga tgccctcatc    420

accgccatca acaatttcac cctcacctcc ttcgagatcc ctcttctgtc tgtgtacgtt    480

caagctgcta accttcacct ttccctcctg cgcgacgccg tgagcttcgg ccagggctgg    540

ggcctcgaca tcgccaccgt gaacaatcac tacaaccgcc tcatcaacct catccaccgc    600

tacaccaagc actgccttga cacctacaac cagggccttg agaacctccg tggcaccaac    660

acccgccagt gggcccgctt caaccagttc cgcagagacc tcaccctcac cgtgctcgac    720

atcgtggcac tcttcccaaa ctacgacgtg cgtacctacc ctatccagac ctccagccag    780

ctcaccaggg aaatctacac ctccagcgtg atcgaggact ctcctgtgtc cgccaacatc    840

cctaacggct tcaaccgcgc cgagttcggc gtgcgccctc ctcacctcat ggacttcatg    900

aactccctct tcgtcactgc cgagaccgtg cgctcccaga ccgtgtgggg cggtcacctc    960

gtgtccagcc gtaacaccgc tggcaacagg atcaacttcc cgtcctacgg cgtgttcaac   1020

ccaggcggtg ccatctggat cgccgatgaa gaccctcgtc ctttctaccg taccctgtcc   1080

gaccctgtgt tcgtgcgtgg cggtttcggc aaccctcact acgtgctggg cctgcgtggc   1140

gtggccttcc agcaaaccgg caccaaccac accaggacgt tccgtaactc cggcaccatc   1200

gacagtcttg acgagatccc tccgcaagac aactccggtg caccttggaa cgactactcc   1260

cacgtgctga accacgtgac cttcgtgagg tggcctggcg aaatctccgg ctccgactcc   1320

tggagggctc ctatgttcag ttggacccac aggagcgcta cgcctaccaa caccatcgac   1380

cctgagcgta tcactcagat ccctctgact aagagcacta acctgggcag cggcactagc   1440

gtggtcaagg gccctggctt cactggcggt gacatcctga ggcggactag ccctggccag   1500

atcagcactc tgagggtgaa catcactgct ccgctgagcc agcgttacag ggtcagaatc   1560
```

-continued

```
cgttacgctt ctactactaa ccttcagttc cacactagca tcgacggccg tccgatcaac   1620

cagggcaact tctctgctac tatgagttct ggcagtaacc tccagtctgg tagtttccgg   1680

actgtcggtt tcactacgcc gttcaacttc tccaacggta gttctgtctt cactctgtct   1740

gctcacgtgt tcaactctgg caacgaggtg tacatcgacc ggatcgagtt cgtccctgct   1800

gaggtgacgt tcgaggccga gtacgacctg gagcgggctc agaaggctgt caacgctctg   1860

ttcacttcta ctaaccagct tggtttgaag actaacgtga ccgactacca cattgatcaa   1920

gtcagtaacc tggtcacgta cctgtctgac gagttctgtc ttgacgagaa gcgggagctg   1980

tctgagaagg tcaagcacgc taagcggctg tctgacgagc ggaacctgct tcaagacagt   2040

aacttcaagg acattaaccg ccagcctgag cgtggttggg gagggtccac gggtattacg   2100

attcaaggag gtgacgatgt ctttaaggag aactatgtga cgctttcggg tacgtttgat   2160

gagtgctatc caacgtacct ttaccagaag attgacgagt cgaagctgaa ggctttcact   2220

cgttaccagc ttcgtggtta cattgaggac tcgcaagacc tcgaaatcta cctcattcgt   2280

tacaacgcta agcacgagac tgtcaacgtc cctggtacgg gtagtctttg gccgctttct   2340

gctcagtcgc cgattggcaa gtgtggcgag ccgaaccgtt gcgctcctca cttggagtgg   2400

aacccggatc tcgattgctc gtgccgtgac ggtgagaagt gcgcgcacca tagtcatcac   2460

tttagccttg acattgatgt cggttgcacg gatcttaacg aggatcttgg agtctgggtg   2520

attttcaaga tcaaaactca ggatgggcac gcgcgtcttg ggaatcttga gttcctggag   2580

gagaagccac ttgtcggtga ggcgcttgcg cgtgtcaagc gtgcggagaa gaaatggcgt   2640

gataagcgtg agaagttgga gtgggagacg aacatcgtgt acaaggaggc gaaggagtcg   2700

gtcgatgcgt tgtttgtcaa tagtcaatac gatcaattgc aagcggatac gaacatcgca   2760

atgattcatg cggcagataa gcgtgtccat tcgattcgtg aggcgtactt gccagagttg   2820

tcggtcatcc caggagttaa tgcggcaatc tttgaggaat tggagggcag aatcttcacg   2880

gcgttctcgt tgtacgatgc aagaaatgtt attaagaatg gagatttcaa caatgggttg   2940

tcatgctgga atgttaaggg tcacgttgat gttgaagaac agaacaacca gagatcagtg   3000

ttggttgtac cagagtggga ggcagaggtt tcacaagagg tgagagtttg cccaggcaga   3060

ggctacatct tgagagttac agcatacaaa gagggatacg gcgagggatg tgttacaatc   3120

cacgaaatcg agaacaatac cgatgagcta aagttctcaa attgtgttga ggaggagatc   3180

tacccgaaca acacggttac ttgtaatgat tacacagtga accaggagga gtatggtggt   3240

gcatacacat caagaaatag aggctacaat gaagcaccat cagttccagc agattatgcc   3300

tcagtttatg aggagaagtc atacacagat ggacgacgtg agaatccatg tgagttcaat   3360

cgaggatacc gagattacac accactacca gttggatacg ttacaaagga actagaatac   3420

ttcccagaaa cagataaagt atggatagag atcggagaaa cagaaggaac attcatcgtt   3480

gattcagtag aactactact tatggaagaa tga                                 3513
```

```
<210> SEQ ID NO 53
<211> LENGTH: 1170
<212> TYPE: PRT
<213> ORGANISM: Artificial
<220> FEATURE:
<223> OTHER INFORMATION: Amino acid sequence of the chimeric protein
      TIC836.

<400> SEQUENCE: 53

Met Glu Asn Asn Ile Gln Asn Gln Cys Val Pro Tyr Asn Cys Leu Asn
1               5                   10                  15
```

-continued

```
Asn Pro Glu Val Glu Ile Leu Asn Glu Glu Arg Ser Thr Gly Arg Leu
            20                  25                  30

Pro Leu Asp Ile Ser Leu Ser Leu Thr Arg Phe Leu Leu Ser Glu Phe
        35                  40                  45

Val Pro Gly Val Gly Val Ala Phe Gly Leu Phe Asp Leu Ile Trp Gly
    50                  55                  60

Phe Ile Thr Pro Ser Asp Trp Ser Leu Phe Leu Leu Gln Ile Glu Gln
65                  70                  75                  80

Leu Ile Glu Gln Arg Ile Glu Thr Leu Glu Arg Asn Arg Ala Ile Thr
                85                  90                  95

Thr Leu Arg Gly Leu Ala Asp Ser Tyr Glu Ile Tyr Ile Glu Ala Leu
            100                 105                 110

Arg Glu Trp Glu Ala Asn Pro Asn Asn Ala Gln Leu Arg Glu Asp Val
        115                 120                 125

Arg Ile Arg Phe Ala Asn Thr Asp Asp Ala Leu Ile Thr Ala Ile Asn
    130                 135                 140

Asn Phe Thr Leu Thr Ser Phe Glu Ile Pro Leu Leu Ser Val Tyr Val
145                 150                 155                 160

Gln Ala Ala Asn Leu His Leu Ser Leu Leu Arg Asp Ala Val Ser Phe
                165                 170                 175

Gly Gln Gly Trp Gly Leu Asp Ile Ala Thr Val Asn Asn His Tyr Asn
            180                 185                 190

Arg Leu Ile Asn Leu Ile His Arg Tyr Thr Lys His Cys Leu Asp Thr
        195                 200                 205

Tyr Asn Gln Gly Leu Glu Asn Leu Arg Gly Thr Asn Thr Arg Gln Trp
    210                 215                 220

Ala Arg Phe Asn Gln Phe Arg Arg Asp Leu Thr Leu Thr Val Leu Asp
225                 230                 235                 240

Ile Val Ala Leu Phe Pro Asn Tyr Asp Val Arg Thr Tyr Pro Ile Gln
                245                 250                 255

Thr Ser Ser Gln Leu Thr Arg Glu Ile Tyr Thr Ser Ser Val Ile Glu
            260                 265                 270

Asp Ser Pro Val Ser Ala Asn Ile Pro Asn Gly Phe Asn Arg Ala Glu
        275                 280                 285

Phe Gly Val Arg Pro Pro His Leu Met Asp Phe Met Asn Ser Leu Phe
    290                 295                 300

Val Thr Ala Glu Thr Val Arg Ser Gln Thr Val Trp Gly Gly His Leu
305                 310                 315                 320

Val Ser Ser Arg Asn Thr Ala Gly Asn Arg Ile Asn Phe Pro Ser Tyr
                325                 330                 335

Gly Val Phe Asn Pro Gly Gly Ala Ile Trp Ile Ala Asp Glu Asp Pro
            340                 345                 350

Arg Pro Phe Tyr Arg Thr Leu Ser Asp Pro Val Phe Val Arg Gly Gly
        355                 360                 365

Phe Gly Asn Pro His Tyr Val Leu Gly Leu Arg Gly Val Ala Phe Gln
    370                 375                 380

Gln Thr Gly Thr Asn His Thr Arg Thr Phe Arg Asn Ser Gly Thr Ile
385                 390                 395                 400

Asp Ser Leu Asp Glu Ile Pro Pro Gln Asp Asn Ser Gly Ala Pro Trp
                405                 410                 415

Asn Asp Tyr Ser His Val Leu Asn His Val Thr Phe Val Arg Trp Pro
            420                 425                 430
```

-continued

```
Gly Glu Ile Ser Gly Ser Asp Ser Trp Arg Ala Pro Met Phe Ser Trp
        435                 440                 445

Thr His Arg Ser Ala Thr Pro Thr Asn Thr Ile Asp Pro Glu Arg Ile
    450                 455                 460

Thr Gln Ile Pro Leu Thr Lys Ser Thr Asn Leu Gly Ser Gly Thr Ser
465                 470                 475                 480

Val Val Lys Gly Pro Gly Phe Thr Gly Gly Asp Ile Leu Arg Arg Thr
                485                 490                 495

Ser Pro Gly Gln Ile Ser Thr Leu Arg Val Asn Ile Thr Ala Pro Leu
            500                 505                 510

Ser Gln Arg Tyr Arg Val Arg Ile Arg Tyr Ala Ser Thr Thr Asn Leu
        515                 520                 525

Gln Phe His Thr Ser Ile Asp Gly Arg Pro Ile Asn Gln Gly Asn Phe
    530                 535                 540

Ser Ala Thr Met Ser Ser Gly Ser Asn Leu Gln Ser Gly Ser Phe Arg
545                 550                 555                 560

Thr Val Gly Phe Thr Thr Pro Phe Asn Phe Ser Asn Gly Ser Ser Val
                565                 570                 575

Phe Thr Leu Ser Ala His Val Phe Asn Ser Gly Asn Glu Val Tyr Ile
            580                 585                 590

Asp Arg Ile Glu Phe Val Pro Ala Glu Val Thr Phe Glu Ala Glu Tyr
        595                 600                 605

Asp Leu Glu Arg Ala Gln Lys Ala Val Asn Ala Leu Phe Thr Ser Thr
    610                 615                 620

Asn Gln Leu Gly Leu Lys Thr Asn Val Thr Asp Tyr His Ile Asp Gln
625                 630                 635                 640

Val Ser Asn Leu Val Thr Tyr Leu Ser Asp Glu Phe Cys Leu Asp Glu
                645                 650                 655

Lys Arg Glu Leu Ser Glu Lys Val Lys His Ala Lys Arg Leu Ser Asp
            660                 665                 670

Glu Arg Asn Leu Leu Gln Asp Ser Asn Phe Lys Asp Ile Asn Arg Gln
        675                 680                 685

Pro Glu Arg Gly Trp Gly Gly Ser Thr Gly Ile Thr Ile Gln Gly Gly
    690                 695                 700

Asp Asp Val Phe Lys Glu Asn Tyr Val Thr Leu Ser Gly Thr Phe Asp
705                 710                 715                 720

Glu Cys Tyr Pro Thr Tyr Leu Tyr Gln Lys Ile Asp Glu Ser Lys Leu
                725                 730                 735

Lys Ala Phe Thr Arg Tyr Gln Leu Arg Gly Tyr Ile Glu Asp Ser Gln
            740                 745                 750

Asp Leu Glu Ile Tyr Leu Ile Arg Tyr Asn Ala Lys His Glu Thr Val
        755                 760                 765

Asn Val Pro Gly Thr Gly Ser Leu Trp Pro Leu Ser Ala Gln Ser Pro
    770                 775                 780

Ile Gly Lys Cys Gly Glu Pro Asn Arg Cys Ala Pro His Leu Glu Trp
785                 790                 795                 800

Asn Pro Asp Leu Asp Cys Ser Cys Arg Asp Gly Glu Lys Cys Ala His
                805                 810                 815

His Ser His His Phe Ser Leu Asp Ile Asp Val Gly Cys Thr Asp Leu
            820                 825                 830

Asn Glu Asp Leu Gly Val Trp Val Ile Phe Lys Ile Lys Thr Gln Asp
        835                 840                 845

Gly His Ala Arg Leu Gly Asn Leu Glu Phe Leu Glu Glu Lys Pro Leu
```

-continued

```
    850                 855                 860

Val Gly Glu Ala Leu Ala Arg Val Lys Arg Ala Glu Lys Lys Trp Arg
865                 870                 875                 880

Asp Lys Arg Glu Lys Leu Glu Trp Glu Thr Asn Ile Val Tyr Lys Glu
                885                 890                 895

Ala Lys Glu Ser Val Asp Ala Leu Phe Val Asn Ser Gln Tyr Asp Gln
            900                 905                 910

Leu Gln Ala Asp Thr Asn Ile Ala Met Ile His Ala Ala Asp Lys Arg
        915                 920                 925

Val His Ser Ile Arg Glu Ala Tyr Leu Pro Glu Leu Ser Val Ile Pro
    930                 935                 940

Gly Val Asn Ala Ala Ile Phe Glu Glu Leu Glu Gly Arg Ile Phe Thr
945                 950                 955                 960

Ala Phe Ser Leu Tyr Asp Ala Arg Asn Val Ile Lys Asn Gly Asp Phe
                965                 970                 975

Asn Asn Gly Leu Ser Cys Trp Asn Val Lys Gly His Val Asp Val Glu
            980                 985                 990

Glu Gln Asn Asn Gln Arg Ser Val  Leu Val Val Pro Glu  Trp Glu Ala
        995                 1000                1005

Glu Val  Ser Gln Glu Val Arg  Val Cys Pro Gly Arg  Gly Tyr Ile
    1010                 1015                1020

Leu Arg  Val Thr Ala Tyr Lys  Glu Gly Tyr Gly Glu  Gly Cys Val
    1025                 1030                1035

Thr Ile  His Glu Ile Glu Asn  Asn Thr Asp Glu Leu  Lys Phe Ser
    1040                 1045                1050

Asn Cys  Val Glu Glu Glu Ile  Tyr Pro Asn Asn Thr  Val Thr Cys
    1055                 1060                1065

Asn Asp  Tyr Thr Val Asn Gln  Glu Glu Tyr Gly Gly  Ala Tyr Thr
    1070                 1075                1080

Ser Arg  Asn Arg Gly Tyr Asn  Glu Ala Pro Ser Val  Pro Ala Asp
    1085                 1090                1095

Tyr Ala  Ser Val Tyr Glu Glu  Lys Ser Tyr Thr Asp  Gly Arg Arg
    1100                 1105                1110

Glu Asn  Pro Cys Glu Phe Asn  Arg Gly Tyr Arg Asp  Tyr Thr Pro
    1115                 1120                1125

Leu Pro  Val Gly Tyr Val Thr  Lys Glu Leu Glu Tyr  Phe Pro Glu
    1130                 1135                1140

Thr Asp  Lys Val Trp Ile Glu  Ile Gly Glu Thr Glu  Gly Thr Phe
    1145                 1150                1155

Ile Val  Asp Ser Val Glu Leu  Leu Leu Met Glu Glu
    1160                 1165                1170
```

CHIMERIC INSECTICIDAL PROTEINS TOXIC OR INHIBITORY TO LEPIDOPTERAN PESTS

REFERENCE TO RELATED APPLICATION

This application is a continuation of U.S. patent application Ser. No. 14/884,469, filed Oct. 15, 2015, which claims the benefit of U.S. provisional application No. 62/064,989, filed Oct. 16, 2014, each of which are herein incorporated by reference in their entireties.

INCORPORATION OF SEQUENCE LISTING

A computer readable form of the Sequence Listing is filed with this application by electronic submission and is incorporated into this application by reference in its entirety. The Sequence Listing is contained in the file created on Dec. 11, 2017, having the file name P34230US03_SEQ.txt, and which is 371,792 bytes in size (as measured in the MS-Windows® operating system).

FIELD OF THE INVENTION

The invention generally relates to the field of insect inhibitory proteins. A novel class of chimeric insecticidal proteins exhibiting insect inhibitory activity against agriculturally-relevant pests of crop plants and seeds is disclosed in this application. In particular, the disclosed class of proteins exhibits insecticidal activity against the Lepidopteran order of insect pests. Plants, plant parts, and seeds containing a recombinant nucleic acid molecule encoding one or more of the disclosed toxin proteins are provided.

BACKGROUND OF THE INVENTION

Improving crop yield from agriculturally-significant plants including, among others, corn, soybean, sugarcane, rice, wheat, vegetables, and cotton, has become increasingly important. In addition to the growing need for agricultural products to feed, clothe and provide energy for a growing human population, climate-related effects and pressure from the growing population to use land other than for agricultural practices are predicted to reduce the amount of arable land available for farming. These factors have led to grim forecasts with respect to food security, particularly in the absence of major improvements in plant biotechnology and agronomic practices. In light of these pressures, environmentally sustainable improvements in technology, agricultural techniques, and pest management are vital tools to expand crop production on the limited amount of arable land available for farming.

Insects, particularly insects within the order Lepidoptera, are considered a major cause of damage to field crops, thereby decreasing crop yields in infested areas. Lepidopteran pest species which negatively impact agriculture include, but are not limited to, fall armyworm (*Spodoptera frugiperda*), beet armyworm (*Spodoptera exigua*), bertha armyworm (*Mamestra configurata*), black cutworm (*Agrotis ipsilon*), cabbage looper (*Trichoplusia ni*), soybean looper (*Chrysodeixis includens*), velvetbean caterpillar (*Anticarsia gemmatalis*), green cloverworm (*Hypena scabra*), tobacco budworm (*Heliothis virescens*), granulate cutworm (*Agrotis subterranea*), armyworm (*Pseudaletia unipuncta*), western cutworm (*Agrotis orthogonia*), European corn borer (*Ostrinia nubilalis*), navel orangeworm (*Amyelois transitella*), corn root webworm (*Crambus caliginosellus*), sod webworm (*Herpetogramma licarsisalis*), sunflower moth (*Homoeosoma electellum*), lesser cornstalk borer (*Elasmopalpus lignosellus*), codling moth (*Cydia pomonella*), grape berry moth (*Endopiza viteana*), oriental fruit moth (*Grapholita molesta*), sunflower bud moth (*Suleima helianthana*), diamondback moth (*Plutella xylostella*), pink bollworm (*Pectinophora gossypiella*), pink stem borer (*Sesamia inferens*), gypsy moth (*Lymantria dispar*), cotton leaf worm (*Alabama argillacea*), fruit tree leaf roller (*Archips argyrospila*), European leafroller (*Archips rosana*), Asiatic rice borer, or rice stem borer (*Chilo suppressalis*), rice leaf roller (*Cnaphalocrocis medinalis*), corn root webworm (*Crambus caliginosellus*), bluegrass webworm (*Crambus teterrellus*), southwestern corn borer (*Diatraea grandiosella*)), surgarcane borer (*Diatraea saccharalis*), spiny bollworm (*Earias insulana*), spotted bollworm (*Earias vittella*), Old World cotton bollworm (*Helicoverpa armigera*), corn earworm, soy podworm or cotton bollworm (*Helicoverpa zea*), sod webworm (*Herpetogramma licarsisalis*), European grape vine moth (*Lobesia botrana*), citrus leafminer (*Phyllocnistis citrella*), large white butterfly (*Pieris brassicae*), imported cabbageworm, or small white butterfly (*Pieris rapae*), tobacco cutworm, or cluster caterpillar (*Spodoptera litura*), and tomato leafminer (*Tuta absoluta*).

Historically, the intensive application of synthetic chemical insecticides was relied upon as the pest control agent in agriculture. Concerns for the environment and human health, in addition to emerging resistance issues, stimulated the research and development of biological pesticides. This research effort led to the progressive discovery and use of various entomopathogenic microbial species, including bacteria.

The biological control paradigm shifted when the potential of entomopathogenic bacteria, especially bacteria belonging to the genus *Bacillus*, was discovered and developed as a biological pest control agent. Strains of the bacterium *Bacillus thuringiensis* (Bt) have been used as a source for insecticidal proteins since it was discovered that Bt strains show a high toxicity against specific insects. Bt strains are known to produce delta-endotoxins that are localized within parasporal crystalline inclusion bodies at the onset of sporulation and during the stationary growth phase (e.g., Cry proteins), and are also known to produce secreted insecticidal protein. Upon ingestion by a susceptible insect, delta-endotoxins as well as secreted toxins exert their effects at the surface of the midgut epithelium, disrupting the cell membrane, leading to cell disruption and death. Genes encoding insecticidal proteins have also been identified in bacterial species other than Bt, including other *Bacillus* and a diversity of other bacterial species, such as *Brevibacillus laterosporus, Lysinibacillus sphaericus* ("Ls" formerly known as *Bacillus sphaericus*) and *Paenibacillus popilliae.*

Crystalline and secreted soluble insecticidal protein toxins are highly specific for their hosts and have gained worldwide acceptance as alternatives to chemical insecticides. For example, insecticidal toxin proteins have been employed in various agricultural applications to protect agriculturally important plants from insect infestations, decrease the need for chemical pesticide applications, and increase yields. Insecticidal toxin proteins are used to control agriculturally-relevant pests of crop plants by mechanical methods, such as spraying to disperse microbial formulations containing various bacteria strains onto plant surfaces, and by using genetic transformation techniques to produce transgenic plants and seeds expressing insecticidal toxin protein.

The use of transgenic plants expressing insecticidal proteins has been globally adopted. For example, in 2012, 26.1 million hectares were planted with transgenic crops expressing Bt toxins (James, C., Global Status of Commercialized Biotech/GM Crops: 2012. ISAAA Brief No. 44). The global use of transgenic insect-protected crops and the limited number of insecticidal proteins used in these crops has created a selection pressure for existing insect alleles that impart resistance to the currently-utilized insecticidal proteins.

The development of resistance in target pests to insecticidal proteins creates the continuing need for discovery and development of new forms of insecticidal proteins that are useful for managing the increase in insect resistance to transgenic crops expressing insecticidal proteins. New insecticidal proteins with improved efficacy and which exhibit control over a broader spectrum of susceptible insect species will reduce the number of surviving insects which can develop resistance alleles. In addition, the use in one plant of two or more transgenic insecticidal proteins toxic to the same insect pest and displaying different modes of action reduces the probability of resistance in any single target insect species.

Consequently, there is a critical need to identify additional insecticidal proteins with improved insecticidal properties such as increased efficacy against a broader spectrum of target insect pests species and different modes of action compared to the toxins currently used in agricultural practices. To meet this need, the present invention discloses novel Cry1 chimeric insecticidal proteins that exhibit activity against significant target Lepidopteran pest species.

Members of the family of Cry1 crystal proteins are known in the art to exhibit bioactivity against Lepidopteran pests. The precursor form of Cry 1 crystal proteins consists of two approximately equal-sized segments. The carboxy-terminal portion of the precursor protein, known as the protoxin segment, stabilizes crystal formation and exhibits no insecticidal activity. The amino-terminal half of the precursor protein comprises the toxin segment of the Cry1 protein and, based on alignment of conserved or substantially conserved sequences within Cry1 family members, can be further sub-divided into three structural domains, domain I, domain II, and domain III. Domain I comprises about the first third of the active toxin segment and has been shown to be essential for channel formation. Domains II and III have both been implicated in receptor binding and insect species specificity, depending on the insect and insecticidal protein being examined.

The likelihood of arbitrarily creating a chimeric protein with enhanced properties from the assortment of the domain structures of the numerous native insecticidal proteins known in the art is remote. This is a result of the complex nature of protein structure, oligomerization, and activation (including correct proteolytic processing of the chimeric precursor, if expressed in such a form) required to release an insecticidal protein segment. Only by careful selection of protoxins and specific targets within each parental protein for the creation of a chimeric structure can functional chimeric insecticidal toxins be constructed that exhibit improved insecticidal activity in comparison to the parental proteins from which the chimeras are derived. It is known in the art that reassembly of the protoxin and toxin domains I, II and III of any two or more toxins that are different from each other often results in the construction of proteins that exhibit faulty crystal formation or the complete lack of any detectable insecticidal activity directed to a preferred target insect pest species. Only by trial and error are effective insecticidal chimeras designed, and even then, the skilled artisan is not certain to end up with a chimera that exhibits insecticidal activity that is equivalent to or improved in comparison to any single parental toxin protein from which the constituent protoxin or toxin domains of the chimera may have been derived. For example, the literature reports numerous examples of the construction or assembly of chimeric proteins from two or more crystal protein precursors. See, e.g. Jacqueline S. Knight, et al. "A Strategy for Shuffling Numerous *Bacillus thuringiensis* Crystal Protein Domains." *J. Economic Entomology,* 97 (6) (2004): 1805-1813; Bosch, et al. (U.S. Pat. No. 6,204,246); Malvar and Gilmer (U.S. Pat. No. 6,017,534). In each of these examples, many of the resultant chimeras failed to exhibit insecticidal or crystal forming properties that were equivalent to or improved in comparison to the precursor proteins from which the components of the chimeras were derived.

SUMMARY OF THE INVENTION

Recombinant nucleic acid molecules are provided that encode chimeric insecticidal proteins toxic to Lepidopteran species of plant pests. Each of the chimeric insecticidal proteins can be used alone or in combination with each other and with other insecticidal proteins and insect inhibitory agents in formulations and in planta; thus providing alternatives to insecticidal proteins and insecticidal chemistries currently in use in agricultural systems.

In certain embodiments disclosed herein is a chimeric insecticidal protein comprising an amino acid sequence as set forth in any of SEQ ID NOs: 21, 10, 28, 7, 4, 13, 16, 19, 23, 25, 30, 33, 36, 39, 41, 43, 45, 47, 50 or 53. This chimeric insecticidal protein exhibits inhibitory activity against an insect species of the order Lepidoptera such as, but not limited to, *Anticarsia gemmatalis, Diatraea saccharalis, Elasmopalpus lignosellus, Helicoverpa zea, Heliothis virescens, Chrysodeixis includens, Spodoptera cosmioides, Spodoptera eridania, Spodoptera frugiperda, Spodoptera exigua, Helicoverpa armigera, Spodoptera litura, Pectinophora gossypiella, Diatraea grandiosella, Earias vitella, Helicoverpa gelotopeon*, and *Rachiplusia nu.*

In another embodiment, a polynucleotide encoding a chimeric insecticidal protein, wherein the polynucleotide is operably linked to a heterologous promoter and the chimeric insecticidal protein comprises the amino acid sequence as set forth in any of SEQ ID NOs: 21, 10, 28, 7, 4, 13, 16, 19, 23, 25, 30, 33, 36, 39, 41, 43, 45, 47, 50 or 53 is disclosed. A polynucleotide encoding a chimeric insecticidal protein, wherein the polynucleotide comprises a nucleotide sequence that optionally: hybridizes under stringent conditions to the reverse complement of the polynucleotide sequence as set forth in any of SEQ ID NOs:1, 2, 3, 5, 6, 8, 9, 11, 12, 14, 15, 17, 18, 20, 22, 24, 26, 27, 29, 31, 32, 34, 35, 37, 38, 40, 42, 44, 46, 48, 49, 51 or 52; or encodes the chimeric insecticidal protein comprising an amino acid sequence as set forth in any of SEQ ID NOs: 21, 10, 28, 7, 4, 13, 16, 19, 23, 25, 30, 33, 36, 39, 41, 43, 45, 47, 50 or 53 is also contemplated.

In other embodiments disclosed herein is a host cell comprising the polynucleotide set forth in any of SEQ ID NO: 1, 2, 3, 5, 6, 8, 9, 11, 12, 14, 15, 17, 18, 20, 22, 24, 26, 27, 29, 31, 32, 34, 35, 37, 38, 40, 42, 44, 46, 48, 49, 51 or 52, wherein the host cell is selected from the group consisting of a bacterial host cell or a plant host cell. Contemplated bacterial host include *Agrobacterium, Rhizobium, Bacillus, Brevibacillus, Escherichia, Pseudomonas, Klebsiella*, and *Erwinia*; and wherein the *Bacillus* species is a *Bacillus*

*cereus* or a *Bacillus thuringiensis*, said *Brevibacillus* is a *Brevibacillus laterosperous*, and said *Escherichia* is an *Escherichia coli*. Contemplated plant cells include monocots and dicots.

Other embodiments disclosed herein include insect inhibitory compositions comprising a chimeric insecticidal protein comprising an amino acid sequence as set forth in any of SEQ ID NOs: 21, 10, 28, 7, 4, 13, 16, 19, 23, 25, 30, 33, 36, 39, 41, 43, 45, 47, 50 or 53. In certain embodiments, the insect inhibitory composition further comprises at least one insect inhibitory agent different from the chimeric insecticidal protein. Contemplated insect inhibitory agents different from the chimeric insecticidal protein include an insect inhibitory protein, an insect inhibitory dsRNA molecule, and an insect inhibitory chemistry. These insect inhibitory agents different from the chimeric insecticidal protein can exhibit activity against one or more pest species of the orders Lepidoptera, Coleoptera, Hemiptera, Homoptera, or Thysanoptera.

In yet another embodiment, disclosed herein is a seed comprising an insect inhibitory effective amount of: a chimeric insecticidal protein comprising the amino acid sequence as set forth in any of SEQ ID NOs: 21, 10, 28, 7, 4, 13, 16, 19, 23, 25, 30, 33, 36, 39, 41, 43, 45, 47, 50 or 53; or a polynucleotide set forth in any of SEQ ID NOs:1, 2, 3, 5, 6, 8, 9, 11, 12, 14, 15, 17, 18, 20, 22, 24, 26, 27, 29, 31, 32, 34, 35, 37, 38, 40, 42, 44, 46, 48, 49, 51 or 52.

Methods of controlling a Lepidopteran pest comprising contacting the Lepidopteran pest with an inhibitory amount of a chimeric insecticidal protein of the invention are also contemplated.

In another embodiment, disclosed herein is a transgenic plant cell, plant or plant part comprising a chimeric insecticidal protein, wherein: the chimeric insecticidal protein comprises any amino acid sequence set forth in any of SEQ ID NO: 21, 10, 28, 7, 4, 13, 16, 19, 23, 25, 30, 33, 36, 39, 41, 43, 45, 47, 50 or 53; or the chimeric insecticidal protein comprises a protein having: at least 94% identical to SEQ ID NOs:21, 10; at least 93% identical to SEQ ID NO:28 at least 87% identical to SEQ ID NO:7; at least 90% identity to SEQ ID NO:4; at least 91% identical to SEQ ID NO:13; at least 64% identical to SEQ ID NO:16; at least 66% identical to SEQ ID NO:19; at least 86% identical to SEQ ID NO:23; at least 91% identical to SEQ ID NO:25; at least 94% identical to SEQ ID NO:30; at least 91% identical to SEQ ID NO:33; at least 64% identical to SEQ ID NO:36; at least 66% identical to SEQ ID NO:39; at least 94% identical to SEQ ID NO:41; at least 84% identical to SEQ ID NO:43; at least 93% identical to SEQ ID NO:45; at least 94% identical to SEQ ID NO: 47; at least 91% identical to SEQ ID NO:50; or at least 93% identical to SEQ ID NO:53. Methods of controlling a Lepidopteran pest which comprise exposing the pest to this transgenic plant cell, plant or plant part, wherein said plant cell, plant or plant part expresses a Lepidopteran inhibitory amount of the chimeric insecticidal protein are also contemplated.

In other embodiments herein, commodity products derived from the plant cell, plant, or plant part wherein the product comprises a detectable amount of the chimeric insecticidal protein are provided. Contemplated commodity products include plant biomass, oil, meal, animal feed, flour, flakes, bran, lint, hulls, and processed seed.

Yet another method disclosed herein is a method of producing a seed comprising a chimeric insecticidal protein, the method comprising: planting at least one seed comprising a chimeric insecticidal protein; growing plants from said seed; and harvesting seed from said plants, wherein said harvested seed comprises the chimeric insecticidal protein.

Recombinant polynucleotide molecules encoding a chimeric insecticidal protein, comprising a nucleotide sequence selected from the group consisting of 1, 2, 3, 5, 6, 8, 9, 11, 12, 14, 15, 17, 18, 20, 22, 24, 26, 27, 29, 31, 32, 34, 35, 37, 38, 40, 42, 44, 46, 48, 49, 51 or 52; and optionally a polynucleotide sequence encoding an insect inhibitory agent different from the chimeric insecticidal protein are also contemplated herein.

Another recombinant nucleic acid molecule contemplated herein comprises a heterologous promoter operably linked to a polynucleotide segment encoding a chimeric insecticidal proteins, wherein: the chimeric insecticidal protein comprises any amino acid sequence set forth in any of SEQ ID NO: 21, 10, 28, 7, 4, 13, 16, 19, 23, 25, 30, 33, 36, 39, 41, 43, 45, 47, 50 or 53; or the chimeric insecticidal protein comprises a protein having: at least 94% identical to SEQ ID NOs:21, 10; at least 93% identical to SEQ ID NO:28; at least 87% identical to SEQ ID NO:7; at least 90% identity to SEQ ID NO:4; at least 91% identical to SEQ ID NO:13; at least 64% identical to SEQ ID NO:16; at least 66% identical to SEQ ID NO:19; at least 86% identical to SEQ ID NO:23; at least 91% identical to SEQ ID NO:25; at least 94% identical to SEQ ID NO:30; at least 91% identical to SEQ ID NO:33; at least 64% identical to SEQ ID NO:36; at least 66% identical to SEQ ID NO:39; at least 94% identical to SEQ ID NO:41; at least 84% identical to SEQ ID NO:43; at least 93% identical to SEQ ID NO:45; at least 94% identical to SEQ ID NO: 47; at least 91% identical to SEQ ID NO:50; or at least 93% identical to SEQ ID NO:53; or the polynucleotide segment hybridizes to a polynucleotide having a nucleotide sequence as set forth in any of SEQ ID NO: 1, 2, 3, 5, 6, 8, 9, 11, 12, 14, 15, 17, 18, 20, 22, 24, 26, 27, 29, 31, 32, 34, 35, 37, 38, 40, 42, 44, 46, 48, 49, 51 or 52.

Other embodiments, features, and advantages of the invention will be apparent from the following detailed description, examples, and claims.

BRIEF DESCRIPTION OF THE SEQUENCES

SEQ ID SEQ ID NO: 1 is a recombinant DNA sequence encoding TIC1100 used for expression in a bacterial cell.

SEQ ID NO: 2 is a synthetic DNA sequence encoding TIC1100 for expression in a plant cell.

SEQ ID NO: 3 is a synthetic DNA sequence encoding TIC1100 for expression in a plant cell.

SEQ ID NO: 4 is the amino acid sequence of TIC1100.

SEQ ID NO: 5 is a recombinant DNA sequence encoding TIC860 used for expression in a bacterial cell.

SEQ ID NO: 6 is a synthetic DNA sequence encoding TIC860 for expression in a plant cell.

SEQ ID NO: 7 is the amino acid sequence of TIC860.

SEQ ID NO: 8 is a recombinant DNA sequence encoding TIC867 used for expression in a bacterial cell.

SEQ ID NO: 9 is a synthetic DNA sequence encoding TIC867 for expression in a plant cell.

SEQ ID NO: 10 is the amino acid sequence of TIC867.

SEQ ID NO: 11 is a recombinant DNA sequence encoding TIC867_20 used for expression in a bacterial cell.

SEQ ID NO: 12 is a synthetic DNA sequence encoding TIC867_20 for expression in a plant cell.

SEQ ID NO: 13 is the amino acid sequence of TIC867_20.

SEQ ID NO: 14 is a recombinant DNA sequence encoding TIC867_21 used for expression in a bacterial cell.

SEQ ID NO: 15 is a synthetic DNA sequence encoding TIC867_21 for expression in a plant cell.

SEQ ID NO: 16 is the amino acid sequence of TIC867_21.

SEQ ID NO: 17 is a recombinant DNA sequence encoding TIC867_22 used for expression in a bacterial cell.

SEQ ID NO: 18 is a synthetic DNA sequence encoding TIC867_22 for expression in a plant cell.

SEQ ID NO: 19 is the amino acid sequence of TIC867_22.

SEQ ID NO: 20 is a synthetic DNA sequence encoding TIC867_23 for expression in the plant cell.

SEQ ID NO: 21 is the amino acid sequence of TIC867_23.

SEQ ID NO: 22 is a synthetic DNA sequence encoding TIC867_24 for expression in a plant cell.

SEQ ID NO: 23 is the amino acid sequence of TIC867_24.

SEQ ID NO: 24 is a synthetic DNA sequence encoding TIC867_24 for expression in a plant cell.

SEQ ID NO: 25 is the amino acid sequence of TIC867_25.

SEQ ID NO: 26 is a recombinant DNA sequence encoding TIC868 used for expression in a bacterial cell.

SEQ ID NO: 27 is a synthetic DNA sequence encoding TIC868 for expression in a plant cell.

SEQ ID NO: 28 is the amino acid sequence of TIC868.

SEQ ID NO: 29 is a synthetic DNA sequence encoding TIC868_9 for expression in a plant cell.

SEQ ID NO: 30 is the amino acid sequence of TIC868_9.

SEQ ID NO: 31 is a recombinant DNA sequence encoding TIC868_10 used for expression in a bacterial cell.

SEQ ID NO: 32 is a synthetic DNA sequence for expression in the plant cell encoding the TIC868 variant, TIC868_10.

SEQ ID NO: 33 is the amino acid sequence of TIC868_10.

SEQ ID NO: 34 is a recombinant DNA sequence encoding TIC868_11 used for expression in a bacterial cell.

SEQ ID NO: 35 is a synthetic DNA sequence encoding TIC868_11 for expression in a plant cell.

SEQ ID NO: 36 is the amino acid sequence of TIC868_11.

SEQ ID NO: 37 is a recombinant DNA sequence encoding TIC868_12 used for expression in a bacterial cell.

SEQ ID NO: 38 is a synthetic DNA sequence encoding TIC868_12 for expression in the plant cell.

SEQ ID NO: 39 is the amino acid sequence of TIC868_12.

SEQ ID NO: 40 is a synthetic DNA sequence encoding TIC868_13 for expression in the plant cell.

SEQ ID NO: 41 is the amino acid sequence of TIC868_13.

SEQ ID NO: 42 is a synthetic DNA sequence encoding TIC868_14 for expression in a plant cell.

SEQ ID NO: 43 is the amino acid sequence of TIC868_14.

SEQ ID NO: 44 is a synthetic DNA sequence encoding TIC868_15 for expression in a plant cell.

SEQ ID NO: 45 is the amino acid sequence of TIC868_15.

SEQ ID NO: 46 is a synthetic DNA sequence encoding TIC868_29 for expression in a plant cell.

SEQ ID NO: 47 is the amino acid sequence of TIC868_29.

SEQ ID NO: 48 is a recombinant DNA sequence encoding TIC869 used for expression in a bacterial cell.

SEQ ID NO: 49 is a synthetic DNA sequence encoding TIC869 for expression in a plant cell.

SEQ ID NO: 50 is the amino acid sequence of TIC869.

SEQ ID NO: 51 is a recombinant DNA sequence encoding TIC836 used for expression in a bacterial cell.

SEQ ID NO: 52 is a synthetic DNA sequence encoding TIC836 for expression in a plant cell.

SEQ ID NO: 53 is the amino acid sequence of TIC836.

DETAILED DESCRIPTION OF THE INVENTION

The problem in the art of agricultural pest control can be characterized as a need for new insecticidal proteins that are efficacious against target pests, exhibit broad spectrum toxicity against target pest species, are capable of being expressed in plants without causing undesirable agronomic issues, and provide an alternative mode of action compared to current toxins that are used commercially in plants. Novel chimeric insecticidal proteins are disclosed herein, and address each of these needs, particularly against a broad spectrum of Lepidopteran insect pests.

In order to avoid the development of, or circumvent insect resistance against currently used insecticidal proteins, new insecticidal proteins with different modes-of-action (MOA), as well as a broad spectrum and efficacy, are needed for Lepidoptera control. One way to address this need is to discover new insecticidal proteins from different biological sources, preferably from bacteria, fungi or plants. Another approach is to interchange segments between various Bt proteins that exhibit structural similarities to create new chimeric Bt proteins having insect inhibitory properties. The likelihood of creating a chimeric protein with enhanced properties from the re-assortment of the domain structures of numerous native insecticidal crystal proteins known in the art is known in the art to be remote. See, e.g. Jacqueline S. Knight, et al. "A Strategy for Shuffling Numerous *Bacillus thuringiensis* Crystal Protein Domains." *J. Economic Entomology,* 97 (6) (2004): 1805-1813.

Disclosed herein are recombinant nucleic acid molecule sequences that encode novel chimeric insecticidal proteins. These insecticidal proteins address the ongoing need in the art to engineer additional toxic insecticidal proteins with improved insecticidal properties such as increased efficacy against a broader spectrum of target insect pests species and different modes of action. Members of this group of proteins, including the exemplary proteins disclosed herein, exhibit insecticidal activity against Lepidopteran insect pest species.

The term "segment" or "fragment" is used in this application to describe consecutive amino acid or nucleic acid sequences that are shorter than the complete amino acid or nucleic acid sequence describing a disclosed chimeric insecticidal protein. A segment or fragment exhibiting insect inhibitory activity is also disclosed in this application if alignment of such segment or fragment, with the corresponding section of the chimeric insecticidal protein, results in amino acid sequence identity of any fraction percentage from about 65 to about 100 percent between the segment or fragment and the corresponding section of the chimeric insecticidal protein.

Reference in this application to the terms "active" or "activity", "pesticidal activity" or "pesticidal", or "insecticidal activity", "insect inhibitory" or "insecticidal" refer to efficacy of a toxic agent, such as an insecticidal protein, in inhibiting (inhibiting growth, feeding, fecundity, or viability), suppressing (suppressing growth, feeding, fecundity, or viability), controlling (controlling the pest infestation, controlling the pest feeding activities on a particular crop containing an effective amount of the insecticidal protein) or killing (causing the morbidity, mortality, or reduced fecundity of) a pest. These terms are intended to include the result of providing a pesticidally effective amount of an insecticidal protein to a pest where the exposure of the pest to the insecticidal protein results in morbidity, mortality, reduced fecundity, or stunting. These terms also include repulsion of the pest from the plant, a tissue of the plant, a plant part, seed, plant cells, or from the particular geographic location where the plant may be growing, as a result of providing a pesticidally effective amount of the insecticidal protein in or on the plant. In general, pesticidal activity refers to the ability of an insecticidal protein to be effective in inhibiting the growth, development, viability, feeding behavior, mating behavior, fecundity, or any measurable decrease in the adverse effects caused by an insect feeding on this protein, protein fragment, protein segment or polynucleotide of a particular target pest, including but not limited to insects of the order Lepidoptera. The insecticidal protein can be produced by the plant or can be applied to the plant or to the environment within the location where the plant is located. The terms "bioactivity", "effective", "efficacious" or variations thereof are also terms interchangeably utilized in this application to describe the effects of the chimeric insecticidal proteins of the present invention on target insect pests.

A pesticidally effective amount of a toxic agent, when provided in the diet of a target pest, exhibits pesticidal activity when the toxic agent contacts the pest. A toxic agent can be an insecticidal protein or one or more chemical agents known in the art. Insecticidal chemical agents and insecticidal protein agents can be used alone or in combinations with each other. Chemical agents include but are not limited to dsRNA molecules targeting specific genes for suppression in a target pest, organochlorides, organophosphates, carbamates, pyrethroids, neonicotinoids, and ryanoids. Insecticidal protein agents include the chimeric insecticidal proteins set forth in this application, as well as other proteinaceous toxic agents including those that target Lepidopteran pest species, as well as protein toxins that are used to control other plant pests such as Cry proteins available in the art for use in controlling Coleopteran, Thysanopteranm, Hemipteran and Homopteran species.

It is intended that reference to a pest, particularly a pest of a crop plant, means insect pests of crop plants, particularly those Lepidopteran insect pests that are controlled by the disclosed chimeric insecticidal proteins. However, reference to a pest can also include Coleopteran, Hemipteran and Homopteran insect pests of plants, as well as nematodes and fungi when toxic agents targeting these pests are co-localized or present together with the chimeric insecticidal protein, or a protein that is 65 to about 100 percent identical to the chimeric insecticidal protein.

The chimeric insecticidal proteins disclosed herein exhibit insecticidal activity towards insect pests from the Lepidopteran insect species, including adults, pupae, larvae, and neonates, as well as Hemipteran insect species, including adults and nymphs. The insects of the order Lepidoptera include, but are not limited to, armyworms, cutworms, loopers, and heliothines in the Family Noctuidae, e.g., fall armyworm (*Spodoptera frugiperda*), beet armyworm (*Spodoptera exigua*), bertha armyworm (*Mamestra configurata*), black cutworm (*Agrotis ipsilon*), cabbage looper (*Trichoplusia ni*), soybean looper (*Pseudoplusia includens*), velvetbean caterpillar (*Anticarsia gemmatalis*), green cloverworm (*Hypena scabra*), tobacco budworm (*Heliothis virescens*), granulate cutworm (*Agrotis subterranea*), armyworm (*Pseudaletia unipuncta*), western cutworm (*Agrotis orthogonia*); borers, casebearers, webworms, coneworms, cabbageworms and skeletonizers from the Family Pyralidae, e.g., European corn borer (*Ostrinia nubilalis*), navel orangeworm (*Amyelois transitella*), corn root webworm (*Crambus caliginosellus*), sod webworm (*Herpetogramma licarsisalis*), sunflower moth (*Homoeosoma electellum*), lesser cornstalk borer (*Elasmopalpus lignosellus*); leafrollers, budworms, seed worms, and fruit worms in the Family Tortricidae, e.g., codling moth (*Cydia pomonella*), grape berry moth (*Endopiza viteana*), oriental fruit moth (*Grapholita molesta*), sunflower bud moth (*Suleima helianthana*); and many other economically important Lepidoptera, e.g., diamondback moth (*Plutella xylostella*), pink bollworm (*Pectinophora gossypiella*) and gypsy moth (*Lymantria dispar*). Other insect pests of order Lepidoptera include, e.g., *Alabama argillacea* (cotton leaf worm), *Archips argyrospila* (fruit tree leaf roller), *Archips rosana* (European leafroller) and other *Archips* species, *Chilo suppressalis* (Asiatic rice borer, or rice stem borer), *Cnaphalocrocis medinalis* (rice leaf roller), *Crambus caliginosellus* (corn root webworm), *Crambus teterrellus* (bluegrass webworm), *Diatraea grandiosella* (southwestern corn borer), *Diatraea saccharalis* (surgarcane borer), *Earias insulana* (spiny bollworm), *Earias vittella* (spotted bollworm), *Helicoverpa armigera* (American bollworm), *Helicoverpa zea* (corn earworm or cotton bollworm), *Heliothis virescens* (tobacco budworm), *Herpetogramma licarsisalis* (sod webworm), *Lobesia botrana* (European grape vine moth), *Phyllocnistis citrella* (citrus leafminer), *Pieris brassicae* (large white butterfly), *Pieris rapae* (imported cabbageworm, or small white butterfly), *Plutella xylostella* (diamondback moth), *Spodoptera exigua* (beet armyworm), *Spodoptera litura* (tobacco cutworm, cluster caterpillar), and *Tuta absoluta* (tomato leafminer).

Reference in this application to an "isolated DNA molecule", or an equivalent term or phrase, is intended to mean that the DNA molecule is one that is present alone or in combination with other compositions, but not within its natural environment. For example, nucleic acid elements such as a coding sequence, intron sequence, untranslated leader sequence, promoter sequence, transcriptional termination sequence, and the like, that are naturally found within the DNA of the genome of an organism are not considered to be "isolated" so long as the element is within the genome of the organism and at the location within the genome in which it is naturally found. However, each of these elements, and subparts of these elements, would be "isolated" within the scope of this disclosure so long as the element is not within the genome of the organism and at the location within the genome in which it is naturally found. Similarly, a nucleotide sequence encoding an insecticidal protein or any naturally occurring insecticidal variant of that protein would be an isolated nucleotide sequence so long as the nucleotide sequence was not within the DNA of the bacterium from which the sequence encoding the protein is naturally found. A synthetic nucleotide sequence encoding the amino acid sequence of the naturally occurring insecticidal protein would be considered to be isolated for the purposes of this disclosure. For the purposes of this disclosure, any transgenic nucleotide sequence, i.e., the nucleotide sequence of the DNA inserted into the genome of the cells of a plant or bacterium, or present in an extrachromosomal vector, would be considered to be an isolated nucleotide sequence whether it is present within the plasmid or similar structure used to transform the cells, within the genome of the plant or bacterium, or present in detectable amounts in tissues, progeny, biological samples or commodity products derived from the plant or bacterium.

As described further in the Examples, through a chimeragenesis effort about eight hundred and forty four (844) nucleotide sequences that encode chimeric insecticidal proteins were constructed from the protoxin and toxin domains of known insecticidal toxins (referred to herein as the "parent proteins"), and expressed and tested in bioassay for Lepidopteran activity. A small number of the constructed chimeric insecticidal proteins exhibited improved Lepidopteran activity or an enhanced Lepidopteran spectrum compared to the parent proteins from which its toxin components were derived.

These novel chimeric insecticidal proteins with improved Lepidopteran activity or an enhanced Lepidopteran spectrum were constructed from the following insecticidal parent protein protoxin and toxin domains: Cry1Ah (Domain I), Cry1Bb1 (Domains I and II), Cry 1Be2 (Domains I and II), Cry1Ja1 (Domains I and II), Cry1Fa1 (Domains I and II), Cry1Ac (Domain II and protoxin), Cry1Ca (Domain III and protoxin), Cry1Ka (Domain III and protoxin), Cry1Jx (Domain III), Cry1Ab (Domain III), Cry1Ab3 (protoxin), Cry1Da1(protoxin), Cry4 (protoxin), Cry9 (protoxin), Cry1Be (protoxin), and Cry1Ka (protoxin).

Specifically, the novel chimeric insecticidal proteins of this invention with improved Lepidopteran activity or an enhanced Lepidopteran spectrum comprise the following protoxin and domain combinations: TIC1100/SEQ ID NO:4 (Domain I—Cry1Ah, Domain II—Cry1Ac, Domain III—Cry1Ca, Protoxin—Cry1Ac), TIC860/SEQ ID NO:7 (Domain I—Cry1Bb1, Domain II—Cry1BB1, Domain III—Cry1Ca, Protoxin—Cry1Ac), TIC867/SEQ ID NO:10 (Domain I—Cry1Be2, Domain II—Cry1Be2, Domain III—Cry1Ka, Protoxin—Cry1Ab3), TIC868/SEQ ID NO:28 (Domain I—Cry1Be2, Domain II—Cry1Be2, and Domain III—Cry1Ca, Protoxin—Cry1Ab3), TIC869/SEQ ID NO:50 (Domain I—Cry1Ja1, Domain II—Cry1Ja1, Domain III—Cry1Jx, Protoxin—Cry1Ab3) and TIC836/SEQ ID NO:53 (Domain I—Cry1Fa1, Domain II—Cry1Fa1, Domain III—Cry1Ab, Protoxin—Cry1Ac).

Variants in which amino acid substitutions or alternate protoxin domains were introduced were also constructed for the chimeric insecticidal proteins TIC867 and TIC868. Specifically, these variants of TIC867 and TIC868 comprise the following amino acid substitutions or alternate protoxin domains: TIC867_20/SEQ ID NO:13 (alternate protoxin domain Cry1Da1), TIC867_21/SEQ ID NO:16 (alternate protoxin domain Cry4), TIC867_22/SEQ ID NO:19 (alternate protoxin domain Cry9), TIC867_23/SEQ ID NO:21 (alternate protoxin domain Cry1Be), TIC867_24/SEQ ID NO:23 (alternate protoxin domain Cry1Ka), TIC867_25/SEQ ID NO: 25 (alternate protoxin domain Cry1Ka), TIC868_9/SEQ ID NO:30 (amino acid modification N240S_Y343QN349T), TIC868_10/SEQ ID NO:33 (alternate protoxin domain Cry1Da1), TIC868_11/SEQ ID NO:36 (alternate protoxin domain Cry4), TIC868_12/SEQ ID NO:39 (alternate protoxin domain Cry9), TIC868_13/SEQ ID NO:41 (alternate protoxin domain Cry1Be), TIC868_14/SEQ ID NO:43 (alternate protoxin domain Cry1Ka), TIC868_15/SEQ ID NO:45 (alternate protoxin domain Cry1Ca), and TIC868_29/SEQ ID NO:47 (amino acid modification Q136Y_Y343Q_N349T).

As demonstrated in the Examples, each of these TIC867 and TIC868 variants altered the Lepidopteran activity and/or reduced the Lepidopteran activity spectrum of the parent chimeric insecticidal protein, thus indicating that the alternate protoxin domain and the amino acid substitutions had a direct consequence on the insecticidal activity and spectrum of the chimeric insecticidal proteins TIC867 and TIC868.

Many of the chimeric insecticidal proteins demonstrate insecticidal activity against multiple Lepidopteran insect pest species. Specifically, the novel chimeric insecticidal proteins disclosed in this application exhibited activity against one or more of the following Lepidopteran insect pests, Velvet bean caterpillar (VBC, *Anticarsia gemmatalis*), Sugarcane borer (SCB, *Diatraea saccharalis*), Lesser cornstalk borer (LSCB, *Elasmopalpus lignosellus*), Corn earworm (CEW, *Helicoverpa zea*), Soybean pod worm (SPW, *Helicoverpa zea*), Cotton bollworm (CBW, *Helicoverpa zea*), Tobacco budworm (TBW, *Heliothis virescens*), Soybean looper (SBL, *Chrysodeixis includens*), Black armyworm (BLAW, *Spodoptera* cosmioides), Southern armyworm (SAW, *Spodoptera eridania*), Fall armyworm (FAW, *Spodoptera frugiperda*), Beet armyworm (BAW, *Spodoptera exigua*), Old World bollworm (OBW, *Helicoverpa armigera*), Oriental leafworm (OLW, *Spodoptera litura*), Pink bollworm (PBW, *Pectinophora gossypiella*), Southwestern Corn Borer (SWCB, *Diatraea grandiosella*), Spotted bollworm (SBW, *Earias* vitella), American bollworm (SABW, *Helicoverpa gelotopeon*), and Sunflower looper (SFL, *Rachiplusia nu*). Thus, the exemplary proteins described in this application are related by common function and exhibit insecticidal activity towards insect pests from the Lepidoptera insect species including adults, larvae and pupae.

Proteins that resemble the chimeric insecticidal proteins can be identified by comparison to each other using various computer based algorithms known in the art. For example, amino acid sequence identities of proteins related to the chimeric insecticidal proteins can be analyzed using a Clustal W alignment using these default parameters: Weight matrix: blosum, Gap opening penalty: 10.0, Gap extension penalty: 0.05, Hydrophilic gaps: On, Hydrophilic residues: GPSNDQERK, Residue-specific gap penalties: On (Thompson, et al (1994) Nucleic Acids Research, 22:4673-4680). Percent amino acid identity is further calculated by the product of 100% multiplied by (amino acid identities/length of the subject protein). Other alignment algorithms are also available in the art, provide results similar to those obtained using Clustal W alignment and are contemplated in this application.

It is intended that a query protein exhibiting insect inhibitory activity is disclosed in this application if alignment of such query protein with the subject chimeric insecticidal proteins set forth in SEQ ID NOs: 4, 7, 10, 13, 16, 19, 21, 23, 25, 28, 30, 33, 36, 39, 41, 43, 45, 47, 50 and 53 and results in at least about 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or about 100% amino acid sequence identity (or any fraction percentage in this range) between the query and subject protein.

As described further in the Examples of this application, synthetic or artificial sequences encoding the chimeric insecticidal proteins were designed for use in plants. Exemplary synthetic nucleotide sequences that were designed for use in plants are set forth in SEQ ID NOs: 2 and 3 (TIC1100), SEQ ID NO:6 (TIC860), SEQ ID NO:9 (TIC867), SEQ ID NO:12 (TIC867_20), SEQ ID NO:15 (TIC867_21), SEQ ID NO:18 (TIC867_22), SEQ ID NO:20 (TIC867_23), SEQ ID NO:22 (TIC867_24), SEQ ID NO: 24 (TIC867_25), SEQ ID NO:27

(TIC868), SEQ ID NO:29 (TIC868_9), SEQ ID NO:32 (TIC868_10), SEQ ID NO:35 (TIC868_11), SEQ ID NO:38 (TIC868_12), SEQ ID NO:40 (TIC868_13), SEQ ID NO:42 (TIC868_14), SEQ ID NO:44 (TIC868_15), SEQ ID NO:46 (TIC868_29), SEQ ID NO:49 (TIC869) and SEQ ID NO:52 (TIC836).

For expression in plant cells, the chimeric insecticidal proteins can be expressed to reside in the cytosol or targeted to various organelles of the plant cell. For example, targeting a protein to the chloroplast may result in increased levels of expressed protein in a transgenic plant while preventing off-phenotypes from occurring. Targeting may also result in an increase in pest resistance efficacy in the transgenic event. A target peptide or transit peptide is a short (3-70 amino acids long) peptide chain that directs the transport of a protein to a specific region in the cell, including the nucleus, mitochondria, endoplasmic reticulum (ER), chloroplast, apoplast, peroxisome and plasma membrane. Some target peptides are cleaved from the protein by signal peptidases after the proteins are transported. For targeting to the chloroplast, proteins contain transit peptides which are around 40-50 amino acids. For descriptions of the use of chloroplast transit peptides, see U.S. Pat. Nos. 5,188,642 and 5,728,925. Many chloroplast-localized proteins are expressed from nuclear genes as precursors and are targeted to the chloroplast by a chloroplast transit peptide (CTP). Examples of such isolated chloroplast proteins include, but are not limited to, those associated with the small subunit (SSU) of ribulose-1,5,-bisphosphate carboxylase, ferredoxin, ferredoxin oxidoreductase, the light-harvesting complex protein I and protein II, thioredoxin F, enolpyruvyl shikimate phosphate synthase (EPSPS), and transit peptides described in U.S. Pat. No. 7,193,133. It has been demonstrated in vivo and in vitro that non-chloroplast proteins may be targeted to the chloroplast by use of protein fusions with a heterologous CTP and that the CTP is sufficient to target a protein to the chloroplast. Incorporation of a suitable chloroplast transit peptide such as the *Arabidopsis thaliana* EPSPS CTP (CTP2) (see, Klee et al., *Mol. Gen. Genet.* 210:437-442, 1987) or the *Petunia hybrida* EPSPS CTP (CTP4) (see, della-Cioppa et al., *Proc. Natl. Acad. Sci. USA* 83:6873-6877, 1986) has been shown to target heterologous EPSPS protein sequences to chloroplasts in transgenic plants (see, U.S. Pat. Nos. 5,627,061; 5,633,435; and 5,312,910; and EP 0218571; EP 189707; EP 508909; and EP 924299). For targeting the chimeric insecticidal proteins to the chloroplast, a sequence encoding a chloroplast transit peptide is placed 5' in operable linkage and in frame to a synthetic coding sequence encoding the chimeric insecticidal protein that has been designed for optimal expression in plant cells.

Expression cassettes and vectors containing these synthetic or artificial nucleotide sequences were constructed and introduced into corn, cotton, and soybean plant cells in accordance with transformation methods and techniques which are known in the art. Transformed cells were regenerated into transformed plants that were observed to be expressing the chimeric insecticidal protein. To test pesticidal activity, bioassays were performed in the presence of Lepidopteran pest larvae using plant leaf disks obtained from the transformed plants. Recombinant nucleic acid molecule compositions that encode the chimeric insecticidal proteins are contemplated. For example, the chimeric insecticidal proteins can be expressed with recombinant DNA constructs in which a polynucleotide molecule with an ORF encoding a chimeric insecticidal protein is operably linked to genetic expression elements such as a promoter and any other regulatory element necessary for expression in the system for which the construct is intended. Non-limiting examples include a plant-functional promoter operably linked to the synthetic chimeric insecticidal protein encoding sequences for expression of the chimeric insecticidal protein in plants or a Bt-functional promoter operably linked to a chimeric insecticidal protein encoding sequence for expression of the protein in a Bt bacterium or other *Bacillus* species. Other elements can be operably linked to the chimeric insecticidal proteins encoding sequences including, but not limited to, enhancers, introns, untranslated leaders, encoded protein immobilization tags (HIS-tag), translocation peptides (i.e., plastid transit peptides, signal peptides), polypeptide sequences for post-translational modifying enzymes, ribosomal binding sites, and RNAi target sites.

Exemplary recombinant polynucleotide molecules provided herein include, but are not limited to, a heterologous promoter operably linked to a polynucleotide such as SEQ ID NOs: 1, 2, 3, 5, 6, 8, 9, 11, 12, 14, 15, 17, 18, 20, 22, 24, 26, 27, 29, 31, 32, 34, 35, 37, 38, 40, 42, 44, 46, 48, 49, 51, and 52, that encodes the polypeptide or protein having the amino acid sequence as set forth in SEQ ID NOs: 4 (TIC1100), 7 (TIC860), 10 (TIC867), 13 (TIC867_20), 16 (TIC867_21), 19 (TIC867_22), 21 (TIC867_23), 23 (TIC867_24), 25 (TIC867_25), 28 (TIC868), 30 (TIC868_9), 33 (TIC868_10), 36 (TIC868_11), 39 (TIC867_12), 41 (TIC867_13), 43 (TIC867_14), 45 (TIC867_15), 47 (TIC867_29), 50 (TIC869) and 53 (TIC836). A heterologous promoter can also be operably linked to synthetic DNA coding sequences encoding a plastid targeted chimeric insecticidal protein and untargeted chimeric insecticidal protein. It is contemplated that the codons of a recombinant nucleic acid molecule encoding for a chimeric insecticidal protein disclosed herein can be substituted by synonymous codons (known in the art as a silent substitution).

A recombinant DNA molecule or construct comprising a chimeric insecticidal protein encoding sequence can further comprise a region of DNA that encodes for one or more toxic agents which can be configured to concomitantly express or co-express with a DNA sequence encoding a chimeric insecticidal protein, a protein different from a chimeric insecticidal protein, an insect inhibitory dsRNA molecule, or an ancillary protein. Ancillary proteins include, but are not limited to, co-factors, enzymes, binding-partners, or other agents that function to aid in the effectiveness of an insect inhibitory agent, for example, by aiding its expression, influencing its stability in plants, optimizing free energy for oligomerization, augmenting its toxicity, and increasing its spectrum of activity. An ancillary protein may facilitate the uptake of one or more insect inhibitory agents, for example, or potentiate the toxic effects of the toxic agent.

A recombinant DNA molecule or construct can be assembled so that all proteins or dsRNA molecules are expressed from one promoter or each protein or dsRNA molecule is under separate promoter control or some combination thereof. The proteins of this invention can be expressed from a multi-gene expression system in which a chimeric insecticidal protein is expressed from a common nucleotide segment which also contains other open reading frames and promoters, depending on the type of expression system selected. For example, a bacterial multi-gene expression system can utilize a single promoter to drive expression of multiply-linked/tandem open reading frames from within a single operon (i.e., polycistronic expression). In another example, a plant multi-gene expression system can utilize multiply-unlinked expression cassettes, each expressing a different protein or other toxic agent such as one or more dsRNA molecules.

Recombinant nucleic acid molecules or recombinant DNA constructs comprising chimeric insecticidal protein encoding sequence can be delivered to host cells by vectors, e.g., a plasmid, baculovirus, synthetic chromosome, virion, cosmid, phagemid, phage, or viral vector. Such vectors can be used to achieve stable or transient expression of a chimeric insecticidal protein encoding sequence in a host cell, or subsequent expression of the encoded polypeptide. An exogenous recombinant polynucleotide or recombinant DNA construct that comprises chimeric insecticidal protein sequence encoding sequence and that is introduced into a host cell is referred herein as a "transgene".

Transgenic bacteria, transgenic plant cells, transgenic plants, and transgenic plant parts that contain a polynucleotide that encodes any one or more of the chimeric insecticidal proteins are provided herein. The term "bacterial cell" or "bacterium" can include, but is not limited to, an *Agrobacterium*, a *Bacillus*, an *Escherichia*, a *Salmonella*, a *Pseudomonas*, or a *Rhizobium* cell. The term "plant cell" or "plant" can include but is not limited to a dicotyledonous cell or a monocotyledonous cell. Contemplated plants and plant cells include, but are not limited to, alfalfa, banana, barley, bean, broccoli, cabbage, brassica, carrot, cassava, castor, cauliflower, celery, chickpea, Chinese cabbage, citrus, coconut, coffee, corn, clover, cotton, a cucurbit, cucumber, Douglas fir, eggplant, eucalyptus, flax, garlic, grape, hops, leek, lettuce, Loblolly pine, millets, melons, nut, oat, olive, onion, ornamental, palm, pasture grass, pea, peanut, pepper, pigeonpea, pine, potato, poplar, pumpkin, Radiata pine, radish, rapeseed, rice, rootstocks, rye, safflower, shrub, sorghum, Southern pine, soybean, spinach, squash, strawberry, sugar beet, sugarcane, sunflower, sweet corn, sweet gum, sweet potato, switchgrass, tea, tobacco, tomato, triticale, turf grass, watermelon, and wheat plant cell or plant. In certain embodiments, transgenic plants and transgenic plant parts regenerated from a transgenic plant cell are provided. In certain embodiments, the transgenic plants can be obtained from a transgenic seed, by cutting, snapping, grinding or otherwise disassociating the part from the plant. In certain embodiments, the plant part can be a seed, a boll, a leaf, a flower, a stem, a root, or any portion thereof, or a non-regenerable portion of a transgenic plant part. As used in this context, a "non-regenerable" portion of a transgenic plant part is a portion that cannot be induced to form a whole plant or that cannot be induced to form a whole plant that is capable of sexual and/or asexual reproduction. In certain embodiments, a non-regenerable portion of a plant part is a portion of a transgenic seed, boll, leaf, flower, stem, or root.

Methods of making transgenic plants that comprise Lepidoptera-inhibitory amounts of a chimeric insecticidal proteins are provided. Such plants can be made by introducing a polynucleotide that encodes the chimeric insecticidal proteins provided in this application into a plant cell, and selecting a plant derived from said plant cell that expresses an insect or Lepidoptera-inhibitory amount of the chimeric insecticidal protein. Plants can be derived from the plant cells by regeneration, seed, pollen, or meristem transformation techniques. Methods for transforming plants are known in the art. For example, *Agrobacterium*-mediated transformation is described in U.S. Patent Application Publications 2009/0138985A1 (soybean), 2008/0280361A1 (soybean), 2009/0142837A1 (corn), 2008/0282432 (cotton), and 2008/0256667 (cotton).

Plants expressing the chimeric insecticidal proteins can be crossed by breeding with transgenic events expressing other insecticidal proteins and/or expressing other transgenic traits such as other insect control traits, herbicide tolerance genes, genes conferring yield or stress tolerance traits, and the like, or such traits can be combined in a single vector so that the traits are all linked.

Processed plant products, wherein the processed product comprises a detectable amount of a chimeric insecticidal protein, an insect inhibitory segment or fragment thereof, or any distinguishing portion thereof, are also disclosed in this application. In certain embodiments, the processed product is selected from the group consisting of plant parts, plant biomass, oil, meal, sugar, animal feed, flour, flakes, bran, lint, hulls, processed seed, and seed. In certain embodiments, the processed product is non-regenerable. The plant product can comprise commodity or other products of commerce derived from a transgenic plant or transgenic plant part, where the commodity or other products can be tracked through commerce by detecting nucleotide segments or expressed RNA or proteins that encode or comprise distinguishing portions of a chimeric insecticidal protein.

Methods of controlling insects, in particular Lepidoptera infestations of crop plants, with the chimeric insecticidal proteins are also disclosed in this application. Such methods can comprise growing a plant comprising an insect- or Lepidoptera-inhibitory amount of the chimeric insecticidal protein. In certain embodiments, such methods can further comprise any one or more of: (i) applying any composition comprising or encoding a chimeric insecticidal protein to a plant or a seed that gives rise to a plant; and (ii) transforming a plant or a plant cell that gives rise to a plant with a polynucleotide encoding a chimeric insecticidal protein. In general, it is contemplated that chimeric insecticidal protein can be provided in a composition, provided in a microorganism, or provided in a transgenic plant to confer insect inhibitory activity against Lepidopteran insects.

In certain embodiments, the chimeric insecticidal protein is the insecticidally active ingredient of an insect inhibitory composition prepared by culturing recombinant *Bacillus* or any other recombinant bacterial cell transformed to express a chimeric insecticidal protein under conditions suitable for expression. Such a composition can be prepared by desiccation, lyophilization, homogenization, extraction, filtration, centrifugation, sedimentation, or concentration of a culture of such recombinant cells expressing/producing the chimeric insecticidal protein. Such a process can result in a *Bacillus* or other entomopathogenic bacterial cell extract, cell suspension, cell homogenate, cell lysate, cell supernatant, cell filtrate, or cell pellet. By obtaining the chimeric insecticidal protein so produced, a composition that includes the chimeric insecticidal protein can include bacterial cells, bacterial spores, and parasporal inclusion bodies and can be formulated for various uses, including as agricultural insect inhibitory spray products or as insect inhibitory formulations in diet bioassays.

The aforementioned compound or formulation can further comprise an agriculturally-acceptable carrier, such as a bait, a powder, dust, pellet, granule, spray, emulsion, a colloidal suspension, an aqueous solution, a *Bacillus* spore or crystal preparation or a seed treatment. The compound or formulation can also further comprise a recombinant plant cell, plant tissue, seed or plant transformed to express one or more of the proteins; or bacterium transformed to express one or more of the proteins. Depending on the level of insect inhibitory or insecticidal inhibition inherent in the recombinant polypeptide and the level of compound or formulation to be applied to a plant or diet assay, the compound or formulation can include various by weight amounts of the recombinant polypeptide, e.g. from 0.0001% to 0.001% to 0.01% to 1% to 99% by weight of the recombinant polypeptide.

In an embodiment, in order to reduce the likelihood of resistance development, an insect inhibitory composition or transgenic plant comprising a chimeric insecticidal protein can further comprise at least one additional toxic agent that exhibits insect inhibitory activity against the same Lepidopteran insect species, but which is different from the chimeric insecticidal protein. Possible additional toxic agents for such a composition include an insect inhibitory protein and an insect inhibitory dsRNA molecule. One example for the use of such ribonucleotide sequences to control insect pests is described in Baum, et al. (U.S. Patent Publication 2006/0021087 A1). Such additional polypeptide(s) for the control of Lepidopteran pests may be selected from the group consisting of an insect inhibitory protein, such as, but not limited to, Cry1A (U.S. Pat. No. 5,880,275), Cry1Ab, Cry1Ac, Cry1A.105, Cry1Ae, Cry1B (U.S. patent Publication Ser. No. 10/525,318), Cry1C (U.S. Pat. No. 6,033,874), Cry1D, Cry1E, Cry1F, and Cry1A/F chimeras (U.S. Pat. Nos. 7,070,982; 6,962,705; and 6,713,063), Cry1G, Cry1H, Cry1I, Cry1J, Cry1K, Cry1L, Cry2A, Cry2Ab (U.S. Pat. No. 7,064,249), Cry2Ae, Cry4B, Cry6, Cry7, Cry8, Cry9, Cry15, Cry43A, Cry43B, Cry51Aa1, ET66, TIC400, TIC800, TIC834, TIC1415, Vip3A, VIP3Ab, VIP3B, AXMI-001, AXMI-002, AXMI-030, AXMI-035, AND AXMI-045 (U.S. Patent Publication 2013-0117884 A1), AXMI-52, AXMI-58, AXMI-88, AXMI-97, AXMI-102, AXMI-112, AXMI-117, AXMI-100 (U.S. Patent Publication 2013-0310543 A1), AXMI-115, AXMI-113, AXMI-005 (U.S. Patent Publication 2013-0104259 A1), AXMI-134 (U.S. Patent Publication 2013-0167264 A1), AXMI-150 (U.S. Patent Publication 2010-0160231 A1), AXMI-184 (U.S. Patent Publication 2010-0004176 A1), AXMI-196, AXMI-204, AXMI-207, AXMI-209 (U.S. Patent Publication 2011-0030096 A1), AXMI-218, AXMI-220 (U.S. Patent Publication 2014-0245491 A1), AXMI-221z, AXMI-222z, AXMI-223z, AXMI-224z, AXMI-225z (U.S. Patent Publication 2014-0196175 A1), AXMI-238 (U.S. Patent Publication 2014-0033363 A1), AXMI-270 (U.S. Patent Publication 2014-0223598 A1), AXMI-345 (U.S. Patent Publication 2014-0373195 A1), DIG-3 (U.S. Patent Publication 2013-0219570 A1), DIG-5 (U.S. Patent Publication 2010-0317569 A1), DIG-11 (U.S. Patent Publication 2010-0319093 A1), AfIP-1A and derivatives thereof (U.S. Patent Publication 2014-0033361 A1), AfIP-1B and derivatives thereof (U.S. Patent Publication 2014-0033361 A1), PIP-1APIP-1B (U.S. Patent Publication 2014-0007292 A1), PSEEN3174 (U.S. Patent Publication 2014-0007292 A1), AECFG-592740 (U.S. Patent Publication 2014-0007292 A1), Pput_1063 (U.S. Patent Publication 2014-0007292 A1), Pput_1064 (U.S. Patent Publication 2014-0007292 A1), GS-135 and derivatives thereof (U.S. Patent Publication 2012-0233726 A1), GS153 and derivatives thereof (U.S. Patent Publication 2012-0192310 A1), GS154 and derivatives thereof (U.S. Patent Publication 2012-0192310 A1), GS155 and derivatives thereof (U.S. Patent Publication 2012-0192310 A1), SEQ ID NO:2 and derivatives thereof as described in U.S. Patent Publication 2012-0167259 A1, SEQ ID NO:2 and derivatives thereof as described in U.S. Patent Publication 2012-0047606 A1, SEQ ID NO:2 and derivatives thereof as described in U.S. Patent Publication 2011-0154536 A1, SEQ ID NO:2 and derivatives thereof as described in U.S. Patent Publication 2011-0112013 A1, SEQ ID NO:2 and 4 and derivatives thereof as described in U.S. Patent Publication 2010-0192256 A1, SEQ ID NO:2 and derivatives thereof as described in U.S. Patent Publication 2010-0077507 A1, SEQ ID NO:2 and derivatives thereof as described in U.S. Patent Publication 2010-0077508 A1, SEQ ID NO:2 and derivatives thereof as described in U.S. Patent Publication 2009-0313721 A1, SEQ ID NO:2 or 4 and derivatives thereof as described in U.S. Patent Publication 2010-0269221 A1, SEQ ID NO:2 and derivatives thereof as described in U.S. Pat. No. 7,772,465 (B2), CF161_0085 and derivatives thereof as described in WO2014/008054 A2, Lepidopteran toxic proteins and their derivatives as described in US Patent Publications US2008-0172762 A1, US2011-0055968 A1, and US2012-0117690 A1; SEQ ID NO:2 and derivatives thereof as described in U.S. Pat. No. 7,510,878(B2), SEQ ID NO:2 and derivatives thereof as described in U.S. Pat. No. 7,812,129(B1); and the like.

In other embodiments, an insect inhibitory composition or transgenic plant can further comprise at least one additional toxic agent that exhibits insect inhibitory activity to an insect pest that is not inhibited by the chimeric insecticidal proteins of the present invention (such as Coleopteran, Hemipteran and Homopteran pests), in order to expand the spectrum of insect inhibition obtained.

Such additional toxic agent for the control of Coleopteran pests may be selected from the group consisting of an insect inhibitory protein, such as, but not limited to, Cry3Bb (U.S. Pat. No. 6,501,009), Cry1C variants, Cry3A variants, Cry3, Cry3B, Cry34/35, 5307, AXMI134 (U.S. Patent Publication 2013-0167264 A1) AXMI-184 (U.S. Patent Publication 2010-0004176 A1), AXMI-205 (U.S. Patent Publication 2014-0298538 A1), axmi207 (U.S. Patent Publication 2013-0303440 A1), AXMI-218, AXMI-220 (U.S. Patent Publication 20140245491A1), AXMI-221z, AXMI-223z (U.S. Patent Publication 2014-0196175 A1), AXMI-279 (U.S. Patent Publication 2014-0223599 A1), AXMI-R1 and variants thereof (U.S. Patent Publication 2010-0197592 A1, TIC407, TIC417, TIC431, TIC807, TIC853, TIC901, TIC1201, TIC3131, DIG-10 (U.S. Patent Publication 2010-0319092 A1), eHIPs (U.S. Patent Application Publication No. 2010/0017914), IP3 and variants thereof (U.S. Patent Publication 2012-0210462 A1), and ω-Hexatoxin-Hv1a (U.S. Patent Application Publication US2014-0366227 A1).

Such additional toxic agent for the control of Hemipteran pests may be selected from the group consisting of Hemipteran-active proteins such as, but not limited to, TIC1415 (US Patent Publication 2013-0097735 A1), TIC807 (U.S. Pat. No. 8,609,936), TIC834 (U.S. Patent Publication 2013-0269060 A1), AXMI-036 (U.S. Patent Publication 2010-0137216 A1), and AXMI-171 (U.S. Patent Publication 2013-0055469 A1). Additional polypeptides for the control of Coleopteran, Lepidopteran, and Hemipteran insect pests can be found on the *Bacillus thuringiensis* toxin nomenclature website maintained by Neil Crickmore (on the world wide web at btnomenclature.info).

Chimeric insecticidal protein-encoding sequences and sequences having a substantial percentage identity to the chimeric insecticidal proteins can be identified using methods known to those of ordinary skill in the art such as polymerase chain reaction (PCR), thermal amplification and hybridization. For example, the chimeric insecticidal proteins can be used to produce antibodies that bind specifically to related proteins, and can be used to screen for and to find other proteins that are closely related.

Furthermore, nucleotide sequences encoding the chimeric insecticidal proteins can be used as probes and primers for screening to identify other members of the class using thermal-cycle or isothermal amplification and hybridization methods. For example, oligonucleotides derived from sequences as set forth in SEQ ID NO:2 can be used to determine the presence or absence of a chimeric insecticidal transgene in a deoxyribonucleic acid sample derived from a commodity product. Given the sensitivity of certain nucleic acid detection methods that employ oligonucleotides, it is anticipated that oligonucleotides derived from sequences as set forth in any of SEQ ID NO:2 can be used to detect the respective chimeric insecticidal protein in commodity products derived from pooled sources where only a fraction of the commodity product is derived from a transgenic plant containing any of SEQ ID NO:2.

EXAMPLES

In view of the foregoing, those of skill in the art will appreciate that the following disclosed embodiments are merely representative of the invention, which may be embodied in various forms. Thus, specific structural and functional details disclosed herein are not to be interpreted as limiting.

sequences encoding novel chimeric insecticidal proteins. The resulting polynucleotide sequences were cloned into a *Bacillus thuringiensis* (Bt) expression plasmid vector. After confirmation of the polynucleotide sequence, the expression plasmid was transformed into Bt and expressed. Preparations of the expressed novel chimeric proteins were assayed for activity against various Lepidopteran pests.

Many polynucleotide sequences encoding chimeric insecticidal proteins were produced and tested in bioassay. Not all of the chimeric insecticidal proteins demonstrated activity. Only a few of the chimeric insecticidal proteins were selected based upon their activity to specific Lepidoptera demonstrated in bioassay. Amino acid variants in which amino acid substitutions, or alternate protoxin domains, were introduced were also produced based upon the original chimeric insecticidal proteins TIC867 and TIC868. The components of the chimeric insecticidal proteins (domains I, II and III and the protoxin) of the present invention are presented in Table 1. The amino acid substitutions in the TIC868 variants relative to the original TIC868 protein sequence are also presented.

TABLE 1

Novel chimeric pesticidal proteins and their components.

| Toxin | PRT SEQ ID NO: | Dom1 | Dom2 | Dom3 | Protox | Amino Acid Modifications* |
|---|---|---|---|---|---|---|
| TIC1100 | 4 | Cry1Ah | Cry1Ac | Cry1Ca | Cry1Ac | |
| TIC860 | 7 | Cry1Bb1 | Cry1Bb1 | Cry1Ca | Cry1Ac | |
| TIC867 | 10 | Cry1Be2 | Cry1Be2 | Cry1Ka | Cry1Ab3 | |
| TIC867_20 | 13 | Cry1Be2 | Cry1Be2 | Cry1Ka | Cry1Da1 | |
| TIC867_21 | 16 | Cry1Be2 | Cry1Be2 | Cry1Ka | Cry4 | |
| TIC867_22 | 19 | Cry1Be2 | Cry1Be2 | Cry1Ka | Cry9 | |
| TIC867_23 | 21 | Cry1Be2 | Cry1Be2 | Cry1Ka | Cry1Be | |
| TIC867_24 | 23 | Cry1Be2 | Cry1Be2 | Cry1Ka | Cry1Ka | |
| TIC867_25 | 25 | Cry1Be2 | Cry1Be2 | Cry1Ka | Cry1Ca | |
| TIC868 | 28 | Cry1Be2 | Cry1Be2 | Cry1Ca | Cry1Ab3 | |
| TIC868_9 | 30 | Cry1Be2 | Cry1Be2 | Cry1Ca | Cry1Ab3 | N240S_Y343Q_N349T |
| TIC868_10 | 33 | Cry1Be2 | Cry1Be2 | Cry1Ca | Cry1Da1 | |
| TIC868_11 | 36 | Cry1Be2 | Cry1Be2 | Cry1Ca | Cry4 | |
| TIC868_12 | 39 | Cry1Be2 | Cry1Be2 | Cry1Ca | Cry9 | |
| TIC868_13 | 41 | Cry1Be2 | Cry1Be2 | Cry1Ca | Cry1Be | |
| TIC868_14 | 43 | Cry1Be2 | Cry1Be2 | Cry1Ca | Cry1Ka | |
| TIC868_15 | 45 | Cry1Be2 | Cry1Be2 | Cry1Ca | Cry1Ca | |
| TIC868_29 | 47 | Cry1Be2 | Cry1Be2 | Cry1Ca | Cry1Ab3 | Q136Y_Y343Q_N349T |
| TIC869 | 50 | Cry1Ja1 | Cry1Ja1 | Cry1Jx | Cry1Ab3 | |
| TIC836 | 53 | Cry1Fa1 | Cry1Fa1 | Cry1Ab | Cry1Ac | |

*The amino acid mutations are identified using the standard IUPAC amino acid code. See IUPAC-IUB Joint Commission on Biochemical Nomenclature. Nomenclature and Symbolism for Amino Acids and Peptides. Eur. J. Biochem. 138: 9-37 (1984). The first amino acid sequence abbreviation indicates the original amino acid in the given scaffold protein, the number represents the position of the amino acid, and the second amino acid sequence abbreviation indicates the amino acid placed in that position in the improved variant protein.

Example 1

Creation and Cloning of Lepidopteran-Active Novel Chimeric Insecticidal Protein Coding Sequences This Example illustrates the creation of the novel chimeric insecticidal proteins and the cloning and expressing of the chimeric insecticidal proteins.

Recombinant nucleic acid sequences were constructed from known Cry protein genes to produce polynucleotide

Example 2

The Novel Chimeric Insecticidal Proteins Demonstrate Activity Against Lepidopteran Pests This Example illustrates the testing of the chimeric insecticidal proteins described in Example 1 and the Lepidopteran activity observed for the chimeric insecticidal proteins.

Polynucleotide sequences encoding chimeric insecticidal proteins were expressed in Bt. The expressed chimeric insecticidal proteins were then assayed against a variety of Lepidoptera known to be pests of corn, sugarcane, soybean and cotton, as well as other crop plants. Specifically, the insecticidal proteins were assayed for activity against Velvetbean caterpillar (VBC, *Anticarsia gemmatalis*), Sugarcane borer (SCB, *Diatraea saccharalis*), Lesser cornstalk borer (LSCB, *Elasmopalpus lignosellus*), Corn earworm (CEW, *Helicoverpa zea*), Tobacco budworm (TBW, *Heliothis virescens*), Soybean looper (SBL, *Chrysodeixis includens*), Black armyworm (BLAW, *Spodoptera* cosmioides), Southern armyworm (SAW, *Spodoptera eridania*), Fall armyworm (FAW, *Spodoptera frugiperda*), Beet armyworm (BAW, *Spodoptera exigua*), Old World bollworm (OBW, *Helicoverpa armigera*), Oriental leafworm (OLW, *Spodoptera litura*), Pink bollworm (PBW, *Pectinophora gossypiella*), Black cutworm (BCW, *Agrotis ipsilon*), Southwestern Corn Borer (SWCB, *Diatraea grandiosella*), Spotted bollworm (SBW, *Earias* vitella), and European corn borer (ECB, *Ostrinia nubilalis*). Corn earworm (CEW, *Helicoverpa zea*) is also referred to as Soybean pod worm (SPW) and Cotton bollworm (CBW). Activity was determined through a combination of mortality and stunting scores as well as MIC50 scores. MIC50 refers to a molt inhibition concentration wherein both the dead larvae and L1 larvae (larvae that failed to molt to second instars) are factored into the score. Table 2 shows the activity of each chimeric insecticidal protein. A '+' sign indicates activity observed to the specific insect pest.

TABLE 2

Bioassay activity against selected Lepidoptera.

| Toxin | PRT SEQ ID NO: | Insect VBC | SCB | LSCB | CEW SPW CBW | BLAW | TBW | SBL | SAW | FAW | BAW | OBW | OLW | PBW | BCW | SWCB | ECB | SBW |
|---|---|---|---|---|---|---|---|---|---|---|---|---|---|---|---|---|---|---|
| TIC1100 | 4 | + | + | | | + | | | + | | + | | + | + | | | | |
| TIC860 | 7 | + | + | + | | + | + | + | + | + | + | | + | + | | + | | + |
| TIC867 | 10 | + | + | | | + | | + | | + | + | + | + | | | + | | |
| TIC867_20 | 13 | | | | | | | | | | | | | | | | | |
| TIC867_21 | 16 | | | | + | | | | | | | | | | | | | |
| TIC867_22 | 19 | | | | + | | | | | + | | | | | | | | |
| TIC868 | 28 | + | + | | | + | | + | | + | + | | + | + | | + | | + |
| TIC868_10 | 33 | | | | | | | | | + | | | | | | | | |
| TIC868_11 | 36 | | | | | | | | | + | | | | | | | | |
| TIC868_12 | 39 | | | | | | | | | + | | | | | | | | |
| TIC869 | 50 | + | + | | | | | + | | + | | | | | | + | | |
| TIC836 | 53 | + | | | | + | | + | + | + | | | | | | | | |

As can be seen in Table 2 above, most of the chimeric insecticidal proteins exhibited activity against one or more Lepidopteran pest species.

Example 3

Synthesis of Genes Encoding Chimeric Insecticidal Proteins and for Expression in Plants This Example illustrates the synthesis of polynucleotides encoding the chimeric insecticidal proteins for expression in plants.

Synthetic coding sequences were constructed for use in expression of the chimeric insecticidal proteins in plants. The synthetic sequences were designed and synthesized according to methods generally described in U.S. Pat. No. 5,500,365, avoiding certain inimical problem sequences such as ATTTA and A/T rich plant polyadenylation sequences while preserving the amino acid sequence of the chimeric insecticidal protein. The nucleotide sequences for these genes encoding the chimeric insecticidal proteins for expression in plants are listed in Table 3.

TABLE 3

Polynucleotide Sequences Encoding Chimeric Insecticidal Proteins Designed for Use in Plants.

| Insecticidal Protein | DNA SEQ ID NO: | PRT SEQ ID NO: |
|---|---|---|
| TIC1100 | 2 | 4 |
| TIC1100 | 3 | 4 |
| TIC860 | 6 | 7 |
| TIC867 | 9 | 10 |
| TIC867_20 | 12 | 13 |
| TIC867_21 | 15 | 16 |
| TIC867_22 | 18 | 19 |
| TIC867_23 | 20 | 21 |
| TIC867_24 | 22 | 23 |
| TIC867_25 | 24 | 25 |
| TIC868 | 27 | 28 |
| TIC868_9 | 29 | 30 |
| TIC868_10 | 32 | 33 |
| TIC868_11 | 35 | 36 |
| TIC868_12 | 38 | 39 |
| TIC868_13 | 40 | 41 |
| TIC868_14 | 42 | 43 |
| TIC868_15 | 44 | 45 |
| TIC868_29 | 46 | 47 |
| TIC869 | 49 | 50 |
| TIC836 | 52 | 53 |

Example 4

Expression Cassettes for the Expression of Chimeric Insecticidal Proteins in Plants This Example illustrates the construction of expression cassettes comprising polynucleotide sequences designed for use in plants which encode chimeric insecticidal proteins.

A variety of plant expression cassettes were constructed with the polynucleotide sequences encoding the chimeric insecticidal proteins designed for plant expression provided in Table 3. Such expression cassettes are useful for transient expression in plant protoplasts or transformation of plant cells. Typical expression cassettes were designed with respect to the eventual placement of the protein within the cell. One set of expression cassettes was designed in a manner to allow the protein to be translated and remain in the cytosol. Another set of expression cassettes was designed to have a transit peptide contiguous with the toxin protein to allow targeting to an organelle of the cell such as the chloroplast or plastid. All expression cassettes were designed to begin at the 5' end with a promoter, which can be comprised of multiple promoter elements, enhancer elements, or other expression elements known to those of ordinary skill in the art operably linked to boost the expression of the transgene. The promoter sequence was usually followed contiguously with one or more leader sequences 3' to the promoter. An intron sequence was usually provided 3' to the leader sequence to improve expression of the transgene. A coding sequence for the toxin or transit peptide and coding sequence for the toxin was usually located 3' to the operably linked promoter, leader and intron configuration. A 3'UTR sequence was usually provided 3' of the coding sequence to facilitate termination of transcription and to provide sequences important for the polyadenylation of the resulting transcript. All of the elements described above were operably linked and arranged sequentially, often with additional sequences provided for the construction of the expression cassette.

Example 5

Lepidopteran Activity of the Chimeric Insecticidal Proteins in Stably Transformed Corn This Example illustrates the inhibitory activity exhibited by the chimeric insecticidal proteins against Lepidopteran pests when expressed in corn plants and provided as a diet to the respective corn insect pest.

Corn variety LH244 was transformed with the binary transformation vectors described in Example 4 using an *Agrobacterium*-mediated transformation method. The transformed cells were induced to form plants by methods known in the art. Bioassays using plant leaf disks were performed analogous to those described in U.S. Pat. No. 8,344,207. A non-transformed LH244 plant was used to obtain tissue to be used as a negative control. Multiple transformation events from each binary vector were assessed against Corn earworm (CEW, *Helicoverpa zea*), Fall armyworm (FAW, *Spodoptera frugiperda*), Black cutworm (BCW, *Agrotis ipsilon*) and Southwestern Corn Borer (SWCB, *Diatraea grandiosella*).

Leaf disc bioassay was performed on $R_0$ and $F_1$ generation transgenic plants. In addition, leaf damage ratings were assessed for whole transgenic $F_1$ plants expressing certain chimeric insecticidal proteins infested with the Lepidopteran insect pests. $F_1$ transgenic events expressing TIC860 and TIC868 were also assessed for activity in the field against FAW, CEW, and SWCB. The assay results are shown in Table 4. A '+' sign indicates activity observed to the specific insect pest. As can be seen in Table 4, most of the chimeric insecticidal proteins and many of the chimeric insecticidal protein variants demonstrated activity against one or more Lepidopteran pest species.

TABLE 4

Bioassay activity of chimeric insecticidal proteins from stably transformed corn leaf tissue.

| | PRT | Insect | | | | | | | | | | | | | | | | |
|---|---|---|---|---|---|---|---|---|---|---|---|---|---|---|---|---|---|---|
| Toxin | SEQ ID NO: | VBC | SCB | LSCB | CEW SPW CBW | BLAW | TBW | SBL | SAW | FAW | BAW | OBW | OLW | PBW | BCW | SWCB | ECB | SBW |
| TIC1100 | 4 | + | + | | | + | | | + | | + | | + | + | | | | |
| TIC860 | 7 | + | + | + | | + | + | + | + | + | + | | + | + | | + | | + |
| TIC867 | 10 | + | + | | | + | | + | | + | + | + | + | | | + | | |
| TIC867_20 | 13 | NT | NT | NT | | NT | NT | NT | NT | | NT | NT | NT | NT | NT | NT | NT | NT |
| TIC867_21 | 16 | NT | NT | NT | + | NT | NT | NT | NT | | NT | NT | NT | NT | NT | NT | NT | NT |
| TIC867_22 | 19 | NT | NT | NT | + | NT | NT | NT | NT | + | NT | NT | NT | NT | NT | NT | NT | NT |
| TIC868 | 28 | + | + | | | + | | + | + | + | + | | + | + | | + | | + |
| TIC868_10 | 33 | NT | NT | NT | + | NT | NT | NT | NT | + | NT | NT | NT | NT | NT | NT | NT | NT |
| TIC868_11 | 36 | NT | NT | NT | + | NT | NT | NT | NT | + | NT | NT | NT | NT | NT | NT | NT | NT |
| TIC868_12 | 39 | NT | NT | NT | + | NT | NT | NT | NT | + | NT | NT | NT | NT | NT | NT | NT | NT |
| TIC869 | 50 | + | + | | | | | + | + | + | | | | | | + | | |
| TIC836 | 53 | + | | | | + | | + | + | + | | | | | | | | |

Example 6

Lepidopteran Activity of the Chimeric Insecticidal Proteins in Stably Transformed Soybean This Example illustrates the inhibitory activity exhibited by the chimeric insecticidal proteins against Lepidopteran pests when expressed in soybean plants and provided as a diet to the respective insect pest.

The coding sequences for selected chimeric insecticidal proteins were redesigned for plant expression, cloned into a binary plant transformation vector, and used to transform soybean plant cells. The plant transformation vectors comprised a first transgene cassette for expression of the chimeric insecticidal protein as described in Example 4 and a second transgene cassette for the selection of transformed plant cells using spectinomycin selection. In some instances, such as in the case of TIC1100, TIC860 and TIC836, a chloroplast transit peptide coding sequence was operably linked to the chimeric insecticidal coding sequence. Assays were performed with plastid targeted and untargeted TIC1100, TIC860 and TIC836. Table 5 below shows the chimeric insecticidal and TIC867 variant chimeric insecticidal protein and associated coding sequences used for expression in stably transformed soybean.

Soybean plant cells were transformed using the binary transformation vectors described above by *Agrobacterium*-mediated transformation. The resulting transformed plant cells were induced to form whole soybean plants. Leaf tissue was harvested and used in bioassay as described in Example 5 or alternatively, lyophilized tissue was used in the insect diet for bioassay. Bioassay was performed against FAW, Southern armyworm (SAW, *Spodoptera eridania*), Soybean looper (SBL, *Chrysodeixis includens*), Soybean Pod Worm (SPW, *Helicoverpa zea*), Velvetbean caterpillar (VBC, *Anticarsia gemmatalis*), Tobacco budworm (TBW, *Heliothis virescens*), Black armyworm (BLAW, *Spodoptera* cosmioides), Lesser cornstalk borer (LSCB, *Elasmopalpus lignosellus*) and Old World bollworm (OBW, *Helicoverpa armigera*).

Table 5 shows the activity against selected species of Lepidoptera for each insecticidal protein in $R_0$ generation plants, wherein '+' indicates activity. As can be seen in Table 5, each of the chimeric insecticidal proteins expressed in stably transformed soybean demonstrated activity against multiple Lepidopteran species. Of particular note is that the TIC867 variant, TIC867_23 demonstrated activity against SPW.

TABLE 5

Bioassay activity of chimeric insecticidal proteins from stably transformed $R_0$ soybean leaf tissue.

| Insecticidal Protein | FAW | SAW | SBL | SPW | VBC | TBW | BLAW | LSCB | OBW |
|---|---|---|---|---|---|---|---|---|---|
| TIC1100 | + | + | + | | + | | + | + | + |
| TIC860 | + | + | + | | + | | | + | |
| TIC867 | + | + | + | | + | + | | + | |
| TIC867_20 | | + | + | | | | | | |
| TIC867_21 | | + | + | | | | | | |
| TIC867_22 | | + | + | | | | | | |
| TIC867_23 | + | + | + | + | | | | | |
| TIC867_24 | | + | + | | | | | | |
| TIC867_25 | | + | + | | | | | | |
| TIC868 | + | | + | | + | | + | + | |
| TIC869 | | | + | | + | + | | + | |
| TIC836 | + | + | + | | + | + | + | | + |

Selected transformed events were allowed to self-pollinate and the resulting seed was grown. Leaf tissue was harvested from the $R_1$ generation plants and used in a feeding bioassay. $R_1$ plants expressing TIC1100, TIC860, TIC867, TIC868, TIC869 and TIC836 were assayed for activity against SAW, SBL, SPW and VBC. Table 6 shows the activity observed in these tests. A '+' sign indicates activity observed to the specific insect pest. As demonstrated in Table 6, most of the expressed chimeric insecticidal proteins from $R_1$ generation plants demonstrated activity to one or more Lepidopteran species.

TABLE 6

Bioassay activity of chimeric insecticidal proteins from stably transformed $R_1$ soybean leaf tissue.

| Toxin | SAW | SBL | SPW | VBC |
|---|---|---|---|---|
| TIC1100 | + | + | | + |
| TIC860 | + | + | | + |
| TIC867 | + | | | |
| TIC868 | + | + | | + |
| TIC869 | + | + | | + |
| TIC836 | + | + | | + |

Table 7 demonstrates the results of field tests conducted in screen houses with stably transformed $R_1$ generation soybean plants expressing TIC1100, TIC860, and TIC836. Species used to infest plants in the screen houses include SAW, SBL and SPW. Resistance was defined as being less than or equal to fifteen percent defoliation in the soybean plants. The resistance observed in these cage trials is consistent with the resistance observed in the $R_1$ generation soybean leaf tissue assay presented in Table 6. A '+' sign indicates activity observed to the specific insect pest.

TABLE 7

Activity Profile of TIC1100, TIC860 and TIC836 Expressed in $R_1$ Generation Soybean Tested in Screen House Field Tests.

| Toxin | SAW | SBL | SPW |
|---|---|---|---|
| TIC1100 | + | + | |
| TIC860 | + | + | |
| TIC836 | + | + | |

Field tests in screen houses with stably transformed $R_1$ generation soybean plants expressing TIC867 and TIC869 were also conducted at two different locations in Argentina, Acevedo and Fontezuela. Species used to infest plants in the screen houses include South American bollworm (SABW, *Helicoverpa gelotopeon*), VBC, BLAW, and Sunflower looper (SFL, *Rachiplusia nu*). Resistance was defined as being less than or equal to fifteen percent defoliation in the soybean plants. Table 8 below shows the resistance observed. A '+' sign indicates activity observed to the specific insect pest. As demonstrated in Table 8, transgenic soybean plants expressing TIC867 demonstrated resistance to BLAW and VBC. Transgenic soybean plants expressing TIC869 demonstrated resistance to SABW, SFL, BLAW, and VBC.

TABLE 8

Activity Profile of TIC867 and TIC869 Expressed in $R_1$ Generation Soybean Tested in Screen House Field Tests.

| | Acevedo | | | Fontezuela | | |
|---|---|---|---|---|---|---|
| Toxin | SABW | SFL | VBC | SABW | BLAW | VBC |
| TIC867 | | | + | | + | + |
| TIC869 | | + | + | + | + | + |

Example 7

Lepidopteran Activity of the Chimeric Insecticidal Proteins in Stably Transformed Cotton This Example illustrates the inhibitory activity exhibited by the chimeric insecticidal proteins against Lepidopteran pests when expressed in cotton plants and provided as a diet to the respective insect pest.

The coding sequences for selected chimeric insecticidal proteins were redesigned for plant expression, cloned into a binary plant transformation vector, and used to transform cotton plant cells. The resulting binary vectors were similar to those described in Example 4 and were used to express plastid targeted and untargeted TIC860 (coding sequence: SEQ ID NO: 6; protein sequence: SEQ ID NO: 7), TIC867 (coding sequence: SEQ ID NO: 9; protein sequence: SEQ ID NO: 10), TIC868 (coding sequence: SEQ ID NO: 27; protein sequence: SEQ ID NO: 28) and TIC867_23 (coding sequence: SEQ ID NO: 20; protein sequence: SEQ ID NO: 23).

Cotton plant cells were transformed by an *Agrobacterium*-mediated transformation method. Transformed cotton cells were induced to form whole plants. Cotton leaf tissue was used in bioassay as described in Example 5 against Cotton Boll Worm (CBW, *Helicoverpa zea*), FAW, TBW and SBL. Table 9 shows the activity observed against these Lepidopteran species for TIC860, TIC867, and TIC868 in stably transformed $R_0$ generation cotton, wherein '+' indicate activity. As can be seen in Table 9, TIC860, TIC867, and TIC868 demonstrated activity against two or more Lepidopteran pest species in stably transformed $R_0$ generation cotton.

TABLE 9

Bioassay activity of TIC860, TIC867 and TIC868 from stably transformed $R_0$ cotton leaf tissue.

| Toxin | CBW | FAW | TBW | SBL |
|---|---|---|---|---|
| TIC860 | | + | | + |
| TIC867 | + | + | + | NT |
| TIC868 | | + | | + |

Selected transformation events were used to produce $R_1$ seed. $R_1$ Plants expressing TIC860, TIC867, and TIC868 were assayed for resistance to CBW, FAW, TBW, and SBL. Leaf, square and boll tissues were used in assay. Table 10 shows the activity observed in these tests. A '+' sign indicates activity observed to the specific insect pest. As demonstrated in Table 10, TIC860 demonstrated activity against FAW in the leaf tissue. Further, the chimeric insecticidal protein TIC867 demonstrated activity against CBW and FAW in the leaf, square and boll tissues, as well as TBW and SBL in the leaf. The chimeric insecticidal protein TIC868 demonstrated activity against FAW in the leaf, square and boll tissues, as well as TBW and SBL in the leaf.

TABLE 10

Bioassay activity of chimeric insecticidal proteins from stably transformed $R_1$ cotton leaf tissue.

| | CBW | | | FAW | | | TBW | SBL |
|---|---|---|---|---|---|---|---|---|
| Toxin | Leaf | Square | Boll | Leaf | Square | Boll | Leaf | Leaf |
| TIC860 | | | | + | | | | |
| TIC867 | + | + | + | + | + | + | + | + |
| TIC868 | | | | + | + | + | + | + |

All of the compositions disclosed and claimed herein can be made and executed without undue experimentation in light of the present disclosure. While the compositions of this invention have been described in terms of the foregoing illustrative embodiments, it will be apparent to those of skill in the art that variations, changes, modifications, and alterations may be applied to the composition described herein, without departing from the true concept, spirit, and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope, and concept of the invention as defined by the appended claims.

All publications and published patent documents cited in the specification are incorporated herein by reference to the same extent as if each individual publication or patent application was specifically and individually indicated to be incorporated by reference.

What is claimed is:

1. A chimeric insecticidal protein comprising SEQ ID NO:7, wherein the chimeric insecticidal protein exhibits inhibitory activity against an insect species of the order Lepidoptera.

2. A polynucleotide encoding the chimeric insecticidal protein of claim 1, wherein the polynucleotide is operably linked to a heterologous promoter.

3. A polynucleotide encoding a chimeric insecticidal protein, wherein the polynucleotide:

a) comprises SEQ ID NO: 6; or b) encodes the chimeric insecticidal protein of claim 1.

4. A host cell comprising the polynucleotide of claim 3, wherein said polynucleotide comprises SEQ ID NO: 6, wherein the host cell is selected from the group consisting of a bacterial host cell and a plant host cell.

5. The host cell of claim 4, wherein the bacterial host cell is selected from the group consisting of *Agrobacterium, Rhizobium, Bacillus, Brevibacillus, Escherichia, Pseudomonas, Klebsiella*, and *Erwinia.*

6. The host cell of claim 4, wherein said plant host cell is selected from the group of plants consisting of monocots and dicots.

7. An insect inhibitory composition comprising the chimeric insecticidal protein of claim 1.

8. The insect inhibitory composition of claim 7, further comprising at least one insect inhibitory agent different from the chimeric insecticidal protein.

9. The insect inhibitory composition of claim 8, wherein said at least one insect inhibitory agent is selected from the group consisting of an insect inhibitory protein and an insect inhibitory dsRNA molecule.

10. The insect inhibitory composition of claim 8, wherein said at least one other pesticidal agent exhibits activity against one or more pest species of the orders Lepidoptera, Coleoptera, Hemiptera, Homoptera, or Thysanoptera.

11. A seed comprising an insect inhibitory effective amount of:

a) the chimeric insecticidal protein of claim 1; or b) the polynucleotide set forth in SEQ ID NO: 6.

12. A method of controlling a Lepidopteran pest, the method comprising contacting the Lepidopteran pest with an inhibitory amount of the chimeric insecticidal protein of claim 1.

13. A transgenic plant cell, plant or plant part comprising a chimeric insecticidal protein, wherein the chimeric insecticidal protein comprises SEQ ID NO: 7.

14. A method of controlling a Lepidopteran pest, comprising exposing the pest to the transgenic plant or plant part of claim 13, wherein said plant or plant part expresses a Lepidopteran inhibitory amount of the chimeric insecticidal protein.

15. A commodity product derived from the plant or plant part of claim 13, wherein the product comprises a detectable amount of the chimeric insecticidal protein.

16. The commodity product of claim 15, wherein the product is selected from the group consisting of plant biomass, oil, meal, animal feed, flour, flakes, bran, lint, hulls, and processed seed.

17. A method of producing a seed comprising the chimeric insecticidal protein of claim 1, the method comprising:

a) planting at least one seed comprising the chimeric insecticidal protein of claim 1;

b) growing at least one plant from said seed; and c) harvesting seeds from said at least one plant, wherein the harvested seeds comprise the chimeric insecticidal protein of claim 1.

18. A recombinant polynucleotide molecule encoding the chimeric insecticidal protein of claim 1, said molecule comprising SEQ ID NO:6 and a polynucleotide sequence encoding an insect inhibitory agent different from the chimeric insecticidal protein.

19. A recombinant nucleic acid molecule comprising a heterologous promoter operably linked to a polynucleotide segment encoding a chimeric insecticidal protein, wherein:

a) in the chimeric insecticidal protein comprises SEQ ID NO: 7; or b) the polynucleotide segment comprises SEQ ID NO: 6;

wherein said chimeric insecticidal protein exhibits inhibitory activity against an insect species of the order Lepidoptera.

* * * * *